US010696958B2

(12) United States Patent
Babe et al.

(10) Patent No.: US 10,696,958 B2
(45) Date of Patent: Jun. 30, 2020

(54) METALLOPROTEASES

(71) Applicant: DANISCO US INC., Palo Alto, CA (US)

(72) Inventors: Lilia M. Babe, Palo Alto, CA (US); Frits Goedegebuur, Palo Alto, CA (US); Roopa Ghirnikar, Palo Alto, CA (US); Xiaogang Gu, Palo Alto, CA (US); Marc Kolkman, Palo Alto, CA (US); Jian Yao, Palo Alto, CA (US)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 15/835,551

(22) Filed: Dec. 8, 2017

(65) Prior Publication Data
US 2018/0087038 A1 Mar. 29, 2018

Related U.S. Application Data

(63) Continuation of application No. 14/893,473, filed as application No. PCT/US2014/039928 on May 29, 2014, now abandoned.

(30) Foreign Application Priority Data

May 29, 2013 (CN) .................... 13/076384
May 29, 2013 (CN) .................... 13/076387
May 29, 2013 (CN) .................... 13/076398
May 29, 2013 (CN) .................... 13/076401
May 29, 2013 (CN) .................... 13/076406
May 29, 2013 (CN) .................... 13/076414
May 29, 2013 (CN) .................... 13/076415
May 29, 2013 (CN) .................... 13/076419

(51) Int. Cl.
C12N 9/52 (2006.01)
C12N 9/48 (2006.01)
C12N 9/54 (2006.01)
C11D 3/386 (2006.01)

(52) U.S. Cl.
CPC .............. C12N 9/52 (2013.01); C11D 3/386 (2013.01); C11D 3/38681 (2013.01); C12N 9/485 (2013.01); C12N 9/54 (2013.01); C12Y 304/24 (2013.01)

(58) Field of Classification Search
None
See application file for complete search history.

(56) References Cited

U.S. PATENT DOCUMENTS 4,261,868 A 4/1981 Hora et al.
5,496,710 A 3/1996 Nagao et al.

FOREIGN PATENT DOCUMENTS

| JP | 2006 197802 A | 8/2006 | |
|---|---|---|---|
| WO | WO98/44127 A1 | 10/1998 | |
| WO | WO2007/044993 A2 | 4/2007 | |
| WO | WO-2007044993 A2 * | 4/2007 | ............ C11D 3/386 |
| WO | WO2009/058303 A2 | 5/2009 | |
| WO | WO2009/058661 A1 | 5/2009 | |
| WO | WO2014/071410 A1 | 5/2014 | |
| WO | WO2014/194032 A1 | 12/2014 | |
| WO | WO2014/194054 A1 | 12/2014 | |
| WO | WO2014/194117 A2 | 12/2014 | |

OTHER PUBLICATIONS

Bowie et al (Science, 1990, 257:1306-1310).*
Bork (Genome Research, 2000, 10:398-400).*
Chang et al., "Roles of the signal peptide and mature domains in the secretion and maturation of the neutral metalloprotease from Streptomyces cacaoi." Biochemical Journal, 321(1): 29-37, 1997.
Database Uniprot: Q75NT6 Bacillus vietnamensis, Jul. 5, 2004.
Database Uniprot, Oct. 5, 2010 "Thermolysin metallopeptidase from Streptomyces griseoflavus Tu4000", retrieved from EBI Database Accession No. D9Y036.
Database Uniprot, Apr. 18, 2012, "Subname: Full=Baillolysin;" Uniprot: H6CMZ7.
Database UniProt, Jul. 24, 2007, Subname: Full=Bacillolysin (Thermolysin-like metalloprotease, peptidase M4), Uniprot: A6CTU8.
Database Geneseq, Oct. 5, 2006, "S. septatus metalloendopeptidase, SEQ ID 2." XP002729913, retrieved from EBI accession No. GSP:AEJ59500, Database accession No. AEJ59500 sequence.
Database Geneseq, Oct. 5, 2006, "S. septatus metalloendopeptidase, SEQ ID 1." XP002729914 retrieved from EBI accession No. GSN:AEJ59499, Database accession No. AEJ59499 sequence.
Database Geneseq, Dec. 13, 2007,"Bacillus polymyxa neutral metalloprotease (npr) protein.", EBI accession No. GSP:ANJ68751.
Database Geneseq, Feb. 8, 1992, "Paenibacillus polymyxa npr gene for extracellular neutral protease, complete cds" retrieved from EBU accession No. EM STD: D00861.
Database Geneseq, Feb. 26, 2013, "Paenibacillus polymyxa strain EJS-3 fibrinolytic enzyme gene, complete cds", retrieved from EBI accession No. KC176802.
Derekova, Anna et al, "Anoxybacillus rupiensis sp. Nov., a novel thermophilic bacterium isolated from Rupi basin (Bulgaria)", Extremophiles, 11:577-583 (2007).
International Search Report for PCT/US2014/039928 dated Sep. 14, 2015.
International Preliminary Report on Patentability for PCT/US2014/039928, dated Dec. 1, 2015.
Simkhada, Jaya Ram et al., "An Oxidant-and Organic Solvent-Resistant Alkaline Metalloprotease from Streptomyces olivochromogenes." Applied Biochemistry and Biotechnology, 162(5): 1457-1470, 2010.
Rao, Mala B et al., "Molecular and Biotechnological aspects of microbial proteases." Microbiology and Molecular Biology Reviews, American Society for Microbiology, US, 62(3): 597-635, 1998.

(Continued)

Primary Examiner — Robert A Zeman

(57) ABSTRACT

Aspects of the present compositions and methods relate to novel metalloproteases, polynucleotides encoding the novel metalloproteases, and compositions and methods for use thereof.

4 Claims, 50 Drawing Sheets

Specification includes a Sequence Listing.

(56) References Cited

OTHER PUBLICATIONS

Mihwah, Kim et al, "Gene cloning and characterization of a Bacillus vietnamensis metalloprotease.", bioscience, biotechnology and biochemistry, vol. 68, No. 7, Jul. 1, 2004, p. 1533-1540.
Strongin, Alex et al., "Sequence regions of Bacilli metalloproteinases that can affect enzyme thermostability", Prot Seq. Data Anal. 4:355-361 (1991).

* cited by examiner

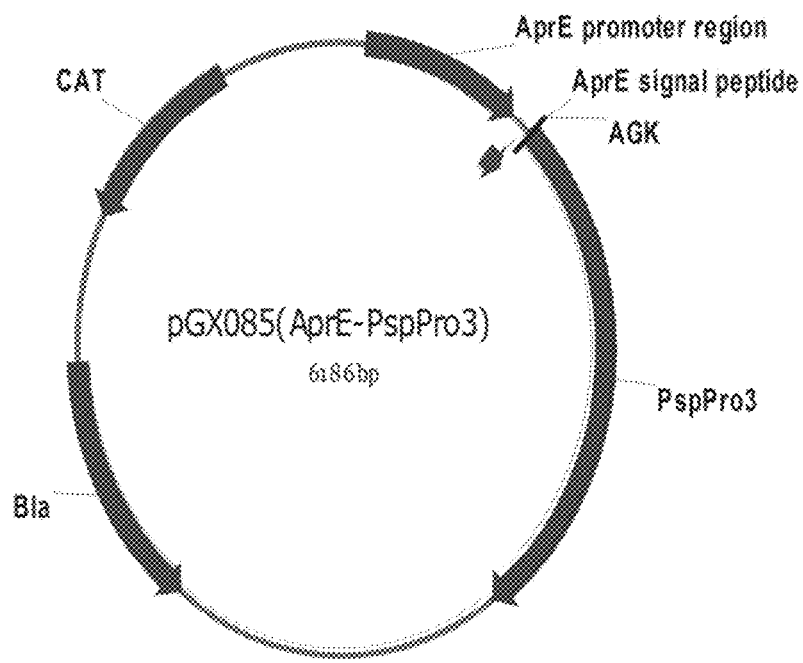
Figure 1.1. Plasmid map of pGX085(AprE-PspPro3).
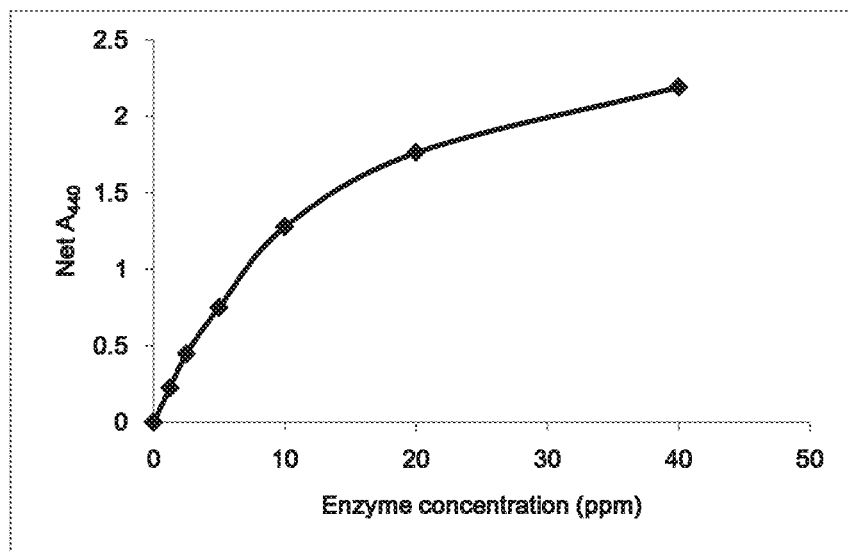
Figure 1.2. Dose response of PspPro3 in azo-casein assay at pH 7.

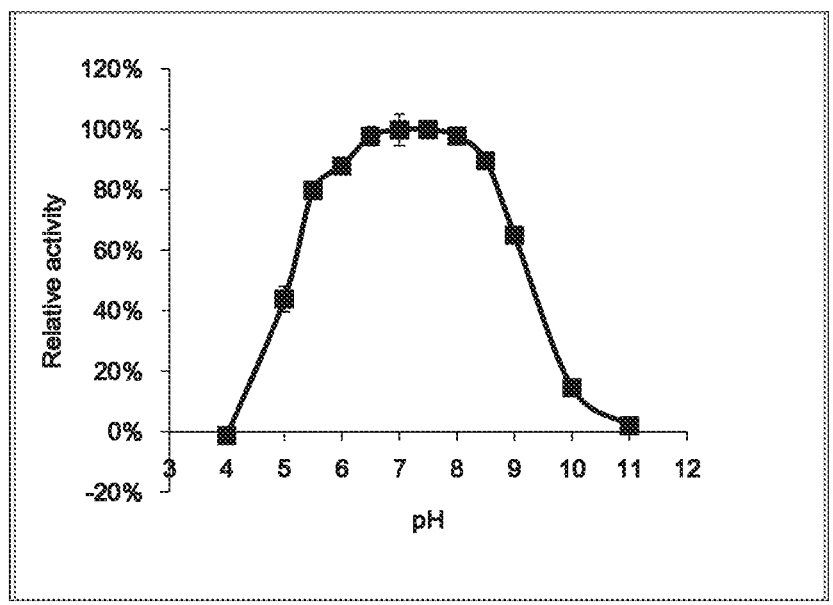
Figure 1.3. pH profile of PspPro3.
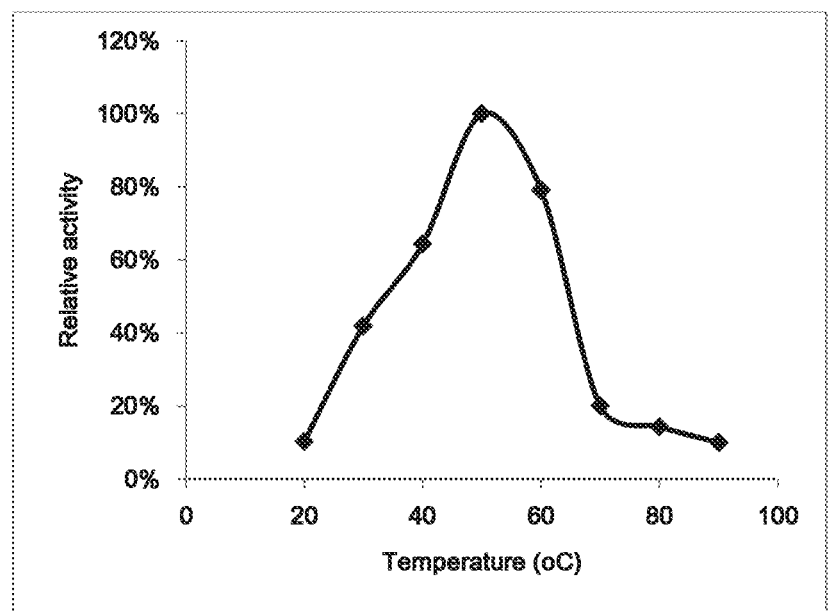
Figure 1.4. Temperature profile of PspPro3.

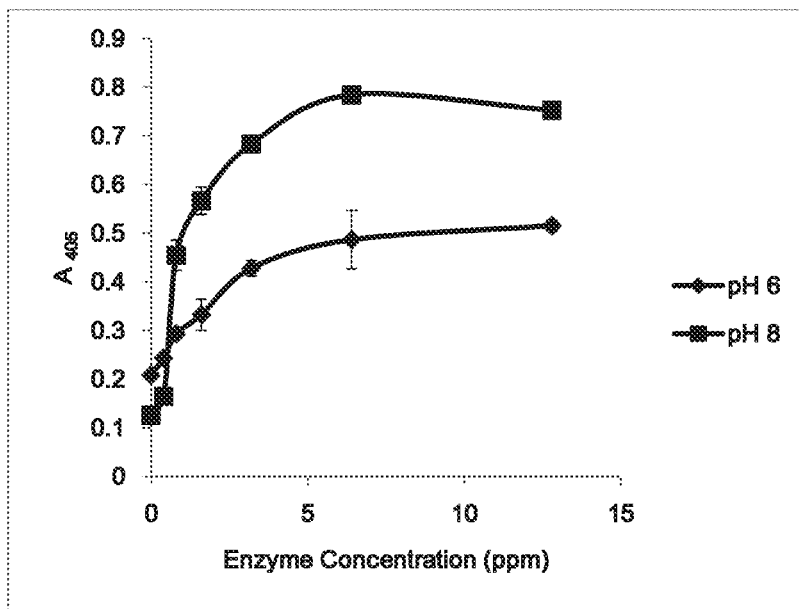
Figure 1.5A. Cleaning performance of PspPro3 at pH 6 and 8 in AT dish detergent.
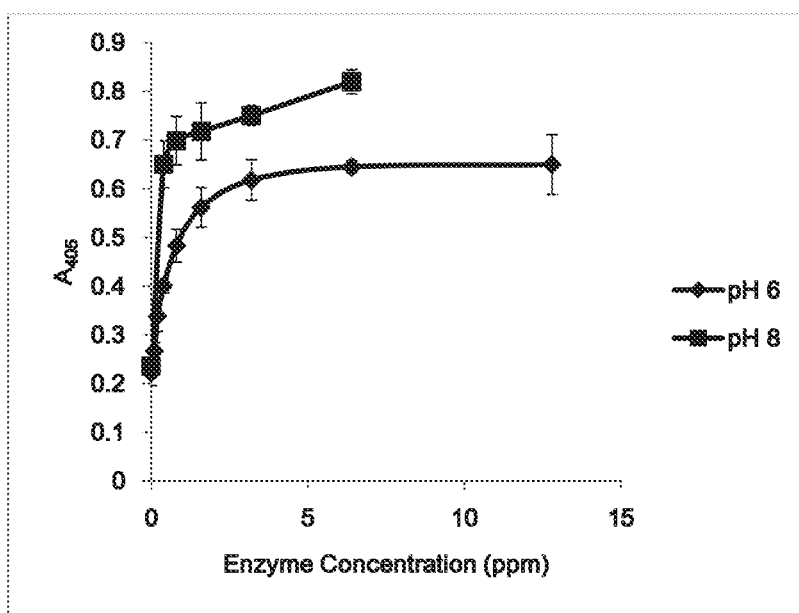
Figure 1.5B. Cleaning performance of PspPro3 at pH 6 and 8 in AT dish detergent with bleach

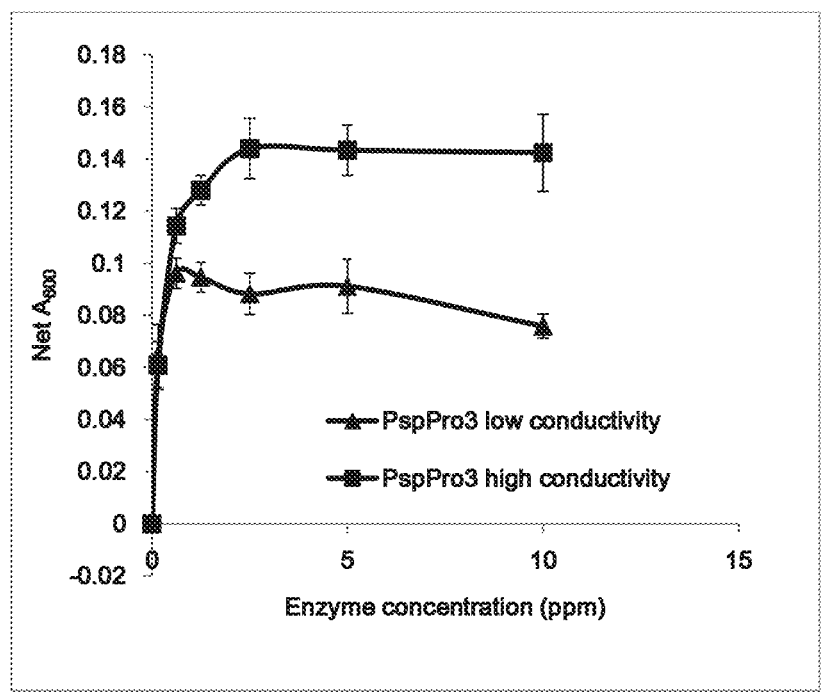
Figure 1.6. Cleaning performance of PspPro3 in liquid laundry detergent at pH 8

```
CLUSTAL W (1.83) multiple sequence alignment

PspPro3                         ------ATGTGKGVLGDTKTFNTTASGSSYQLRDTTRGNGIVTYTASNRQS
Paenibacillus_sp_Aloe-11        ---NEATGTGKGVLGDTKTFNTTASGSSYQLRDTTRGNGIVTYTASNRQS
B_thermoproteolyticus_P00800    ITGTSTVGVGRGVLGDQKNINTTYS-TYYYLQDNTRGNGIFTYDAKYRTT
                                    :.*.*:***** *.:*** * : * *;*.******.** *. * :

PspPro3                         IPGTILTDADNVWN---DPAGVDAHAYAAKTYDYYKEKFNPNSIDGRGLQ
Paenibacillus_sp_Aloe-11        IPGTILTDADNVWN---DPAGVDAHAYAAKTYDYYKEKFNPNSIDGRGLQ
B_thermoproteolyticus_P00800    LPGSLWADADNQFFASYDAPAVDAHYYAGVTYDYYKNVHNRLSYDGNNAA
                                :**:: :**** :    *..,**** **. ******: .** * **..

PspPro3                         LRSTVHYGNRYNNAFWNGSQMTYGDGDGTTFIAFSGDPDVVGHELTHGVT
Paenibacillus_sp_Aloe-11        LRSTVHYGNRYNNAFWNGSQMTYGDGDGTTFIAFSGDPDVVGHELTHGVT
B_thermoproteolyticus_P00800    IRSSVHYSQGYNNAFWNGSQMVYGDGDGQTFIPLSGGIDVVAHELTHAVT
                                :**:***.: **********.****** ***.:**. ***.***** **

PspPro3                         EYTSNLEYYGESGALNEAFSDIIGNDIQ-------RKNWLVGDDIYTPRIAG
Paenibacillus_sp_Aloe-11        EYTSNLEYYGESGALNEAFSDIIGNDIQ-------RKNWLVGDDIYTPRIAG
B_thermoproteolyticus_P00800    DYTAGLIYQNESGAINEAISDIFGTLVEFYANKNPDWEIGEDVYTPGISG
                                :**:.* * ,****:****:****:*. ::        . :* :*:*:*** *:*

PspPro3                         DALRSMSNPTLYDQPDHYSNLYRGSSDNGGVHINSGIINKAYYLLAQGGT
Paenibacillus_sp_Aloe-11        DALRSMSNPTLYDQPDHYSNLYRGSSDNGGVHINSGIINKAYYLLAQGGT
B_thermoproteolyticus_P00800    DSLRSMSDPAKYGDPDHYSKRYTGTQDNGGVHINSGIINKAAYLISQGGT
                                *:*****:*: *.;****** * *:.****** ******** **;:****

PspPro3                         FHGVTVNGIGRDAAVQIYYSAFTNYLTSSSDFSNARDAVVQAAKDLYGAS
Paenibacillus_sp_Aloe-11        FHGVTVNGIGRDAAVQIYYSAFTNYLTSSSDFSNARDAVVQAAKDLYGAS
B_thermoproteolyticus_P00800    HYGVSVVGIGRDKLGKIFYRALTQYLTPTSNFSQLRAAAVQSAIDLYGST
                                .:**:* *****    :*:* *;:***.;*;**; * *.**;*.****::

PspPro3                         SAQATAAAKSFDAVGVN    (SEQ ID NO: 3)
Paenibacillus_sp_Aloe-11        SAQATAAAKSFDAVGVN    (SEQ ID NO: 44)
B_thermoproteolyticus_P00800    SQEVASVKQAFDAVGVK    (SEQ ID NO: 45)
                                * :.::. ::*******:
```

Figure 1.7. Alignment of PspPro3 with protease homologs

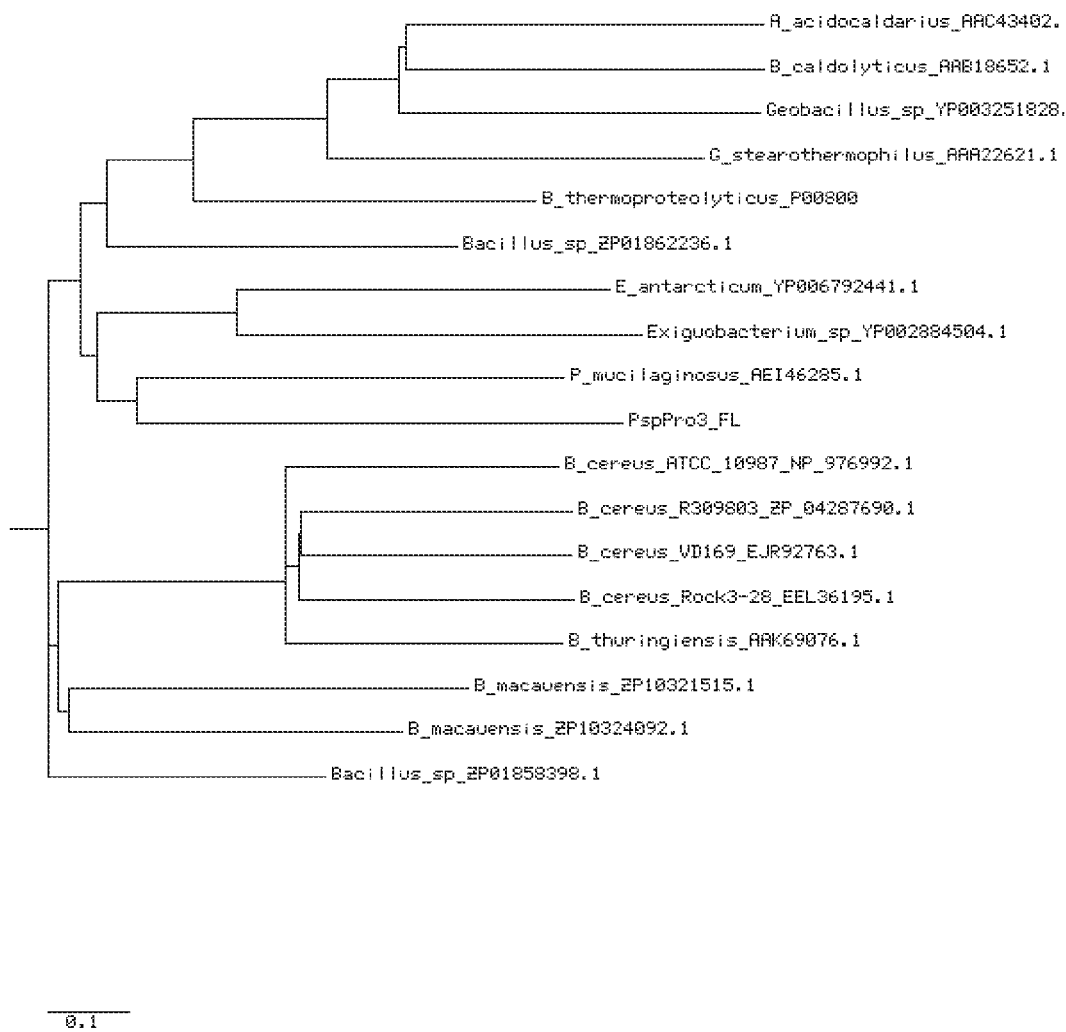
Figure 1.8. Phylogenetic tree of PspPro3 and homologs.

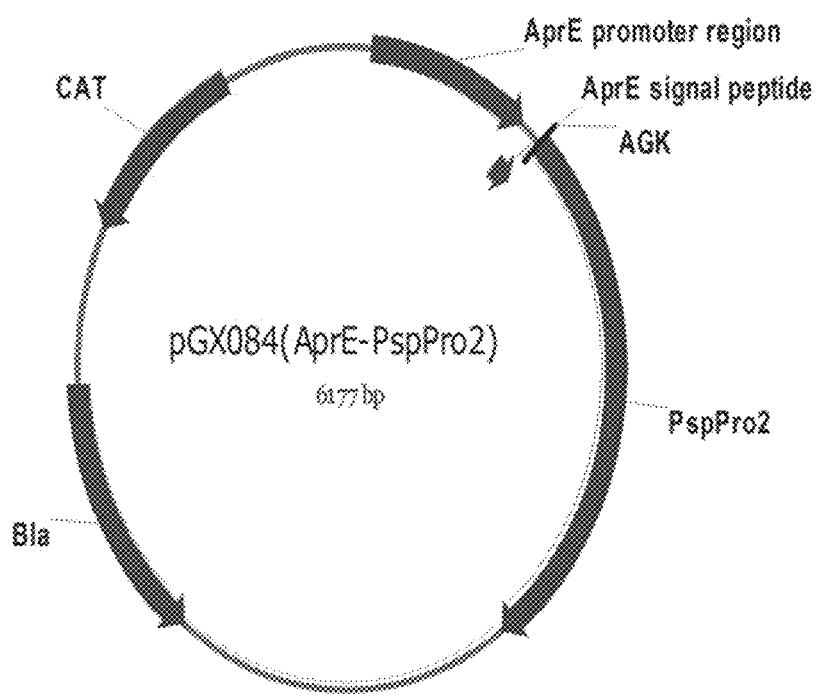
Figure 2.1. The map of plasmid pGX084(AprE-PspPro2).

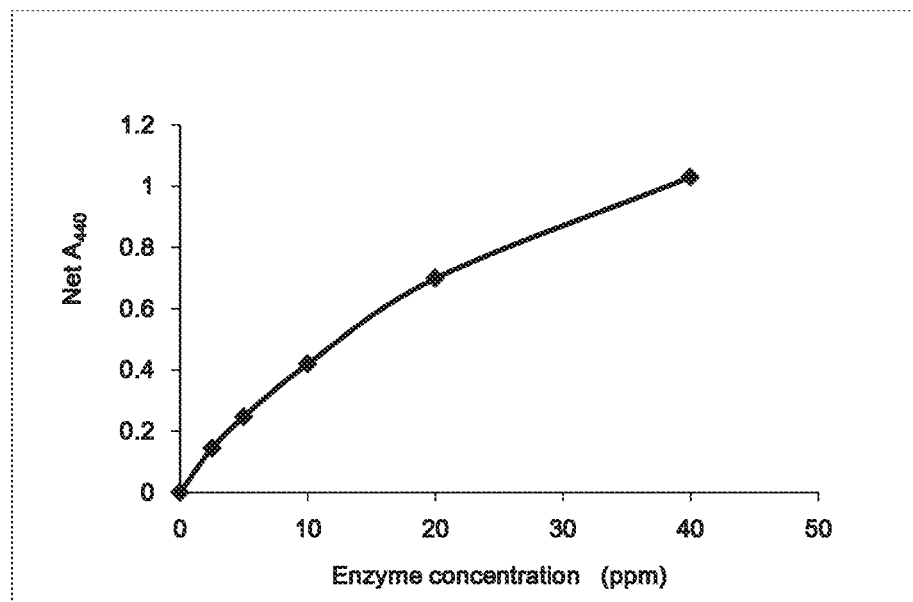
Figure 2.2. Dose response curve of PspPro2 in azo-casein assay at pH 7.
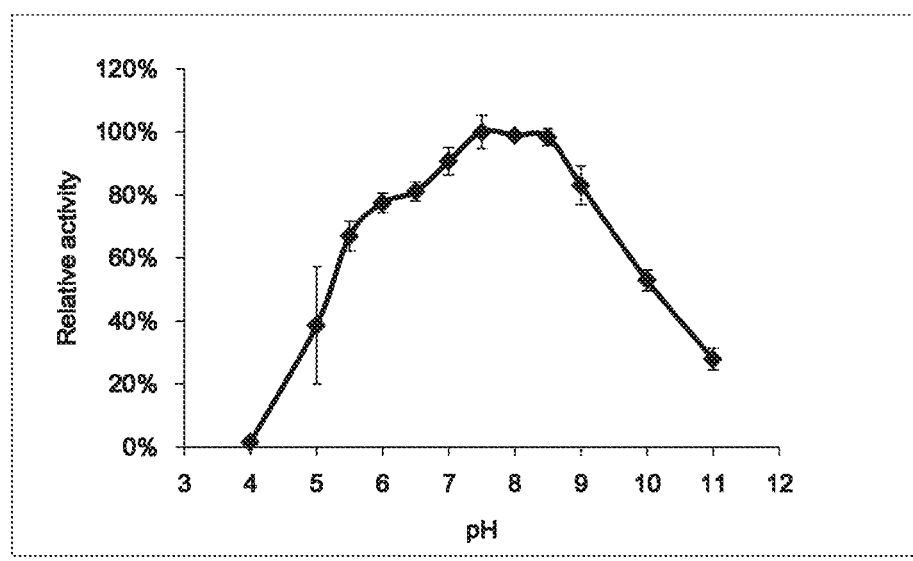
Figure 2.3. pH profile of purified PspPro2.

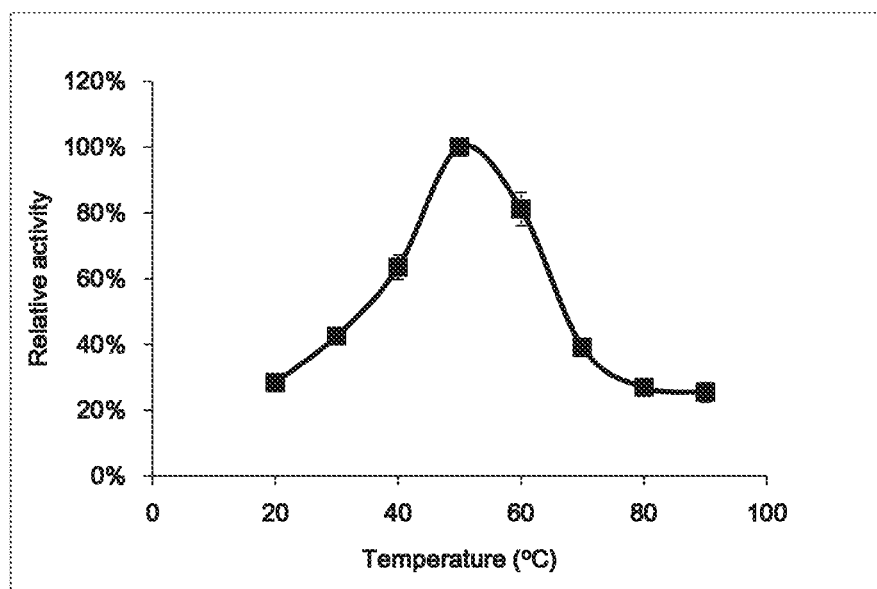
Figure 2.4. Temperature profile of purified PspPro2.

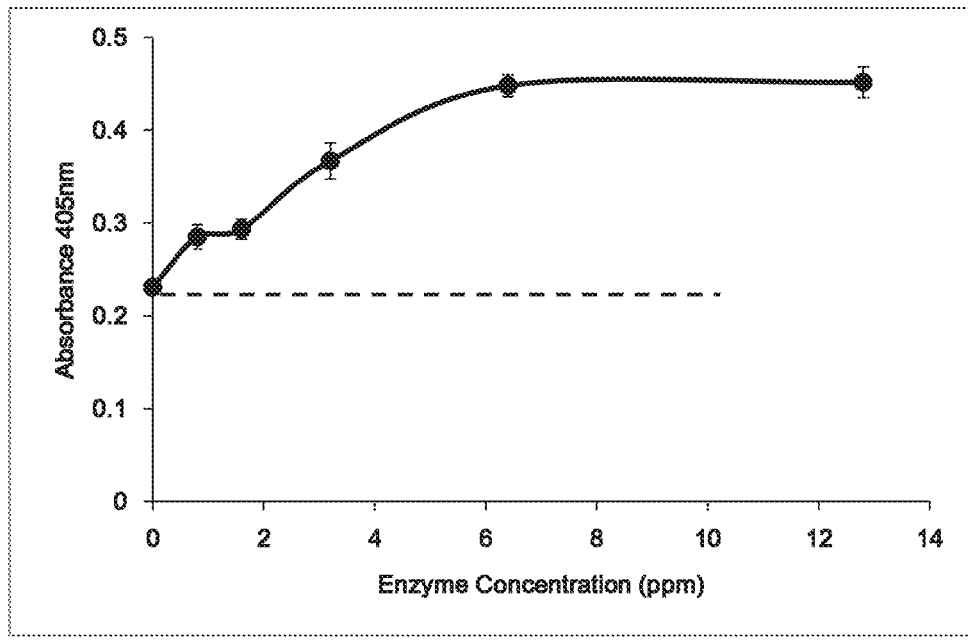
Figure 2.5A. Cleaning performance of PspPro2 protein at pH 6 in AT detergent with bleach.
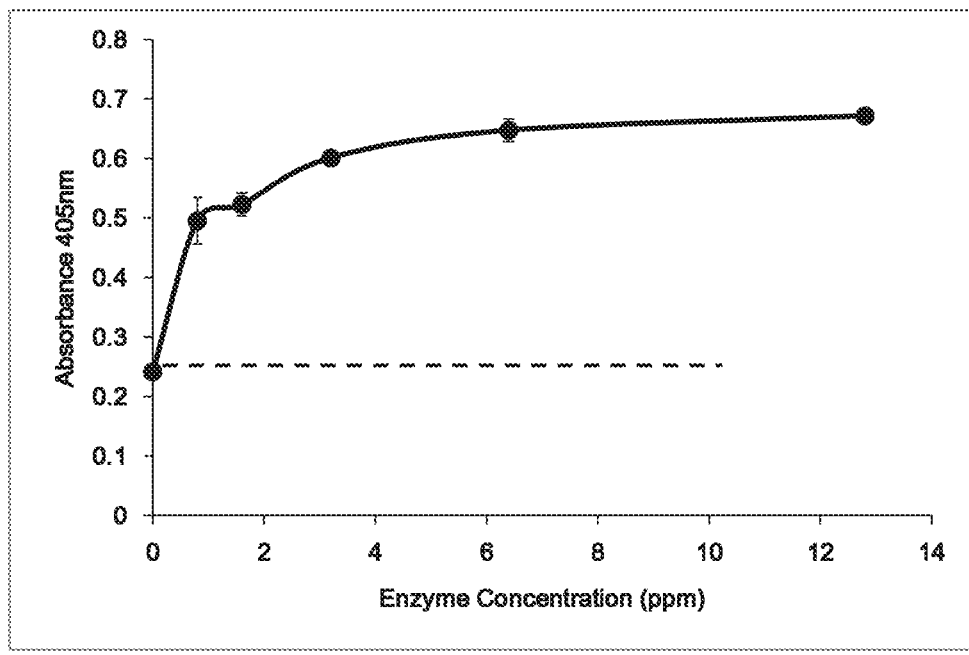
Figure 2.5B. Cleaning performance of PspPro2 protein at pH 8 in AT detergent with bleach.

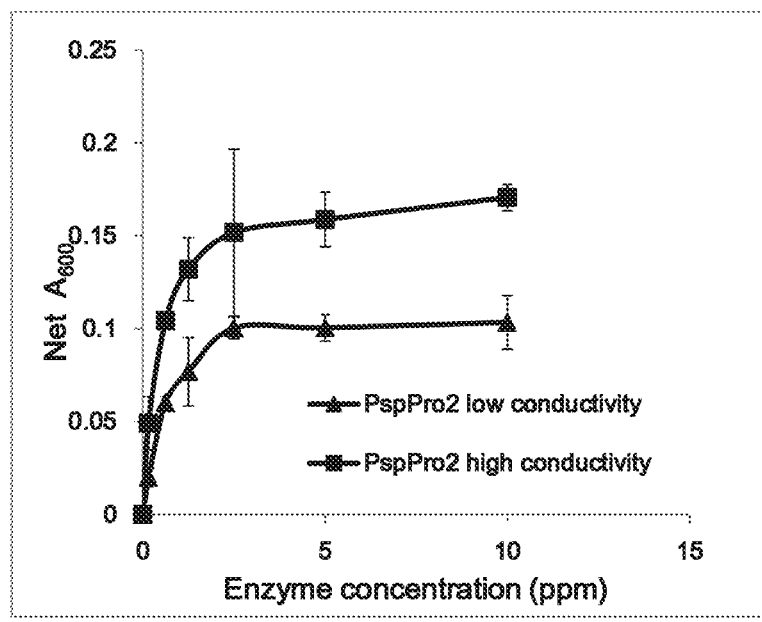
Figure 2.6A. Cleaning performance of PspPro2 protein in liquid laundry detergent.
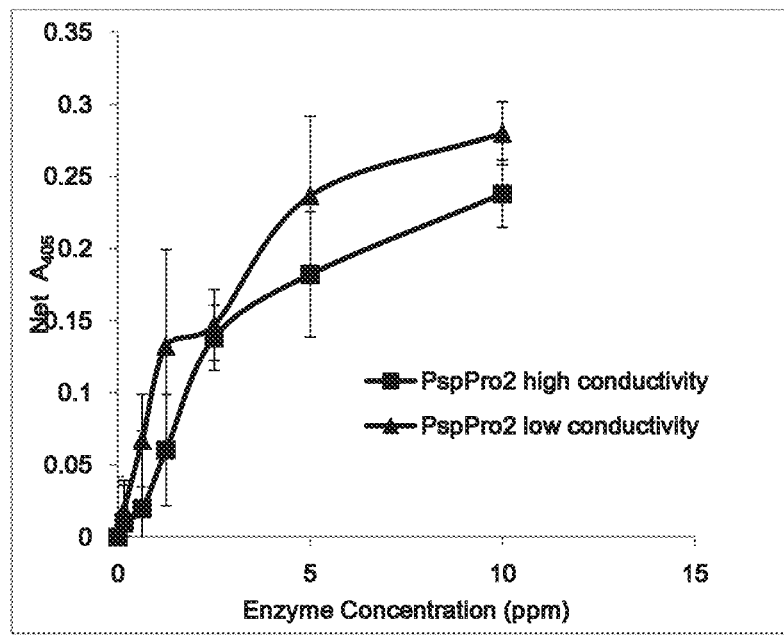
Figure 2.6B. Cleaning performance of PspPro2 protein in powder laundry detergent.

```
CLUSTAL W (1.83) multiple sequence alignment

PspPro2                            -----ATGTGRGVDGKTKSFTTTASGNRYQLKDTTRSNGIVTYTAGNRQT
ZP_09775365.1_P_sp_Aloe-11         -----ATGTGRGVDGKTKSFTTTASGNRYQLKDTTRSNGIVTYTAGNRQT
B_thermoproteolyticus_P00800       ITGTSTVGVGRGVLGDQKNINTTYS-TYYYLQDNTRGNGIFTYDAKYRTT
                                        :.*.****  *. *.:.**  * . * *;*.**.***.**  *  * *

PspPro2                            TPGTILTDTDNVW----EDPAAVDAHAYAIKTYDYYKNKFGRDSIDGRGMQ
ZP_09775365.1_P_sp_Aloe-11         TPGTILTDTDNVW----EDPAAVDAHAYAIKTYDYYKNKFGRDSIDGRGMQ
B_thermoproteolyticus_P00800       LPGSLWADADNQFFASYDAPAVDAHYYAGVTYDYYKNVHNRLSYDGNNAA
                                    **:: :*:**  :     *.:***** **  *******.* * **..

PspPro2                            IRSTVHYGKKYNNAFWNGSQMTYGDGDGSTFTFFSGDPDVVGHELTHGVT
ZP_09775365.1_P_sp_Aloe-11         IRSTVHYGKKYNNAFWNGSQMTYGDGDGSTFTFFSGDPDVVGHELTHGVT
B_thermoproteolyticus_P00800       IRSSVHYSQGYNNAFWNGSQMVYGDGDGQTFIPLSGGIDVVAHELTHAVT
                                    ***:***.:  ***********,******.**   ;**. ***.*****.**

PspPro2                            EFTSNLEYYGESGALNEAFSDIIGNDID------GTSWLLGDGIYTPNIPG
ZP_09775365.1_P_sp_Aloe-11         EFTSNLEYYGESGALNEAFSDIIGNDID------GTSWLLGDGIYTPNIPG
B_thermoproteolyticus_P00800       DYTAGLIYQNESGAINEAISDIFGTLVEFYANKNPDWEIGEDVYTPGISG
                                   ::;*:.* *  .****;***;**:*.  ::     ...* :*:.:****.*,*

PspPro2                            DALRSLSDPTRFGQPDHYSNFYPDPNNDDEGGVHTNSGIINKAYYLLAQG
ZP_09775365.1_P_sp_Aloe-11         DALRSLSDPTRFGQPDHYSNFYPDPNNDDEGGVHTNSGIINKAYYLLAQG
B_thermoproteolyticus_P00800       DSLRSMSDPAKYGDPDHYSKRYT---GTQDNGGVHINSGIINKAAYLISQG
                                   *;***;***::;:*.*****:  *.  ,..;*:****  ******* **::**

PspPro2                            GTSHGVTVTGIGREAAVFIYYNAFTNYLTSTSNFSNARAAVIQAAKDFYG
ZP_09775365.1_P_sp_Aloe-11         GTSHGVTVTGIGREAAVFIYYNAFTNYLTSTSNFSNARAAVIQAAKDFYG
B_thermoproteolyticus_P00800       GTHYGVSVVGIGRDKLGKIFYRALTQYLTPTSNFSQLRAAAVQSATDLYG
                                   ** ;**;*.****;    *;*.*;*;***.*****;  ***.;*;*.*;**

PspPro2                            ADSLAVTSAIQSFDAVGIK    SEQ ID NO: 8
ZP_09775365.1_P_sp_Aloe-11         ADSLAVTSAIQSFDAVGIK    SEQ ID NO: 46
B_thermoproteolyticus_P00800       STSQEVASVKQAFDAVGVK    SEQ ID NO: 45
                                   : *   *;*. *;*****;*
```

Figure 2.7: Alignment of PspPro2 protein with homologous protease sequences.

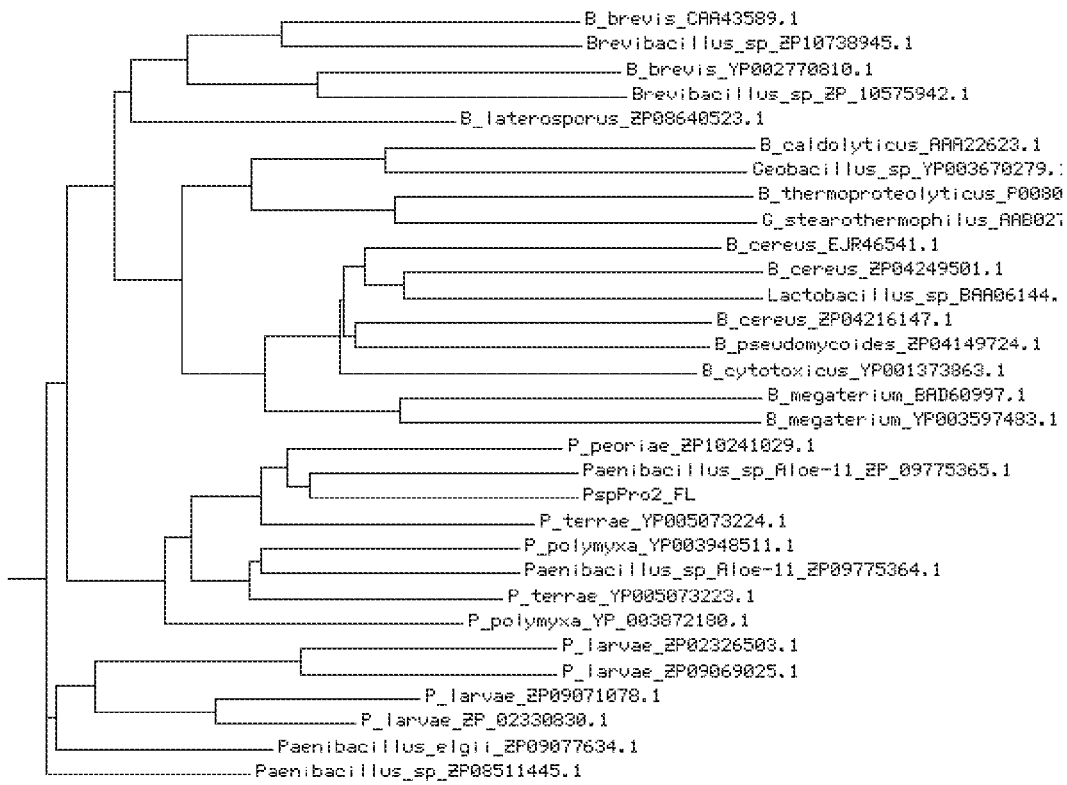
Figure 2.8: Phylogenetic tree for PspPro2 and its homologs

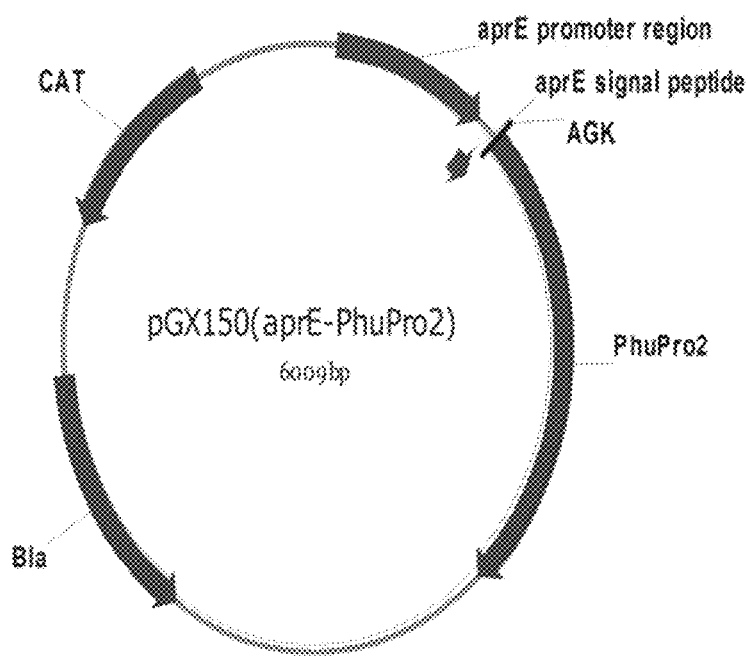
Figure 3.1. The plasmid map of pGX150 (AprE-PhuPro2).
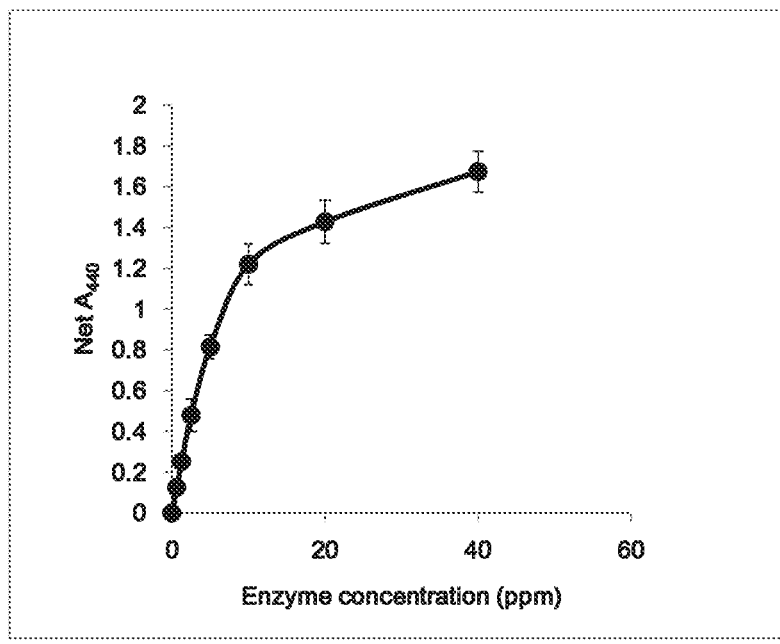
Figure 3.2. Dose response curve of PhuPro2 in azo-casein assay at pH 7.

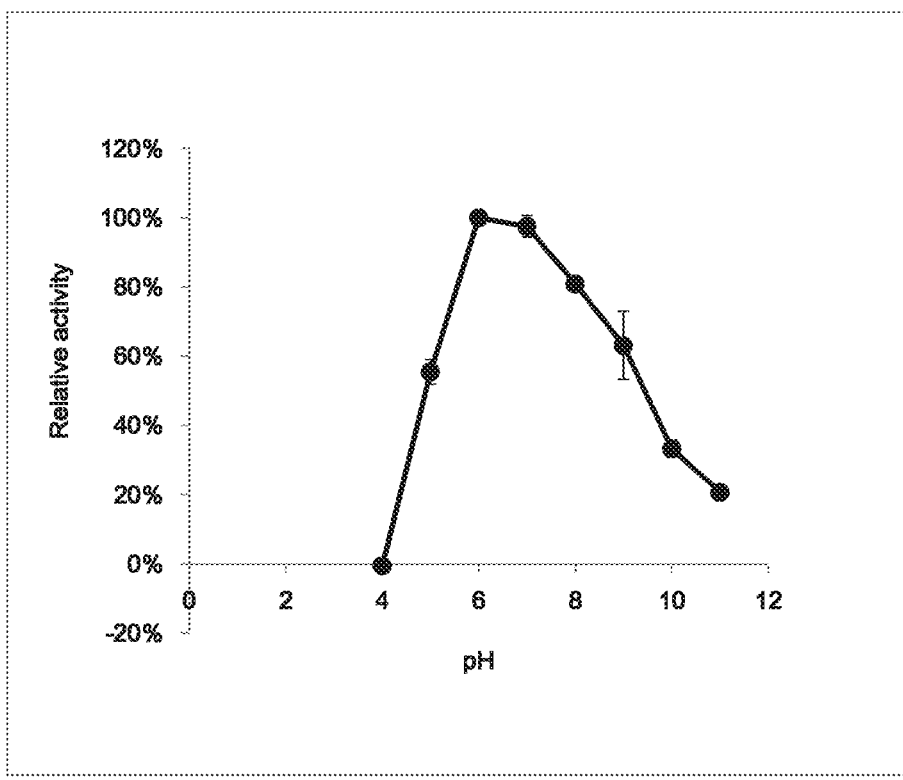
Figure 3.3. pH profile of PhuPro2.
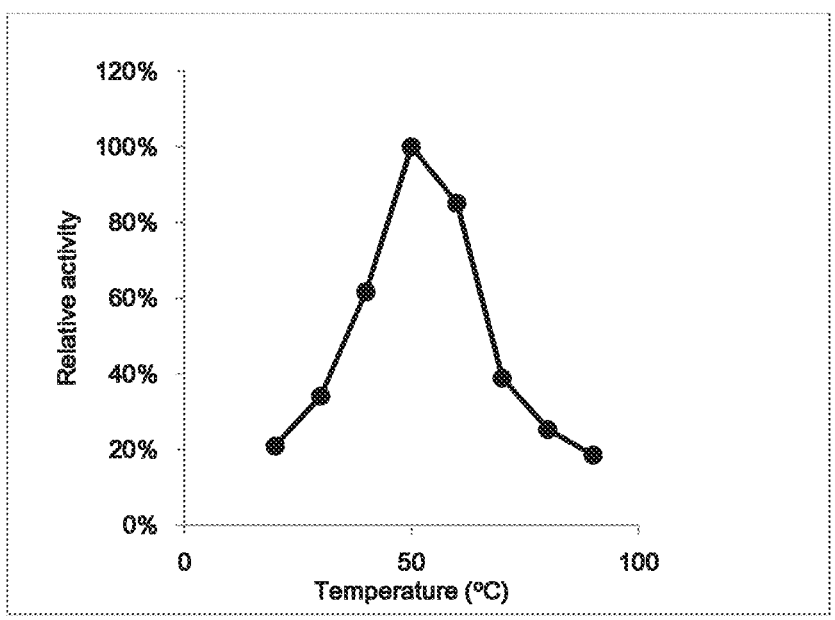
Figure 3.4. Temperature profile of PhuPro2.

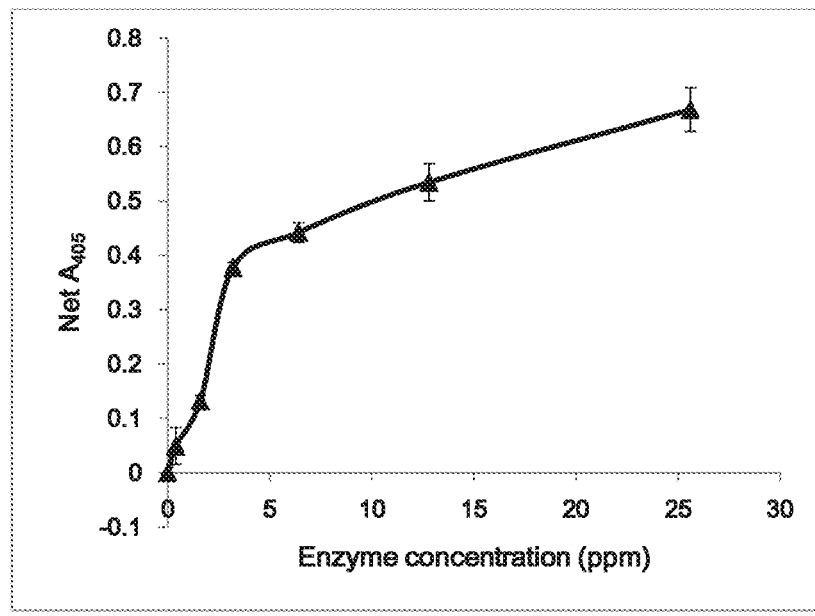
Figure 3.5A. Cleaning performance of PhuPro2 in AT dish detergent at pH 6.
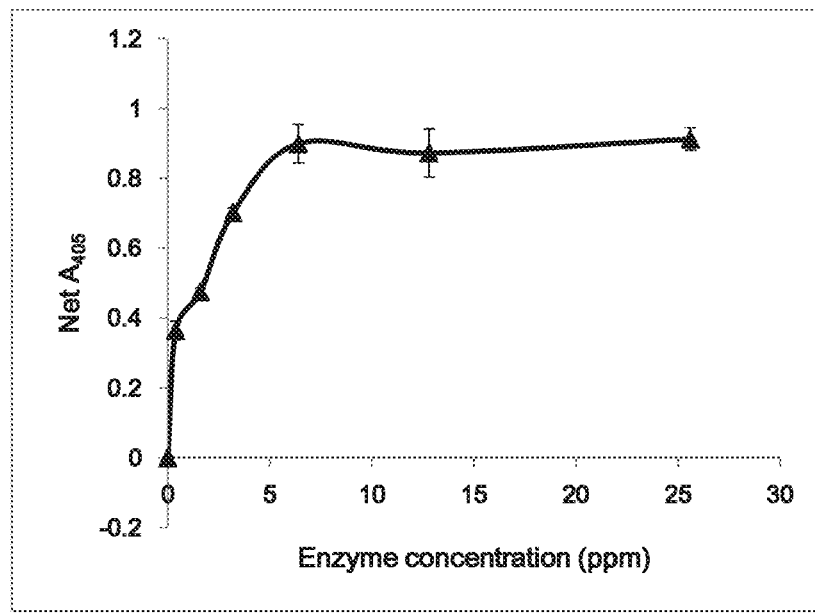
Figure 3.5B. Cleaning performance of PhuPro2 in AT dish detergent at pH 8.

```
CLUSTAL W (1.83) multiple sequence alignment

PhuPro2                             -----ATGSGIGVLGDNKTFQTTLSGSTYQLKDTTRGNGIYTYIASNRTT
P_terrae_HPL-003_YP_005073223.      -----ATGTGKGVLGDTKSFNTTQSGSSYQLKDTTRGNGIVTYTASNRQT
B_thermoproteolyticus_P00800        ITGTSTVGVGRGVLGDQKNINTTYS-TYYYLQDNTRGNGIFTYDAKYRTT
                                         :.* * ***** *,::** * : * *;*,****** ** *, * *

PhuPro2                             IPGTLLTDADNVWT----DGAAVDAHTYAGKVYDFYKTKFGRNSLDGNGLL
P_terrae_HPL-003_YP_005073223.      IPGTLLTDADNVWN----DPAGVDAHAYAAKTYDYYKDKFGRNSIDGRGLQ
B_thermoproteolyticus_P00800        LPGSLWADADNQFFASYDAPAVDAHYYAGVTYDYYKNVHNRLSYDGNNAA
                                    :**:* ;****  :       * ..**** **, .**;**  ..* * **..

PhuPro2                             IRSSVHYSSRYNNAFWNGTQIVFGDGDGSTFIPLSGDLDVVGHELSHGVI
P_terrae_HPL-003_YP_005073223.      LRSTVHYGSRYNNAFWNGSQMTYGDGDGTTFIAFSGDPDVVGHELTHGVT
B_thermoproteolyticus_P00800        IRSSVHYSQGYNNAFWNGSQMVYGDGDGQTFIPLSGGIDVVAHELTHAVT
                                    :**:***.. *********:*;: ;***** ***.;**. ***.***:*.*

PhuPro2                             EYTSNLQYLNESGALNESYADVLGNSIQ-----AKNWLIGDDVYTPGISG
P_terrae_HPL-003_YP_005073223.      EYTSNLDYYGESGALNESFSDIIGNDIQ-----RKNWLVGDDIYTPSIAG
B_thermoproteolyticus_P00800        DYTAGLIYQNESGAINEAISDIFGTLVEFYANKNPDWEIGEDVYTPGISG
                                    :**:.* * .****:**; :*::*. ::         :* ;*:*;***.*:*

PhuPro2                             DALRSMSNPTLYGQPDNYANRYTGSSDNGGVHTNSGITNKAFYLLAQGGT
P_terrae_HPL-003_YP_005073223.      DALRSMSNPTLYDQPDHYSNLYKGSSDNGGVHTNSGIINKAYYLLAQGGT
B_thermoproteolyticus_P00800        DSLRSMSDPAKYGDPDHYSKRYTGTQDNGGVHINSGIINKAAYLISQGGT
                                    *:*****;*:* .;.**;:; *.*;.****** **** *** **;;****

PhuPro2                             QNGVTVAGIGRDAAVNIFYNIVAYYLTSTSNFAAAKNASIQAAKDLYGTG
P_terrae_HPL-003_YP_005073223.      FHNVTVSGIGRDAAVQIYYSAFTNYLTSTSNFSNTRAAVVQAAKDLYGAN
B_thermoproteolyticus_P00800        HYGVSVVGIGRDKLGKIFYRALTQYLTPTSNFSQLRAAAVQSATDLYGST
                                      .*;* *****   :;* :.: ***.****; ; * :*:*,****;

PhuPro2                             SSYVTSVTNAFRAVGL-   SEQ ID NO: 13
P_terrae_HPL-003_YP_005073223.      SAQATAAAKSFDAVGVN   SEQ ID NO: 47
B_thermoproteolyticus_P00800        SQEVASVKQAFDAVGVK   SEQ ID NO: 45
                                    *   ,::. ::* ***;
```

Figure 3.6: Alignment of PhuPro2 with homologous protease sequences.

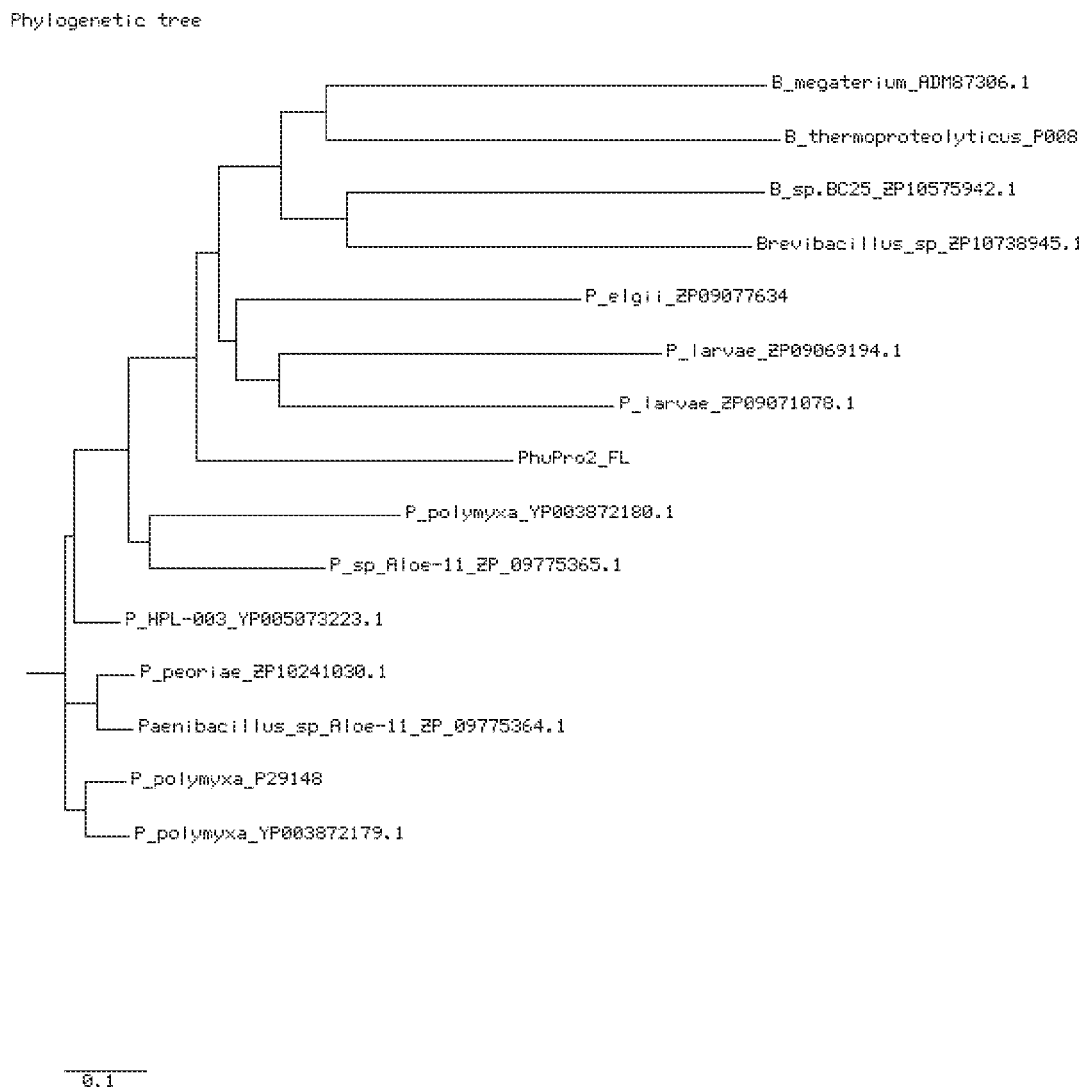
Figure 3.7: Phylogenetic tree for PhuPro2 and homologs.

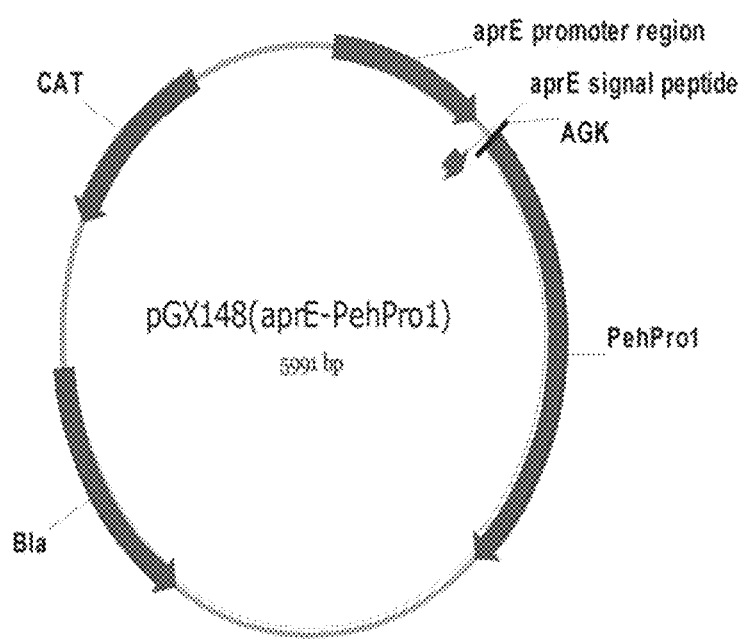
Figure 4.1. The plasmid map of pGX148 (AprE-PehPro1).

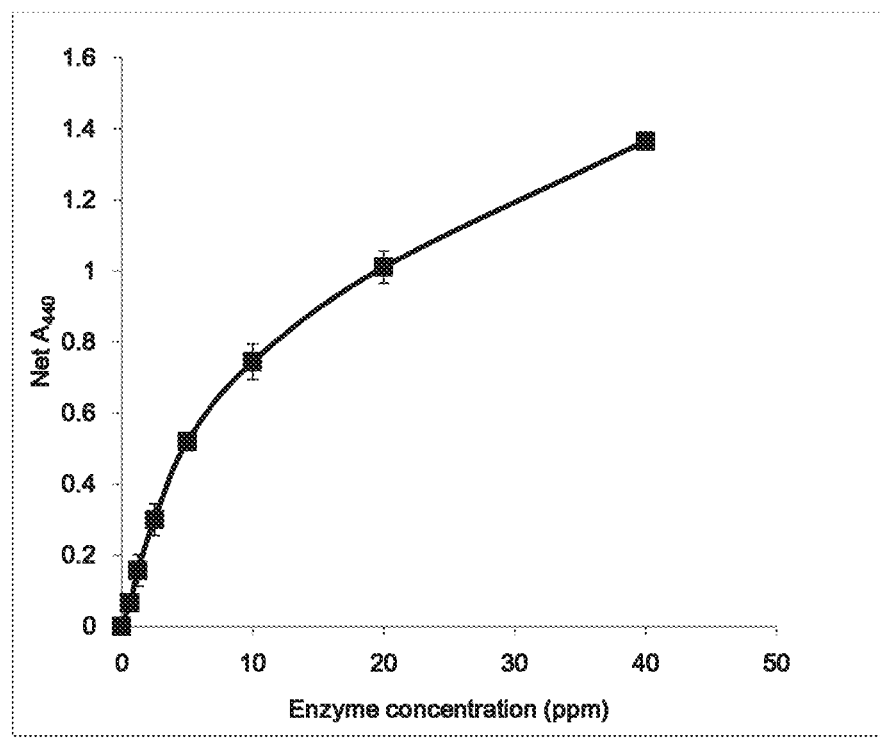
Figure 4.2. Dose response curve of PehPro1 in azo-casein assay at pH 7.
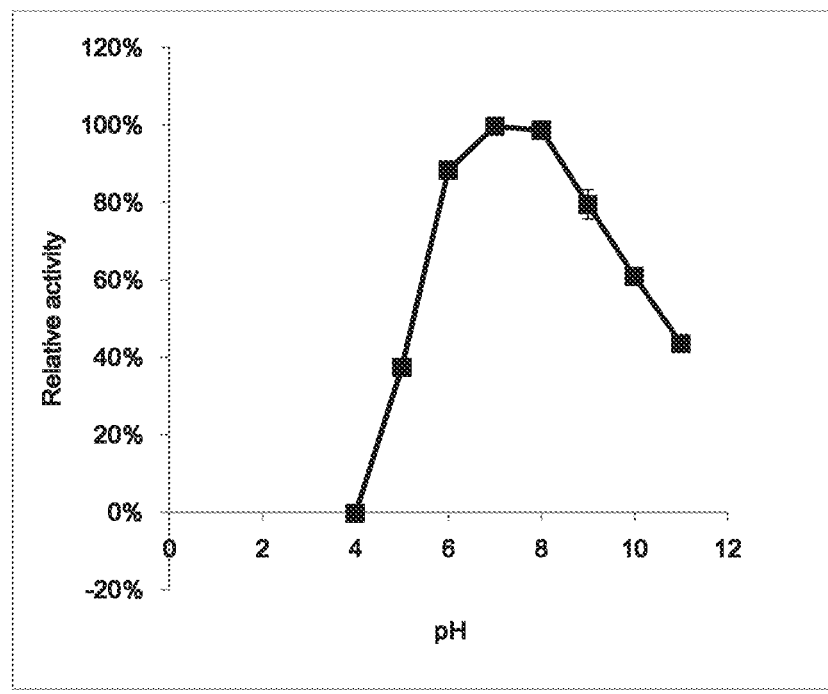
Figure 4.3. pH profile of PehPro1.

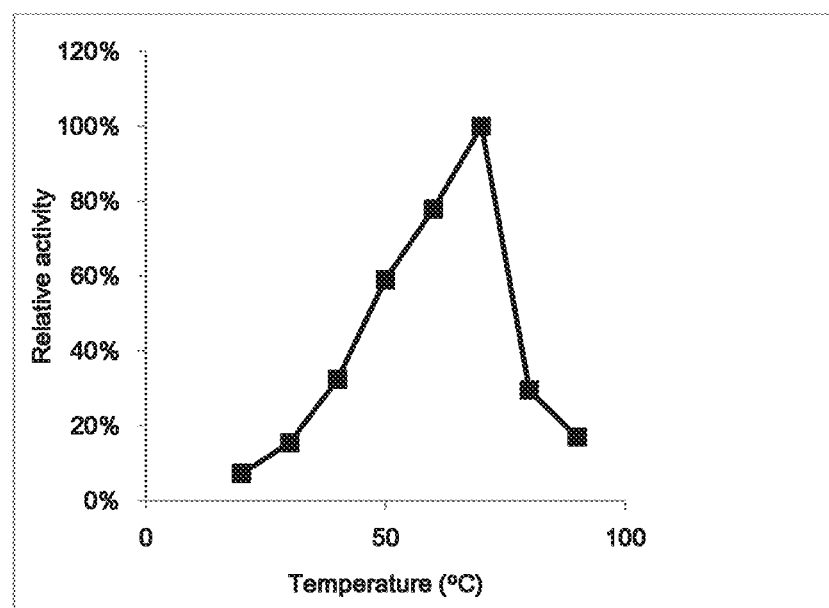
Figure 4.4. Temperature profile of PehPro1.

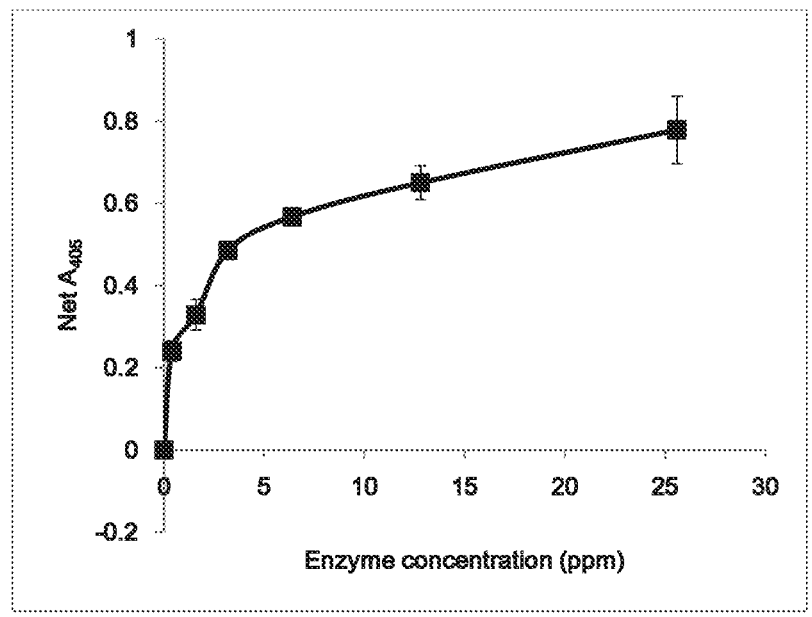
Figure 4.5A: Cleaning performance of PehPro1 in AT detergent at pH 6.
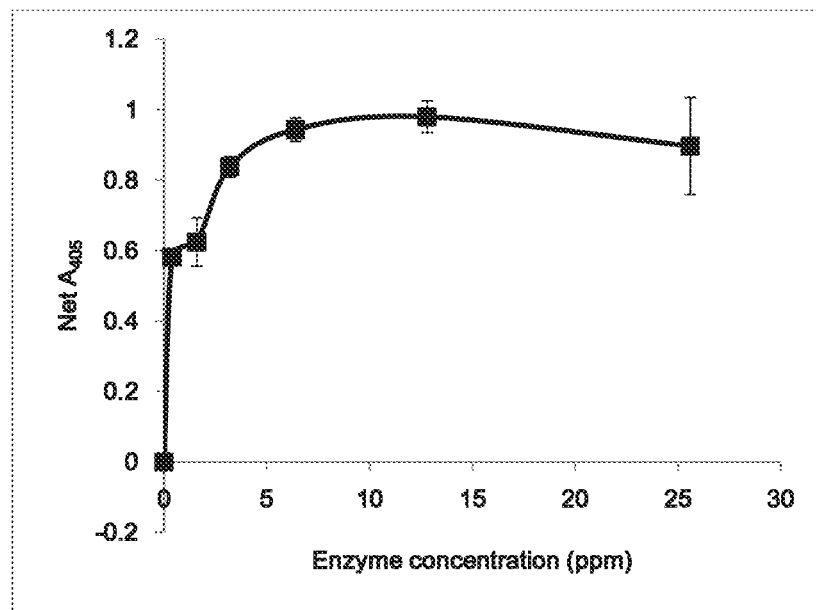
Figure 4.5B: Cleaning performance of PehPro1 in AT detergent at pH 8.

```
CLUSTAL W (1.83) multiple sequence alignment

PehProl_mature                     --------ATGTGKGVLGDTKSFTTTQSGSTYQLKDTTRGQGIVTYSAGNRSS
Paenibacillus_elgii_B69_ZP_090     --------ATGTGKGVLGDTKSFITTQSGSSYQLKDTTRGQGIVTYSAGNRTS
B_thermoproteolyticus_P00800       ITGTSTVGVGRGVLGDQKNINTTYS--TYYYLQDNTRGNGIFTYDAKYRTT
                                           :.*.*:***** *.:.** * : * *:*.***:**.**.* *::

PehProl_mature                     LPGTLLTSSSNIWN---DGAAVDAHAYTAKVYDYYKNKFGRNSIDGNGFQ
Paenibacillus_elgii_B69_ZP_090     LPGSLLTSTNNIWN---DGSAVDAHAYTGKVYDYYKNKFGRNSIDGNGLQ
B_thermoproteolyticus_P00800       LPGSLWADADNQFFASYDAPAVDAHYYAGVTYDYYKNVHNPLSYDGNNAA
                                   ***:*  :.:.*  :    *..***** *:. .*****  ..* * ***.

PehProl_mature                     LKSTVHYSSPYNNAFWNGVQMVYGDGDGVTFIPFSADPDVIGHELTHGVT
Paenibacillus_elgii_B69_ZP_090     LKSTVHYSTRYNNAFWNGVQMVYGDGDGVTFPSFPADPDVIGHELTHGVT
B_thermoproteolyticus_P00800       IRSSVHYSQGYNNAFWNGSQMVYGDGDGQTFIPLSGGIDVVAHELTHAVT
                                   ::*:****  ********  ******** ** ..:..  **:.*****.**

PehProl_mature                     EHTAGLEYYGESGALNESISDIIGNAID------GKNWLIGDLIYTPNIPG
Paenibacillus_elgii_B69_ZP_090     ESTAGLEYYGESGALNESISDIFGNAIE------GKNWLIGDLI----TLNA
B_thermoproteolyticus_P00800       DYTAGLIYQNESGAINEAISDIFGTLVEFYANKNPDWEIGEDVYTPGISG
                                   : **** *  .****:**;**:****:*.  ::       .:* **: :   .

PehProl_mature                     DALRSMENPKLYNQPDRYQDRYTGPSDNGGVHINSGINNKAFYLIAQGGT
Paenibacillus_elgii_B69_ZP_090     GALRSMENPKLYRQPDRYQDRYTGPSDNGGVHTNSGINNKAFHLIAQGGT
B_thermoproteolyticus_P00800       DSLRSMSDPAKYGDPDHYSKRYTGTQDNGGVHINSGIINKAAYLISQGGT
                                   .:****.:*  * :**:*..****.*.*****.**** *** :**:****

PehProl_mature                     HYGVTVNGIGRDAAVQIFYDALINYLTPTSNFSAMPAAAIQAATDLYGAN
Paenibacillus_elgii_B69_ZP_090     HYGVTVNGIGRSAAEQIFYDALIHYLTPTSNFSAIPAAAIQAATDSFGAN
B_thermoproteolyticus_P00800       HYGVSVVGIGRDKLGKIFYRALTQYLTPTSNFSQLPAAAVQSATDLYGST
                                   ****:* ****.   :*** ** :********* :****:*:***  *.:

PehProl_mature                     SSQVNAVKKAYTAVGVN    SEQ ID NO: 18
Paenibacillus_elgii_B69_ZP_090     SSQVDAVKKAYNAVGVN    SEQ ID NO: 48
B_thermoproteolyticus_P00800       SQEVASVKQAFDAVGVK    SEQ ID NO: 45
                                   *.:* :**:*: ****:
```

Figure 4.6: Alignment of PehPro1 protein with homologous protease sequences.

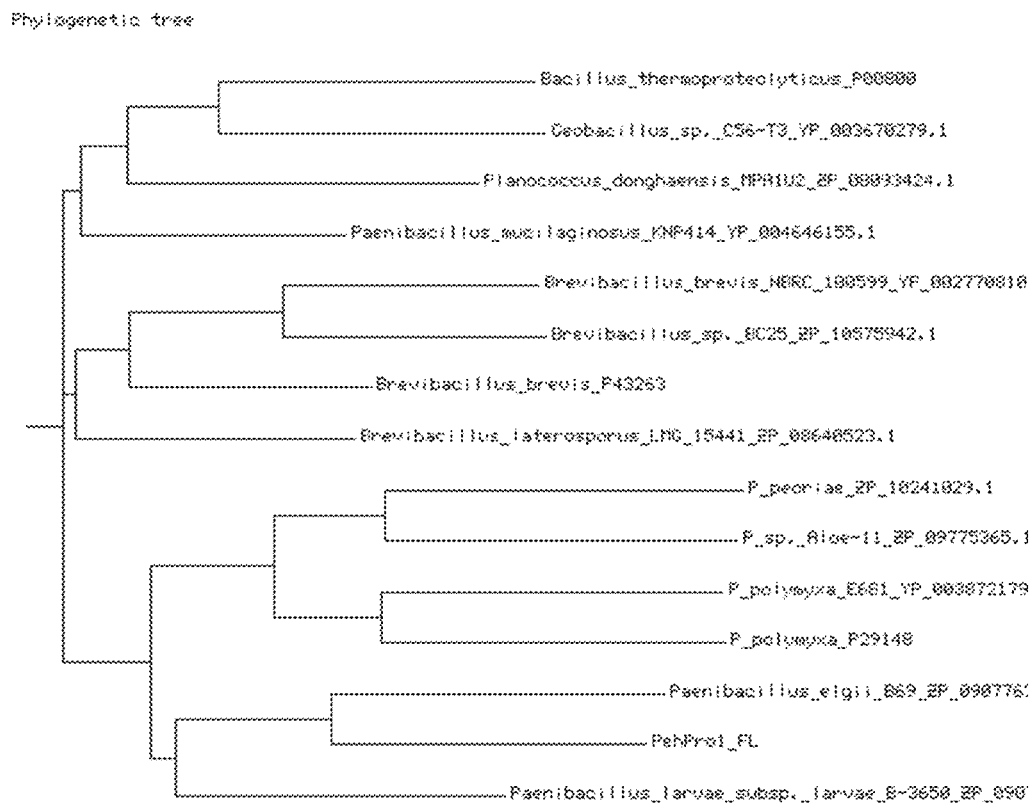
Figure 4.7: Phylogenetic tree for PehPro1 and its homologs.

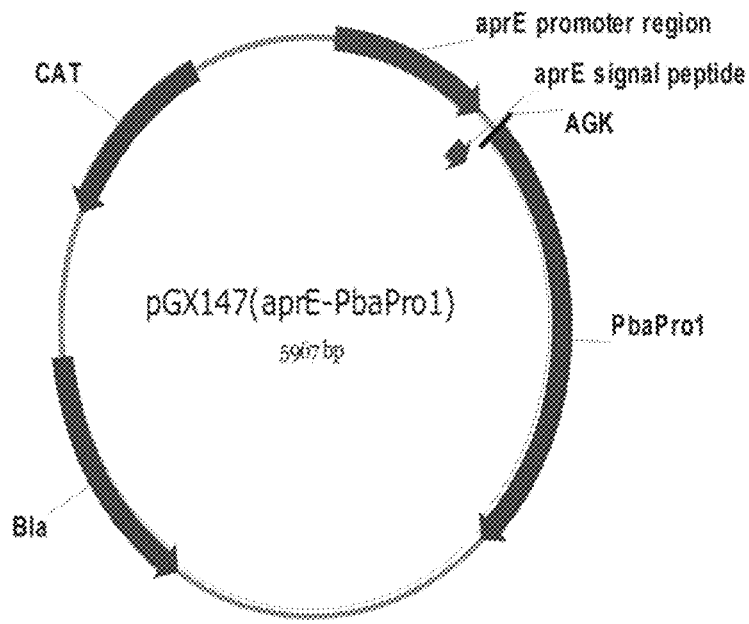
Figure 5.1. The plasmid map of pGX147(AprE-PbaPro1).
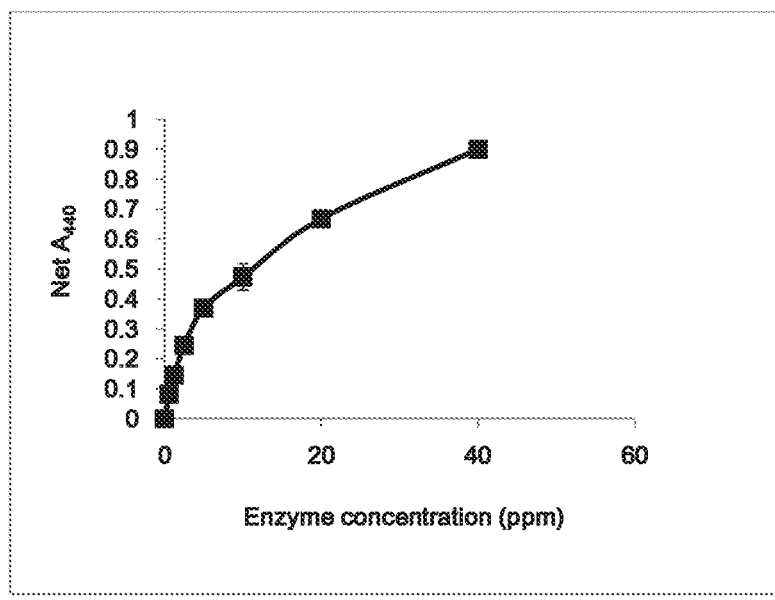
Figure 5.2. Dose response curve of PbaPro1 in azo-casein assay at pH 7.

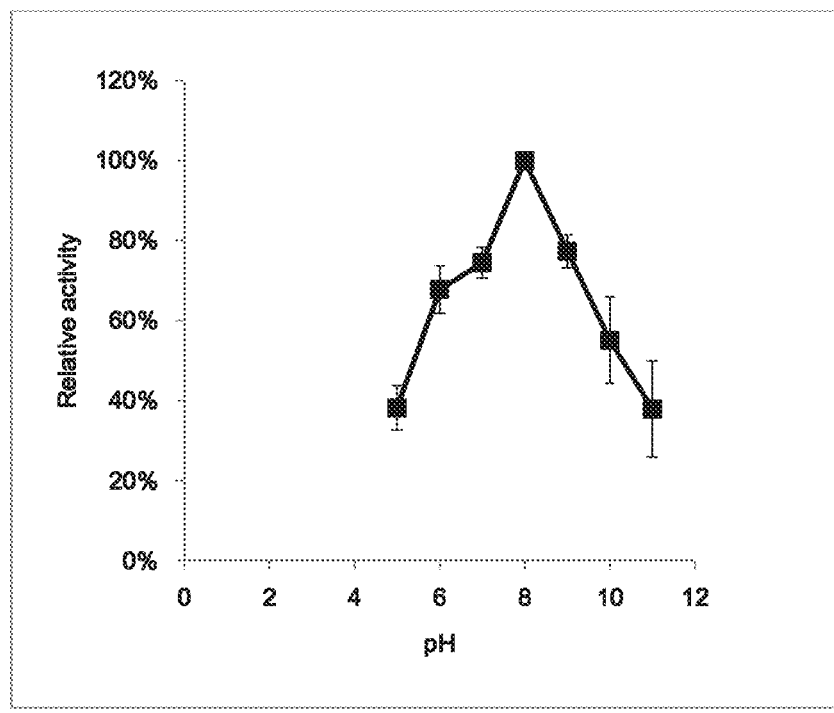
Figure 5.3. pH profile of PbaPro1.
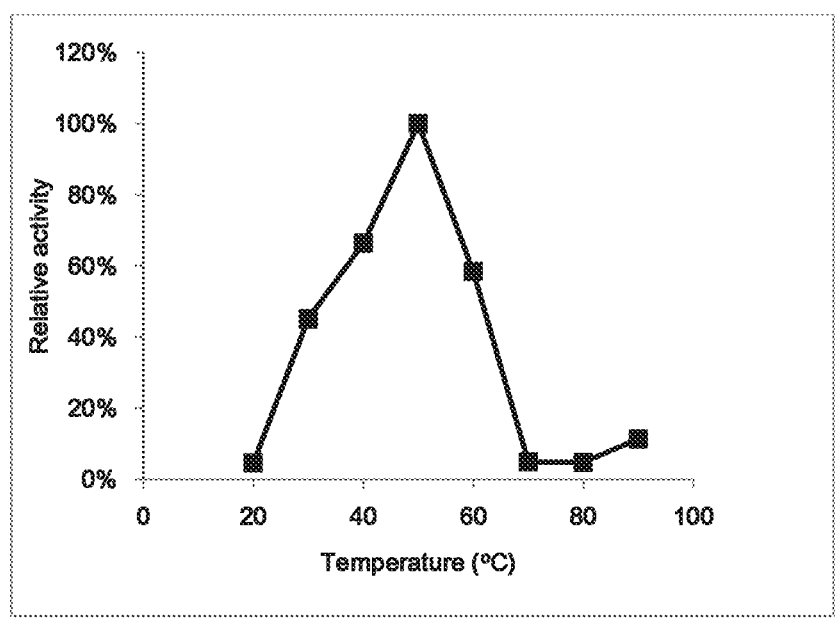
Figure 5.4. Temperature profile of PbaPro1.

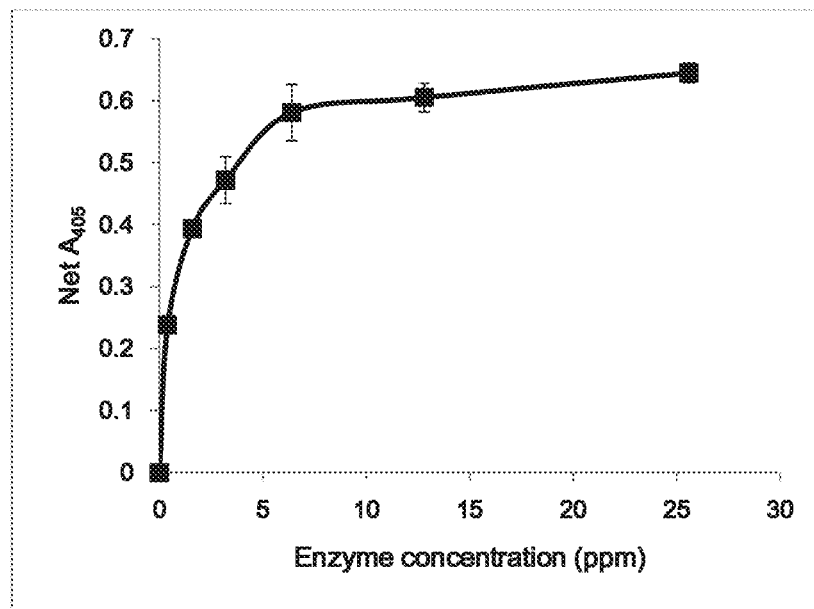
Figure 5.5A: Cleaning performance of PbaPro1 in AT dish detergent at pH 6.
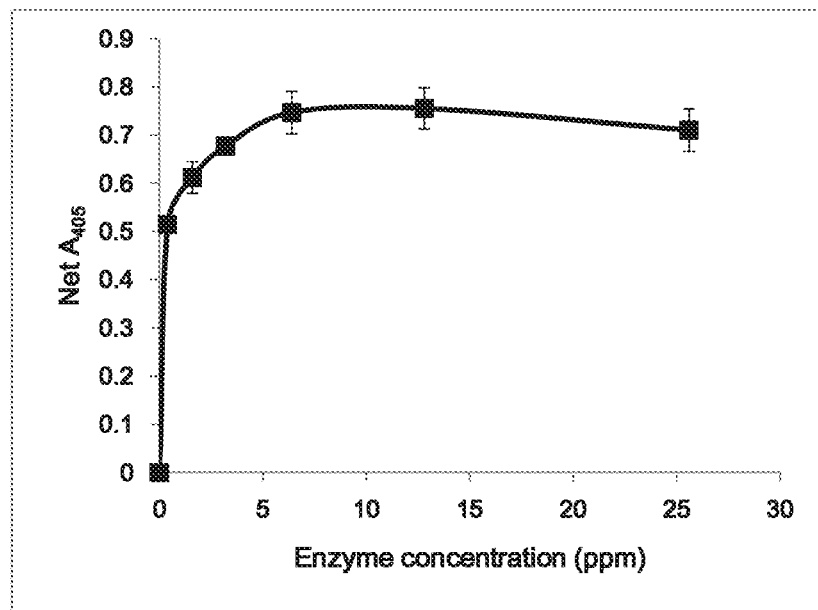
Figure 5.5B: Cleaning performance of PbaPro1 in AT dish detergent at pH 8.

```
CLUSTAL W (1.83) multiple sequence alignment

PbaPro1                       ------ATGTGTGVHGDTKILTTTQSGSTYQLKDTTRGKGIQTYIANNRSS
P_polymyxa_SC2                ---NEATGTGKGVLGDSKSFTTTASGSSYQLKDTTRGNGIVTYTASNRQS
B_thermoproteolyticus_P00800  ITGTSTVGVGRGVLGDQKNINTTYS-TYYYLQDNTRGNGIFTYDAKYRTT
                                 :.*.* **.**.*.:.** *.:.* *;*.***;** **.*..*.:

PbaPro1                       LPGSLSTSSNNVWT---DRAAVDAHAYAAATYDFYKNKFNRNGIDGNGLL
P_polymyxa_SC2                IPGTILTDADNVWN---DPAGVDAHAYAAKTYDYYKAKFGRNSIDGRGLQ
B_thermoproteolyticus_P00800  LPGSLWADADNQFFASYDAPAVDAHYYAGVTYDYYKNVHNRLSYDGNNAA
                              :**::.:.::*.:......*..****.**.****:**...*...**..

PbaPro1                       IRSTVHYGSNYKNAFWNGAQIVYGDGDGIEFGPFSGDLDVVGHELTHGVI
P_polymyxa_SC2                LRSTVHYGSRYNNAFWNGSQMTYGDGDGSTFIAFSGDPDVVGHELTHGVT
B_thermoproteolyticus_P00800  IRSSVHYSQGYNNAFWNGSQMVYGDGDGQTFIPLSGGIDVVAHELTHAVT
                              :**:***.. *:******:*:.****** *..:** ***.*****.*

PbaPro1                       EYTANLEYRNEPGALNEAFADIMGNTIE-----SKNWLLGDGIYTPNIPG
P_polymyxa_SC2                EYTSNLEYYGESGALNEAFSDVIGNDIQ-----RKNWLVGDDIYTPNIAG
B_thermoproteolyticus_P00800  DYTAGLIYQNESGAINEAISDIFGTLVEFYANKNPDWEIGEDVYTPGISG
                              :**:.* *.*.*.**:***::*::*..::.          :*.:*::***.*.*

PbaPro1                       DALRSLSDPTLYNQPDKYSDRYTGSQDNGGVHINSGIINKAYYLAAQGGT
P_polymyxa_SC2                DALRSMSNPTLYDQPDHYSNLYRGSSDNGGVHTNSGIINKAYYLLAQGGN
B_thermoproteolyticus_P00800  DSLRSMSDPAKYGDPDHYSKRYTGTQDNGGVHINSGIINKAAYLISQGGT
                              *:***:*:*: *.:**:**. * *:.******.********.**.:***.

PbaPro1                       HNGVTVSGIGRDKAVRIFYSTLVNYLTPTSKFAAAKTATIQAAKDLYGAN
P_polymyxa_SC2                FHGVTVNGIGRDAAVQIYYSAFTNYLTSSSDFSNARAAVIQAAKDLYGAN
B_thermoproteolyticus_P00800  HYGVSVVGIGRDKLGKIFYPALTQYLTPTSNFSQLRAAAVQSATDLYGST
                              .**:* *****    :*:* ::.:***.:*.*:   ::*.:*:*.****:.

PbaPro1                       SAEATAITKAYQAVGL-  SEQ ID NO: 23
P_polymyxa_SC2                SAEATAAAKSFDAVGVN  SEQ ID NO: 49
B_thermoproteolyticus_P00800  SQEVASVKQAFDAVGVK  SEQ ID NO: 45
                              * *.::  :::***:
```

Figure 5.6: Alignment of PbaPro1 protein with homologous protease sequences.

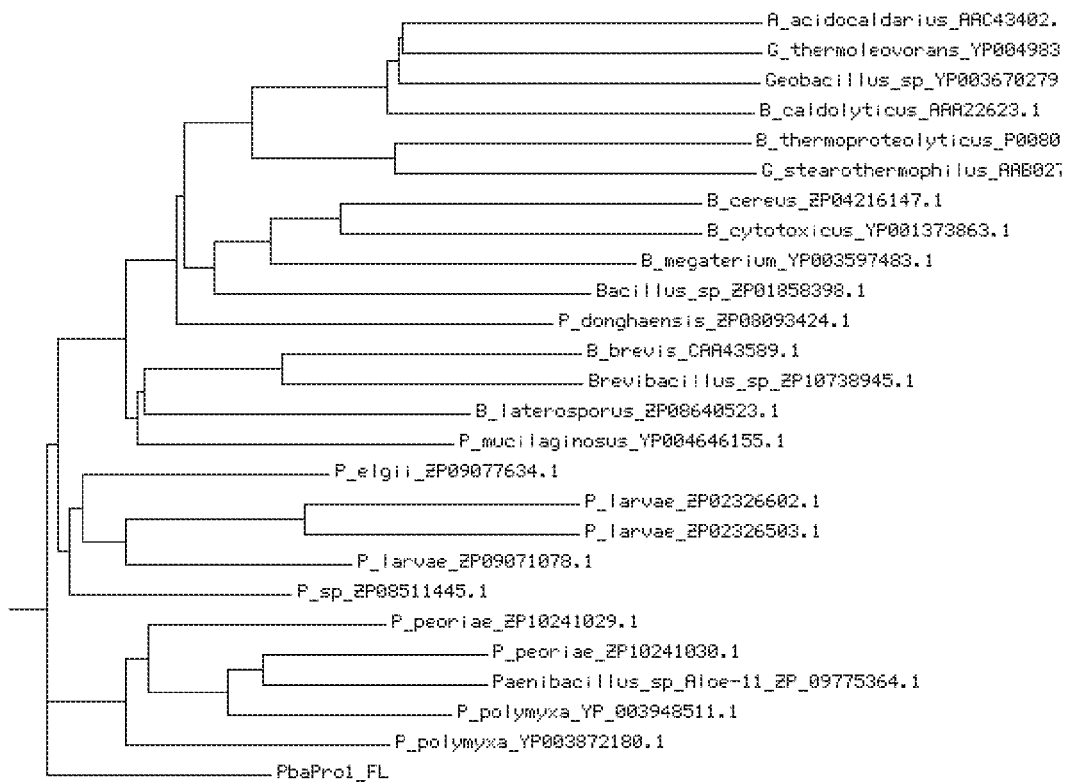
Figure 5.7: Phylogenetic tree for PbaPro1 and homologs.

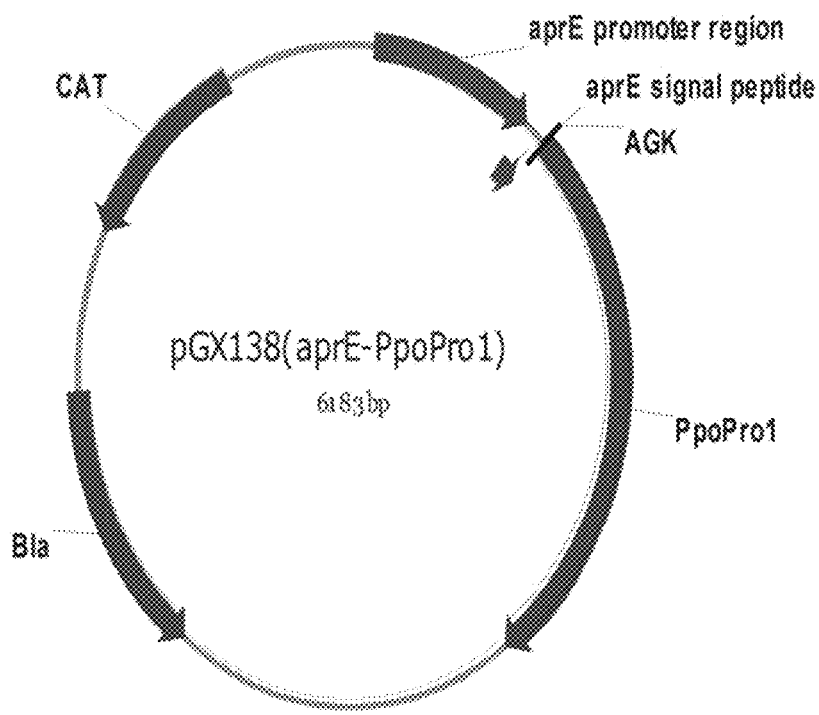
Figure 6.1. The plasmid map of pGX138 (AprE-PpoPro1).
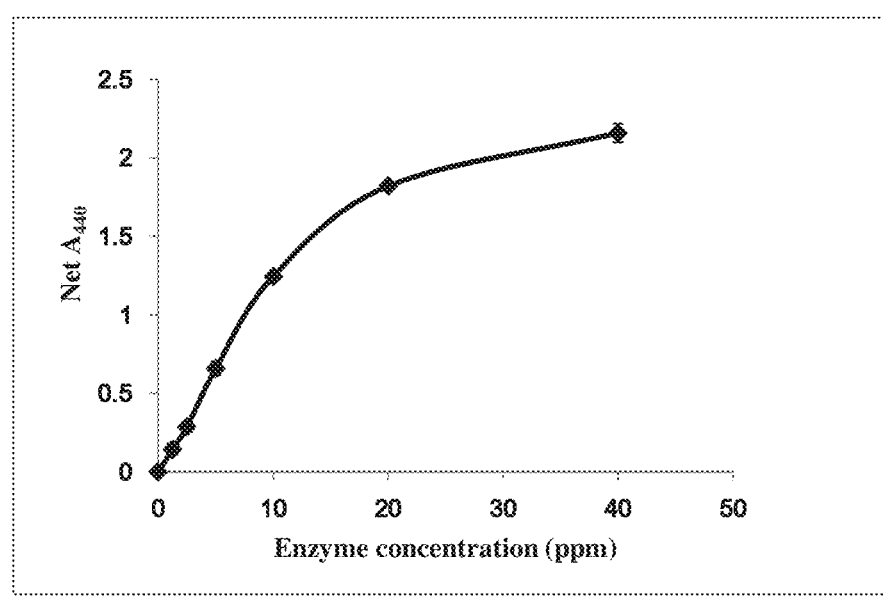
Figure 6.2. Dose response of PpoPro1 in azo-casein assay at pH 7.

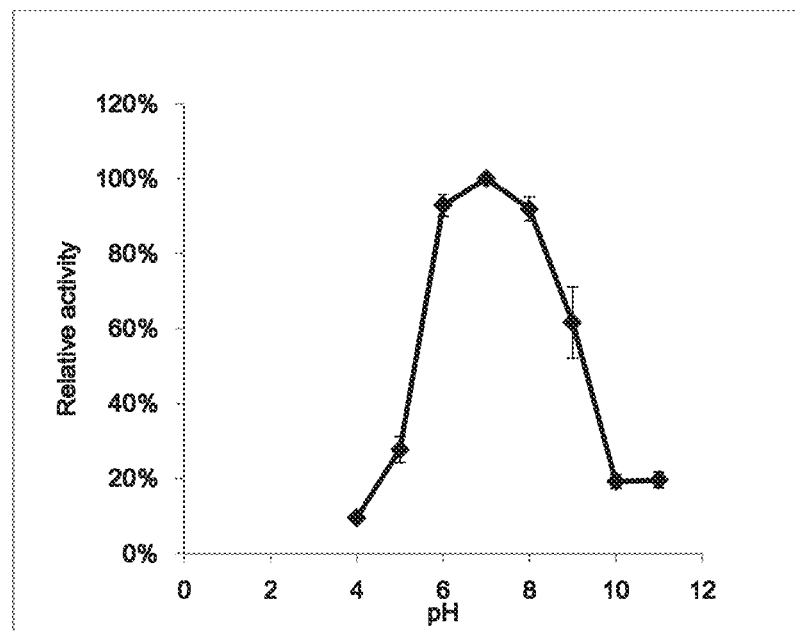
Figure 6.3. pH profile of purified PpoPro1.
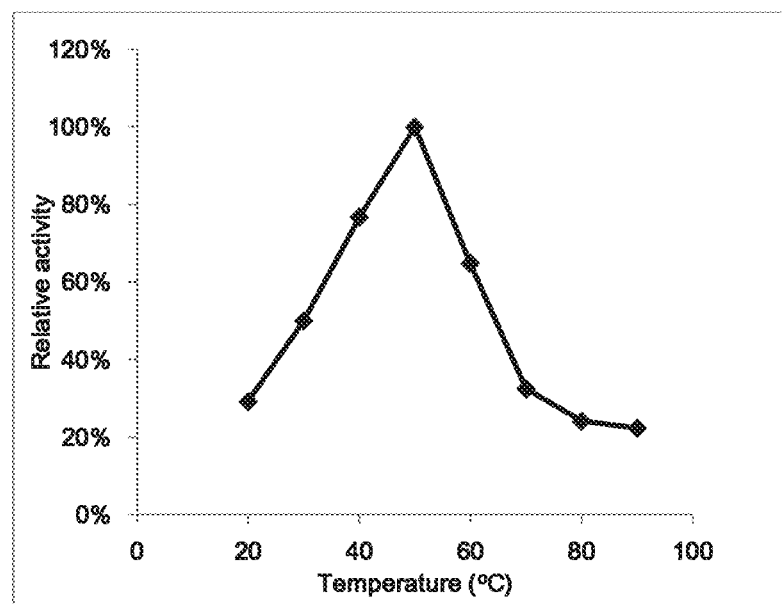
Figure 6.4. Temperature profile of purified PpoPro1.

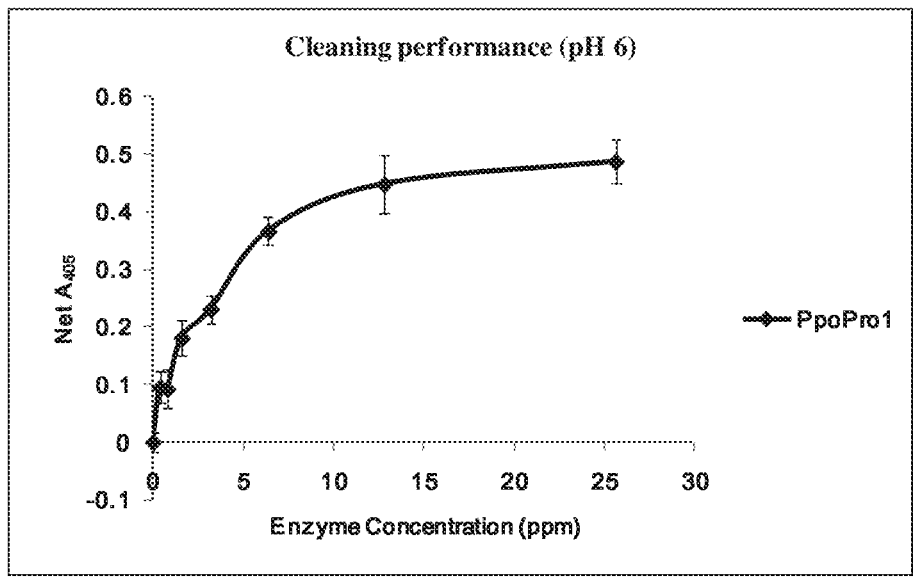
Figure 6.5A: Cleaning performance of PpoPro1 at pH 6 in AT detergent with PAP.
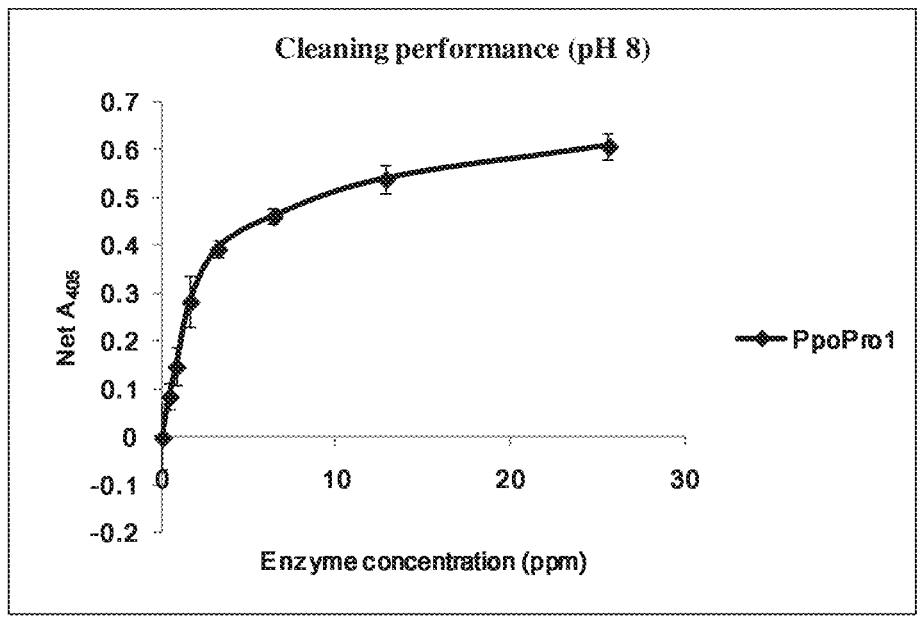
Figure 6.5B: Cleaning performance of PpoPro1 at pH 8 in AT detergent with PAP.

```
CLUSTAL W (1.83) multiple sequence alignment

PpoPro1                         -----ATGTGKGVLGDSKSFTTTASGSSYQLKDTTRGNGIVTYTASNRQS
P_polymyxa_SC2_YP_003948511.1   ---NEATGTGKGVLGDSKSFTTTASGSSYQLKDTTRGNGIVTYTASNRQS
B_thermoproteolyticus_P00800    ITGTSTVGVGRGVLGDQKNINTTYS-TYYYLQDNTRGNGIFTYDAKYRTT
                                  .*.*:*****.*.:.** * : * *;*,******.** *. * :

PpoPro1                         IPGTILTDADNVWN---DPAGVDAHAYAAKTYDYYKAKFGRNSIDGRGLQ
P_polymyxa_SC2_YP_003948511.1   IPGTILTDADNVWN---DPAGVDAHAYAAKTYDYYKAKFGRNSIDGRGLQ
B_thermoproteolyticus_P00800    LPGSLWADADNQFFASYDAPAVDAHYYAGVIYDYYKNVHNRLSYDGNNAA
                                :**:: :**** :    *...**** **. ****** ..* * **..

PpoPro1                         LRSTVHYGSRYNNAFWNGSQMTYGDGDGSTFIAFSGDPDVVGHELTHGVT
P_polymyxa_SC2_YP_003948511.1   LRSTVHYGSRYNNAFWNGSQMTYGDGDGSTFIAFSGDPDVVGHELTHGVT
B_thermoproteolyticus_P00800    IRSSVHYSQGYNNAFWNGSQMVYGDGDGQTFIPLSGGIDVVAHELTHAVT
                                :**:***.. **********.******.***.:**. ***.*****.**

PpoPro1                         EYTSNLEYYGESGALNEAFSDVIGNDIQ------RKNWLVGDDIYTPNIAG
P_polymyxa_SC2_YP_003948511.1   EYTSNLEYYGESGALNEAFSDVIGNDIQ------RKNWLVGDDIYTPNIAG
B_thermoproteolyticus_P00800    DYTAGLIYQNESGAINEAISDIFGTLVEFYANKNPDWEIGEDVYTPGISG
                                :**;.* * .****;***:**::*. ::      . :* :*:*;***.*;*

PpoPro1                         DALRSMSNPTLYDQPDHYSNLYRGSSDNGGVHTNSGIINKAYYLLAQGGN
P_polymyxa_SC2_YP_003948511.1   DALRSMSNPTLYDQPDHYSNLYRGSSDNGGVHTNSGIINKAYYLLAQGGN
B_thermoproteolyticus_P00800    DSLRSMSDPAKYGDPDHYSKRYTGTQDNGGVHINSGIINKAAYLISQGGT
                                *:*****:*: *.:*****; * *;.****** ******** **:;***.

PpoPro1                         FHGVTVNGIGRDAAVQIYYSAFTNYLTSSSDFSNARAAVIQAAKDLYGAN
P_polymyxa_SC2_YP_003948511.1   FHGVTVNGIGRDAAVQIYYSAFTNYLTSSSDFSNARAAVIQAAKDLYGAN
B_thermoproteolyticus_P00800    HYGVSVVGIGRDKLGKIFYRALTQYLTPTSNFSQLRAAAVQSATDLYGST
                                .:**:* *****   (*:* *:*:***.:*:**: ***.:*:*.****;.

PpoPro1                         SAEATAAAKSFDAVGVN    SEQ ID NO: 28
P_polymyxa_SC2_YP_003948511.1   SAEATAAAKSFDAVGVN    SEQ ID NO: 50
B_thermoproteolyticus_P00800    SQEVASVKQAFDAVGVK    SEQ ID NO: 45
                                * *.::. ::******;
```

Figure 6.6. Alignment of PpoPro1 with protease homologs.

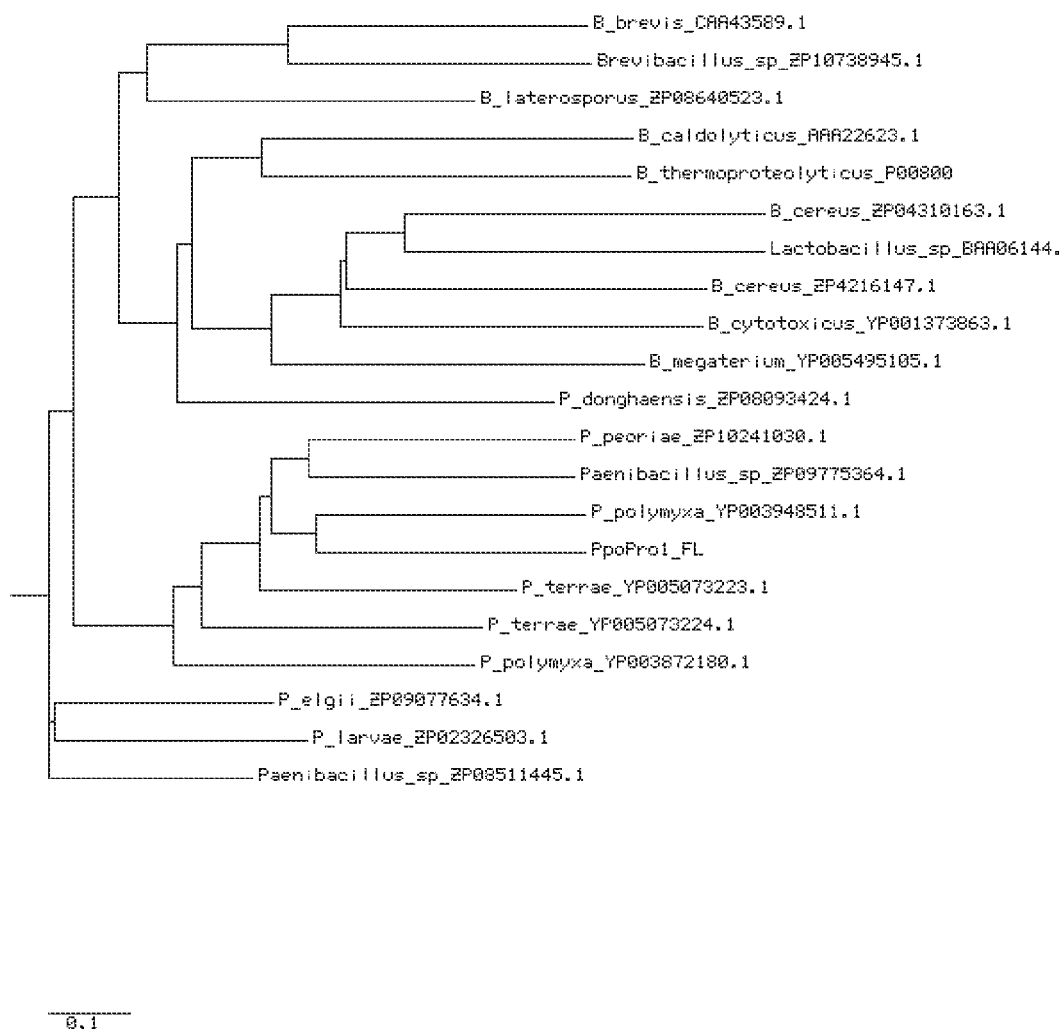
Figure 6.7. Phylogenetic tree of PpoPro1 and homologs.

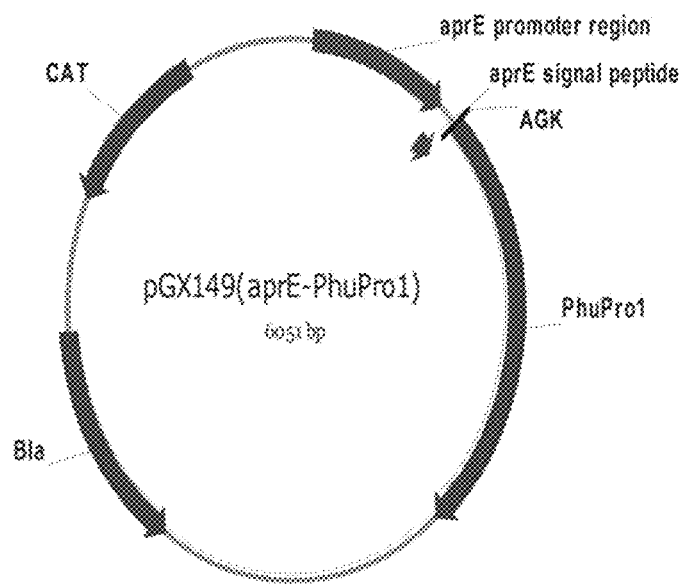
Figure 7.1. The plasmid map of pGX149(AprE-PhuPro1).
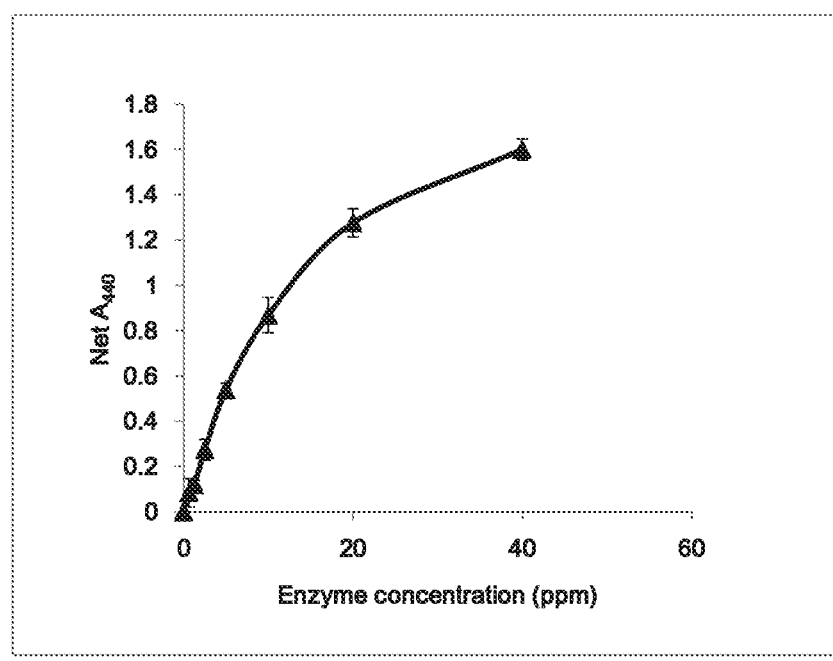
Figure 7.2. Dose response curve of PhuPro1 in azo-casein assay at pH 7.

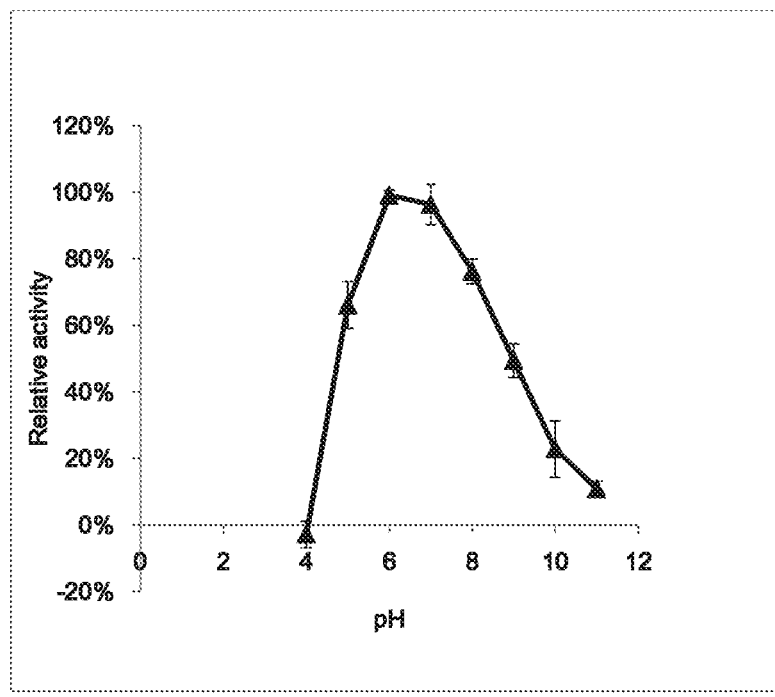
Figure 7.3. pH profile of PhuPro1.
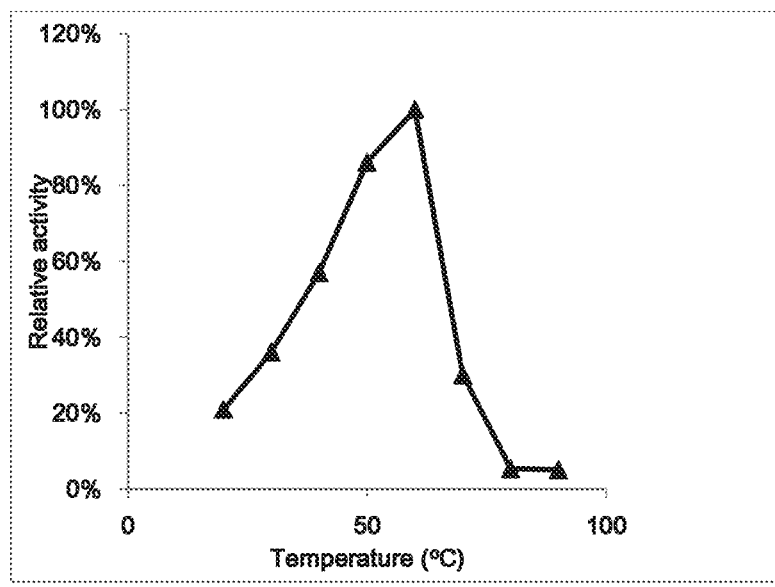
Figure 7.4. Temperature profile of PhuPro1.

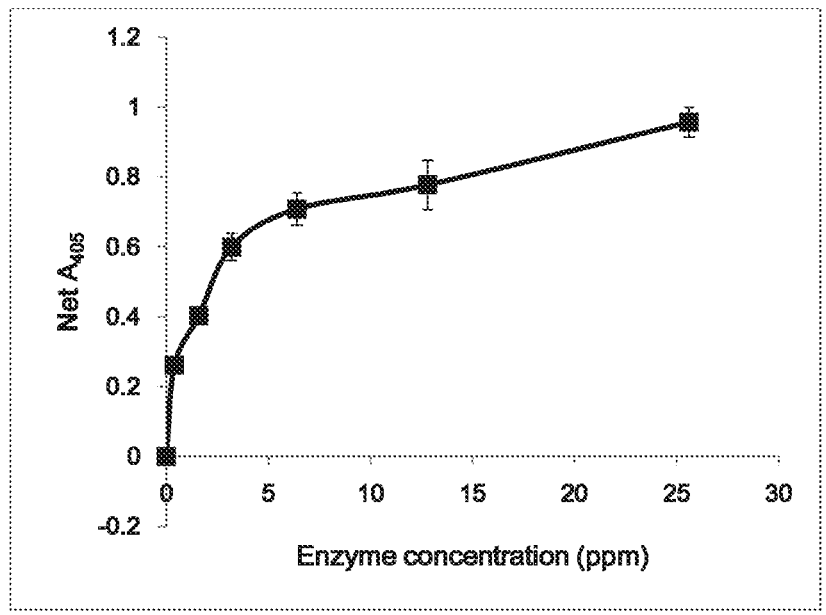
Figure 7.5A. Cleaning performance of PhuPro1 in dish detergent at pH 6.
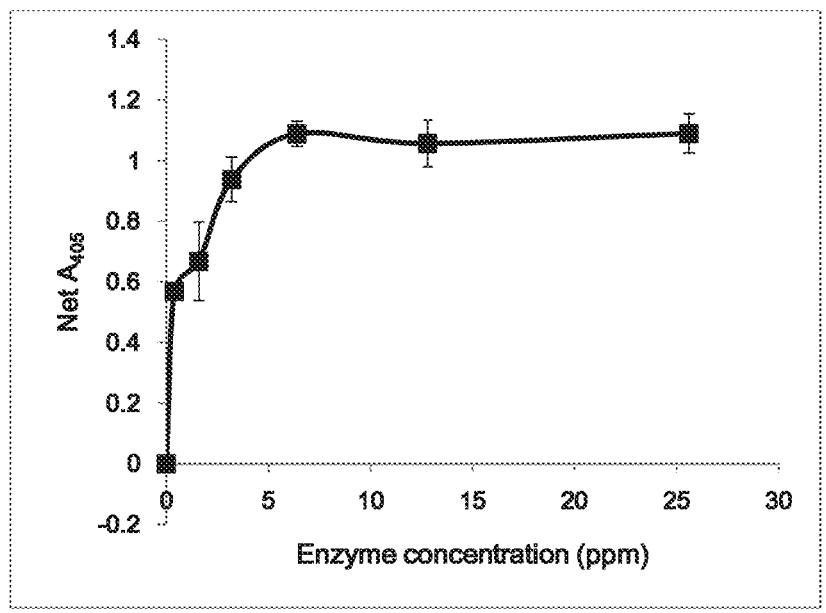
Figure 7.5B. Cleaning performance of PhuPro1 in dish detergent at pH 8.

```
CLUSTAL W (1.83) multiple sequence alignment

PhuPro1                            ---------ATGTGKGVLGDTKSFTVGTSGSSYVMTDSTRGKGIQTYTASNRTS
P_terrae_HPL-003_YP_005073223.     ---------ATGTGKGVLGDTKSFNITQSGSSYQLKDTTRGNGIVIYTASNRQT
B_thermoproteolyticus_P00800       ITGTSTVGVGRGVLGDQKNINTTYS-TYYYLQDNTRGNGIFTYDAKYRTT
                                            :.*.*:***** *:..   * : * : *.***:** ** *. * :

PhuPro1                            LPGSTVTSSSSTPN----DPASVDAHAYAQKVYDFYKSNFNRNSIDGNGLA
P_terrae_HPL-003_YP_005073223.     IPGTLLTDADNVWN----DPAGVDAHAYAAKTYDYYKDKFGRNSIDGRGLQ
B_thermoproteolyticus_P00800       LPGSLWADADNQFFASYDAPAVDAHYYAGVTYDYYKNVHNRLSYDGNNAA
                                   :**:  :.:..    :   *...****.**  .**;**. ..* * **..

PhuPro1                            IRSTTHYSTRYNNAFWNGSQMVYGDGDGSQFIAFSGDLDVVGHELTHGVT
P_terrae_HPL-003_YP_005073223.     LRSTVHYGSRYNNAFWNGSQMTYGDGDGTTFIAFSGDPDVVGHELTHGVT
B_thermoproteolyticus_P00800       IRSSVHYSQGYNNAFWNGSQMVYGDGDGQTFIPLSGGIDVVAHELTHAVT
                                   :**:.**.  ***********.******  **.;**. ***.*****.**

PhuPro1                            EYTANLEYYGQSGALNESISDIFGNTIE------GKNWMVGDAIYTPGVSG
P_terrae_HPL-003_YP_005073223.     EYTSNLDYYGESGALNESFSDIIGNDIQ------RKNWLVGDDIYTPSIAG
B_thermoproteolyticus_P00800       DYTAGLIYQNESGAINEAISDIFGTLVEFYANKNPDWEIGEDVYTPGISG
                                   :**:.* * .:***:**::***:*. ::      :* :*: :***.::*

PhuPro1                            DALRYMDDPTKGGQPARMADYNNTSADNGGVHTNSGIPNKAYYLLAQGGT
P_terrae_HPL-003_YP_005073223.     DALRSMSNPTLYDQPDHYSNLYKGSSDNGGVHTNSGIINKAYYLLAQGGT
B_thermoproteolyticus_P00800       DSLRSMSDPAKYGDPDHYSKRYTGIQDNGGVHINSGIINKAAYLISQGGT
                                   *:** *.:*:   .:* : :.   .: : ****** **** *** **;:****

PhuPro1                            FGGVNVTGIGRSQAIQIVYRALTYYLTSTSNFSNYRSAMVQASTDLYGAN
P_terrae_HPL-003_YP_005073223.     FHNVTVSGIGRDAAVQIYYSAFTNYLTSTSNFSNTRAAVVQAAKDLYGAN
B_thermoproteolyticus_P00800       HYGVSVVGIGRDKLGKIFYRALTQYLIPTSNFSQLRAAAVQSATDLYGST
                                   .  .*.* ****.   :* * *:* ***.*****: *:* **::.***:.

PhuPro1                            STQTTAVKNSLSAVGIN    SEQ ID NO: 33
P_terrae_HPL-003_YP_005073223.     SAQATAAAKSFDAVGVN    SEQ ID NO: 51
B_thermoproteolyticus_P00800       SQEVASVKQAFDAVGVK    SEQ ID NO: 45
                                   * :.::.  :::.**::
```

Figure 7.6: Alignment of PhuPro1 with homologous protease sequences.

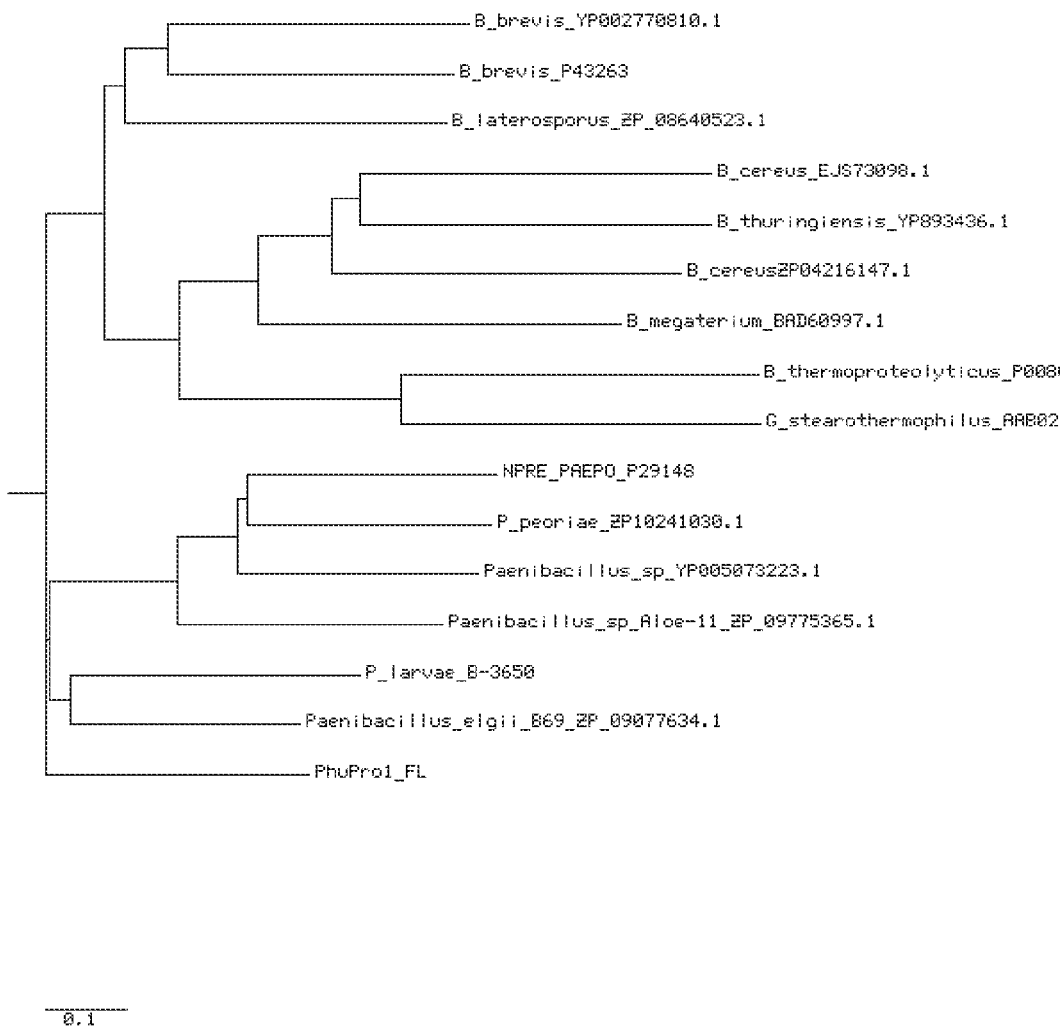
Figure7.7: Phylogenetic tree for PhuPro1 and homologs.

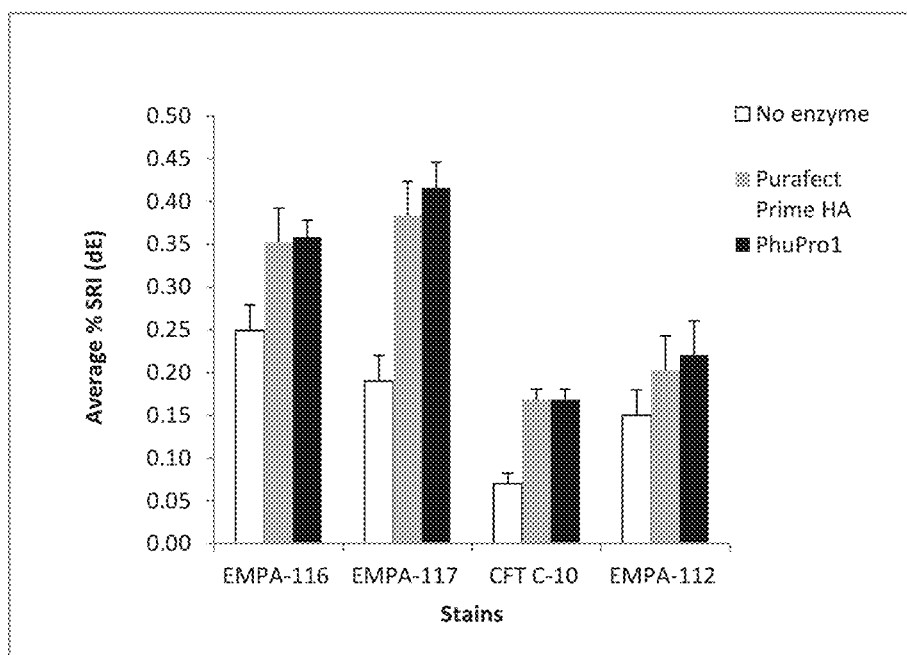
Figure 7.8A: Cleaning performance in Terg-o-Tometer assay at 32°C, on four technical stains.
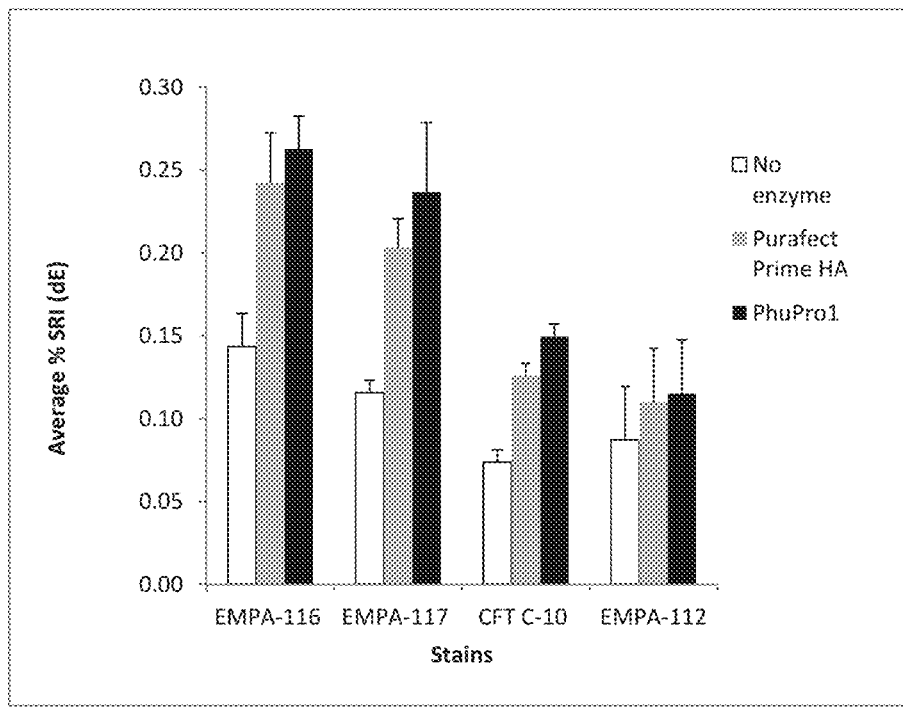
Figure 7.8B: Cleaning performance in Terg-o-Tometer assay at 16°C, on four technical stains.

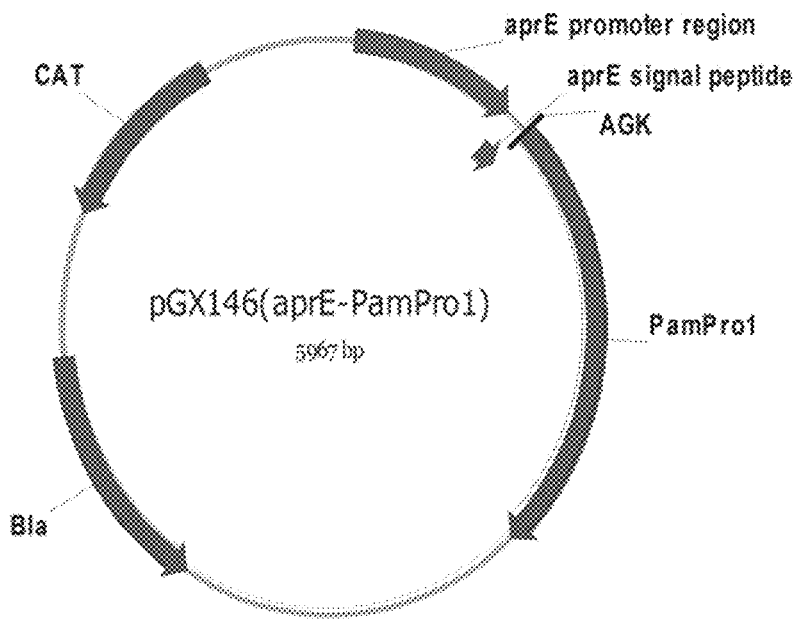
Figure 8.1. The plasmid map of pGX146(AprE-PamPro1).
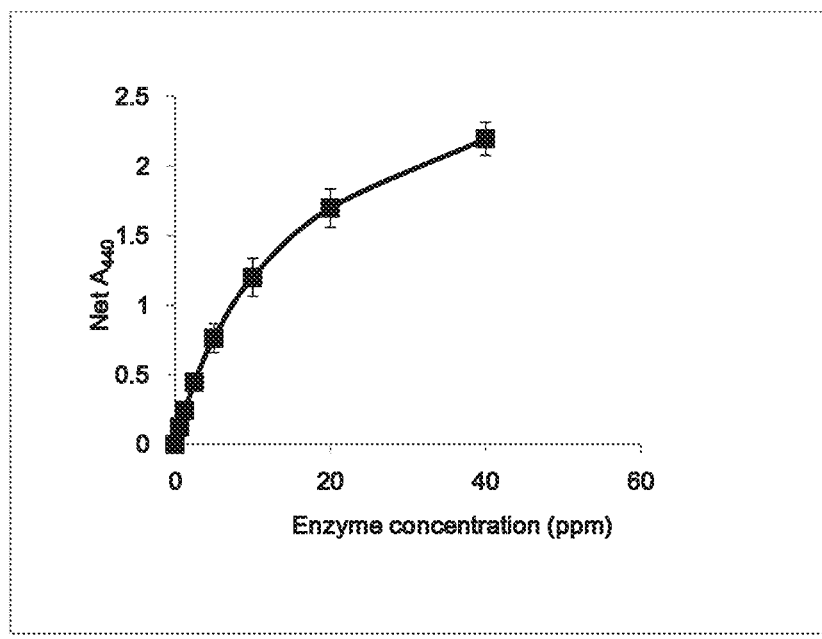
Figure 8.2. Dose response curve of PamPro1 the azo-casein assay at pH 7.

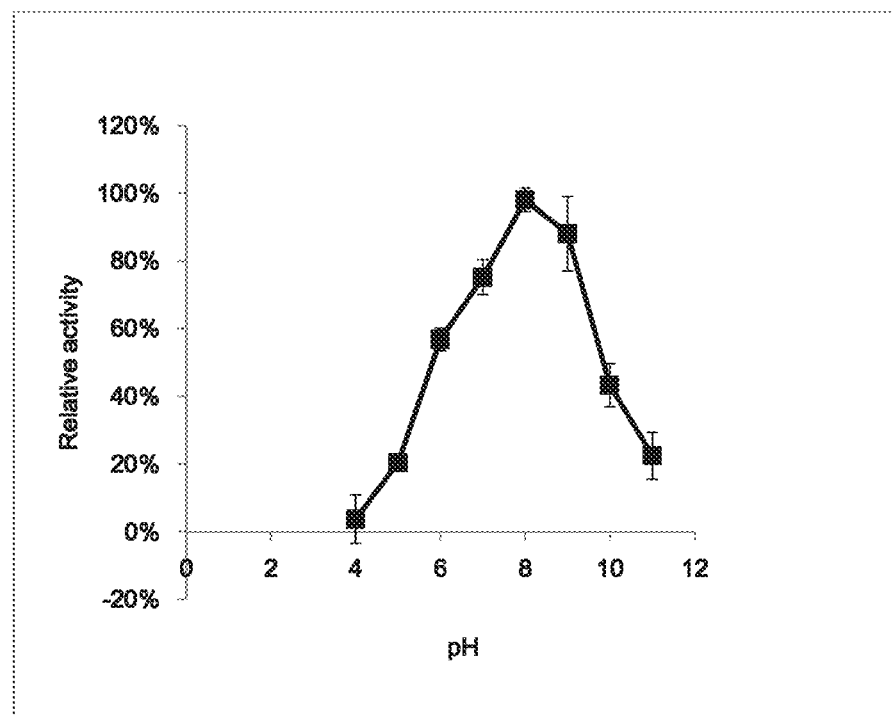
Figure 8.3. pH profile of PamPro1.
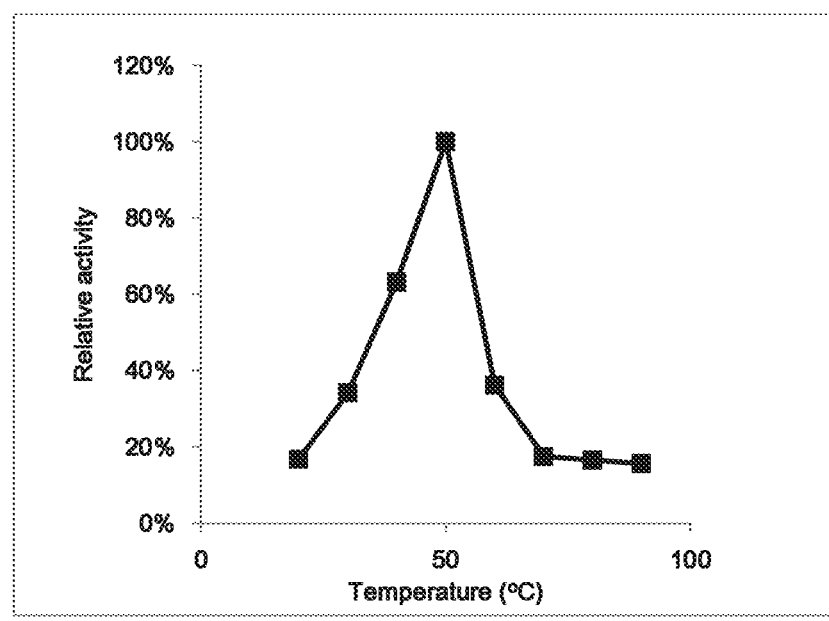
Figure 8.4. Temperature profile of PamPro1.

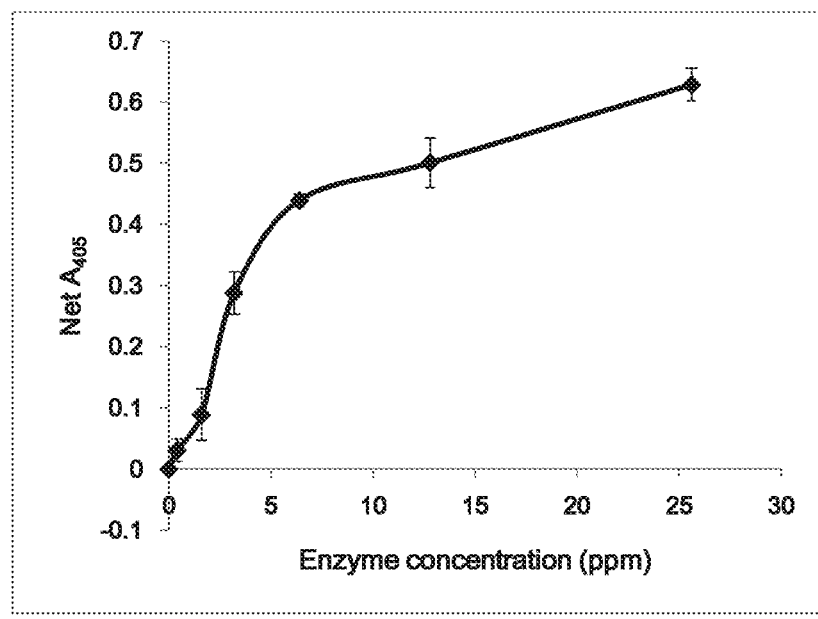
Figure 8.5A: Cleaning performance of PamPro1 in AT dish detergent at pH 6.
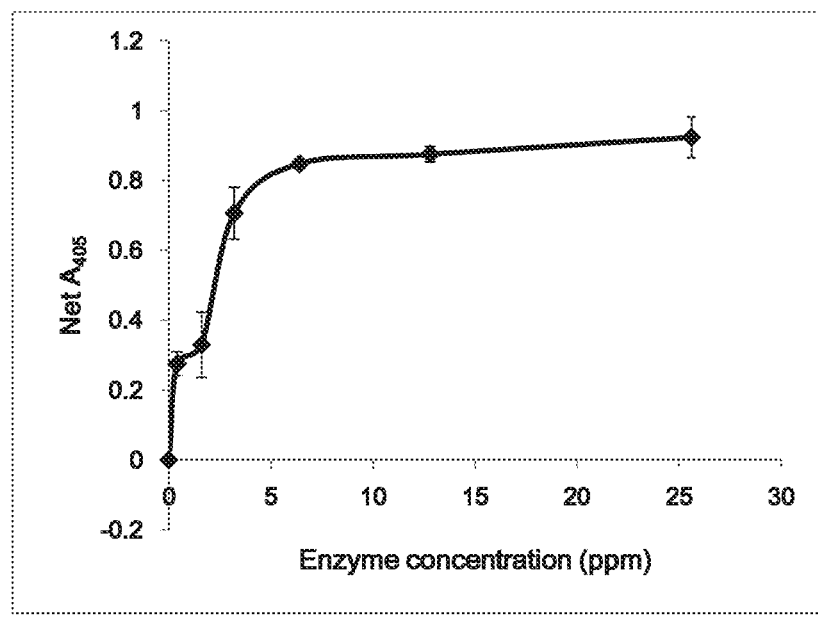
Figure 8.5B: Cleaning performance of PamPro1 in AT dish detergent at pH 8.

```
CLUSTAL W (1.83) multiple sequence alignment

PamPro1                          ------ATGTGTGVLGDTKILTTTQSGSTFQLKDTTRGNGIQTYIANNGSS
P_peoriae_KCTC                   DIINEATGTGKGVLGDTKSFTTTASGSSYQLRDTTRGNGIVTYIASNRQS
B_thermoproteolyticus_P00800     IIGTSTVGVGRGVLGDQKNINTTYS-TYYYLQDNTRGNGIFTYDAKYRTT
                                   :.*.* ***** *.:.** * : ; *;*.****** ** *.   ;

PamPro1                          LPGSLLTDSDNVWT----DPAGVDAHAHAAATYDFYKNKFNRNGINGNGLL
P_peoriae_KCTC                   IPGTILTDADNVWN---DPAGVDAHAYAAKTYDYYKEKFNRNSIDGRGLQ
B_thermoproteolyticus_P00800     LPGSLWADADNQFFASYDAPAVDAHYYAGVTYDYYKNVHNRLSYDGNNAA
                                 :**:: :*:** :    * ..**** :*. ***:**: .** . :*..

PamPro1                          IRSTVHYGSNYNNAFWNGAQIVFGDGDGTMFRSLSGDLDVVGHELTHGVI
P_peoriae_KCTC                   LRSTVHYGNRYNNAFWNGSQMTYGDGDGTIFIAFSGDPDVVGHELTHGVT
B_thermoproteolyticus_P00800     IRSSVHYSQGYNNAFWNGSQMVYGDGDGQTFIPLSGGIDVVAHELTHAVT
                                 :**:***.. ********:*:.:***** * ..**. ***.*****.*

PamPro1                          EYTANLEYRNEPGALNEAFADIFGNTIQ-----SKNWLLGDDIYTPNTPG
P_peoriae_KCTC                   EYTSNLEYYGESGALNESFSDIIGNDIQ-----RKNWLVGDDIYTPRIAG
B_thermoproteolyticus_P00800     DYTAGLIYQNESGAINEAISDIFGTLVEFYANKNPDWEIGEDVYTPGISG
                                 :**:.* * .*.**:**::*:*.  ::         :* :*:*:*** .*

PamPro1                          DALRSLSNPTLYGQPDKYSDRYTGSQDNGGVHINSGIINKAYFLAAQGGT
P_peoriae_KCTC                   DALRSMSNPTLYDQPDHYSNLYRGSSDNGGVHTNSGIINKAYYLLAQGGT
B_thermoproteolyticus_P00800     DSLRSMSDPAKYGDPDHYSKRYTGTQDNGGVHINSGIINKAAYLISQGGT
                                 *:***:*:*: *.:**;**.  * *:.****** ********* :* :****

PamPro1                          HNGVTVTGIGRDKAIQIFYSTLVNYLTPTSKFAAAKTATIQAAKDLYGAT
P_peoriae_KCTC                   FHGVTVNGIGRDAAVQIYYSAFTNYLTSSSDFSNARDAVVQAAKDLYGAS
B_thermoproteolyticus_P00800     HYGVSVVGIGRDKLGKIFYPALTQYLTPTSNFSQLRAAAVQSATDLYGST
                                 . **:* *****   :*:* ::.:***.:*,*:  : *.:.*:*.****::

PamPro1                          SAEATAITKAYQAVGL-    SEQ ID NO: 38
P_peoriae_KCTC                   SAQATAAAKAFDAVGVN    SEQ ID NO: 52
B_thermoproteolyticus_P00800     SQEVASVKQAFDAVGVK    SEQ ID NO: 45
                                 * ;.:: :*::****:
```

Figure 8.6: Alignment of PamPro1 with homologous protease sequences

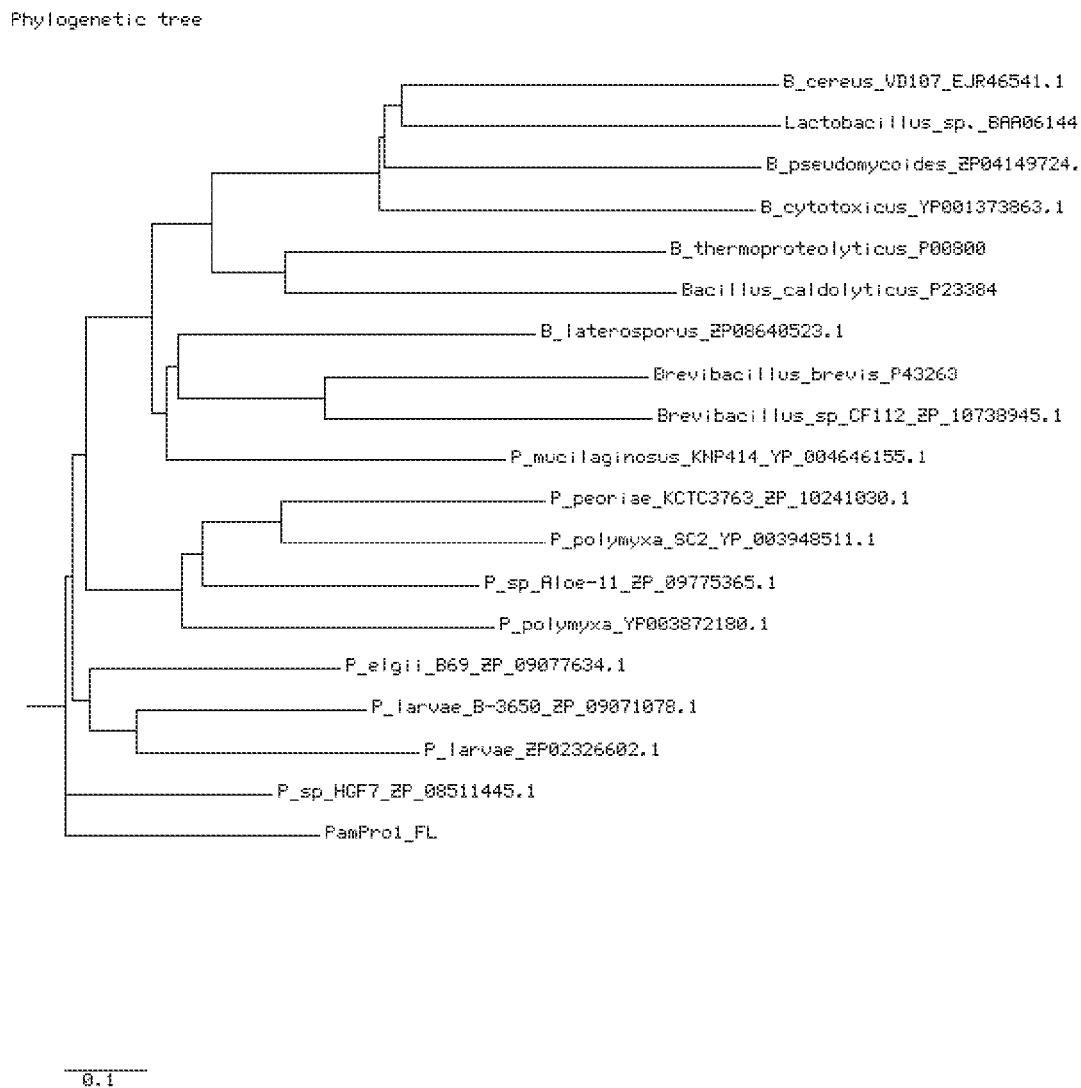
Figure 8.7: Phylogenetic tree for PamPro1 and homologs

```
1KEI.A                       ITGISTVGVGRGVLGDQKNINTTYSTYY---YLQDNTRGNGIFTYDAKYR
B_caldolyticus_AAA22623.1    ---TSTVGVGRGVLGDQKYINTTYSSYYGYYYLQDNTRGSGIFTYDGRNR
B_anthracis_NP843132.1       VTGINAVGTGKGVLGDTKSLNTTLSASS--YYLQDNTRGATIFTYDAKNR
B_thuringiensis_YP893436.1   VTGINAVGTGKGVLGDTKSLNTTLSASS--YYLQDNTRGATIFTYDAKNR
B_cereus_ZP04310163.1        ---INAVGTGKGVLGDTKSLNTTLSASS--YYLQDNTRGATIFTYDAKNR
Lactobacillus_sp_BAA06144.1  VTGINAVGTGKGVLGDTKSLNTTLSASS--YYLQDNTRGATIFTYDAKNR
1NPC.A                       VTGINKVGTGKGVLGDTKSLNTTLSGSS--YYLQDNTRGATIFTYDAKNR
B_cytotoxicus_YP001373863.1  VTGINAVGTGTGVLGDKKSINTTLSGST--YYLQDNTRGAQIFTYDAKNR
B_megaterium_YP005495105.1   ---INAIGSGKGVLGDTKSLKTTLSGSA--YYLQDNTRGATIYTYDAKNR
B_sp_SG-1_ZP01858398.1       VSGIDQVGTGKGVLGDTKSLNTTLSNGT--YYLQDNTRGGGIMTYDMKNR
PamPro1                      ------ATGTGTGVLGDTKTLITTQSGST--FQLKDTTRGNGIQTYIANNG
PbaPro1                      ------ATGTGTGVRGDTKTLITTQSGST--YQLKDTTRGKGIQTYIANNR
PhuPro2                      ------ATGSGTGVLGDNKTFQTTLSGST--YQLKDTTRGNGIYTYIASNR
PpePro1                      ------ATGTGRGVDGVTKSFITTASGNG--YQLKDTTRSNGIVTYIANNR
PspPro2                      ------ATGTGRGVDGKTKSFITTASGNR--YQLKDTTRSNGIVTYIAGNR
PpoPro1                      ------ATGTGKGVLGDSKSFTTTASGSS---YQLKDTTRGNGIVTYTASNR
PpoPro2                      ------ATGTGKGVLGDTKSFTTTASGSS---YQLKDTTRGNGIVTYTASNR
PspPro3                      ------ATGTGKGVLGDTKTFNTTASGSS---YQLRDTTRGNGIVTYTASNR
PehPro1                      ------ATGTGKGVLGDTKSFTTTQSGST---YQLKDTTRGQGIVTYSAGNR
PhuPro1                      ------ATGTGKGVLGDTKSFTVGTSGSS---YVMTDSTRGKGIQTYTASNR
PtePro1                      ------ATGTGVGVLGDTKTFTTTQSGTQ---YVMQDTTRGGGIVTYSAGNT
BbrPro1                      ------VTATGKGVLGDTKQFETTKQGST---YMLKDTTRGKGIETYTANNR
NprE                         ----AATTGTGTTLKGRTVSLNISSESGKYVLRDLSKPTGTQIITYDLQNR
NprE_variant                 ----AATTGTGTTLKGRTVSLNISSESGKYVLRDLSKPTGTQIITYDLQNR
                                .  *   :  *      :    .        ...  .  *  **

1KEI.A                       TT------LPGSLWADADNQFFASYDAPAVDAHYYAGVTYDYYKNVHNRLS
B_caldolyticus_AAA22623.1    TV------LPGSLWADGDNQFFASYDAAAVDAHYYAGVVYDYYKNVHGRLS
B_anthracis_NP843132.1       ST------LPGTLWVDADNVFNAAYDAAAVDAHYYAGRTYDYYKATFNRNS
B_thuringiensis_YP893436.1   ST------LPGTLWVDADNVFNAAYDAAAVDAHYYAGKTYDYYKATFNRNS
B_cereus_ZP04310163.1        ST------LPGTLWVDADNVFNAAYDAAAVDAHYYAGKTYDYYKATFNRNS
Lactobacillus_sp_BAA06144.1  ST------LPGTLWVDADNVFNAAYDAAAVDAHYYAGKTYDYYKATFNRNS
1NPC.A                       ST------LPGTLWADADNVFNAAYDAAAVDAHYYAGKTYDYYKATFNRNS
B_cytotoxicus_YP001373863.1  SS------LPGTLWADVDNAFHAKYDAAAVDAHYYAGVTYDYYKNTFNRNS
B_megaterium_YP005495105.1   TS------LPGTLWADTDNTYNATRDAAAVDAHYYAGVTYDYYKNKFNRNS
B_sp_SG-1_ZP01858398.1       TFFPQFYLPGSLWSDADNVYNQAYDAAAVDAHYFAGATFDYYKDVFGRNS
PamPro1                      SS---------LPGSLLTDSDNVWTDRAGVDAHAHAAATYDFYKNKFNRNG
PbaPro1                      SS---------LPGSLSTSSNNVWTDRAAVDAHAYAAATYDFYKNKFNRNG
PhuPro2                      TT---------IPGTLLTDADNVWTDGAAVDAHTYAGKVYDFYKTKFGRNS
PpePro1                      QT---------TPGTIMTDADNVWNDPAAVDAHAYAIKTYDYYKNKFGRDS
PspPro2                      QT---------TPGTILTDTDNVWEDPAAVDAHAYAIKTYDYYKNKFGRDS
PpoPro1                      QS---------IPGTILTDADNVWNDPAGVDAHAYAAKTYDYYKAKFGRNS
PpoPro2                      QS---------IPGTLLTDADNVWNDPAGVDAHAYAAKTYDYYKSKFGRDS
PspPro3                      QS---------IPGTILTDADNVWNDPAGVDAHAYAAKTYDYYKEKFNRNS
PehPro1                      SS---------LPGTLLTSSSNIWNDGAAVDAHAYTAKVYDYYKNKFGRNS
PhuPro1                      TS---------LPGSTVTSSSSTFNDPASVDAHAYAQKVYDFYKSNFNRNS
PtePro1                      QS---------LPGTLMRDTDNVWTDPAAVDAHAYAAVVYDYFKNNFNRDS
BbrPro1                      TS---------LPGTLMTDSDNYWTDGAAVDAHAHAQKTYDFYRNVHNRNS
NprE                         EYN------LPGILVSSTTNQFTISSQRAAVDAHYNLGKVYDYFYQKFNRNS
NprE_variant                 EYN------LPGILVSSTTNQFTISSQRAAVDAHYNLGKVYDYFYQKFNRNS
                                     .  : ..****         .:*::    ..* .
```

Figure 9.1A CLUSTAL 2.0.10 multiple sequence alignment of the various Paenibacillus metalloproteases with other bacterial metalloprotease homologs.

```
1KEI.A                       YDGNNAAIRSSVHYSQGYNNAFWNGSQMVYGDGDGQTFIPLSGGIDVVAH
B_caldolyticus_AAA22623.1    YDGSNAAIRSTVHYGRGYNNAFWNGSQMVYGDGDGQTFLPFSGGIDVVGH
B_anthracis_NP843132.1       INDAGAPLKSTVHYGSRYNNAFWNGSQMVYGDGDGVTFTSLSGGIDVIGH
B_thuringiensis_YP893436.1   INDAGAPLKSTVHYGSRYNNAFWNGSQMVYGDGDGVTFTSLSGGIDVIGH
B_cereus_ZP04310163.1        INDAGAPLKSTVHYGSRYNNAFWNGSQMVYGDGDGVTFTSLSGGIDVIGH
Lactobacillus_sp_BAA06144.1  INDAGAPLKSTVHYGSRYNNAFWNGSQMVYGDGDGVTFTSLSGGIDVIGH
1NPC.A                       INDAGAPLKSTVHYGSNYNNAFWNGSQMVYGDGDGVTFTSLSGGIDVIGH
B_cytotoxicus_YP001373863.1  INDAGAALKSTVHYGSNYNNAFWNGSQMVYGDGDGVTFTSLSGGIDVIGH
B_megaterium_YP005495105.1   YDNAGAPLKSTVHYSSGYNNAFWNGSQMVYGDGDGTTFVPLSGGLDVIGH
B_sp_SG-1_ZP01858398.1       YDNKGTTIQSSVHYSKNYNNAFWNGSQMVYGDGDGTTFIPLSGGLDVVAH
PamPro1                      INGNGLLIRSTVHYGSNYNNAFWNGAQIVFGDGDGTMFRSLSGDLDVVGH
PbaPro1                      IDGNGLLIRSTVHYGSNYKNAFWNGAQIVYGDGDGIEFGPFSGDLDVVGH
PhuPro2                      LDGNGLLIRSSVHYSSRYNNAFWNGTQIVFGDGDGSTFIPLSGDLDVVGH
PpePro1                      IDGRGMQIRSTVHYGKKYVNAFWNGSQMIYGDGDGSTFTFFSGDPDVVGH
PspPro2                      IDGRGMQIRSTVHYGKKYNNAFWNGSQMIYGDGDGSTFTFFSGDPDVVGH
PpoPro1                      IDGRGLQLRSTVHYGSRYNNAFWNGSQMTYGDGDGSTFIAFSGDPDVVGH
PpoPro2                      VDGRGLQLRSTVHYGSRYNNAFWNGSQMTYGDGDGSTFIAFSGDPDVVGH
PspPro3                      IDGRGLQLRSTVHYGNRYNNAFWNGSQMTYGDGDGTTFIAFSGDPDVVGH
PehPro1                      IDGNGFQLKSTVHYSSRYNNAFWNGVQMVYGDGDGVTFIPFSADPDVIGH
PhuPro1                      IDGNGLAIRSTTHYSTRYNNAFWNGSQMVYGDGDGSQFIAFSGDLDVVGH
PtePro1                      LDGRGMAIKSTVHYGSRYNNAFWNGTQIAYGDGDGTTFRAFSGDLDVIGH
BbrPro1                      YDGNGAVIRSTVHYSTRYNNAFWNGSQMVYGDGDGTTFLPLSGGLDVVAH
NprE                         YDNKGGKIVSSVHYGSRYNNAAWIGDQMIYGDGDGSFFSPLSGSMDVTAH
NprE_variant                 YDNKGGKIVSSVHYGSRYNNAAWIGDQMIYGDGDGILFSPLSGSLDVTAH
                             :.  ,   : *:.**.  * ** * * *; :*****   *  :*.. ** .*

1KEI.A                       ELTHAVTDYTAGLIYQNESGAINEAISDIFGTLVEFYANKNPDWEIGEDV
B_caldolyticus_AAA22623.1    ELTHAVTDYTAGLVYQNESGAINEAMSDIFGTLVEFYANRNPDWEIGEDI
B_anthracis_NP843132.1       ELTHAVTEYSSDLIYQNESGALNEAISDVFGTLVEYYDNRNPDWEIGEDI
B_thuringiensis_YP893436.1   ELTHAVTEYSSDLIYQNESGALNEAISDVFGTLVEFYDNRNPDWEIGEDI
B_cereus_ZP04310163.1        ELTHAVTEYSSDLIYQNESGALNEAISDVFGTLVEFYDNRNPDWEIGEDI
Lactobacillus_sp_BAA06144.1  ELTHAVTEYSSDLIYQNESGALNEAISDVFGTLVEYYDNRNPDWEIGEDI
1NPC.A                       ELTHAVTENSSNLIYQNESGALNEAISDIFGTLVEFYDNRNPDWEIGEDI
B_cytotoxicus_YP001373863.1  ELTHAVTEYSSNLIYQYESGALNEAISDVFGTLVEYYDNRNPDWEIGEDI
B_megaterium_YP005495105.1   ELTHAVTERSSNLIYQYESGALNEAISDIFGTLVEYYDNRNPDWEIGEDI
B_sp_SG-1_ZP01858398.1       ELTHAVTDTSSDLVYQNESGALNEAISDIFGTLVEYHENHNPDFEIGEDI
PamPro1                      ELTHGVIEYTANLEYRNEPGALNEAFADIFGNTIQ-------SKNWLLGDDI
PbaPro1                      ELTHGVIEYTANLEYRNEPGALNEAFADIMGNTIE-------SKNWLLGDGI
PhuPro2                      ELSHGVIEYTSNLQYLNESGALNESYADVLGNSIQ-------AKNWLIGDDV
PpePro1                      ELTHGVTEFTSNLEYYGESGALNEAFSDIIGNDID-------GANWLLGDGI
PspPro2                      ELTHGVTEYTSNLEYYGESGALNEAFSDIIGNDID-------GTSWLLGDGI
PpoPro1                      ELTHGVTEYTSNLEYYGESGALNEAFSDVIGNDIQ-------RKNWLVGDDI
PpoPro2                      ELTHGVTEYTSNLEYYGESGALNEAFSDVIGNDIQ-------RKNWLVGDDI
PspPro3                      ELTHGVTEYTSNLEYYGESGALNEAFSDIIGNDIQ-------RKNWLVGDDI
PehPro1                      ELTHGVTEHTAGLEYYGESGALNESISDIIGNAID-------GKNWLIGDLI
PhuPro1                      ELTHGVTEYTANLEYYGQSGALNESISDIFGNTIE-------GKNWMVGDAI
PtePro1                      ELTHGITEKTAGLIYQGESGALNESISDVFGNTIQ-------GKNWLIGDDI
BbrPro1                      ELTHAVTERTAGLVYQNESGALNESMSDIFGAMVD-------NDDWLMGEDI
NprE                         EMTHGVTQETANLNYENQPGALNESFSDVFGYFND-------TEDWDIGEDI
NprE_variant                 EMTHGVTQETANLNYENQPGALNESFSDVFGYFND-------TEDWDIGEDI
                             *:;*.:  :  ::.* *   :.**:**; :*::*      :    .: :*: :
```

Figure 9.1B CLUSTAL 2.0.10 multiple sequence alignment of the various Paenibacillus metalloproteases with other bacterial metalloprotease homologs.

```
1KEI.A                        YTPGISGDSLRSMSDPAKYGDPDHYSKRYT----GTQDNGGVHINSGIIN
B_caldolyticus_AAA22623.1     YTPGVAGDALRSMSDPAKYGDPDHYSKRYT----GTQDNGGVHTNSGIIN
B_anthracis_NP843132.1        YTPGKAGDALRSMSDPTKYGDPDHYSKRYT----GTGDNGGVHTNSGIIN
B_thuringiensis_YP893436.1    YTPGKAGDALRSMSDPTKYGDPDHYSKRYT----GTGDNGGVHTNSGIIN
B_cereus_ZP04310163.1         YTPGKAGDALRSMSDPTKYGDPDHYSKRYT----GTGDNGGVHTNSGIIN
Lactobacillus_sp_BAA06144.1   YTPGKAGDALRSMSDPTKYGDPDHYSKRYT----GTSDNGGVHTNSGIIN
1NPC.A                        YTPGKAGDALRSMSDPTKYGDPDHYSKRYT----GSSDNGGVHTNSGIIN
B_cytotoxicus_YP001373863.1   YTPGKAGDALRSMSDPTKYGDPDHYSKRYT----GSGDNGGVHTNSGIIN
B_megaterium_YP005495105.1    YTPGTSGDALRSMSNPAKYGDPDHYSKRYT----GSSDNGGVHTNSGIIN
B_sp_SG-1_ZP01858398.1        YTPNTPNDALRSMSDPAKYGDPDHYSVRYT----GTQDNGGVHINSGIIN
PamPro1                       YTPNTPGDALRSLSNPTLYGQPDKYSDRYT----GSQDNGGVHINSGIIN
PbaPro1                       YTPNIPGDALRSLSDPTLYNQPDKYSDRYT----GSQDNGGVHINSGIIN
PhuPro2                       YTPGISGDALRSMSNPTLYGQPDNYANRYT----GSSDNGGVHTNSGIIN
PpePro1                       YTPGIPGDALRSLSDPTRFGQPDHYSNFYPDP--NNDDEGGVHTNSGIIN
PspPro2                       YTPNIPGDALRSLSDPTRFGQPDHYSNFYPDP--NNDDEGGVHTNSGIIN
PpoPro1                       YTPNIAGDALRSMSNPTLYDQPDHYSNLYR----GSSDNGGVHTNSGIIN
PpoPro2                       YTPNIAGDALRSMSNPTLYDQPDHYSNLYK----GSSDNGGVHTNSGIIN
PspPro3                       YTPRIAGDALRSMSNPTLYDQPDHYSNLYR----GSSDNGGVHTNSGIIN
PehPro1                       YTPNTPGDALRSMENPKLYNQPDRYQDRYT----GPSDNGGVHINSGINN
PhuPro1                       YTPGVSGDALRYMDDPTKGGQPARMADYNN----TSADNGGVHTNSGIPN
PtePro1                       YTPSIPGDALRSMENPTLFNQPDHYSNIYR----GSDDNGGVHTNSGIPN
BbrPro1                       YTPGRSGDALRSLQDPAAYGDPDHYSKRYT----GSQDNGGVHTNSGINN
NprE                          ---TVSQPALRSLSNPTKYGQPDNFKNYKNLPNTDAGDYGGVHTNSGIPN
NprE_variant                  ---TISQPALRSLSNPTKYGQPDNFKNYKNLPNTPAGDYGGVHTNSGIPN
                                 .:**   :.:*    .:*  .        *  **** **** *

1KEI.A                        KAAYLISQGGTHYGVSVVGIGRDKLGKIFYRALTQYLTPTSNFSQLRAAA
B_caldolyticus_AAA22623.1     KAAYLLSQGGVHYGVSVTGIGRDKMGKIFYRALVYYLTPTSNFSQLRAAC
B_anthracis_NP843132.1        KAAYLLANGGTHYGVTVNGIGKDKVGAIYYRANTQYFTQSTTFSQARAGL
B_thuringiensis_YP893436.1    KAAYLLANGGTHYGVTVNGIGKDKVGAIYYRANTQYFTQSTTFSQARAGL
B_cereus_ZP04310163.1         KAAYLLANGGTHYGVTVNGIGKDKVGAIYYRANTQYFTQSTTFSQARAGL
Lactobacillus_sp_BAA06144.1   KAAYLLANGGTHYGVTVNGIGKDKVGAIYYRANTQYFTQSTTFSQARAGL
1NPC.A                        KQAYLLANGGTHYGVTVTGIGKDKLGAIYYRANTQYFTQSTTFSQARAGA
B_cytotoxicus_YP001373863.1   KAAYLLANGGTHYGVTVNGIGKDKVGAIYYRANTQYFTQSTTFSQARAGL
B_megaterium_YP005495105.1    KAAYLLANGGTHYGVTVTGIGGDKLGKIYYRANTLYFTQSTTFSQARAGL
B_sp_SG-1_ZP01858398.1        KQAYLLSEGGTHYGVNVTGIGREKLGEIYYRMNTVYLTASSTFSQARSAA
PamPro1                       KAYFLAAQGGTHNGVTVTGIGRDKAIQIFYSTLVNYLTPTSKFAAAKTAT
PbaPro1                       KAYYLAAQGGTHNGVTVSGIGRDKAVRIFYSTLVNYLTPTSKFAAAKTAT
PhuPro2                       KAFYLLAQGGTQNGVTVAGIGRDAAVNIFYNTVAYYLTSTSNFAAAKNAS
PpePro1                       KAYYLLAQGGTSHGVKVTGIGREAAVFIYYNAFTNYLTSTSNFSNARAAV
PspPro2                       KAYYLLAQGGTSHGVTVTGIGREAAVFIYYNAFTNYLTSTSNFSNARAAV
PpoPro1                       KAYYLLAQGGNFHGVTVNGIGRDAAVQIYYSAFTNYLTSSSDFSNARAAV
PpoPro2                       KAYYLLAQGGSTFHGVAVNGIGRDAAVQIYYSAFTNYLTSSSDFSNARAAV
PspPro3                       KAYYLLAQGGSTFHGVTVNGIGRDAAVQIYYSAFTNYLTSSSDFSNARDAV
PehPro1                       KAFYLIAQGGTHYGVTVNGIGRDAAVQIFYDALINYLTPTSNFSAMRAAA
PhuPro1                       KAYYLLAQGGTFGGVNVTGIGRSQAIQIVYRALTYYLTSTSNFSNYRSAM
PtePro1                       KAFYLLAQGGTHRGVSVTGIGRGDAAKIVYKALTYYLTSTSNFAAMRQAA
BbrPro1                       KAAYLLAEGGTHYGVRVNGIGRTDIAKIYYHALTHYLTPYSNFSAMRRAA
NprE                          KAAYN------------TITKIGVNKAEQIYYRALTVYLTPSSTFKDAKAAL
NprE_variant                  KAAYN------------TITKIGVNKAEQIYYRALTVYLTPSSTFKDAKAAL
                              *  :               ;  **   *  *   *:*  : *   :  .
```

Figure 9.1C CLUSTAL 2.0.10 multiple sequence alignment of the various Paenibacillus metalloproteases with other bacterial metalloprotease homologs.

```
1KEI.A                       VQSATDLYGSTSQEVASVKQAFDAVGVK    SEQ ID NO: 53
B_caldolyticus_AAA22623.1    VQAAADLYGSTSQEVNSVKQAFNAVGVY    SEQ ID NO: 54
B_anthracis_NP843132.1       VQA-------------------------    SEQ ID NO: 55
B_thuringiensis_YP893436.1   VQAATDLYGASSAEVAAVKQSYSAVGVN    SEQ ID NO: 56
B_cereus_ZP04310163.1        VQAAADLYGASSAEVAAVKQSYSAVGVN    SEQ ID NO: 57
Lactobacillus_sp_BAA06144.1  VQAAADLYGASSAEVAAVKQSYSAVGVN    SEQ ID NO: 58
1NPC.A                       VQAAADLYGANSAEVAAVKQSFSAVGVN    SEQ ID NO: 59
B_cytotoxicus_YP001373863.1  VQAAADLYGANSAEVTAVKQSYDAVGVK    SEQ ID NO: 60
B_megaterium_YP005495105.1   VQAAADLYGSGSQEVISVGKSFDAVGVQ    SEQ ID NO: 61
B_sp_SG-1_ZP01858398.1       VQAASDLYGSNSPEVQSVNQSFDAVGIN    SEQ ID NO: 62
PamPro1                      IQAAKDLYGATSAEATAITKAYQAVGL-    SEQ ID NO: 38
PbaPro1                      IQAAKDLYGANSAEATAITKAYQAVGL-    SEQ ID NO: 23
PhuPro2                      IQAAKDLYGTGSSYVTSVTNAFRAVGL-    SEQ ID NO: 13
PpePro1                      IQAAKDFYGADSLAVTSAIKSFDAVGIK    SEQ ID NO: 63
PspPro2                      IQAAKDFYGADSLAVTSAIQSFDAVGIK    SEQ ID NO: 8
PpoPro1                      IQAAKDLYGANSAEATAAAKSFDAVGVN    SEQ ID NO: 28
PpoPro2                      IQAAKDLYGANSAEATAAAKSFDAVGVN    SEQ ID NO: 64
PspPro3                      VQAAKDLYGASSAQATAAAKSFDAVGVN    SEQ ID NO: 3
PehPro1                      IQAATDLYGANSSQVNAVKKAYTAVGVN    SEQ ID NO: 18
PhuPro1                      VQASTDLYGANSTQTTAVKNSLSAVGIN    SEQ ID NO: 33
PtePro1                      ISSATDLFGANSAQVNSVKAAYAAVGI-    SEQ ID NO: 65
EbrPro1                      VLSATDLFGANSRQVQAVNAAYDAVGVK    SEQ ID NO: 66
NprE                         IQSARDLYGSQDAASVEAAWNAVGL---    SEQ ID NO: 67
NprE_variant                 IQSARDLYGSQDAASVEAAWNAVGL---    SEQ ID NO: 68
                                 :  :
```

Figure 9.1D CLUSTAL 2.0.10 multiple sequence alignment of the various Paenibacillus metalloproteases with other bacterial metalloprotease homologs.

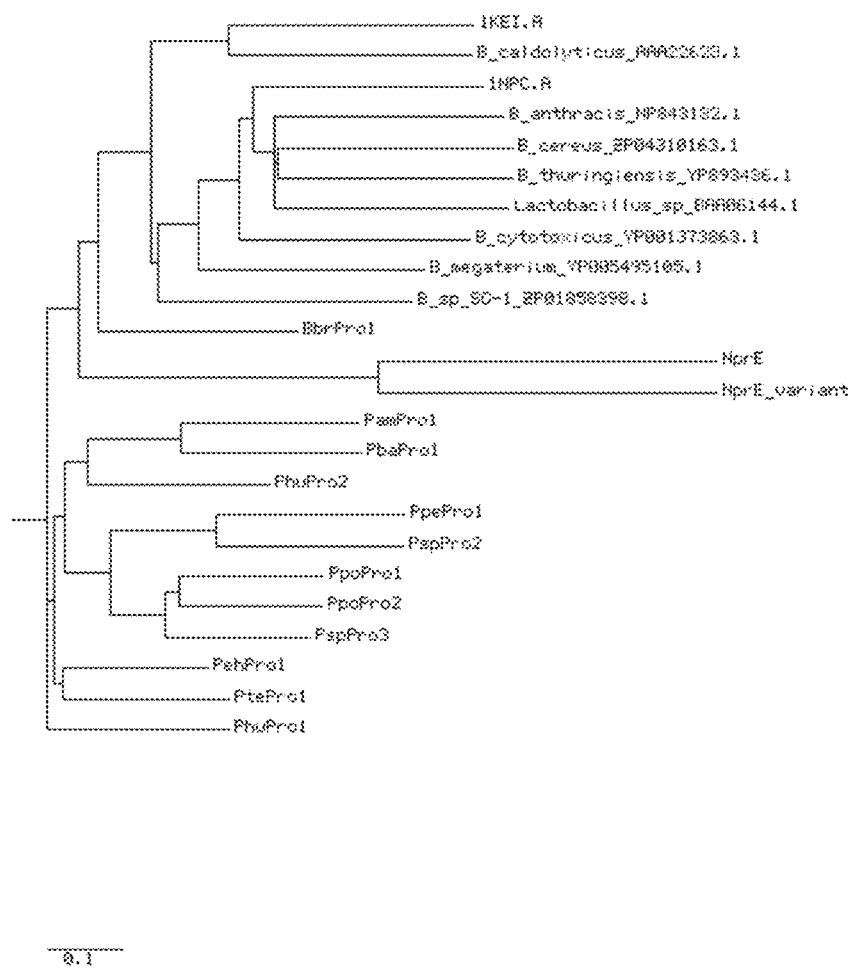
Figure 9.2 The phylogenetic tree of the various Paenibacillus metalloproteases with other bacterial metalloprotease homologs.

SEQUENCE LISTING

```
<160> NUMBER OF SEQ ID NOS: 68

<210> SEQ ID NO 1
<211> LENGTH: 1785
<212> TYPE: DNA
<213> ORGANISM: Paenibacillus sp.
<220> FEATURE:
<221> NAME/KEY: misc_feature
<222> LOCATION: (1)..(1785)
<223> OTHER INFORMATION: nucleotide sequence of the PspPro3 gene
      isolated from Paenibacillus sp.

<400> SEQUENCE: 1
atgttaatga aaaagtatg ggtttcgctt cttggaggag cgatgttatt agggtctgta      60
gcgtctggtg catcagcagc ggagagttcc gtttcggggc cggctcagct tacgccaacc     120
ttccatgccg aacaatggaa agcaccttca tcggtatcgg gtgatgacat cgtatggagc     180
tatttaaatc ggcaaaagaa aacgttgctg ggtacggaca gcaccagtgt ccgtgatcaa     240
ttccgtatcg tagatcgcac aagcgacaaa tccggcgtga gccattatcg gctgaagcaa     300
tatgtaaacg gaattcccgt atatggagct gaacagacca ttcatgtggg caaatccggt     360
gaagtgacct cttatctggg agccgtgatt actgaggatc agcaagaaga agctacgcaa     420
ggtacaactc cgaaaatcag cgcttctgaa gcggtccata ccgcatatca ggaggcagct     480
acacgggttc aagccctccc tacctccgat gatacgattt ctaaagatgc ggaggagcca     540
agcagtgtaa gcaaagacac ttactccgaa gcagctaaca acggaaaaac gagttctgtt     600
gaaaaggaca agctcagcct tgagaaagcg gctgacctga agatagcaa aattgaagcg     660 gtggaggcag agccaaactc cattgccaaa atcgccaacc tgcagcctga ggtagatcct     720
aaagccgaac tatattccta tgcgaagggc gatgcattgc agctggttta tgtgactgag     780
gttaatattt tgcagcctgc gccgctgcgt acacgctaca tcattgacgc caatgatggc     840
aaaatcgtat cccagtatga catcattaat gaagcgacag gcacaggcaa aggtgtactc     900
ggtgatacca aaacattcaa cactactgct tccggcagca gctaccagtt aagagatacg     960
actcgcggga atgaatcgt gacttacacg gcctccaacc gtcaaagcat cccaggtacg    1020
atcctgaccg atgccgataa cgtatggaat gatccagccg gcgtggatgc ccacgcttat    1080
gcagccaaaa cctatgatta ttataaggaa aagttcaatc gcaacagcat tgacggacga    1140
```

```
ggcctgcagc tccgttcgac agttcattac ggcaatcgtt acaacaacgc cttctggaac    1200
ggctcccaaa tgacttatgg agacggagac ggcaccacat ttatcgcttt tagcggtgat    1260
ccggatgtag ttggtcatga actcacacac ggtgttacgg agtatacttc caatttggaa    1320
tattacggag aatccggtgc gttgaacgag gccttctcgg acatcatcgg caatgacatc    1380
cagcgtaaaa actggcttgt aggcgatgat atttacacgc cacgcattgc gggtgatgca    1440
cttcgttcta tgtccaatcc tacgctgtac gatcaaccgg atcactattc gaacttgtac    1500
agaggcagct ccgataacgg cggcgttcat acgaacagcg gtattataaa taaagcctat    1560
tatctgttgg cacaaggcgg caccttccat ggtgtaactg tcaatgggat tggccgcgat    1620
gcagcggttc aaatttacta cagcgccttt acgaactacc tgacttcttc ttctgacttc    1680
tccaatgcac gtgatgccgt tgtacaagcg gcaaaagatc tctacggcgc gagctcggca    1740
caagctaccg cagcagccaa atcttttgat gctgtaggcg ttaac                   1785
```

<210> SEQ ID NO 2
<211> LENGTH: 595
<212> TYPE: PRT
<213> ORGANISM: Paenibacillus sp.
<220> FEATURE:
<221> NAME/KEY: misc_feature
<222> LOCATION: (1)..(595)
<223> OTHER INFORMATION: amino acid sequence of the PspPro3 precursor protein

<400> SEQUENCE: 2

```
Met Leu Met Lys Lys Val Trp Val Ser Leu Leu Gly Gly Ala Met Leu
1               5                   10                  15

Leu Gly Ser Val Ala Ser Gly Ala Ser Ala Ala Glu Ser Ser Val Ser
                20                  25                  30

Gly Pro Ala Gln Leu Thr Pro Thr Phe His Ala Glu Gln Trp Lys Ala
            35                  40                  45

Pro Ser Ser Val Ser Gly Asp Asp Ile Val Trp Ser Tyr Leu Asn Arg
        50                  55                  60

Gln Lys Lys Thr Leu Leu Gly Thr Asp Ser Thr Ser Val Arg Asp Gln
65                  70                  75                  80

Phe Arg Ile Val Asp Arg Thr Ser Asp Lys Ser Gly Val Ser His Tyr
                85                  90                  95

Arg Leu Lys Gln Tyr Val Asn Gly Ile Pro Val Tyr Gly Ala Glu Gln
                100                 105                 110

Thr Ile His Val Gly Lys Ser Gly Glu Val Thr Ser Tyr Leu Gly Ala
            115                 120                 125

Val Ile Thr Glu Asp Gln Gln Glu Ala Thr Gln Gly Thr Thr Pro
        130                 135                 140

Lys Ile Ser Ala Ser Glu Ala Val His Thr Ala Tyr Gln Glu Ala Ala
145                 150                 155                 160

Thr Arg Val Gln Ala Leu Pro Thr Ser Asp Asp Thr Ile Ser Lys Asp
                165                 170                 175

Ala Glu Glu Pro Ser Ser Val Ser Lys Asp Thr Tyr Ser Glu Ala Ala
            180                 185                 190

Asn Asn Gly Lys Thr Ser Ser Val Glu Lys Asp Lys Leu Ser Leu Glu
        195                 200                 205

Lys Ala Ala Asp Leu Lys Asp Ser Lys Ile Glu Ala Val Glu Ala Glu
    210                 215                 220

Pro Asn Ser Ile Ala Lys Ile Ala Asn Leu Gln Pro Glu Val Asp Pro
```

```
                225                 230                 235                 240
Lys Ala Glu Leu Tyr Phe Tyr Ala Lys Gly Asp Ala Leu Gln Leu Val
                    245                 250                 255

Tyr Val Thr Glu Val Asn Ile Leu Gln Pro Ala Pro Leu Arg Thr Arg
                    260                 265                 270

Tyr Ile Ile Asp Ala Asn Asp Gly Lys Ile Val Ser Gln Tyr Asp Ile
                    275                 280                 285

Ile Asn Glu Ala Thr Gly Thr Gly Lys Gly Val Leu Gly Asp Thr Lys
290                 295                 300

Thr Phe Asn Thr Thr Ala Ser Gly Ser Ser Tyr Gln Leu Arg Asp Thr
305                 310                 315                 320

Thr Arg Gly Asn Gly Ile Val Thr Tyr Thr Ala Ser Asn Arg Gln Ser
                    325                 330                 335

Ile Pro Gly Thr Ile Leu Thr Asp Ala Asp Asn Val Trp Asn Asp Pro
                    340                 345                 350

Ala Gly Val Asp Ala His Ala Tyr Ala Ala Lys Thr Tyr Asp Tyr Tyr
                    355                 360                 365

Lys Glu Lys Phe Asn Arg Asn Ser Ile Asp Gly Arg Gly Leu Gln Leu
                    370                 375                 380

Arg Ser Thr Val His Tyr Gly Asn Arg Tyr Asn Asn Ala Phe Trp Asn
385                 390                 395                 400

Gly Ser Gln Met Thr Tyr Gly Asp Gly Asp Gly Thr Thr Phe Ile Ala
                    405                 410                 415

Phe Ser Gly Asp Pro Asp Val Val Gly His Glu Leu Thr His Gly Val
                    420                 425                 430

Thr Glu Tyr Thr Ser Asn Leu Glu Tyr Tyr Gly Glu Ser Gly Ala Leu
                    435                 440                 445

Asn Glu Ala Phe Ser Asp Ile Ile Gly Asn Asp Ile Gln Arg Lys Asn
                    450                 455                 460

Trp Leu Val Gly Asp Asp Ile Tyr Thr Pro Arg Ile Ala Gly Asp Ala
465                 470                 475                 480

Leu Arg Ser Met Ser Asn Pro Thr Leu Tyr Asp Gln Pro Asp His Tyr
                    485                 490                 495

Ser Asn Leu Tyr Arg Gly Ser Ser Asp Asn Gly Gly Val His Thr Asn
                    500                 505                 510

Ser Gly Ile Ile Asn Lys Ala Tyr Tyr Leu Leu Ala Gln Gly Gly Thr
                    515                 520                 525

Phe His Gly Val Thr Val Asn Gly Ile Gly Arg Asp Ala Ala Val Gln
                    530                 535                 540

Ile Tyr Tyr Ser Ala Phe Thr Asn Tyr Leu Thr Ser Ser Ser Asp Phe
545                 550                 555                 560

Ser Asn Ala Arg Asp Ala Val Gln Ala Ala Lys Asp Leu Tyr Gly
                    565                 570                 575

Ala Ser Ser Ala Gln Ala Thr Ala Ala Lys Ser Phe Asp Ala Val
                    580                 585                 590

Gly Val Asn
        595

<210> SEQ ID NO 3
<211> LENGTH: 304
<212> TYPE: PRT
<213> ORGANISM: Paenibacillus sp.
<220> FEATURE:
<221> NAME/KEY: misc_feature
<222> LOCATION: (1)..(304)
```

<223> OTHER INFORMATION: amino acid sequence of the predicted mature
      form of PspPro3

<400> SEQUENCE: 3

```
Ala Thr Gly Thr Gly Lys Gly Val Leu Gly Asp Thr Lys Thr Phe Asn
1               5                   10                  15

Thr Thr Ala Ser Gly Ser Ser Tyr Gln Leu Arg Asp Thr Thr Arg Gly
            20                  25                  30

Asn Gly Ile Val Thr Tyr Thr Ala Ser Asn Arg Gln Ser Ile Pro Gly
        35                  40                  45

Thr Ile Leu Thr Asp Ala Asp Asn Val Trp Asn Asp Pro Ala Gly Val
    50                  55                  60

Asp Ala His Ala Tyr Ala Ala Lys Thr Tyr Asp Tyr Lys Glu Lys
65                  70                  75                  80

Phe Asn Arg Asn Ser Ile Asp Gly Arg Gly Leu Gln Leu Arg Ser Thr
                85                  90                  95

Val His Tyr Gly Asn Arg Tyr Asn Asn Ala Phe Trp Asn Gly Ser Gln
            100                 105                 110

Met Thr Tyr Gly Asp Gly Asp Gly Thr Thr Phe Ile Ala Phe Ser Gly
            115                 120                 125

Asp Pro Asp Val Val Gly His Glu Leu Thr His Gly Val Thr Glu Tyr
        130                 135                 140

Thr Ser Asn Leu Glu Tyr Tyr Gly Glu Ser Gly Ala Leu Asn Glu Ala
145                 150                 155                 160

Phe Ser Asp Ile Ile Gly Asn Asp Ile Gln Arg Lys Asn Trp Leu Val
                165                 170                 175

Gly Asp Asp Ile Tyr Thr Pro Arg Ile Ala Gly Asp Ala Leu Arg Ser
            180                 185                 190

Met Ser Asn Pro Thr Leu Tyr Asp Gln Pro Asp His Tyr Ser Asn Leu
            195                 200                 205

Tyr Arg Gly Ser Ser Asp Asn Gly Gly Val His Thr Asn Ser Gly Ile
        210                 215                 220

Ile Asn Lys Ala Tyr Tyr Leu Leu Ala Gln Gly Gly Thr Phe His Gly
225                 230                 235                 240

Val Thr Val Asn Gly Ile Gly Arg Asp Ala Ala Val Gln Ile Tyr Tyr
                245                 250                 255

Ser Ala Phe Thr Asn Tyr Leu Thr Ser Ser Asp Phe Ser Asn Ala
            260                 265                 270

Arg Asp Ala Val Val Gln Ala Ala Lys Asp Leu Tyr Gly Ala Ser Ser
        275                 280                 285

Ala Gln Ala Thr Ala Ala Ala Lys Ser Phe Asp Ala Val Gly Val Asn
    290                 295                 300
```

<210> SEQ ID NO 4
<211> LENGTH: 1803
<212> TYPE: DNA
<213> ORGANISM: Artificial Sequence
<220> FEATURE:
<223> OTHER INFORMATION: Synthetic: nucleotide sequence of the
      synthesized PspPro3 gene in plasmid pGX085(AprE- PspPro3)

<400> SEQUENCE: 4

```
gtgagaagca aaaaattgtg gatcagcttg ttgtttgcgt taacgttaat ctttacgatg      60
gcgttcagca acatgagcgc gcaggctgct ggaaaagcag aatcatcagt gtcaggaccg     120
gctcagctta cgccgacgtt tcatgcagag cagtggaaag caccgagcag cgttagcgga     180
```

-continued

```
gatgacatcg tgtggagcta cctgaacaga cagaagaaaa cgcttcttgg cacggacagc      240
acgagcgtca gagaccagtt cagaatcgtg gatagaacaa gcgacaaaag cggcgtcagc      300
cattatagac tgaagcagta tgtgaacgga atcccggttt atggcgcaga acaaacaatc      360
catgtcggaa agagcggcga agttacgagc tatctgggcg cggttattac agaggaccag      420
caagaggagg ctacacaagg cacgacaccg aaaatttcag catcagaggc agttcatacg      480
gcctaccaag aagctgcaac gagagttcaa gccctgccta cgtcagatga tacaatcagc      540
aaagacgctg aggaacctag ctcagttagc aaggacacgt atagcgaagc cgcgaacaat      600
ggcaagacgt caagcgtgga aaaagacaag ctttcactgg agaaggccgc tgatctgaaa      660
gactcaaaga tcgaggctgt ggaagcggaa ccgaatagca ttgcaaagat tgccaacctg      720
caaccggagg tggaccccga aggcggagctg tatttctacg ctaaaggcga tgcactgcaa      780
ctggtttacg tcacggaggt taacatcctg cagccggcac cgcttagaac gagatacatc      840
attgacgcga acgacggcaa gatcgtgagc cagtacgaca ttatcaacga ggccacggga      900
acgggcaagg gagtccttgg cgacacgaag acattcaata caacggcctc aggctcatca      960
taccagctga gagacacgac gagaggcaac ggaatcgtca cgtacacggc tagcaataga     1020
cagagcattc cgggcacaat ccttacggac gcagacaatg tgtggaatga cccggcaggc     1080
gtggacgcac atgcctacgc agcgaagacg tacgactact acaaggagaa gttcaacaga     1140
aacagcatcg acggaagagg actgcaactt agaagcacgg tgcattacgg caacagatac     1200
aacaacgctt tctggaacgg cagccaaatg acgtatggag acggcgatgg aacaacgttt     1260
atcgcattct caggcgaccc tgacgttgtg ggacatgaac tgacgcatgg agtcacagaa     1320
tacacgagca atctggagta ttacggagaa tcaggcgcac ttaatgaggc cttcagcgac     1380
atcatcggaa acgacatcca gagaaagaac tggctggttg gcgatgatat ctacacgccg     1440
agaattgcgg gcgacgcgct gagatcaatg agcaaccta cgctgtacga tcagccggat     1500
cattacagca acctgtatag aggctcaagc gataatggcg gcgtgcatac aaacagcggc     1560
atcatcaaca aagcctatta tctgctggcg caaggcggca cattccatgg cgttacagtt     1620
aatggcattg gcagagacgc agccgtgcag atctactaca gcgcattcac gaattacctg     1680
acatcaagca gcgactttc aaaatgcaaga gatgcagtgg tgcaggcggc taaagacctt     1740
tatggagctt caagcgctca ggccacagct gcggcaaaaa gcttcgacgc ggttggagtg     1800
aat                                                                   1803
```

<210> SEQ ID NO 5
<211> LENGTH: 601
<212> TYPE: PRT
<213> ORGANISM: Artificial Sequence
<220> FEATURE:
<223> OTHER INFORMATION: Synthetic: amino acid sequence of the PspPro3
      precursor protein expressed from plasmid pGX085(AprE- PspPro3)

<400> SEQUENCE: 5

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ala Glu Ser Ser Val Ser Gly Pro Ala Gln Leu Thr Pro Thr Phe His
        35                  40                  45

Ala Glu Gln Trp Lys Ala Pro Ser Ser Val Ser Gly Asp Asp Ile Val
    50                  55                  60
```

```
Trp Ser Tyr Leu Asn Arg Gln Lys Lys Thr Leu Gly Thr Asp Ser
 65                  70                  75                  80

Thr Ser Val Arg Asp Gln Phe Arg Ile Val Asp Arg Thr Ser Asp Lys
                 85                  90                  95

Ser Gly Val Ser His Tyr Arg Leu Lys Gln Tyr Val Asn Gly Ile Pro
            100                 105                 110

Val Tyr Gly Ala Glu Gln Thr Ile His Val Gly Lys Ser Gly Glu Val
        115                 120                 125

Thr Ser Tyr Leu Gly Ala Val Ile Thr Glu Asp Gln Gln Glu Glu Ala
    130                 135                 140

Thr Gln Gly Thr Thr Pro Lys Ile Ser Ala Ser Glu Ala Val His Thr
145                 150                 155                 160

Ala Tyr Gln Glu Ala Ala Thr Arg Val Gln Ala Leu Pro Thr Ser Asp
                165                 170                 175

Asp Thr Ile Ser Lys Asp Ala Glu Glu Pro Ser Ser Val Ser Lys Asp
            180                 185                 190

Thr Tyr Ser Glu Ala Ala Asn Asn Gly Lys Thr Ser Ser Val Glu Lys
        195                 200                 205

Asp Lys Leu Ser Leu Glu Lys Ala Ala Asp Leu Lys Asp Ser Lys Ile
    210                 215                 220

Glu Ala Val Glu Ala Glu Pro Asn Ser Ile Ala Lys Ile Ala Asn Leu
225                 230                 235                 240

Gln Pro Glu Val Asp Pro Lys Ala Glu Leu Tyr Phe Tyr Ala Lys Gly
                245                 250                 255

Asp Ala Leu Gln Leu Val Tyr Val Thr Glu Val Asn Ile Leu Gln Pro
            260                 265                 270

Ala Pro Leu Arg Thr Arg Tyr Ile Ile Asp Ala Asn Asp Gly Lys Ile
        275                 280                 285

Val Ser Gln Tyr Asp Ile Ile Asn Glu Ala Thr Gly Thr Gly Lys Gly
    290                 295                 300

Val Leu Gly Asp Thr Lys Thr Phe Asn Thr Thr Ala Ser Gly Ser Ser
305                 310                 315                 320

Tyr Gln Leu Arg Asp Thr Thr Arg Gly Asn Gly Ile Val Thr Tyr Thr
                325                 330                 335

Ala Ser Asn Arg Gln Ser Ile Pro Gly Thr Ile Leu Thr Asp Ala Asp
            340                 345                 350

Asn Val Trp Asn Asp Pro Ala Gly Val Asp Ala His Ala Tyr Ala Ala
        355                 360                 365

Lys Thr Tyr Asp Tyr Tyr Lys Glu Lys Phe Asn Arg Asn Ser Ile Asp
    370                 375                 380

Gly Arg Gly Leu Gln Leu Arg Ser Thr Val His Tyr Gly Asn Arg Tyr
385                 390                 395                 400

Asn Asn Ala Phe Trp Asn Gly Ser Gln Met Thr Tyr Gly Asp Gly Asp
                405                 410                 415

Gly Thr Thr Phe Ile Ala Phe Ser Gly Asp Pro Asp Val Val Gly His
            420                 425                 430

Glu Leu Thr His Gly Val Thr Glu Tyr Thr Ser Asn Leu Glu Tyr Tyr
        435                 440                 445

Gly Glu Ser Gly Ala Leu Asn Glu Ala Phe Ser Asp Ile Ile Gly Asn
    450                 455                 460

Asp Ile Gln Arg Lys Asn Trp Leu Val Gly Asp Asp Ile Tyr Thr Pro
465                 470                 475                 480

Arg Ile Ala Gly Asp Ala Leu Arg Ser Met Ser Asn Pro Thr Leu Tyr
```

```
                485                 490                 495
Asp Gln Pro Asp His Tyr Ser Asn Leu Tyr Arg Gly Ser Ser Asp Asn
            500                 505                 510

Gly Gly Val His Thr Asn Ser Gly Ile Ile Asn Lys Ala Tyr Tyr Leu
        515                 520                 525

Leu Ala Gln Gly Gly Thr Phe His Gly Val Thr Val Asn Gly Ile Gly
        530                 535                 540

Arg Asp Ala Ala Val Gln Ile Tyr Tyr Ser Ala Phe Thr Asn Tyr Leu
545                 550                 555                 560

Thr Ser Ser Ser Asp Phe Ser Asn Ala Arg Asp Ala Val Val Gln Ala
                565                 570                 575

Ala Lys Asp Leu Tyr Gly Ala Ser Ser Ala Gln Ala Thr Ala Ala Ala
                580                 585                 590

Lys Ser Phe Asp Ala Val Gly Val Asn
                595                 600

<210> SEQ ID NO 6
<211> LENGTH: 1770
<212> TYPE: DNA
<213> ORGANISM: Paenibacillus sp.
<220> FEATURE:
<221> NAME/KEY: misc_feature
<222> LOCATION: (1)..(1770)
<223> OTHER INFORMATION: nucleotide sequence of the PspPro2 gene
      isolated from Paenibacillus sp.

<400> SEQUENCE: 6
atgaaaaaag tatgggtttc acttcttgga ggagcgatgt tattagggc tgtagcacca        60 ggtgcatcag cagcagagca ttctgttcct gatcctactc agctaacacc gaccttcac       120 gccgagcaat ggaaggctcc ttccacggta accggcgaca atattgtatg gagctatttg      180
aatcgacaaa agaaaacctt attgaataca gacagcacca gtgtgcgtga tcagttccgc      240
atcattgatc gtacaagcga caaatccggt gcaagccatt atcggctcaa gcaatatgta      300
aacgggatcc ccgtatatgg ggctgaacag accattcatg tgaacaacgc cggtaaagta      360
acctcttatt tgggtgctgt catttcagag gatcagcagc aagacgcgac cgaagatacc      420
actccaaaaa tcagcgcgac tgaagccgtt tataccgcat atgcagaagc cgctgcccgg      480
attcaatcct tcccttccat caatgatagt ctttctgagg ctagtgagga acaagggagt      540
gagaatcaag gcaatgagat tcaaaacatt gggattaaaa gcagtgtaag taatgacact      600
tacgcagagg cgcataacaa cgtacttta acccccgttg accaagcaga gcaaagttac      660
attgccaaaa ttgctaatct ggagccaagt gtagagccca agcagaatt atacatctat       720 ccagatggtg agactacacg actggtttat gtaacagagg ttaatattct tgaacctgcg      780
cctctgcgca cacgctactt cattgatgcg aaaaccggca aaatcgtatt ccagtatgac      840
atcctcaacc acgcaacagg caccggccgc ggcgtggatg gcaaaacaaa atcatttacg      900
actacagctt caggcaaccg gtatcagttg aaagacacga ctcgcagcaa tggaatcgtg      960
acttacaccg ctggcaatcg ccagacgacg ccaggtacga ttttgaccga tacagataat     1020
gtatgggagg accctgcggc tgttgatgcc catgcctacg ccattaaaac ctatgactat     1080
tataagaata aattcggtcg cgacagtatt gatggacgtg gcatgcaaat tcgttcgaca     1140
gtccattacg gcaaaaaata taacaatgcc ttctggaacg gctcgcaaat gacctacgga     1200
gacggagacg ggtccacatt taccttcttc agcggcgatc ccgatgtcgt ggggcatgag     1260
ctcacccacg gcgtcaccga gttcacctcc aatttggagt attatggtga gtccggtgca     1320
```

```
ttgaacgaag ccttctcgga tattatcggt aatgatatag atggcaccag ttggcttctt    1380
ggcgacggca tttatacgcc taatattcca ggcgacgctc tgcgttccct gtccgatcct    1440
acacgattcg gccagccgga tcactactcc aatttctatc cggaccccaa caatgatgat    1500
gaaggcggag tccatacgaa cagcggtatt atcaacaaag cctattattt gctggcacaa    1560
ggcggtacgt cccatggtgt aacggtaact ggtatcggac gcgaagcggc tgtattcatt    1620
tactacaatg cctttaccaa ctatttgacc tctacctcca acttctctaa cgcacgcgct    1680
gctgttatac aggcagccaa ggatttttat ggtgctgatt cgctggcagt aaccagtgct    1740
attcaatcct ttgatgcggt aggaatcaaa                                     1770
```

<210> SEQ ID NO 7
<211> LENGTH: 590
<212> TYPE: PRT
<213> ORGANISM: Paenibacillus sp.
<220> FEATURE:
<221> NAME/KEY: misc_feature
<222> LOCATION: (1)..(590)
<223> OTHER INFORMATION: amino acid sequence of the PspPro2 precursor
      protein

<400> SEQUENCE: 7

```
Met Lys Lys Val Trp Val Ser Leu Leu Gly Gly Ala Met Leu Leu Gly
1               5                   10                  15

Ala Val Ala Pro Gly Ala Ser Ala Ala Glu His Ser Val Pro Asp Pro
                20                  25                  30

Thr Gln Leu Thr Pro Thr Phe His Ala Glu Gln Trp Lys Ala Pro Ser
            35                  40                  45

Thr Val Thr Gly Asp Asn Ile Val Trp Ser Tyr Leu Asn Arg Gln Lys
        50                  55                  60

Lys Thr Leu Leu Asn Thr Asp Ser Thr Ser Val Arg Asp Gln Phe Arg
65                  70                  75                  80

Ile Ile Asp Arg Thr Ser Asp Lys Ser Gly Ala Ser His Tyr Arg Leu
                85                  90                  95

Lys Gln Tyr Val Asn Gly Ile Pro Val Tyr Gly Ala Glu Gln Thr Ile
            100                 105                 110

His Val Asn Asn Ala Gly Lys Val Thr Ser Tyr Leu Gly Ala Val Ile
        115                 120                 125

Ser Glu Asp Gln Gln Gln Asp Ala Thr Glu Asp Thr Thr Pro Lys Ile
130                 135                 140

Ser Ala Thr Glu Ala Val Tyr Thr Ala Tyr Ala Glu Ala Ala Arg
145                 150                 155                 160

Ile Gln Ser Phe Pro Ser Ile Asn Asp Ser Leu Ser Glu Ala Ser Glu
                165                 170                 175

Glu Gln Gly Ser Glu Asn Gln Gly Asn Glu Ile Gln Asn Ile Gly Ile
            180                 185                 190

Lys Ser Ser Val Ser Asn Asp Thr Tyr Ala Glu Ala His Asn Asn Val
        195                 200                 205

Leu Leu Thr Pro Val Asp Gln Ala Glu Gln Ser Tyr Ile Ala Lys Ile
210                 215                 220

Ala Asn Leu Glu Pro Ser Val Glu Pro Lys Ala Glu Leu Tyr Ile Tyr
225                 230                 235                 240

Pro Asp Gly Glu Thr Thr Arg Leu Val Tyr Val Thr Glu Val Asn Ile
                245                 250                 255

Leu Glu Pro Ala Pro Leu Arg Thr Arg Tyr Phe Ile Asp Ala Lys Thr
```

```
                260                 265                 270
Gly Lys Ile Val Phe Gln Tyr Asp Ile Leu Asn His Ala Thr Gly Thr
            275                 280                 285

Gly Arg Gly Val Asp Gly Lys Thr Lys Ser Phe Thr Thr Ala Ser
        290                 295                 300

Gly Asn Arg Tyr Gln Leu Lys Asp Thr Thr Arg Ser Asn Gly Ile Val
305                 310                 315                 320

Thr Tyr Thr Ala Gly Asn Arg Gln Thr Thr Pro Gly Thr Ile Leu Thr
                325                 330                 335

Asp Thr Asp Asn Val Trp Glu Asp Pro Ala Ala Val Asp Ala His Ala
            340                 345                 350

Tyr Ala Ile Lys Thr Tyr Asp Tyr Lys Asn Lys Phe Gly Arg Asp
        355                 360                 365

Ser Ile Asp Gly Arg Gly Met Gln Ile Arg Ser Thr Val His Tyr Gly
370                 375                 380

Lys Lys Tyr Asn Asn Ala Phe Trp Asn Gly Ser Gln Met Thr Tyr Gly
385                 390                 395                 400

Asp Gly Asp Gly Ser Thr Phe Thr Phe Phe Ser Gly Asp Pro Asp Val
                405                 410                 415

Val Gly His Glu Leu Thr His Gly Val Thr Glu Phe Thr Ser Asn Leu
            420                 425                 430

Glu Tyr Tyr Gly Glu Ser Gly Ala Leu Asn Glu Ala Phe Ser Asp Ile
        435                 440                 445

Ile Gly Asn Asp Ile Asp Gly Thr Ser Trp Leu Leu Gly Asp Gly Ile
450                 455                 460

Tyr Thr Pro Asn Ile Pro Gly Asp Ala Leu Arg Ser Leu Ser Asp Pro
465                 470                 475                 480

Thr Arg Phe Gly Gln Pro Asp His Tyr Ser Asn Phe Tyr Pro Asp Pro
                485                 490                 495

Asn Asn Asp Asp Glu Gly Gly Val His Thr Asn Ser Gly Ile Ile Asn
            500                 505                 510

Lys Ala Tyr Tyr Leu Leu Ala Gln Gly Gly Thr Ser His Gly Val Thr
        515                 520                 525

Val Thr Gly Ile Gly Arg Glu Ala Ala Val Phe Ile Tyr Tyr Asn Ala
        530                 535                 540

Phe Thr Asn Tyr Leu Thr Ser Thr Ser Asn Phe Ser Asn Ala Arg Ala
545                 550                 555                 560

Ala Val Ile Gln Ala Ala Lys Asp Phe Tyr Gly Ala Asp Ser Leu Ala
                565                 570                 575

Val Thr Ser Ala Ile Gln Ser Phe Asp Ala Val Gly Ile Lys
            580                 585                 590

<210> SEQ ID NO 8
<211> LENGTH: 306
<212> TYPE: PRT
<213> ORGANISM: Paenibacillus sp.
<220> FEATURE:
<221> NAME/KEY: misc_feature
<222> LOCATION: (1)..(306)
<223> OTHER INFORMATION: amino acid sequence of the predicted mature
      form of PspPro2

<400> SEQUENCE: 8

Ala Thr Gly Thr Gly Arg Gly Val Asp Gly Lys Thr Lys Ser Phe Thr
1               5                   10                  15

Thr Thr Ala Ser Gly Asn Arg Tyr Gln Leu Lys Asp Thr Thr Arg Ser
```

```
                    20                  25                  30
Asn Gly Ile Val Thr Tyr Thr Ala Gly Asn Arg Gln Thr Thr Pro Gly
            35                  40                  45

Thr Ile Leu Thr Asp Thr Asp Asn Val Trp Glu Asp Pro Ala Ala Val
        50                  55                  60

Asp Ala His Ala Tyr Ala Ile Lys Thr Tyr Asp Tyr Lys Asn Lys
65                  70                  75                  80

Phe Gly Arg Asp Ser Ile Asp Gly Arg Gly Met Gln Ile Arg Ser Thr
                85                  90                  95

Val His Tyr Gly Lys Lys Tyr Asn Asn Ala Phe Trp Asn Gly Ser Gln
            100                 105                 110

Met Thr Tyr Gly Asp Gly Asp Gly Ser Thr Phe Thr Phe Phe Ser Gly
        115                 120                 125

Asp Pro Asp Val Val Gly His Glu Leu Thr His Gly Val Thr Glu Phe
    130                 135                 140

Thr Ser Asn Leu Glu Tyr Tyr Gly Glu Ser Gly Ala Leu Asn Glu Ala
145                 150                 155                 160

Phe Ser Asp Ile Ile Gly Asn Asp Ile Asp Gly Thr Ser Trp Leu Leu
                165                 170                 175

Gly Asp Gly Ile Tyr Thr Pro Asn Ile Pro Gly Asp Ala Leu Arg Ser
            180                 185                 190

Leu Ser Asp Pro Thr Arg Phe Gly Gln Pro Asp His Tyr Ser Asn Phe
        195                 200                 205

Tyr Pro Asp Pro Asn Asn Asp Asp Glu Gly Gly Val His Thr Asn Ser
    210                 215                 220

Gly Ile Ile Asn Lys Ala Tyr Tyr Leu Leu Ala Gln Gly Gly Thr Ser
225                 230                 235                 240

His Gly Val Thr Val Thr Gly Ile Gly Arg Glu Ala Ala Val Phe Ile
                245                 250                 255

Tyr Tyr Asn Ala Phe Thr Asn Tyr Leu Thr Ser Thr Ser Asn Phe Ser
            260                 265                 270

Asn Ala Arg Ala Ala Val Ile Gln Ala Ala Lys Asp Phe Tyr Gly Ala
        275                 280                 285

Asp Ser Leu Ala Val Thr Ser Ala Ile Gln Ser Phe Asp Ala Val Gly
    290                 295                 300

Ile Lys
305

<210> SEQ ID NO 9
<211> LENGTH: 1794
<212> TYPE: DNA
<213> ORGANISM: Artificial Sequence
<220> FEATURE:
<223> OTHER INFORMATION: Synthetic: nucleotide sequence of the
      synthesized PspPro2 gene in plasmid pGX084 (AprE-PspPro2)

<400> SEQUENCE: 9
gtgagaagca aaaaattgtg gatcagcttg ttgtttgcgt taacgttaat ctttacgatg     60
gcgttcagca acatgagcgc gcaggctgct ggaaaagcag agcattcagt tcctgacccg    120
acgcaactta caccgacatt tcatgctgag cagtggaagg caccgagcac ggtcacgggc    180
gacaacatcg tgtggagcta cctgaacaga cagaaaaaga cgctgctgaa cacggactca    240
acgagcgtga gagaccagtt cagaatcatc gacagaacga gcgacaagtc aggcgcgtca    300
cattatagac tgaagcagta cgtgaacggc atcccggtct acggagccga gcaaacgatc    360
```

```
catgtgaata atgcgggcaa agttacatca tacctgggcg ccgtcatctc agaagaccag    420
cagcaagatg caacggagga tacaacaccg aagatcagcg ccacagaagc ggtctatacg    480
gcttacgccg aagcggctgc aagaatccag agcttcccgt caattaatga cagcctgagc    540
gaagcatcag aggaacaagg cagcgagaac cagggcaatg aaatccaaaa catcggcatc    600
aagagcagcg tgtcaaacga cacgtatgcg gaggctcata caacgttct gctgacaccg    660 gtcgatcagg ccgaacagag ctatattgca aagatcgcga atctggagcc gtcagtcgag    720
ccgaaggccg agctgtatat ctatccggac ggcgagacga cgagactggt gtacgttacg    780
gaggtcaaca tccttgagcc tgcgccgctg agaacaagat actttatcga cgccaagacg    840
ggcaagatcg tgtttcagta cgatatcctg aaccatgcga cgggaacagg cagaggcgtg    900
gacggcaaaa caaatcatt cacgacaacg gcaagcggca acagatacca gctgaaggac    960
acaacaagat caaatggcat cgtcacatac acggccggaa atagacagac gacgccggga    1020
acgattctga cggatacaga taacgtgtgg gaagatccgg cagcagttga tgcacatgca    1080
tacgcgatca agacgtacga ctactacaag aacaaattcg gaagagattc aatcgatgga    1140
agaggcatgc aaatcagatc aacggttcat tatggcaaaa agtacaacaa tgccttctgg    1200
aacggcagcc aaatgacata cggcgatgga gacggctcaa cgtttacatt cttttcaggc    1260
gacccggacg tcgtcggcca tgaactgacg catggcgtta cagagttcac gagcaacctg    1320
gagtattacg gcgaatcagg cgcactgaat gaggcttttca gcgacatcat tggcaacgac    1380
attgatggca tcatggct gcttggcgac ggcattttaca cacctaacat tccgggcgat    1440
gcactgagaa gcctgtcaga ccctacgaga ttcggccaac ctgaccatta cagcaacttc    1500
tacccggatc ctaataacga tgatgagggc ggagtgcata cgaacagcgg cattatcaac    1560
aaagcgtact atctgctggc acaaggcgga acgtcacatg gagtgacggt gacaggaatc    1620
ggcagagagg cggcagtgtt tatctactac aacgccttca caaactacct gacgagcacg    1680
tcaaatttca gcaacgctag agcggcggtc atccaggcag caaaggactt ttatggagca    1740
gactcactgg cagttacgtc agcaattcag tcattcgacg cagttggaat taag         1794
```

<210> SEQ ID NO 10
<211> LENGTH: 598
<212> TYPE: PRT
<213> ORGANISM: Artificial Sequence
<220> FEATURE:
<223> OTHER INFORMATION: Synthetic: amino acid sequence of the PspPro2
      precursor protein expressed from plasmid pGX084(AprE-PspPro2)

<400> SEQUENCE: 10

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Gly Lys
            20                  25                  30

Ala Glu His Ser Val Pro Asp Pro Thr Gln Leu Thr Pro Thr Phe His
        35                  40                  45

Ala Glu Gln Trp Lys Ala Pro Ser Thr Val Thr Gly Asp Asn Ile Val
    50                  55                  60

Trp Ser Tyr Leu Asn Arg Gln Lys Lys Thr Leu Leu Asn Thr Asp Ser
65                  70                  75                  80

Thr Ser Val Arg Asp Gln Phe Arg Ile Ile Asp Arg Thr Ser Asp Lys
                85                  90                  95

Ser Gly Ala Ser His Tyr Arg Leu Lys Gln Tyr Val Asn Gly Ile Pro
            100                 105                 110
```

-continued

Val Tyr Gly Ala Glu Gln Thr Ile His Val Asn Asn Ala Gly Lys Val
    115                 120                 125

Thr Ser Tyr Leu Gly Ala Val Ile Ser Glu Asp Gln Gln Asp Ala
130                 135                 140

Thr Glu Asp Thr Thr Pro Lys Ile Ser Ala Thr Glu Ala Val Tyr Thr
145                 150                 155                 160

Ala Tyr Ala Glu Ala Ala Arg Ile Gln Ser Phe Pro Ser Ile Asn
        165                 170                 175

Asp Ser Leu Ser Glu Ala Ser Glu Glu Gln Gly Ser Glu Asn Gln Gly
            180                 185                 190

Asn Glu Ile Gln Asn Ile Gly Ile Lys Ser Ser Val Ser Asn Asp Thr
        195                 200                 205

Tyr Ala Glu Ala His Asn Asn Val Leu Leu Thr Pro Val Asp Gln Ala
    210                 215                 220

Glu Gln Ser Tyr Ile Ala Lys Ile Ala Asn Leu Glu Pro Ser Val Glu
225                 230                 235                 240

Pro Lys Ala Glu Leu Tyr Ile Tyr Pro Asp Gly Glu Thr Thr Arg Leu
                245                 250                 255

Val Tyr Val Thr Glu Val Asn Ile Leu Glu Pro Ala Pro Leu Arg Thr
            260                 265                 270

Arg Tyr Phe Ile Asp Ala Lys Thr Gly Lys Ile Val Phe Gln Tyr Asp
        275                 280                 285

Ile Leu Asn His Ala Thr Gly Thr Arg Gly Val Asp Gly Lys Thr
    290                 295                 300

Lys Ser Phe Thr Thr Thr Ala Ser Gly Asn Arg Tyr Gln Leu Lys Asp
305                 310                 315                 320

Thr Thr Arg Ser Asn Gly Ile Val Thr Tyr Thr Ala Gly Asn Arg Gln
                325                 330                 335

Thr Thr Pro Gly Thr Ile Leu Thr Asp Thr Asp Asn Val Trp Glu Asp
            340                 345                 350

Pro Ala Ala Val Asp Ala His Ala Tyr Ala Ile Lys Thr Tyr Asp Tyr
        355                 360                 365

Tyr Lys Asn Lys Phe Gly Arg Asp Ser Ile Asp Gly Arg Gly Met Gln
    370                 375                 380

Ile Arg Ser Thr Val His Tyr Gly Lys Lys Tyr Asn Asn Ala Phe Trp
385                 390                 395                 400

Asn Gly Ser Gln Met Thr Tyr Gly Asp Gly Asp Gly Ser Thr Phe Thr
                405                 410                 415

Phe Phe Ser Gly Asp Pro Asp Val Val Gly His Glu Leu Thr His Gly
            420                 425                 430

Val Thr Glu Phe Thr Ser Asn Leu Glu Tyr Tyr Gly Glu Ser Gly Ala
        435                 440                 445

Leu Asn Glu Ala Phe Ser Asp Ile Ile Gly Asn Asp Ile Asp Gly Thr
    450                 455                 460

Ser Trp Leu Leu Gly Asp Gly Ile Tyr Thr Pro Asn Ile Pro Gly Asp
465                 470                 475                 480

Ala Leu Arg Ser Leu Ser Asp Pro Thr Arg Phe Gly Gln Pro Asp His
                485                 490                 495

Tyr Ser Asn Phe Tyr Pro Asp Pro Asn Asn Asp Glu Gly Gly Val
            500                 505                 510

His Thr Asn Ser Gly Ile Ile Asn Lys Ala Tyr Tyr Leu Leu Ala Gln
        515                 520                 525

```
Gly Gly Thr Ser His Gly Val Thr Val Thr Gly Ile Gly Arg Glu Ala
    530                 535                 540

Ala Val Phe Ile Tyr Tyr Asn Ala Phe Thr Asn Tyr Leu Thr Ser Thr
545                 550                 555                 560

Ser Asn Phe Ser Asn Ala Arg Ala Ala Val Ile Gln Ala Ala Lys Asp
                565                 570                 575

Phe Tyr Gly Ala Asp Ser Leu Ala Val Thr Ser Ala Ile Gln Ser Phe
            580                 585                 590

Asp Ala Val Gly Ile Lys
            595

<210> SEQ ID NO 11
<211> LENGTH: 1599
<212> TYPE: DNA
<213> ORGANISM: Paenibacillus humicus
<220> FEATURE:
<221> NAME/KEY: misc_feature
<222> LOCATION: (1)..(1599)
<223> OTHER INFORMATION: nucleotide sequence of the PhuPro2 gene
      isolated from Paenibacillus humicus

<400> SEQUENCE: 11
atgaaaaaaa tgattcctac tctgctcggt accgtattgc tgctttcttc cgcttccgct      60
gtcgctgctg aatcgccaag cctcggagcg gccggaactc ccggggtcag cgtcgtgaac     120
aatcagctcg tgactcaatt catcgaggct tccaaggatg ccaagattgt cccgggctct     180
tccgaggata aaatctgggc tttccttgaa ggccagcaag caaagctggg tgtatccgca     240
gcggatgtaa aacctcgtt cctgatccag aagaaggaag tcgatccgac ttcgggcgtc      300
gagcatttcc gcctgcagca atatgtgaat ggcatcccgg tatatggcgg tgaccaaacc     360
attcacatcg acaaggccgg ccaggttacg tcgttcgtag agctgttcct gccggctcaa     420
aatcaaatca cggcaaaatc cagcgtacca gccataagcg catccgacgc tctggctatc     480
gcggcgaagg aagccagttc ccgcatcggc gagctgggag cacaggagaa gactccgtcg     540
gctcagctgt acgtatatcc ggaaggcaac gggtcgcgtc tcgtctacca gacggaagtg     600
aatgtgcttg agccgcagcc tctgcgcacc cgctatctta tcgatgcggc cgacggccat     660
atcgtgcagc agtacgatct gatcgagacg gcgaccggtt cgggcacggg cgtgctgggc     720
gacaataaga cgttccagac gactctttcc ggcagcacgt accagctgaa agacaccact     780
cgcggcaacg gcatctacac ctacacagcc agcaatcgga ccacgattcc gggcacgctg     840
ctgacggacg ccgacaacgt atggacggat ggagccgccg tcgatgccca tacttatgcc     900
ggaaaagtat atgatttcta caaaacgaag ttcggacgca acagcctcga cggcaacggc     960
ctgctgatcc gttcctcggt ccactacagc agcaggtaca caatgccttc tggaacggc     1020 acccagattg tattcggcga cggcgacggc tcgacgttca ttccgctgtc gggcgatctc     1080
gacgtggtcg ccatgagct gtcccacgga gtcatcgagt cacgtccaa ccttcaatac     1140 ctcaatgaat ccggcgcgct gaacgagtcc tatgccgacg tcctcggcaa ctcgatccag     1200
gcgaaaaact ggcttatcgg cgacgatgtc tatacgcctg gcatctccgg agatgctctc     1260
cgttccatgt ccaacccgac gctttacggg cagccggaca actatgccaa ccgctatacg     1320
ggatcttccg acaacggcgg cgttcatacg aacagcggca tcacgaacaa agcgttctac     1380
ctgctcgccc aaggcggcac ccagaacggc gttaccgtcg ccggcatcgg cgcgacgca      1440 gccgtgaaca ttttctacaa cacagtggcc tattaccta cttccacttc caacttcgcc      1500
gcggcgaaga acgcctcgat ccaggcagcc aaagacctgt acggaacggg ctcctcttat     1560
```
gtcacctcgg tgaccaatgc attcagagcc gtaggcctg                                            1599

<210> SEQ ID NO 12
<211> LENGTH: 533
<212> TYPE: PRT
<213> ORGANISM: Paenibacillus humicus
<220> FEATURE:
<221> NAME/KEY: misc_feature
<222> LOCATION: (1)..(533)
<223> OTHER INFORMATION: amino acid sequence of the PhuPro2 precursor
      protein

<400> SEQUENCE: 12

Met Lys Lys Met Ile Pro Thr Leu Leu Gly Thr Val Leu Leu Leu Ser
1               5                   10                  15

Ser Ala Ser Ala Val Ala Ala Glu Ser Pro Ser Leu Gly Ala Ala Gly
            20                  25                  30

Thr Pro Gly Val Ser Val Val Asn Asn Gln Leu Val Thr Gln Phe Ile
        35                  40                  45

Glu Ala Ser Lys Asp Ala Lys Ile Val Pro Gly Ser Ser Glu Asp Lys
    50                  55                  60

Ile Trp Ala Phe Leu Glu Gly Gln Gln Ala Lys Leu Gly Val Ser Ala
65                  70                  75                  80

Ala Asp Val Lys Thr Ser Phe Leu Ile Gln Lys Lys Glu Val Asp Pro
                85                  90                  95

Thr Ser Gly Val Glu His Phe Arg Leu Gln Gln Tyr Val Asn Gly Ile
            100                 105                 110

Pro Val Tyr Gly Gly Asp Gln Thr Ile His Ile Asp Lys Ala Gly Gln
        115                 120                 125

Val Thr Ser Phe Val Gly Ala Val Leu Pro Ala Gln Asn Gln Ile Thr
130                 135                 140

Ala Lys Ser Ser Val Pro Ala Ile Ser Ala Ser Asp Ala Leu Ala Ile
145                 150                 155                 160

Ala Ala Lys Glu Ala Ser Ser Arg Ile Gly Glu Leu Gly Ala Gln Glu
                165                 170                 175

Lys Thr Pro Ser Ala Gln Leu Tyr Val Tyr Pro Glu Gly Asn Gly Ser
            180                 185                 190

Arg Leu Val Tyr Gln Thr Glu Val Asn Val Leu Glu Pro Gln Pro Leu
        195                 200                 205

Arg Thr Arg Tyr Leu Ile Asp Ala Ala Asp Gly His Ile Val Gln Gln
210                 215                 220

Tyr Asp Leu Ile Glu Thr Ala Thr Gly Ser Gly Thr Gly Val Leu Gly
225                 230                 235                 240

Asp Asn Lys Thr Phe Gln Thr Thr Leu Ser Gly Ser Thr Tyr Gln Leu
                245                 250                 255

Lys Asp Thr Thr Arg Gly Asn Gly Ile Tyr Thr Tyr Thr Ala Ser Asn
            260                 265                 270

Arg Thr Thr Ile Pro Gly Thr Leu Leu Thr Asp Ala Asp Asn Val Trp
        275                 280                 285

Thr Asp Gly Ala Ala Val Asp Ala His Thr Tyr Ala Gly Lys Val Tyr
290                 295                 300

Asp Phe Tyr Lys Thr Lys Phe Gly Arg Asn Ser Leu Asp Gly Asn Gly
305                 310                 315                 320

Leu Leu Ile Arg Ser Ser Val His Tyr Ser Ser Arg Tyr Asn Asn Ala
                325                 330                 335

-continued

```
Phe Trp Asn Gly Thr Gln Ile Val Phe Gly Asp Gly Ser Thr
            340                 345                 350

Phe Ile Pro Leu Ser Gly Asp Leu Asp Val Val Gly His Glu Leu Ser
        355                 360                 365

His Gly Val Ile Glu Tyr Thr Ser Asn Leu Gln Tyr Leu Asn Glu Ser
    370                 375                 380

Gly Ala Leu Asn Glu Ser Tyr Ala Asp Val Leu Gly Asn Ser Ile Gln
385                 390                 395                 400

Ala Lys Asn Trp Leu Ile Gly Asp Asp Val Tyr Thr Pro Gly Ile Ser
                405                 410                 415

Gly Asp Ala Leu Arg Ser Met Ser Asn Pro Thr Leu Tyr Gly Gln Pro
            420                 425                 430

Asp Asn Tyr Ala Asn Arg Tyr Thr Gly Ser Ser Asp Asn Gly Gly Val
        435                 440                 445

His Thr Asn Ser Gly Ile Thr Asn Lys Ala Phe Tyr Leu Leu Ala Gln
    450                 455                 460

Gly Gly Thr Gln Asn Gly Val Thr Val Ala Gly Ile Gly Arg Asp Ala
465                 470                 475                 480

Ala Val Asn Ile Phe Tyr Asn Thr Val Ala Tyr Tyr Leu Thr Ser Thr
                485                 490                 495

Ser Asn Phe Ala Ala Ala Lys Asn Ala Ser Ile Gln Ala Ala Lys Asp
            500                 505                 510

Leu Tyr Gly Thr Gly Ser Ser Tyr Val Thr Ser Val Thr Asn Ala Phe
        515                 520                 525

Arg Ala Val Gly Leu
    530

<210> SEQ ID NO 13
<211> LENGTH: 303
<212> TYPE: PRT
<213> ORGANISM: Paenibacillus humicus
<220> FEATURE:
<221> NAME/KEY: misc_feature
<222> LOCATION: (1)..(303)
<223> OTHER INFORMATION: amino acid sequence of the predicted mature
      form of PhuPro2

<400> SEQUENCE: 13

Ala Thr Gly Ser Gly Thr Gly Val Leu Gly Asp Asn Lys Thr Phe Gln
1               5                   10                  15

Thr Thr Leu Ser Gly Ser Thr Tyr Gln Leu Lys Asp Thr Thr Arg Gly
            20                  25                  30

Asn Gly Ile Tyr Thr Tyr Thr Ala Ser Asn Arg Thr Thr Ile Pro Gly
        35                  40                  45

Thr Leu Leu Thr Asp Ala Asp Asn Val Trp Thr Asp Gly Ala Ala Val
    50                  55                  60

Asp Ala His Thr Tyr Ala Gly Lys Val Tyr Asp Phe Tyr Lys Thr Lys
65                  70                  75                  80

Phe Gly Arg Asn Ser Leu Asp Gly Asn Gly Leu Leu Ile Arg Ser Ser
                85                  90                  95

Val His Tyr Ser Ser Arg Tyr Asn Asn Ala Phe Trp Asn Gly Thr Gln
            100                 105                 110

Ile Val Phe Gly Asp Gly Asp Gly Ser Thr Phe Ile Pro Leu Ser Gly
        115                 120                 125

Asp Leu Asp Val Val Gly His Glu Leu Ser His Gly Val Ile Glu Tyr
    130                 135                 140
```

```
Thr Ser Asn Leu Gln Tyr Leu Asn Glu Ser Gly Ala Leu Asn Glu Ser
145                 150                 155                 160

Tyr Ala Asp Val Leu Gly Asn Ser Ile Gln Ala Lys Asn Trp Leu Ile
                165                 170                 175

Gly Asp Asp Val Tyr Thr Pro Gly Ile Ser Gly Asp Ala Leu Arg Ser
            180                 185                 190

Met Ser Asn Pro Thr Leu Tyr Gly Gln Pro Asp Asn Tyr Ala Asn Arg
        195                 200                 205

Tyr Thr Gly Ser Ser Asp Asn Gly Gly Val His Thr Asn Ser Gly Ile
    210                 215                 220

Thr Asn Lys Ala Phe Tyr Leu Leu Ala Gln Gly Gly Thr Gln Asn Gly
225                 230                 235                 240

Val Thr Val Ala Gly Ile Gly Arg Asp Ala Ala Val Asn Ile Phe Tyr
                245                 250                 255

Asn Thr Val Ala Tyr Tyr Leu Thr Ser Thr Asn Phe Ala Ala Ala
            260                 265                 270

Lys Asn Ala Ser Ile Gln Ala Ala Lys Asp Leu Tyr Gly Thr Gly Ser
        275                 280                 285

Ser Tyr Val Thr Ser Val Thr Asn Ala Phe Arg Ala Val Gly Leu
    290                 295                 300

<210> SEQ ID NO 14
<211> LENGTH: 1629
<212> TYPE: DNA
<213> ORGANISM: Artificial Sequence
<220> FEATURE:
<223> OTHER INFORMATION: Synthetic: nucleotide sequence of the
      synthesized PhuPro2 gene in plasmid pGX150(AprE- PhuPro2)

<400> SEQUENCE: 14
gtgagaagca aaaaattgtg atcagcttg ttgtttgcgt taacgttaat ctttacgatg      60
gcgttcagca acatgagcgc gcaggctgct ggaaaagaat caccgagcct tggcgctgca    120
ggaacaccgg gcgttagcgt tgtgaataac caactggtca cgcagttcat cgaagcatca    180
aaagacgcga aaattgtccc tgatcaagc gaagataaga tttgggcatt tctggaaggc    240
cagcaagcaa agcttggcgt ctcagctgcc gacgtgaaga cgagcttcct gatccagaag    300
aaggaggttg acccgacatc aggcgttgag cactttagac tgcaacagta cgtcaacggc    360
atcccggttt atggaggcga tcaaacaatc catattgata aggcaggcca ggtcacatca    420
ttcgtcggag ctgtcctgcc ggctcagaac caaattacag caaaatcatc agttccggca    480
atttcagcct cagacgctct ggcaatcgct gccaaggagg caagctcaag aattggcgaa    540
ctgggcgcac aagaaaagac accgagcgcc caactttatg tctatccgga gggcaacgga    600
agcagactgg tgtaccagac agaggtcaat gttctggagc cgcaaccgct gagaacgaga    660
taccttatcg atgctgcgga tggccacatt gttcagcaat cgacctgat tgagacagca    720 acaggaagcg gaacgggcgt gctgggcgac aacaagacgt tcagacaac acttagcggc    780 agcacgtacc aacttaagga cacgacgaga ggcaatggca tttacacgta cacggcctca    840
aacagaacga caatcccagg cacactgctg acggatgcag acaatgtttg gacggacggc    900
gcagcagttg acgcacacac gtacgccggc aaggtgtacg acttttacaa gacgaagttc    960
ggcagaaaca gccttgatgg aaatggactg ctgatcagaa gcagcgtcca ctacagcagc   1020
agatacaata acgccttctg gaacggcaca caaatcgtct ttggcgatgg agacggatca   1080
acattcatcc cgctgtcagg cgacctggac gttgtgggcc acgagctgag ccacggcgtc   1140
```

```
atcgagtaca cgagcaacct gcagtacctg aatgaaagcg gcgcactgaa cgagtcatat    1200
gctgatgtgc ttggcaatag catccaggcc aagaactggc ttatcggaga cgacgtctac    1260
acacctggca tcagcggcga tgctctgaga agcatgagca atcctacact ttacggccaa    1320
ccggacaact acgcgaatag atatacgggc agcagcgaca atggcggcgt tcatacaaac    1380
tcaggcatca cgaacaaggc gttctacctg ctggcacagg gaggcacgca aaacggcgtt    1440
acagttgcgg gcattggcag agatgcggcc gtcaacatct tctacaacac agtcgcctac    1500
tacctgacga gcacgtcaaa cttcgcagcg gcaaagaacg catcaattca agcagcaaag    1560
gatctgtacg gaacaggcag ctcatatgtc acgtcagtta cgaatgcgtt tagagccgtc    1620
ggcctttaa                                                            1629
```

<210> SEQ ID NO 15
<211> LENGTH: 542
<212> TYPE: PRT
<213> ORGANISM: Artificial Sequence
<220> FEATURE:
<223> OTHER INFORMATION: Synthetic: amino acid sequence of the PhuPro2
      precursor protein expressed from plasmid pGX150(AprE- PhuPro2)

<400> SEQUENCE: 15

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Glu Ser Pro Ser Leu Gly Ala Ala Gly Thr Pro Gly Val Ser Val Val
        35                  40                  45

Asn Asn Gln Leu Val Thr Gln Phe Ile Glu Ala Ser Lys Asp Ala Lys
    50                  55                  60

Ile Val Pro Gly Ser Ser Glu Asp Lys Ile Trp Ala Phe Leu Glu Gly
65                  70                  75                  80

Gln Gln Ala Lys Leu Gly Val Ser Ala Ala Asp Val Lys Thr Ser Phe
                85                  90                  95

Leu Ile Gln Lys Lys Glu Val Asp Pro Thr Ser Gly Val Glu His Phe
            100                 105                 110

Arg Leu Gln Gln Tyr Val Asn Gly Ile Pro Val Tyr Gly Gly Asp Gln
        115                 120                 125

Thr Ile His Ile Asp Lys Ala Gly Gln Val Thr Ser Phe Val Gly Ala
    130                 135                 140

Val Leu Pro Ala Gln Asn Gln Ile Thr Ala Lys Ser Ser Val Pro Ala
145                 150                 155                 160

Ile Ser Ala Ser Asp Ala Leu Ala Ile Ala Ala Lys Glu Ala Ser Ser
                165                 170                 175

Arg Ile Gly Glu Leu Gly Ala Gln Glu Lys Thr Pro Ser Ala Gln Leu
            180                 185                 190

Tyr Val Tyr Pro Glu Gly Asn Gly Ser Arg Leu Val Tyr Gln Thr Glu
        195                 200                 205

Val Asn Val Leu Glu Pro Gln Pro Leu Arg Thr Arg Tyr Leu Ile Asp
    210                 215                 220

Ala Ala Asp Gly His Ile Val Gln Gln Tyr Asp Leu Ile Glu Thr Ala
225                 230                 235                 240

Thr Gly Ser Gly Thr Gly Val Leu Gly Asp Asn Lys Thr Phe Gln Thr
                245                 250                 255

Thr Leu Ser Gly Ser Thr Tyr Gln Leu Lys Asp Thr Thr Arg Gly Asn
            260                 265                 270
```

Gly Ile Tyr Thr Tyr Thr Ala Ser Asn Arg Thr Thr Ile Pro Gly Thr
         275                 280                 285

Leu Leu Thr Asp Ala Asp Asn Val Trp Thr Asp Gly Ala Ala Val Asp
     290                 295                 300

Ala His Thr Tyr Ala Gly Lys Val Tyr Asp Phe Tyr Lys Thr Lys Phe
305                 310                 315                 320

Gly Arg Asn Ser Leu Asp Gly Asn Gly Leu Leu Ile Arg Ser Ser Val
             325                 330                 335

His Tyr Ser Ser Arg Tyr Asn Asn Ala Phe Trp Asn Gly Thr Gln Ile
         340                 345                 350

Val Phe Gly Asp Gly Asp Gly Ser Thr Phe Ile Pro Leu Ser Gly Asp
         355                 360                 365

Leu Asp Val Val Gly His Glu Leu Ser His Gly Val Ile Glu Tyr Thr
     370                 375                 380

Ser Asn Leu Gln Tyr Leu Asn Glu Ser Gly Ala Leu Asn Glu Ser Tyr
385                 390                 395                 400

Ala Asp Val Leu Gly Asn Ser Ile Gln Ala Lys Asn Trp Leu Ile Gly
             405                 410                 415

Asp Asp Val Tyr Thr Pro Gly Ile Ser Gly Asp Ala Leu Arg Ser Met
         420                 425                 430

Ser Asn Pro Thr Leu Tyr Gly Gln Pro Asp Asn Tyr Ala Asn Arg Tyr
         435                 440                 445

Thr Gly Ser Ser Asp Asn Gly Gly Val His Thr Asn Ser Gly Ile Thr
     450                 455                 460

Asn Lys Ala Phe Tyr Leu Leu Ala Gln Gly Gly Thr Gln Asn Gly Val
465                 470                 475                 480

Thr Val Ala Gly Ile Gly Arg Asp Ala Ala Val Asn Ile Phe Tyr Asn
             485                 490                 495

Thr Val Ala Tyr Tyr Leu Thr Ser Thr Ser Asn Phe Ala Ala Ala Lys
         500                 505                 510

Asn Ala Ser Ile Gln Ala Ala Lys Asp Leu Tyr Gly Thr Gly Ser Ser
         515                 520                 525

Tyr Val Thr Ser Val Thr Asn Ala Phe Arg Ala Val Gly Leu
     530                 535                 540

<210> SEQ ID NO 16
<211> LENGTH: 1581
<212> TYPE: DNA
<213> ORGANISM: Paenibacillus ehimensis
<220> FEATURE:
<221> NAME/KEY: misc_feature
<222> LOCATION: (1)..(1581)
<223> OTHER INFORMATION: nucleotide sequence of the PehPro1 gene
      isolated from Paenibacillus ehimensis

<400> SEQUENCE: 16
atgttaaaag tatgggcatc gattattaca ggagcatttt tgctcgggag cgtgcaaggg      60
gtgcaagctg ctccacaaga tcaagctgct cccttcggag gattcacccc tcaattgatt     120
accggggaaa gctggagtgc gccgcaagga gtatcgggag aggaaaaaat ctggaagtat     180
ctcgaatcca agcaggaaag cttccaaatc ggccaaaccg ttgatctgaa aaagcaattg     240
aaaattatcg ccaaacgac cgacgagaaa cgggaaccaa cgcattaccg tctacagcag     300
tatgtgggag gcgtccccgt atacggcggc gtacaaacga tccatgtcaa caagaaggaa     360 caagttaccct cgctgatcgg cagcctgctt cccgaccagc agcagcaagt ttcgaaaagc     420

```
ttgaattcgc aaatcagcga agcgcaagcc atcgccgtgg cccagaaaga taccgaggcc    480
gccgtcggca agctgggtga accgcaaaag acaccggaag cggatctgta cgtttattta    540
cacaacggac aaccggtcct cgcttatgtg accgaggtta acgttctcga accggaggca    600
atccggacgc gctacttcat cagcgccgaa gacggcagca ttttattcaa gtacgacatc    660
ctcgctcacg ctacaggtac cggaaaaggc gtgctcggag atacgaaatc gttcacgacc    720
acgcaatccg gctccactta tcaattgaag gatacgacgc gcgggcaagg tatcgtcact    780
tacagcgctg caaccggtc ctctctgccg ggaacgctgc tcaccagctc agcaatatt     840
tggaacgacg cgcggcggt cgatgcgcat gcctataccg ccaaagtgta cgattactat    900
aaaaacaaat ttggccgcaa cagcattgac ggcaacggct ccagcttaa atcgaccgtg     960
cactattcct ccagatacaa caacgccttc tggaacggtg tgcaaatggt gtacggcgac   1020
ggcgacggcg taaccttcat tccgttctcc gccgatccgg acgtcatcgg ccacgaattg   1080
acccacggcg ttacgaaaca tacggccggc ctggaatact acggcgaatc cggagcgctg   1140
aacgaatcga tctccgatat tatcggcaac gcgatcgacg gcaaaaactg gctgatcggc   1200
gacttgattt atacgccgaa tactcccggg gacgccctcc gctctatgga gaaccccaag   1260
ctgtataacc aacccgaccg ctatcaagac cgctatacgg gaccttccga taacggcggc   1320
gtgcatatta acagcggtat caacaacaaa gccttctacc tgatcgccca aggcggcacg   1380
cactatggcg tcaccgtgaa cgggatcgga cgcgatgcgc tgtgcaaat tttctatgac   1440
gccctcatca attacctgac tccaacttcg aacttctcgg cgatgcgcgc agcagccatt   1500
caagcggcaa ccgacctgta cggagcgaat tcttctcaag taaacgctgt caaaaaagcg   1560
tatactgccg tcggcgtgaa c                                             1581
```

<210> SEQ ID NO 17
<211> LENGTH: 527
<212> TYPE: PRT
<213> ORGANISM: Paenibacillus ehimensis
<220> FEATURE:
<221> NAME/KEY: misc_feature
<222> LOCATION: (1)..(527)
<223> OTHER INFORMATION: amino acid sequence of the PehPro1 precursor protein

<400> SEQUENCE: 17

Met Leu Lys Val Trp Ala Ser Ile Ile Thr Gly Ala Phe Leu Leu Gly
1               5                   10                  15

Ser Val Gln Gly Val Gln Ala Ala Pro Gln Asp Gln Ala Ala Pro Phe
            20                  25                  30

Gly Gly Phe Thr Pro Gln Leu Ile Thr Gly Glu Ser Trp Ser Ala Pro
        35                  40                  45

Gln Gly Val Ser Gly Glu Glu Lys Ile Trp Lys Tyr Leu Glu Ser Lys
    50                  55                  60

Gln Glu Ser Phe Gln Ile Gly Gln Thr Val Asp Leu Lys Lys Gln Leu
65                  70                  75                  80

Lys Ile Ile Gly Gln Thr Thr Asp Glu Lys Thr Gly Thr Thr His Tyr
                85                  90                  95

Arg Leu Gln Gln Tyr Val Gly Gly Val Pro Val Tyr Gly Gly Val Gln
            100                 105                 110

Thr Ile His Val Asn Lys Glu Gly Gln Val Thr Ser Leu Ile Gly Ser
        115                 120                 125

Leu Leu Pro Asp Gln Gln Gln Val Ser Lys Ser Leu Asn Ser Gln
    130                 135                 140

Ile Ser Glu Ala Gln Ala Ile Ala Val Ala Gln Lys Asp Thr Glu Ala
145                 150                 155                 160

Ala Val Gly Lys Leu Gly Glu Pro Gln Lys Thr Pro Glu Ala Asp Leu
            165                 170                 175

Tyr Val Tyr Leu His Asn Gly Gln Pro Val Leu Ala Tyr Val Thr Glu
            180                 185                 190

Val Asn Val Leu Glu Pro Glu Ala Ile Arg Thr Arg Tyr Phe Ile Ser
            195                 200                 205

Ala Glu Asp Gly Ser Ile Leu Phe Lys Tyr Asp Ile Leu Ala His Ala
            210                 215                 220

Thr Gly Thr Gly Lys Gly Val Leu Gly Asp Thr Lys Ser Phe Thr Thr
225                 230                 235                 240

Thr Gln Ser Gly Ser Thr Tyr Gln Leu Lys Asp Thr Thr Arg Gly Gln
            245                 250                 255

Gly Ile Val Thr Tyr Ser Ala Gly Asn Arg Ser Ser Leu Pro Gly Thr
            260                 265                 270

Leu Leu Thr Ser Ser Ser Asn Ile Trp Asn Asp Gly Ala Ala Val Asp
            275                 280                 285

Ala His Ala Tyr Thr Ala Lys Val Tyr Asp Tyr Tyr Lys Asn Lys Phe
            290                 295                 300

Gly Arg Asn Ser Ile Asp Gly Asn Gly Phe Gln Leu Lys Ser Thr Val
305                 310                 315                 320

His Tyr Ser Ser Arg Tyr Asn Asn Ala Phe Trp Asn Gly Val Gln Met
            325                 330                 335

Val Tyr Gly Asp Gly Asp Gly Val Thr Phe Ile Pro Phe Ser Ala Asp
            340                 345                 350

Pro Asp Val Ile Gly His Glu Leu Thr His Gly Val Thr Glu His Thr
            355                 360                 365

Ala Gly Leu Glu Tyr Tyr Gly Glu Ser Gly Ala Leu Asn Glu Ser Ile
            370                 375                 380

Ser Asp Ile Ile Gly Asn Ala Ile Asp Gly Lys Asn Trp Leu Ile Gly
385                 390                 395                 400

Asp Leu Ile Tyr Thr Pro Asn Thr Pro Gly Asp Ala Leu Arg Ser Met
            405                 410                 415

Glu Asn Pro Lys Leu Tyr Asn Gln Pro Asp Arg Tyr Gln Asp Arg Tyr
            420                 425                 430

Thr Gly Pro Ser Asp Asn Gly Gly Val His Ile Asn Ser Gly Ile Asn
            435                 440                 445

Asn Lys Ala Phe Tyr Leu Ile Ala Gln Gly Gly Thr His Tyr Gly Val
            450                 455                 460

Thr Val Asn Gly Ile Gly Arg Asp Ala Ala Val Gln Ile Phe Tyr Asp
465                 470                 475                 480

Ala Leu Ile Asn Tyr Leu Thr Pro Thr Ser Asn Phe Ser Ala Met Arg
            485                 490                 495

Ala Ala Ala Ile Gln Ala Ala Thr Asp Leu Tyr Gly Ala Asn Ser Ser
            500                 505                 510

Gln Val Asn Ala Val Lys Lys Ala Tyr Thr Ala Val Gly Val Asn
            515                 520                 525

<210> SEQ ID NO 18
<211> LENGTH: 304
<212> TYPE: PRT
<213> ORGANISM: Paenibacillus ehimensis
<220> FEATURE:

<221> NAME/KEY: misc_feature
<222> LOCATION: (1)..(304)
<223> OTHER INFORMATION: amino acid sequence of the predicted mature
      form of PehPro1

<400> SEQUENCE: 18

Ala Thr Gly Thr Gly Lys Gly Val Leu Gly Asp Thr Lys Ser Phe Thr
1               5                   10                  15

Thr Thr Gln Ser Gly Ser Thr Tyr Gln Leu Lys Asp Thr Thr Arg Gly
            20                  25                  30

Gln Gly Ile Val Thr Tyr Ser Ala Gly Asn Arg Ser Ser Leu Pro Gly
        35                  40                  45

Thr Leu Leu Thr Ser Ser Asn Ile Trp Asn Asp Gly Ala Ala Val
    50                  55                  60

Asp Ala His Ala Tyr Thr Ala Lys Val Tyr Asp Tyr Lys Asn Lys
65                  70                  75                  80

Phe Gly Arg Asn Ser Ile Asp Gly Asn Gly Phe Gln Leu Lys Ser Thr
                85                  90                  95

Val His Tyr Ser Ser Arg Tyr Asn Asn Ala Phe Trp Asn Gly Val Gln
            100                 105                 110

Met Val Tyr Gly Asp Gly Asp Gly Val Thr Phe Ile Pro Phe Ser Ala
        115                 120                 125

Asp Pro Asp Val Ile Gly His Glu Leu Thr His Gly Val Thr Glu His
130                 135                 140

Thr Ala Gly Leu Glu Tyr Tyr Gly Glu Ser Gly Ala Leu Asn Glu Ser
145                 150                 155                 160

Ile Ser Asp Ile Ile Gly Asn Ala Ile Asp Gly Lys Asn Trp Leu Ile
                165                 170                 175

Gly Asp Leu Ile Tyr Thr Pro Asn Thr Pro Gly Asp Ala Leu Arg Ser
            180                 185                 190

Met Glu Asn Pro Lys Leu Tyr Asn Gln Pro Asp Arg Tyr Gln Asp Arg
        195                 200                 205

Tyr Thr Gly Pro Ser Asp Asn Gly Gly Val His Ile Asn Ser Gly Ile
210                 215                 220

Asn Asn Lys Ala Phe Tyr Leu Ile Ala Gln Gly Gly Thr His Tyr Gly
225                 230                 235                 240

Val Thr Val Asn Gly Ile Gly Arg Asp Ala Ala Val Gln Ile Phe Tyr
                245                 250                 255

Asp Ala Leu Ile Asn Tyr Leu Thr Pro Thr Ser Asn Phe Ser Ala Met
            260                 265                 270

Arg Ala Ala Ala Ile Gln Ala Ala Thr Asp Leu Tyr Gly Ala Asn Ser
        275                 280                 285

Ser Gln Val Asn Ala Val Lys Lys Ala Tyr Thr Ala Val Gly Val Asn
    290                 295                 300

<210> SEQ ID NO 19
<211> LENGTH: 1611
<212> TYPE: DNA
<213> ORGANISM: Artificial Sequence
<220> FEATURE:
<223> OTHER INFORMATION: Synthetic: nucleotide sequence of the
      synthesized PehPro1 gene in plasmid pGX148(AprE- PehPro1)

<400> SEQUENCE: 19
gtgagaagca aaaaattgtg gatcagcttg ttgttttgcgt taacgttaat ctttacgatg      60
gcgttcagca acatgagcgc gcaggctgct ggaaaagcac ctcaagatca ggcagcacct     120

-continued

```
tttggaggct  ttacaccgca  acttatcaca  ggcgaatcat  ggtcagcacc  gcagggcgtt   180
tcaggcgagg  aaaagatctg  gaagtacctt  gagagcaagc  aggagtcatt  tcaaatcggc   240
cagacagtcg  acctgaaaaa  gcaactgaag  atcatcggcc  aaacaacgga  cgaaaagacg   300
ggcacgacgc  attatagact  gcaacaatat  gttggcggcg  tgccggttta  tggaggcgtg   360
caaacaatcc  acgtgaacaa  ggaaggacag  gtcacgtcac  tgatcggcag  cctgctgccg   420
gatcagcagc  aacaagtctc  aaagagcctg  aactcacaaa  ttagcgaggc  acaagcgatt   480
gcagttgcac  aaaaggacac  ggaagcagct  gtcggcaagc  tgggcgaacc  gcaaaaaaca   540
cctgaggctg  acctttacgt  ctacctgcat  aacggccagc  cggtccttgc  gtacgttacg   600
gaagttaacg  tgctggagcc  ggaggccatc  agaacgagat  acttcattag  cgcggaggat   660
ggaagcattc  tgtttaagta  cgatattctt  gctcacgcga  caggcacagg  caagggcgtc   720
cttggcgaca  caaaaagctt  cacgacaacg  cagagcggat  caacgtacca  gctgaaagat   780
acaacaagag  acaaggcat   cgttacgtat  tcagcgggca  atagatcaag  cctgccgggc   840
acactgctga  catcaagctc  aaacatttgg  aatgacggcg  cagcagttga  tgcccatgcg   900
tacacagcca  aggtgtacga  ctactataag  aacaagtttg  gcagaaatag  catcgacgga   960
aatggatttc  aacttaaatc  aacggtgcac  tactcatcaa  gatataacaa  tgcgttttgg  1020
aacggagtgc  agatggtcta  cggagacggc  gacggcgtga  catttattcc  gtttagcgcc  1080
gacccggacg  tgattggaca  tgaactgaca  catggagtga  cagagcatac  ggcgggactg  1140
gaatattacg  gcgaaagcgg  cgcactgaac  gaaagcatct  cagacattat  tggaaacgca  1200
atcgatggca  aaaactggct  gattggcgat  ctgatttata  cgccgaatac  accgggcgat  1260
gcactgagat  caatggagaa  tccgaagctg  tacaaccaac  cggacagata  ccaagataga  1320
tacacaggac  cgtcagacaa  cggcggagtc  catatcaaca  gcggaatcaa  taacaaagcc  1380
ttttacctga  tcgcccaagg  cggaacgcac  tatggcgtta  cagtcaatgg  catcggaaga  1440
gatgccgcag  ttcagatttt  ctatgacgcg  ctgatcaact  atctgacgcc  tacaagcaat  1500
ttctcagcaa  tgagagccgc  agcaatccaa  gcagccacgg  atctgtatgg  agccaattca  1560
tcacaagtta  atgctgttaa  gaaggcttat  acggcagtgg  gagttaacta  a            1611
```

<210> SEQ ID NO 20
<211> LENGTH: 536
<212> TYPE: PRT
<213> ORGANISM: Artificial Sequence
<220> FEATURE:
<223> OTHER INFORMATION: Synthetic: amino acid sequence of the PehPro1
     precursor protein expressed from plasmid pGX148(AprE- PehPro1)

<400> SEQUENCE: 20

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ala Pro Gln Asp Gln Ala Ala Pro Phe Gly Gly Phe Thr Pro Gln Leu
        35                  40                  45

Ile Thr Gly Glu Ser Trp Ser Ala Pro Gln Gly Val Ser Gly Glu Glu
    50                  55                  60

Lys Ile Trp Lys Tyr Leu Glu Ser Lys Gln Glu Ser Phe Gln Ile Gly
65                  70                  75                  80

Gln Thr Val Asp Leu Lys Lys Gln Leu Lys Ile Ile Gly Gln Thr Thr
                85                  90                  95
```

-continued

```
Asp Glu Lys Thr Gly Thr Thr His Tyr Arg Leu Gln Gln Tyr Val Gly
            100                 105                 110

Gly Val Pro Val Tyr Gly Val Gln Thr Ile His Val Asn Lys Glu
        115                 120                 125

Gly Gln Val Thr Ser Leu Ile Gly Ser Leu Leu Pro Asp Gln Gln Gln
    130                 135                 140

Gln Val Ser Lys Ser Leu Asn Ser Gln Ile Ser Glu Ala Gln Ala Ile
145                 150                 155                 160

Ala Val Ala Gln Lys Asp Thr Glu Ala Ala Val Gly Lys Leu Gly Glu
                165                 170                 175

Pro Gln Lys Thr Pro Glu Ala Asp Leu Tyr Val Tyr Leu His Asn Gly
            180                 185                 190

Gln Pro Val Leu Ala Tyr Val Thr Glu Val Asn Val Leu Glu Pro Glu
        195                 200                 205

Ala Ile Arg Thr Arg Tyr Phe Ile Ser Ala Glu Asp Gly Ser Ile Leu
    210                 215                 220

Phe Lys Tyr Asp Ile Leu Ala His Ala Thr Gly Thr Gly Lys Gly Val
225                 230                 235                 240

Leu Gly Asp Thr Lys Ser Phe Thr Thr Thr Gln Ser Gly Ser Thr Tyr
                245                 250                 255

Gln Leu Lys Asp Thr Thr Arg Gly Gln Gly Ile Val Thr Tyr Ser Ala
            260                 265                 270

Gly Asn Arg Ser Ser Leu Pro Gly Thr Leu Leu Thr Ser Ser Ser Asn
        275                 280                 285

Ile Trp Asn Asp Gly Ala Ala Val Asp Ala His Ala Tyr Thr Ala Lys
    290                 295                 300

Val Tyr Asp Tyr Tyr Lys Asn Lys Phe Gly Arg Asn Ser Ile Asp Gly
305                 310                 315                 320

Asn Gly Phe Gln Leu Lys Ser Thr Val His Tyr Ser Ser Arg Tyr Asn
                325                 330                 335

Asn Ala Phe Trp Asn Gly Val Gln Met Val Tyr Gly Asp Gly Asp Gly
            340                 345                 350

Val Thr Phe Ile Pro Phe Ser Ala Asp Pro Asp Val Ile Gly His Glu
        355                 360                 365

Leu Thr His Gly Val Thr Glu His Thr Ala Gly Leu Glu Tyr Tyr Gly
    370                 375                 380

Glu Ser Gly Ala Leu Asn Glu Ser Ile Ser Asp Ile Ile Gly Asn Ala
385                 390                 395                 400

Ile Asp Gly Lys Asn Trp Leu Ile Gly Asp Leu Ile Tyr Thr Pro Asn
                405                 410                 415

Thr Pro Gly Asp Ala Leu Arg Ser Met Glu Asn Pro Lys Leu Tyr Asn
            420                 425                 430

Gln Pro Asp Arg Tyr Gln Asp Arg Tyr Thr Gly Pro Ser Asp Asn Gly
        435                 440                 445

Gly Val His Ile Asn Ser Gly Ile Asn Asn Lys Ala Phe Tyr Leu Ile
    450                 455                 460

Ala Gln Gly Gly Thr His Tyr Gly Val Thr Val Asn Gly Ile Gly Arg
465                 470                 475                 480

Asp Ala Ala Val Gln Ile Phe Tyr Asp Ala Leu Ile Asn Tyr Leu Thr
                485                 490                 495

Pro Thr Ser Asn Phe Ser Ala Met Arg Ala Ala Ile Gln Ala Ala
            500                 505                 510

Thr Asp Leu Tyr Gly Ala Asn Ser Ser Gln Val Asn Ala Val Lys Lys
```

```
                515                 520                 525
Ala Tyr Thr Ala Val Gly Val Asn
    530                 535

<210> SEQ ID NO 21
<211> LENGTH: 1563
<212> TYPE: DNA
<213> ORGANISM: Paenibacillus barcinonensis
<220> FEATURE:
<221> NAME/KEY: misc_feature
<222> LOCATION: (1)..(1563)
<223> OTHER INFORMATION: nucleotide sequence of the PbaPro1 gene
      isolated from Paenibacillus barcinonensis

<400> SEQUENCE: 21
atgaaattga ccaaaattat gccaacaatt cttgcaggag ctcttttgct cacatccctg      60
tcctctgcag cagcaatgcc gttatctgac tcatccattc catttgaggg ccccctacacc    120 tccgaggaga gtattctgtt gaacaacaac ccggacgaaa tgatttataa ttttcttgca    180
caacaagagc aatttctgaa tgccgacgtc aaaggacagc tcaaaatcat taaacgcaac    240
acagacactt ccggcatcag acactttcgt ctgaagcaat acatcaaagg tgttccggtt    300
tacggcgcag aacaaacgat ccatctggac aagaacggag ctgtaacttc cgcactcggc    360
gatcttccgc caattgaaga caggctgtt ccgaatgatg cgttcccgc aatcagtgca     420 gacgatgcca tccgtgccgc cgagaatgaa gccacctccc gtcttggaga gcttggcgca    480
ccagagcttg agccaaaggc cgaattaaac atttatcatc atgaagatga cggacaaacc    540
tacctcgttt acattacgga agttaacgtg cttgagcctt ccccgctacg gaccaaatat    600
tttattaacg cccttgatgg aagcatcgta tctcaatacg atattatcaa ctttgccaca    660
ggcaccggta caggcgtgca tggtgatacc aaaacactga cgacaactca atccggcagc    720
acctatcagc tgaaagatac aactcgtgga aaaggcattc aaacctatac tgcgaacaat    780
cgctcctcgc ttccaggcag cttgtctacc agttccaata acgtatggac agaccgtgca    840
gctgtagatg cgcacgccta tgctgccgcc acatatgact tctacaaaaa caaattcaat    900
cgcaacggca ttgacggaaa cgggctgttg attcgctcta cagtgcatta tggctccaac    960
tataaaaacg ccttctggaa cggagcacag attgtctatg agatggcga tggcatcgag    1020 ttcggtccct tctccggtga tctcgatgtt gtcggacatg aattgacaca cggggtgatt    1080
gaatatacag ccaatctcga atatcgcaat gagccgggtg ctttaaacga gcttttgcc    1140 gacattatgg ggaacaccat cgaaagcaaa aactggctgc ttggcgacgg aatctatact    1200
ccaaacattc caggtgatgc cctgcgctcg ttatccgacc ctacgctgta taaccagcct    1260
gacaaataca gtgatcgcta cactggctct caggataatg cggtgtgca tatcaacagc    1320 gggatcatta acaaagcata ttatcttgca gcccaaggcg gtactcataa cggggtaacc    1380
gttagcggca tcggccggga taaagcagta cgtattttct atagcacgct ggtgaactac    1440
ctgacgccaa cctccaaatt tgcagcagcc aaaacagcga caattcaggc agccaaggac    1500
ctgtacggtg ccaattccgc tgaagctacg gcaatcacca aagcttatca agcggtaggt    1560
ttg                                                                 1563

<210> SEQ ID NO 22
<211> LENGTH: 521
<212> TYPE: PRT
<213> ORGANISM: Paenibacillus barcinonensis
<220> FEATURE:
<221> NAME/KEY: misc_feature
```

<222> LOCATION: (1)..(521)
<223> OTHER INFORMATION: amino acid sequence of the PbaPro1 precursor
      protein

<400> SEQUENCE: 22

```
Met Lys Leu Thr Lys Ile Met Pro Thr Ile Leu Ala Gly Ala Leu Leu
1               5                   10                  15

Leu Thr Ser Leu Ser Ser Ala Ala Met Pro Leu Ser Asp Ser Ser
            20                  25                  30

Ile Pro Phe Glu Gly Pro Tyr Thr Ser Glu Glu Ser Ile Leu Leu Asn
        35                  40                  45

Asn Asn Pro Asp Glu Met Ile Tyr Asn Phe Leu Ala Gln Gln Glu Gln
50                  55                  60

Phe Leu Asn Ala Asp Val Lys Gly Gln Leu Lys Ile Lys Arg Asn
65                  70                  75                  80

Thr Asp Thr Ser Gly Ile Arg His Phe Arg Leu Lys Gln Tyr Ile Lys
                85                  90                  95

Gly Val Pro Val Tyr Gly Ala Glu Gln Thr Ile His Leu Asp Lys Asn
                100                 105                 110

Gly Ala Val Thr Ser Ala Leu Gly Asp Leu Pro Pro Ile Glu Glu Gln
            115                 120                 125

Ala Val Pro Asn Asp Gly Val Pro Ala Ile Ser Ala Asp Asp Ala Ile
130                 135                 140

Arg Ala Ala Glu Asn Glu Ala Thr Ser Arg Leu Gly Glu Leu Gly Ala
145                 150                 155                 160

Pro Glu Leu Glu Pro Lys Ala Glu Leu Asn Ile Tyr His His Glu Asp
                165                 170                 175

Asp Gly Gln Thr Tyr Leu Val Tyr Ile Thr Glu Val Asn Val Leu Glu
            180                 185                 190

Pro Ser Pro Leu Arg Thr Lys Tyr Phe Ile Asn Ala Leu Asp Gly Ser
        195                 200                 205

Ile Val Ser Gln Tyr Asp Ile Ile Asn Phe Ala Thr Gly Thr Gly Thr
210                 215                 220

Gly Val His Gly Asp Thr Lys Thr Leu Thr Thr Thr Gln Ser Gly Ser
225                 230                 235                 240

Thr Tyr Gln Leu Lys Asp Thr Thr Arg Gly Lys Gly Ile Gln Thr Tyr
                245                 250                 255

Thr Ala Asn Asn Arg Ser Ser Leu Pro Gly Ser Leu Ser Thr Ser Ser
            260                 265                 270

Asn Asn Val Trp Thr Asp Arg Ala Ala Val Asp Ala His Ala Tyr Ala
        275                 280                 285

Ala Ala Thr Tyr Asp Phe Tyr Lys Asn Lys Phe Asn Arg Asn Gly Ile
290                 295                 300

Asp Gly Asn Gly Leu Leu Ile Arg Ser Thr Val His Tyr Gly Ser Asn
305                 310                 315                 320

Tyr Lys Asn Ala Phe Trp Asn Gly Ala Gln Ile Val Tyr Gly Asp Gly
                325                 330                 335

Asp Gly Ile Glu Phe Gly Pro Phe Ser Gly Asp Leu Asp Val Val Gly
            340                 345                 350

His Glu Leu Thr His Gly Val Ile Glu Tyr Thr Ala Asn Leu Glu Tyr
        355                 360                 365

Arg Asn Glu Pro Gly Ala Leu Asn Glu Ala Phe Ala Asp Ile Met Gly
370                 375                 380

Asn Thr Ile Glu Ser Lys Asn Trp Leu Leu Gly Asp Gly Ile Tyr Thr
```

```
                385                 390                 395                 400
        Pro Asn Ile Pro Gly Asp Ala Leu Arg Ser Leu Ser Asp Pro Thr Leu
                        405                 410                 415

Tyr Asn Gln Pro Asp Lys Tyr Ser Asp Arg Tyr Thr Gly Ser Gln Asp
                        420                 425                 430

Asn Gly Gly Val His Ile Asn Ser Gly Ile Ile Asn Lys Ala Tyr Tyr
                        435                 440                 445

Leu Ala Ala Gln Gly Gly Thr His Asn Gly Val Thr Val Ser Gly Ile
                    450                 455                 460

Gly Arg Asp Lys Ala Val Arg Ile Phe Tyr Ser Thr Leu Val Asn Tyr
        465                 470                 475                 480

Leu Thr Pro Thr Ser Lys Phe Ala Ala Ala Lys Thr Ala Thr Ile Gln
                        485                 490                 495

Ala Ala Lys Asp Leu Tyr Gly Ala Asn Ser Ala Glu Ala Thr Ala Ile
                        500                 505                 510

Thr Lys Ala Tyr Gln Ala Val Gly Leu
                        515                 520

<210> SEQ ID NO 23
<211> LENGTH: 303
<212> TYPE: PRT
<213> ORGANISM: Paenibacillus barcinonensis
<220> FEATURE:
<221> NAME/KEY: misc_feature
<222> LOCATION: (1)..(303)
<223> OTHER INFORMATION: amino acid sequence of the predicted mature
      form of PbaPro1

<400> SEQUENCE: 23

Ala Thr Gly Thr Gly Thr Gly Val His Gly Asp Thr Lys Thr Leu Thr
        1               5                   10                  15

Thr Thr Gln Ser Gly Ser Thr Tyr Gln Leu Lys Asp Thr Thr Arg Gly
                        20                  25                  30

Lys Gly Ile Gln Thr Tyr Thr Ala Asn Asn Arg Ser Ser Leu Pro Gly
                        35                  40                  45

Ser Leu Ser Thr Ser Ser Asn Asn Val Trp Thr Asp Arg Ala Ala Val
                    50                  55                  60

Asp Ala His Ala Tyr Ala Ala Thr Tyr Asp Phe Tyr Lys Asn Lys
        65                  70                  75                  80

Phe Asn Arg Asn Gly Ile Asp Gly Asn Gly Leu Leu Ile Arg Ser Thr
                        85                  90                  95

Val His Tyr Gly Ser Asn Tyr Lys Asn Ala Phe Trp Asn Gly Ala Gln
                        100                 105                 110

Ile Val Tyr Gly Asp Gly Asp Gly Ile Glu Phe Gly Pro Phe Ser Gly
                        115                 120                 125

Asp Leu Asp Val Val Gly His Glu Leu Thr His Gly Val Ile Glu Tyr
                    130                 135                 140

Thr Ala Asn Leu Glu Tyr Arg Asn Glu Pro Gly Ala Leu Asn Glu Ala
        145                 150                 155                 160

Phe Ala Asp Ile Met Gly Asn Thr Ile Glu Ser Lys Asn Trp Leu Leu
                        165                 170                 175

Gly Asp Gly Ile Tyr Thr Pro Asn Ile Pro Gly Asp Ala Leu Arg Ser
                        180                 185                 190

Leu Ser Asp Pro Thr Leu Tyr Asn Gln Pro Asp Lys Tyr Ser Asp Arg
                        195                 200                 205

Tyr Thr Gly Ser Gln Asp Asn Gly Gly Val His Ile Asn Ser Gly Ile
```

```
                210                 215                 220
Ile Asn Lys Ala Tyr Tyr Leu Ala Ala Gln Gly Gly Thr His Asn Gly
225                 230                 235                 240

Val Thr Val Ser Gly Ile Gly Arg Asp Lys Ala Val Arg Ile Phe Tyr
                245                 250                 255

Ser Thr Leu Val Asn Tyr Leu Thr Pro Thr Ser Lys Phe Ala Ala Ala
                260                 265                 270

Lys Thr Ala Thr Ile Gln Ala Ala Lys Asp Leu Tyr Gly Ala Asn Ser
            275                 280                 285

Ala Glu Ala Thr Ala Ile Thr Lys Ala Tyr Gln Ala Val Gly Leu
            290                 295                 300

<210> SEQ ID NO 24
<211> LENGTH: 1587
<212> TYPE: DNA
<213> ORGANISM: Artificial Sequence
<220> FEATURE:
<223> OTHER INFORMATION: Synthetic: nucleotide sequence of the
      synthesized PbaPro1 gene in plasmid pGX147(AprE- PbaPro1)

<400> SEQUENCE: 24
gtgagaagca aaaaattgtg gatcagcttg ttgtttgcgt taacgttaat ctttacgatg      60
gcgttcagca acatgagcgc gcaggctgct ggaaaaatgc ctctgtcaga cagcagcatt     120
ccgtttgagg gcccgtacac atcagaagaa agcatcctgc tgaacaacaa cccggacgag     180
atgatctaca atttcctggc acagcaggag cagttcctga acgcagacgt gaagggccag     240
ctgaaaatca tcaaaagaaa cacagacacg agcggcatca gacacttcag actgaagcag     300
tacatcaagg gcgtcccggt ttacggcgct gagcagacaa tccacctgga caaaaatggc     360
gcagtgacga gcgcacttgg agatctgccg ccgattgaag agcaagcagt cccgaacgat     420
ggcgttccgg cgattagcgc tgatgacgct atcagagccg cggaaaacga agcgacgtca     480
agactgggag aacttggcgc accggaactt gaaccgaagg cggaactgaa catctatcac     540
cacgaagacg atggacagac gtacctggtg tacatcacgg aggtgaatgt gctggagccg     600
tcaccgctga aacaaaaata cttcatcaat gcgctggatg cagcatcgt tagccaatac     660 gacatcatta acttcgccac aggcacgggc acaggcgttc atggcgacac aaaaacgctt     720
acgacaacac agtcaggctc aacgtaccag ctgaaagaca caacaagagg caagggcatc     780
cagacgtata cagccaataa cagaagctca cttccgggct cactgtcaac aagcagcaat     840
aatgtctgga cggacagagc tgcagtggac gcgcacgcgt atgctgcggc cacgtacgac     900
ttctacaaga caagttcaa cagaaacggc attgatggca acggcctgct tattagaagc     960
acggtccact acggctcaaa ctacaagaat gcgttttgga acggcgccca aattgtttat    1020
ggcgatggag acggcatcga gttcggacct tttagcggcg acctggatgt ggtcggacat    1080
gaactgacgc acggcgttat cgagtatacg gcgaatctgg aatacagaaa tgaaccgggc    1140
gctctgaatg aggccttcgc ggatatcatg ggcaacacaa ttgagagcaa aaactggctt    1200
ctgggcgacg gaatctacac gccgaacatt ccgggagatg cactgagatc actgagcgac    1260
cctacgctgt acaaccagcc ggacaaatac agcgacagat acgggatc acaggacaat    1320 ggcggcgtcc atattaactc aggcatcatc aacaaagcgt attatctggc agctcaaggc    1380
ggcacgcata tggcgtcac agttagcgga atcggcagag acaaggccgt cagaattttc    1440
tactcaacgt tggtgaacta cctgacaccg acaagcaagt tgcagccgc caaaacagcc    1500 acgattcagg cagcaaagga cctgtacgga gcgaactcag cagaggccac agcgattacg    1560
```
aaggcttatc aagccgtggg actgtaa    1587

<210> SEQ ID NO 25
<211> LENGTH: 528
<212> TYPE: PRT
<213> ORGANISM: Artificial Sequence
<220> FEATURE:
<223> OTHER INFORMATION: Synthetic: amino acid sequence of the PbaPro1
      precursor protein expressed from plasmid pGX147(AprE-PbaPro1)

<400> SEQUENCE: 25

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Met Pro Leu Ser Asp Ser Ser Ile Pro Phe Glu Gly Pro Tyr Thr Ser
        35                  40                  45

Glu Glu Ser Ile Leu Leu Asn Asn Asn Pro Asp Glu Met Ile Tyr Asn
50                  55                  60

Phe Leu Ala Gln Gln Glu Gln Phe Leu Asn Ala Asp Val Lys Gly Gln
65                  70                  75                  80

Leu Lys Ile Ile Lys Arg Asn Thr Asp Thr Ser Gly Ile Arg His Phe
                85                  90                  95

Arg Leu Lys Gln Tyr Ile Lys Gly Val Pro Val Tyr Gly Ala Glu Gln
            100                 105                 110

Thr Ile His Leu Asp Lys Asn Gly Ala Val Thr Ser Ala Leu Gly Asp
        115                 120                 125

Leu Pro Pro Ile Glu Glu Gln Ala Val Pro Asn Asp Gly Val Pro Ala
130                 135                 140

Ile Ser Ala Asp Asp Ala Ile Arg Ala Ala Glu Asn Glu Ala Thr Ser
145                 150                 155                 160

Arg Leu Gly Glu Leu Gly Ala Pro Glu Leu Glu Pro Lys Ala Glu Leu
                165                 170                 175

Asn Ile Tyr His His Glu Asp Asp Gly Gln Thr Tyr Leu Val Tyr Ile
            180                 185                 190

Thr Glu Val Asn Val Leu Glu Pro Ser Pro Leu Arg Thr Lys Tyr Phe
        195                 200                 205

Ile Asn Ala Leu Asp Gly Ser Ile Val Ser Gln Tyr Asp Ile Ile Asn
210                 215                 220

Phe Ala Thr Gly Thr Gly Thr Gly Val His Gly Asp Thr Lys Thr Leu
225                 230                 235                 240

Thr Thr Thr Gln Ser Gly Ser Thr Tyr Gln Leu Lys Asp Thr Thr Arg
                245                 250                 255

Gly Lys Gly Ile Gln Thr Tyr Thr Ala Asn Asn Arg Ser Ser Leu Pro
            260                 265                 270

Gly Ser Leu Ser Thr Ser Ser Asn Asn Val Trp Thr Asp Arg Ala Ala
        275                 280                 285

Val Asp Ala His Ala Tyr Ala Ala Thr Tyr Asp Phe Tyr Lys Asn
290                 295                 300

Lys Phe Asn Arg Asn Gly Ile Asp Gly Asn Gly Leu Leu Ile Arg Ser
305                 310                 315                 320

Thr Val His Tyr Gly Ser Asn Tyr Lys Asn Ala Phe Trp Asn Gly Ala
                325                 330                 335

Gln Ile Val Tyr Gly Asp Gly Asp Gly Ile Glu Phe Gly Pro Phe Ser
            340                 345                 350
```

```
Gly Asp Leu Asp Val Val Gly His Glu Leu Thr His Gly Val Ile Glu
            355                 360                 365

Tyr Thr Ala Asn Leu Glu Tyr Arg Asn Glu Pro Gly Ala Leu Asn Glu
    370                 375                 380

Ala Phe Ala Asp Ile Met Gly Asn Thr Ile Glu Ser Lys Asn Trp Leu
385                 390                 395                 400

Leu Gly Asp Gly Ile Tyr Thr Pro Asn Ile Pro Gly Asp Ala Leu Arg
                405                 410                 415

Ser Leu Ser Asp Pro Thr Leu Tyr Asn Gln Pro Asp Lys Tyr Ser Asp
            420                 425                 430

Arg Tyr Thr Gly Ser Gln Asp Asn Gly Val His Ile Asn Ser Gly
            435                 440                 445

Ile Ile Asn Lys Ala Tyr Tyr Leu Ala Ala Gln Gly Gly Thr His Asn
    450                 455                 460

Gly Val Thr Val Ser Gly Ile Gly Arg Asp Lys Ala Val Arg Ile Phe
465                 470                 475                 480

Tyr Ser Thr Leu Val Asn Tyr Leu Thr Pro Thr Ser Lys Phe Ala Ala
                485                 490                 495

Ala Lys Thr Ala Thr Ile Gln Ala Ala Lys Asp Leu Tyr Gly Ala Asn
            500                 505                 510

Ser Ala Glu Ala Thr Ala Ile Thr Lys Ala Tyr Gln Ala Val Gly Leu
    515                 520                 525

<210> SEQ ID NO 26
<211> LENGTH: 1779
<212> TYPE: DNA
<213> ORGANISM: Paenibacillus polymyxa SC2
<220> FEATURE:
<221> NAME/KEY: misc_feature
<222> LOCATION: (1)..(1779)
<223> OTHER INFORMATION: nucleotide sequence of the PpoPro1 gene
      identified from NCBI database

<400> SEQUENCE: 26
atgaaaaaag tatgggtttc gcttcttgga ggagctatgt tattagggtc tgtcgcgtct      60
ggtgcatctg cggagagttc cgtttcgggg ccagctcagc ttacaccgac cttccacgcc     120
gagcaatgga aagcacctac ctcggtatcg ggggatgaca ttgtatggag ctatttaaat     180
cgacaaagaa atcgttgct gggtgtggat agctccagtg tacgtgaaca attccgaatc     240
gttgatcgca caagcgacaa atccggtgta agccattatc gactgaagca gtatgtaaac     300
ggaattcccg tgtatggagc tgaacaaact attcatgtgg gcaaatctgg tgaggtcacc     360
tcttacttag gagcggtggt taatgaggat cagcaggcag aagctacgca aggtacaact     420
ccaaaaatca gcgcttctga gcggtctac accgcatata agaagcagc tgcacggatt     480 gaagccctcc ctacctccga cgatactatt tctaaagacg ctgaggagcc aagcagtgta     540
agtaaagata cttacgccga agcagctaac aacgaaaaaa cgctttctgt tgataaggac     600
gagctgagtc ttgatcaggc atctgtcctg aaagatagca aaattgaagc agtggaacca     660 gaaaaagtt ccattgccaa aatcgctaat ctgcagcctg aagtagatcc taaagcagaa     720
ctctactact accctaaggg ggatgacctg ctgctggttt atgtaacaga agttaatgtt     780
ttagaacctg ccccactgcg tacccgctac attattgatg ccaatgacgg cagcatcgta     840
ttccagtatg acatcattaa tgaagcgaca ggcacaggta aggtgtgct tggtgattcc     900 aaatcgttca ctactaccgc ttccggcagt agctaccagt taaagataca acacgcggt     960
```

-continued

```
aacggaatcg tgacttacac ggcctccaac cgtcaaagca tcccaggtac cattttgaca    1020
gatgccgata atgtatggaa tgatccagct ggtgtggacg cccatgcgta tgctgctaaa    1080
acctatgatt actataaagc caaatttgga cgcaacagca ttgacggacg cggtctgcaa    1140
cttcgttcga cggtccatta cggtagtcgc tacaacaatg ccttctggaa cggctcccaa    1200
atgacttatg gagatggaga tggtagcaca tttatcgcct tcagcgggga ccccgatgta    1260
gtaggacatg aacttacgca tggtgtcaca gagtatactt cgaatttgga atattacgga    1320
gagtccggcg cattgaatga agctttctca gacgttatcg ggaatgacat tcagcgcaaa    1380
aactggcttg taggcgatga tatttacacg ccaaacattg caggcgatgc ccttcgctca    1440
atgtccaatc caaccctgta cgatcaacca gatcactatt ccaacctgta cagaggcagc    1500
tccgataacg gcggtgttca caccaacagc ggtattatca taaagctta ctacttgtta    1560 gcacaaggtg gtaatttcca tggcgtaact gtaaatggaa ttggccgtga tgcagcggtg    1620
caaatttact acagtgcctt tacgaactac ctgacttctt cttccgactt ctccaacgca    1680
cgtgctgctg tgatccaagc cgcaaaagat ctgtacgggg cgaactcagc agaagcaact    1740
gcagctgcca agtcttttga cgctgtaggc gtaaactaa                           1779
```

<210> SEQ ID NO 27
<211> LENGTH: 592
<212> TYPE: PRT
<213> ORGANISM: Paenibacillus polymyxa SC2
<220> FEATURE:
<221> NAME/KEY: misc_feature
<222> LOCATION: (1)..(592)
<223> OTHER INFORMATION: amino acid sequence of the PpoPro1 precursor
      protein

<400> SEQUENCE: 27

```
Met Lys Lys Val Trp Val Ser Leu Leu Gly Gly Ala Met Leu Leu Gly
1               5                   10                  15

Ser Val Ala Ser Gly Ala Ser Ala Glu Ser Ser Val Ser Gly Pro Ala
            20                  25                  30

Gln Leu Thr Pro Thr Phe His Ala Glu Gln Trp Lys Ala Pro Thr Ser
        35                  40                  45

Val Ser Gly Asp Asp Ile Val Trp Ser Tyr Leu Asn Arg Gln Lys Lys
    50                  55                  60

Ser Leu Leu Gly Val Asp Ser Ser Val Arg Glu Gln Phe Arg Ile
65                  70                  75                  80

Val Asp Arg Thr Ser Asp Lys Ser Gly Val Ser His Tyr Arg Leu Lys
                85                  90                  95

Gln Tyr Val Asn Gly Ile Pro Val Tyr Gly Ala Glu Gln Thr Ile His
            100                 105                 110

Val Gly Lys Ser Gly Glu Val Thr Ser Tyr Leu Gly Ala Val Val Asn
        115                 120                 125

Glu Asp Gln Gln Ala Glu Ala Thr Gln Gly Thr Thr Pro Lys Ile Ser
    130                 135                 140

Ala Ser Glu Ala Val Tyr Thr Ala Tyr Lys Glu Ala Ala Ala Arg Ile
145                 150                 155                 160

Glu Ala Leu Pro Thr Ser Asp Asp Thr Ile Ser Lys Asp Ala Glu Glu
                165                 170                 175

Pro Ser Ser Val Ser Lys Asp Thr Tyr Ala Glu Ala Ala Asn Asn Glu
            180                 185                 190

Lys Thr Leu Ser Val Asp Lys Asp Glu Leu Ser Leu Asp Gln Ala Ser
        195                 200                 205
```

Val Leu Lys Asp Ser Lys Ile Glu Ala Val Glu Pro Glu Lys Ser Ser
    210                 215                 220

Ile Ala Lys Ile Ala Asn Leu Gln Pro Glu Val Asp Pro Lys Ala Glu
225                 230                 235                 240

Leu Tyr Tyr Tyr Pro Lys Gly Asp Asp Leu Leu Leu Val Tyr Val Thr
                245                 250                 255

Glu Val Asn Val Leu Glu Pro Ala Pro Leu Arg Thr Arg Tyr Ile Ile
        260                 265                 270

Asp Ala Asn Asp Gly Ser Ile Val Phe Gln Tyr Asp Ile Ile Asn Glu
    275                 280                 285

Ala Thr Gly Thr Gly Lys Gly Val Leu Gly Asp Ser Lys Ser Phe Thr
290                 295                 300

Thr Thr Ala Ser Gly Ser Ser Tyr Gln Leu Lys Asp Thr Thr Arg Gly
305                 310                 315                 320

Asn Gly Ile Val Thr Tyr Thr Ala Ser Asn Arg Gln Ser Ile Pro Gly
                325                 330                 335

Thr Ile Leu Thr Asp Ala Asp Asn Val Trp Asn Asp Pro Ala Gly Val
        340                 345                 350

Asp Ala His Ala Tyr Ala Ala Lys Thr Tyr Asp Tyr Tyr Lys Ala Lys
    355                 360                 365

Phe Gly Arg Asn Ser Ile Asp Gly Arg Gly Leu Gln Leu Arg Ser Thr
370                 375                 380

Val His Tyr Gly Ser Arg Tyr Asn Asn Ala Phe Trp Asn Gly Ser Gln
385                 390                 395                 400

Met Thr Tyr Gly Asp Gly Asp Gly Ser Thr Phe Ile Ala Phe Ser Gly
                405                 410                 415

Asp Pro Asp Val Val Gly His Glu Leu Thr His Gly Val Thr Glu Tyr
        420                 425                 430

Thr Ser Asn Leu Glu Tyr Tyr Gly Glu Ser Gly Ala Leu Asn Glu Ala
    435                 440                 445

Phe Ser Asp Val Ile Gly Asn Asp Ile Gln Arg Lys Asn Trp Leu Val
450                 455                 460

Gly Asp Asp Ile Tyr Thr Pro Asn Ile Ala Gly Asp Ala Leu Arg Ser
465                 470                 475                 480

Met Ser Asn Pro Thr Leu Tyr Asp Gln Pro Asp His Tyr Ser Asn Leu
                485                 490                 495

Tyr Arg Gly Ser Ser Asp Asn Gly Gly Val His Thr Asn Ser Gly Ile
        500                 505                 510

Ile Asn Lys Ala Tyr Tyr Leu Leu Ala Gln Gly Gly Asn Phe His Gly
    515                 520                 525

Val Thr Val Asn Gly Ile Gly Arg Asp Ala Ala Val Gln Ile Tyr Tyr
530                 535                 540

Ser Ala Phe Thr Asn Tyr Leu Thr Ser Ser Ser Asp Phe Ser Asn Ala
545                 550                 555                 560

Arg Ala Ala Val Ile Gln Ala Ala Lys Asp Leu Tyr Gly Ala Asn Ser
                565                 570                 575

Ala Glu Ala Thr Ala Ala Ala Lys Ser Phe Asp Ala Val Gly Val Asn
        580                 585                 590

<210> SEQ ID NO 28
<211> LENGTH: 304
<212> TYPE: PRT
<213> ORGANISM: Paenibacillus polymyxa SC2
<220> FEATURE:

<221> NAME/KEY: misc_feature
<222> LOCATION: (1)..(304)
<223> OTHER INFORMATION: amino acid sequence of the predicted mature
      form of PpoPro1

<400> SEQUENCE: 28

Ala Thr Gly Thr Gly Lys Gly Val Leu Gly Asp Ser Lys Ser Phe Thr
1               5                   10                  15

Thr Thr Ala Ser Gly Ser Ser Tyr Gln Leu Lys Asp Thr Thr Arg Gly
            20                  25                  30

Asn Gly Ile Val Thr Tyr Thr Ala Ser Asn Arg Gln Ser Ile Pro Gly
        35                  40                  45

Thr Ile Leu Thr Asp Ala Asp Asn Val Trp Asn Asp Pro Ala Gly Val
    50                  55                  60

Asp Ala His Ala Tyr Ala Ala Lys Thr Tyr Asp Tyr Lys Ala Lys
65                  70                  75                  80

Phe Gly Arg Asn Ser Ile Asp Gly Arg Gly Leu Gln Leu Arg Ser Thr
                85                  90                  95

Val His Tyr Gly Ser Arg Tyr Asn Asn Ala Phe Trp Asn Gly Ser Gln
            100                 105                 110

Met Thr Tyr Gly Asp Gly Asp Gly Ser Thr Phe Ile Ala Phe Ser Gly
        115                 120                 125

Asp Pro Asp Val Val Gly His Glu Leu Thr His Gly Val Thr Glu Tyr
    130                 135                 140

Thr Ser Asn Leu Glu Tyr Tyr Gly Glu Ser Gly Ala Leu Asn Glu Ala
145                 150                 155                 160

Phe Ser Asp Val Ile Gly Asn Asp Ile Gln Arg Lys Asn Trp Leu Val
                165                 170                 175

Gly Asp Asp Ile Tyr Thr Pro Asn Ile Ala Gly Asp Ala Leu Arg Ser
            180                 185                 190

Met Ser Asn Pro Thr Leu Tyr Asp Gln Pro Asp His Tyr Ser Asn Leu
        195                 200                 205

Tyr Arg Gly Ser Ser Asp Asn Gly Gly Val His Thr Asn Ser Gly Ile
    210                 215                 220

Ile Asn Lys Ala Tyr Tyr Leu Leu Ala Gln Gly Gly Asn Phe His Gly
225                 230                 235                 240

Val Thr Val Asn Gly Ile Gly Arg Asp Ala Ala Val Gln Ile Tyr Tyr
                245                 250                 255

Ser Ala Phe Thr Asn Tyr Leu Thr Ser Ser Ser Asp Phe Ser Asn Ala
            260                 265                 270

Arg Ala Ala Val Ile Gln Ala Ala Lys Asp Leu Tyr Gly Ala Asn Ser
        275                 280                 285

Ala Glu Ala Thr Ala Ala Lys Ser Phe Asp Ala Val Gly Val Asn
    290                 295                 300

<210> SEQ ID NO 29
<211> LENGTH: 1800
<212> TYPE: DNA
<213> ORGANISM: Artificial Sequence
<220> FEATURE:
<223> OTHER INFORMATION: Synthetic: nucleotide sequence of the
      synthesized PpoPro1 gene in plasmid pGX138(AprE-PpoPro1)

<400> SEQUENCE: 29
gtgagaagca aaaaattgtg gatcagcttg ttgtttgcgt taacgttaat ctttacgatg      60
gcgttcagca acatgagcgc gcaggctgct ggaaaagaat catcagtgtc aggaccggct     120

| | |
|---|---|
| cagcttacac cgacatttca cgcagaacaa tggaaggctc cgacgtcagt ttcaggagac | 180 |
| gacatcgtgt ggagctacct gaatagacag aagaaaagcc tgctgggagt ggatagcagc | 240 |
| agcgtcagag agcagttcag aatcgttgac agaacgagcg acaaaagcgg agtcagccat | 300 |
| tatagactga agcagtacgt gaatggcatc ccggtttatg cgcagagca acaattcat | 360 |
| gttggcaaga gcggagaagt cacaagctat ctgggcgctg tggtcaatga agatcaacaa | 420 |
| gccgaggcta cagggaac aacgccgaaa attagcgcct cagaggcagt ctacacggcg | 480 |
| tacaaagaag cggctgcaag aatcgaagcc ctgccgacat cagacgatac aatttcaaaa | 540 |
| gatgcggagg agccgagctc agttagcaag gatacatacg cggaagccgc aaacaatgag | 600 |
| aaaacactga gcgtggacaa ggacgagctg tcacttgatc aggctagcgt ccttaaagac | 660 |
| agcaagatcg aggccgttga gcctgaaaag tcatcaattg cgaaaatcgc caatctgcaa | 720 |
| cctgaagtcg acccgaaggc ggaactgtac tactacccga aaggcgatga cctgcttctg | 780 |
| gtgtacgtca cggaagtgaa cgtcctggaa ccggcaccgc tgagaacaag atacatcatc | 840 |
| gacgcgaacg acggaagcat cgtcttccag tatgacatta tcaacgaagc aacgggaacg | 900 |
| ggcaaaggcg ttcttggaga ctcaaagagc ttcacgacaa cggcttcagg aagcagctac | 960 |
| cagctgaaag acacgacgag aggaaacgga atcgtcacat atacggcgtc aaacagacaa | 1020 |
| agcatccctg gcacaatcct gacggatgct gacaacgttt ggaatgatcc ggctggcgtg | 1080 |
| gatgcccatg cttatgcggc aaaaacgtat gactattaca aggcgaagtt cggcagaaat | 1140 |
| tcaatcgatg gcagaggact gcagcttaga agcacggtgc actacggatc aagatataac | 1200 |
| aatgccttct ggaacggcag ccagatgaca tacgagacg gagatggaag cacatttatt | 1260 |
| gcattcagcg gcgaccctga tgtggttggc catgagctga cgcatggcgt tacagaatat | 1320 |
| acgagcaatc ttgaatacta cggcgagtca ggcgctctga cgaggcatt tagcgatgtt | 1380 |
| atcggcaatg acatccagag aaaaaactgg ctggtgggcg acgatattta cacgcctaat | 1440 |
| atcgctggcg atgcccttag atcaatgtca aacccgacgc tgtatgatca gcctgaccac | 1500 |
| tactcaaacc tgtatagagg ctcatcagat aacggaggcg tccatacgaa tagcggcatc | 1560 |
| attaacaagg catattatct tctggcccag ggcggcaatt ttcatggagt gacggttaat | 1620 |
| ggaattggaa gagacgcagc cgtccaaatc tactacagcg ctttcacgaa ctaccttaca | 1680 |
| tcaagctcag actttagcaa tgccagagct gctgttatcc aggcagcgaa ggatctttac | 1740 |
| ggcgccaact cagccgaagc tacggccgca gctaaatcat ttgatgcagt gggcgttaat | 1800 |

<210> SEQ ID NO 30
<211> LENGTH: 600
<212> TYPE: PRT
<213> ORGANISM: Artificial Sequence
<220> FEATURE:
<223> OTHER INFORMATION: Synthetic: amino acid sequence of the PpoPro1
      precursor protein expressed from plasmid pGX138(AprE-PpoPro1)

<400> SEQUENCE: 30

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Glu Ser Ser Val Ser Gly Pro Ala Gln Leu Thr Pro Thr Phe His Ala
        35                  40                  45

Glu Gln Trp Lys Ala Pro Thr Ser Val Ser Gly Asp Asp Ile Val Trp
    50                  55                  60

-continued

```
Ser Tyr Leu Asn Arg Gln Lys Lys Ser Leu Leu Gly Val Asp Ser Ser
 65                  70                  75                  80

Ser Val Arg Glu Gln Phe Arg Ile Val Asp Arg Thr Ser Asp Lys Ser
                 85                  90                  95

Gly Val Ser His Tyr Arg Leu Lys Gln Tyr Val Asn Gly Ile Pro Val
            100                 105                 110

Tyr Gly Ala Glu Gln Thr Ile His Val Gly Lys Ser Gly Glu Val Thr
        115                 120                 125

Ser Tyr Leu Gly Ala Val Val Asn Glu Asp Gln Gln Ala Glu Ala Thr
    130                 135                 140

Gln Gly Thr Thr Pro Lys Ile Ser Ala Ser Glu Ala Val Tyr Thr Ala
145                 150                 155                 160

Tyr Lys Glu Ala Ala Arg Ile Glu Ala Leu Pro Thr Ser Asp Asp
                165                 170                 175

Thr Ile Ser Lys Asp Ala Glu Glu Pro Ser Ser Val Ser Lys Asp Thr
                180                 185                 190

Tyr Ala Glu Ala Ala Asn Asn Glu Lys Thr Leu Ser Val Asp Lys Asp
            195                 200                 205

Glu Leu Ser Leu Asp Gln Ala Ser Val Leu Lys Asp Ser Lys Ile Glu
        210                 215                 220

Ala Val Glu Pro Glu Lys Ser Ser Ile Ala Lys Ile Ala Asn Leu Gln
225                 230                 235                 240

Pro Glu Val Asp Pro Lys Ala Glu Leu Tyr Tyr Pro Lys Gly Asp
                245                 250                 255

Asp Leu Leu Leu Val Tyr Val Thr Glu Val Asn Val Leu Glu Pro Ala
            260                 265                 270

Pro Leu Arg Thr Arg Tyr Ile Ile Asp Ala Asn Asp Gly Ser Ile Val
        275                 280                 285

Phe Gln Tyr Asp Ile Ile Asn Glu Ala Thr Gly Thr Gly Lys Gly Val
    290                 295                 300

Leu Gly Asp Ser Lys Ser Phe Thr Thr Ala Ser Gly Ser Ser Tyr
305                 310                 315                 320

Gln Leu Lys Asp Thr Thr Arg Gly Asn Gly Ile Val Thr Tyr Thr Ala
                325                 330                 335

Ser Asn Arg Gln Ser Ile Pro Gly Thr Ile Leu Thr Asp Ala Asp Asn
            340                 345                 350

Val Trp Asn Asp Pro Ala Gly Val Asp Ala His Ala Tyr Ala Ala Lys
        355                 360                 365

Thr Tyr Asp Tyr Tyr Lys Ala Lys Phe Gly Arg Asn Ser Ile Asp Gly
    370                 375                 380

Arg Gly Leu Gln Leu Arg Ser Thr Val His Tyr Gly Ser Arg Tyr Asn
385                 390                 395                 400

Asn Ala Phe Trp Asn Gly Ser Gln Met Thr Tyr Gly Asp Gly Asp Gly
                405                 410                 415

Ser Thr Phe Ile Ala Phe Ser Gly Asp Pro Asp Val Val Gly His Glu
            420                 425                 430

Leu Thr His Gly Val Thr Glu Tyr Thr Ser Asn Leu Glu Tyr Tyr Gly
        435                 440                 445

Glu Ser Gly Ala Leu Asn Glu Ala Phe Ser Asp Val Ile Gly Asn Asp
    450                 455                 460

Ile Gln Arg Lys Asn Trp Leu Val Gly Asp Ile Tyr Thr Pro Asn
465                 470                 475                 480

Ile Ala Gly Asp Ala Leu Arg Ser Met Ser Asn Pro Thr Leu Tyr Asp
```

|  |  |  | 485 |  |  |  | 490 |  |  |  | 495 |  |
|---|---|---|---|---|---|---|---|---|---|---|---|---|

Gln Pro Asp His Tyr Ser Asn Leu Tyr Arg Gly Ser Ser Asp Asn Gly
                500                 505                 510

Gly Val His Thr Asn Ser Gly Ile Ile Asn Lys Ala Tyr Tyr Leu Leu
                515                 520                 525

Ala Gln Gly Gly Asn Phe His Gly Val Thr Val Asn Gly Ile Gly Arg
                530                 535                 540

Asp Ala Ala Val Gln Ile Tyr Tyr Ser Ala Phe Thr Asn Tyr Leu Thr
545                 550                 555                 560

Ser Ser Ser Asp Phe Ser Asn Ala Arg Ala Ala Val Ile Gln Ala Ala
                565                 570                 575

Lys Asp Leu Tyr Gly Ala Asn Ser Ala Glu Ala Thr Ala Ala Ala Lys
                580                 585                 590

Ser Phe Asp Ala Val Gly Val Asn
                595                 600

<210> SEQ ID NO 31
<211> LENGTH: 1641
<212> TYPE: DNA
<213> ORGANISM: Paenibacillus hunanensis
<220> FEATURE:
<221> NAME/KEY: misc_feature
<222> LOCATION: (1)..(1641)
<223> OTHER INFORMATION: nucleotide sequence of the PhuPro1 gene
      isolated from Paenibacillus hunanensis

<400> SEQUENCE: 31

| ttgaaaaaaa cagttggtct tttacttgca ggtagcttgc tcgttggtgc tacaacgtcc | 60 |
|---|---|
| gctttcgcag cagaagcaaa tgatctggca ccactcggtg attacacgcc aaaattgatt | 120 |
| acgcaagcaa caggcatcac tggcgctagt ggcgatgcta agtatggaa gttcctggag | 180 |
| aagcaaaaac gtaccatcgt aaccgatgat gcagcttctg ctgatgtgaa ggaattgttt | 240 |
| gagatcacaa aacgtcaatc cgattctcaa accggtacag agcactatcg cctgaaccaa | 300 |
| acctttaaag gcatcccagt ctatggcgca gagcaaacac tgcactttga caaatccggc | 360 |
| aatgtatctc tgtacatggg tcaggttgtt gaggatgtgt ccgctaaaact ggaagcttcc | 420 |
| gattccaaaa aaggcgtaac tgaggatgta tacgcttcgg atacgaaaaa tgatctggta | 480 |
| acaccagaaa tcagcgcttc tcaagccatc tcgattgctg aaaaggatgc agcttccaaa | 540 |
| atcggctccc tcggcgaagc acaaaaaacg ccagaagcga agctgtatat ctacgctcct | 600 |
| gaggatcaag cagcacgtct ggcttatgtg acagaagtaa acgtactgga gccatctccg | 660 |
| ctgcgtactc gctattttgt agatgcaaaa acaggttcga tcctgttcca atatgatctg | 720 |
| attgagcatg caacaggtac aggtaaaggg gtactgggtg ataccaagtc cttcactgta | 780 |
| ggtacttccg gttcttccta tgtgatgact gatagcacgc gtggaaaagg tatccaaacc | 840 |
| tacacggcgt ctaaccgcac atcactgcca ggtagcactg taacgagcag cagcagcaca | 900 |
| tttaacgatc cagcatctgt cgatgcccat gcgtatgcac aaaaagtata tgatttctac | 960 |
| aaatccaact ttaaccgcaa cagcatcgac ggtaatggtc tggctatccg ctccactacg | 1020 |
| cactattcca cacgttataa caatgcgttc tggaatggtt cccaaatggt atacggtgat | 1080 |
| ggcgatggtt cgcaattcat cgcattctcc ggcgaccttg acgtagtagg tcacgagctg | 1140 |
| acacacggtg taaccgagta cacagcgaac ctggaatact atggtcaatc cggtgcactg | 1200 |
| aacgaatcca tttcggatat cttttggtaac acaatcgaag gtaaaaactg gatggtaggc | 1260 |
| gatgcgatct acacaccagg cgtatccggc gatgctcttc gctacatgga tgatccaaca | 1320 |

-continued

```
aaaggtggac aaccagcgcg tatggcagat tacaacaaca caagcgctga taatggcggt    1380
gtacacacaa acagtggtat cccgaataaa gcatactact tgctggcaca gggtggcaca    1440
tttggcggtg taaatgtaac aggtatcggt cgctcgcaag cgatccagat cgtttaccgt    1500
gcactaacat actacctgac atccacatct aacttctcga actaccgttc tgcaatggtg    1560
caagcatcta cagacctgta cggtgcaaac tctacacaaa caacagcggt gaaaaactcg    1620
ctgagcgcag taggcattaa c                                              1641
```

<210> SEQ ID NO 32
<211> LENGTH: 547
<212> TYPE: PRT
<213> ORGANISM: Paenibacillus hunanensis
<220> FEATURE:
<221> NAME/KEY: misc_feature
<222> LOCATION: (1)..(547)
<223> OTHER INFORMATION: amino acid sequence of the PhuPro1 precursor
      protein

<400> SEQUENCE: 32

Met Lys Lys Thr Val Gly Leu Leu Ala Gly Ser Leu Leu Val Gly
1               5                   10                  15

Ala Thr Thr Ser Ala Phe Ala Ala Glu Ala Asn Asp Leu Ala Pro Leu
            20                  25                  30

Gly Asp Tyr Thr Pro Lys Leu Ile Thr Gln Ala Thr Gly Ile Thr Gly
        35                  40                  45

Ala Ser Gly Asp Ala Lys Val Trp Lys Phe Leu Glu Lys Gln Lys Arg
    50                  55                  60

Thr Ile Val Thr Asp Asp Ala Ala Ser Ala Asp Val Lys Glu Leu Phe
65                  70                  75                  80

Glu Ile Thr Lys Arg Gln Ser Asp Ser Gln Thr Gly Thr Glu His Tyr
                85                  90                  95

Arg Leu Asn Gln Thr Phe Lys Gly Ile Pro Val Tyr Gly Ala Glu Gln
            100                 105                 110

Thr Leu His Phe Asp Lys Ser Gly Asn Val Ser Leu Tyr Met Gly Gln
        115                 120                 125

Val Val Glu Asp Val Ser Ala Lys Leu Glu Ala Ser Asp Ser Lys Lys
    130                 135                 140

Gly Val Thr Glu Asp Val Tyr Ala Ser Asp Thr Lys Asn Asp Leu Val
145                 150                 155                 160

Thr Pro Glu Ile Ser Ala Ser Gln Ala Ile Ser Ile Ala Glu Lys Asp
                165                 170                 175

Ala Ala Ser Lys Ile Gly Ser Leu Gly Glu Ala Gln Lys Thr Pro Glu
            180                 185                 190

Ala Lys Leu Tyr Ile Tyr Ala Pro Glu Asp Gln Ala Ala Arg Leu Ala
        195                 200                 205

Tyr Val Thr Glu Val Asn Val Leu Glu Pro Ser Leu Arg Thr Arg
    210                 215                 220

Tyr Phe Val Asp Ala Lys Thr Gly Ser Ile Leu Phe Gln Tyr Asp Leu
225                 230                 235                 240

Ile Glu His Ala Thr Gly Thr Gly Lys Gly Val Leu Gly Asp Thr Lys
                245                 250                 255

Ser Phe Thr Val Gly Thr Ser Gly Ser Ser Tyr Val Met Thr Asp Ser
            260                 265                 270

Thr Arg Gly Lys Gly Ile Gln Thr Tyr Thr Ala Ser Asn Arg Thr Ser
        275                 280                 285

-continued

Leu Pro Gly Ser Thr Val Thr Ser Ser Ser Thr Phe Asn Asp Pro
290                 295                 300

Ala Ser Val Asp Ala His Ala Tyr Ala Gln Lys Val Tyr Asp Phe Tyr
305                 310                 315                 320

Lys Ser Asn Phe Asn Arg Asn Ser Ile Asp Gly Asn Gly Leu Ala Ile
                325                 330                 335

Arg Ser Thr Thr His Tyr Ser Thr Arg Tyr Asn Asn Ala Phe Trp Asn
                340                 345                 350

Gly Ser Gln Met Val Tyr Gly Asp Gly Asp Gly Ser Gln Phe Ile Ala
                355                 360                 365

Phe Ser Gly Asp Leu Asp Val Val Gly His Glu Leu Thr His Gly Val
370                 375                 380

Thr Glu Tyr Thr Ala Asn Leu Glu Tyr Gly Gln Ser Gly Ala Leu
385                 390                 395                 400

Asn Glu Ser Ile Ser Asp Ile Phe Gly Asn Thr Ile Glu Gly Lys Asn
                405                 410                 415

Trp Met Val Gly Asp Ala Ile Tyr Thr Pro Gly Val Ser Gly Asp Ala
                420                 425                 430

Leu Arg Tyr Met Asp Asp Pro Thr Lys Gly Gly Gln Pro Ala Arg Met
                435                 440                 445

Ala Asp Tyr Asn Asn Thr Ser Ala Asp Asn Gly Val His Thr Asn
450                 455                 460

Ser Gly Ile Pro Asn Lys Ala Tyr Tyr Leu Leu Ala Gln Gly Thr
465                 470                 475                 480

Phe Gly Gly Val Asn Val Thr Gly Ile Gly Arg Ser Gln Ala Ile Gln
                485                 490                 495

Ile Val Tyr Arg Ala Leu Thr Tyr Tyr Leu Thr Ser Ser Asn Phe
                500                 505                 510

Ser Asn Tyr Arg Ser Ala Met Val Gln Ala Ser Thr Asp Leu Tyr Gly
                515                 520                 525

Ala Asn Ser Thr Gln Thr Thr Ala Val Lys Asn Ser Leu Ser Ala Val
530                 535                 540

Gly Ile Asn
545

<210> SEQ ID NO 33
<211> LENGTH: 304
<212> TYPE: PRT
<213> ORGANISM: Paenibacillus hunanensis
<220> FEATURE:
<221> NAME/KEY: misc_feature
<222> LOCATION: (1)..(304)
<223> OTHER INFORMATION: amino acid sequence of the predicted mature
      form of PhuPro1

<400> SEQUENCE: 33

Ala Thr Gly Thr Gly Lys Gly Val Leu Gly Asp Thr Lys Ser Phe Thr
1               5                   10                  15

Val Gly Thr Ser Gly Ser Ser Tyr Val Met Thr Asp Ser Thr Arg Gly
                20                  25                  30

Lys Gly Ile Gln Thr Tyr Thr Ala Ser Asn Arg Thr Ser Leu Pro Gly
                35                  40                  45

Ser Thr Val Thr Ser Ser Ser Thr Phe Asn Asp Pro Ala Ser Val
                50                  55                  60

Asp Ala His Ala Tyr Ala Gln Lys Val Tyr Asp Phe Tyr Lys Ser Asn
65                  70                  75                  80

```
Phe Asn Arg Asn Ser Ile Asp Gly Asn Gly Leu Ala Ile Arg Ser Thr
                85                  90                  95

Thr His Tyr Ser Thr Arg Tyr Asn Asn Ala Phe Trp Asn Gly Ser Gln
            100                 105                 110

Met Val Tyr Gly Asp Gly Asp Ser Gln Phe Ile Ala Phe Ser Gly
        115                 120                 125

Asp Leu Asp Val Val Gly His Glu Leu Thr His Gly Val Thr Glu Tyr
    130                 135                 140

Thr Ala Asn Leu Glu Tyr Tyr Gly Gln Ser Gly Ala Leu Asn Glu Ser
145                 150                 155                 160

Ile Ser Asp Ile Phe Gly Asn Thr Ile Glu Gly Lys Asn Trp Met Val
                165                 170                 175

Gly Asp Ala Ile Tyr Thr Pro Gly Val Ser Gly Asp Ala Leu Arg Tyr
            180                 185                 190

Met Asp Asp Pro Thr Lys Gly Gly Gln Pro Ala Arg Met Ala Asp Tyr
            195                 200                 205

Asn Asn Thr Ser Ala Asp Asn Gly Val His Thr Asn Ser Gly Ile
    210                 215                 220

Pro Asn Lys Ala Tyr Tyr Leu Leu Ala Gln Gly Gly Thr Phe Gly Gly
225                 230                 235                 240

Val Asn Val Thr Gly Ile Gly Arg Ser Gln Ala Ile Gln Ile Val Tyr
            245                 250                 255

Arg Ala Leu Thr Tyr Tyr Leu Thr Ser Thr Ser Asn Phe Ser Asn Tyr
            260                 265                 270

Arg Ser Ala Met Val Gln Ala Ser Thr Asp Leu Tyr Gly Ala Asn Ser
            275                 280                 285

Thr Gln Thr Thr Ala Val Lys Asn Ser Leu Ser Ala Val Gly Ile Asn
            290                 295                 300

<210> SEQ ID NO 34
<211> LENGTH: 1671
<212> TYPE: DNA
<213> ORGANISM: Artificial Sequence
<220> FEATURE:
<223> OTHER INFORMATION: Synthetic: nucleotide sequence of the
      synthesized PhuPro1 gene in plasmid pGX149(AprE- PhuPro1)

<400> SEQUENCE: 34
gtgagaagca aaaaattgtg gatcagcttg ttgtttgcgt taacgttaat ctttacgatg      60
gcgttcagca acatgagcgc gcaggctgct ggaaaagcag aagctaatga tcttgccccg     120
cttggcgatt atacaccgaa gcttattaca caggcaacgg gaattacagg cgcatcaggc     180
gatgcgaagg tgtggaagtt cctggagaag cagaagagaa cgattgtcac ggacgacgcc     240
gcaagcgcgg atgtcaagga gctgttcgag atcacgaaga acagagcga tagccagacg      300 ggaacggagc attacagact gaaccagacg ttcaagggca ttccggtcta cggagctgaa     360
caaacgctgc attttgataa agcggcaac gtctcactgt acatgggcca agtcgttgag      420
gacgttagcg ccaaacttga ggctagcgac agcaagaaag gcgtcacaga agatgtctac     480
gcgtcagaca cgaaaaacga cctggttaca ccggaaatct cagcttcaca ggccatctca     540
attgcagaga agacgcagc gtcaaaaatc ggctcactgg gcgaggctca gaaaacgccg     600
gaggcgaaac tttacatcta cgcccctgag gaccaggctg cgagactggc ttacgtgaca     660
gaagttaatg tgctggagcc gtcaccgctt agaacgagat atttcgtgga cgcaaagacg     720
ggcagcattc tgtttcagta cgatcttatc gaacacgcga caggcacagg aaagggagtt     780
```

```
ctgggagaca caaaaagctt cacggttggc acgtcaggca gcagctacgt gatgacagac      840
agcacgagag gcaagggcat tcaaacgtat acagcgagca acagaacaag cctgccggga      900
agcacagtca cgagctcatc atcaacgttt aatgacccgg cctcagtgga tgctcacgca      960
tacgcgcaga aagtgtacga cttctacaaa agcaacttca atagaaacag catcgacgga     1020
aacggccttg cgatcagaag cacgacgcac tacagcacaa gatacaacaa cgccttctgg     1080
aacggcagcc aaatggttta cggcgatggc gacggatcac agtttatcgc atttagcgga     1140
gacctggacg tcgttggcca tgagctgaca catggcgtta cggagtacac agcaaacctg     1200
gaatactatg gccagtcagg cgcccttaac gagagcatca gcgacatttt tggcaatacg     1260
atcgaaggaa agaactggat ggtcggcgac gcaatctaca caccgggcgt ttcaggcgat     1320
gcactgagat atatggacga cccgacaaag ggcggacagc cggccagaat ggcggattac     1380
aataatacgt cagcagataa cggcggcgtg catacaaata gcggcatccc taacaaagca     1440
tattacctgc ttgcgcaagg aggaacattt ggcggcgtga atgttacggg cattggcaga     1500
tcacaagcga ttcagatcgt ttacagagcg ctgacgtact accttacgag cacgagcaat     1560
tttagcaact acagaagcgc aatggtgcag gcaagcacgg atctgtatgg cgcaaattca     1620
acacaaacga cggcggtcaa gaatagcctt tcagcagtgg gcattaacta a             1671
```

<210> SEQ ID NO 35
<211> LENGTH: 556
<212> TYPE: PRT
<213> ORGANISM: Artificial Sequence
<220> FEATURE:
<223> OTHER INFORMATION: Synthetic: amino acid sequence of the PhuPro1
     precursor protein expressed from plasmid pGX149(AprE- PhuPro1)

<400> SEQUENCE: 35

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ala Glu Ala Asn Asp Leu Ala Pro Leu Gly Asp Tyr Thr Pro Lys Leu
        35                  40                  45

Ile Thr Gln Ala Thr Gly Ile Thr Gly Ala Ser Gly Asp Ala Lys Val
    50                  55                  60

Trp Lys Phe Leu Glu Lys Gln Lys Arg Thr Ile Val Thr Asp Asp Ala
65                  70                  75                  80

Ala Ser Ala Asp Val Lys Glu Leu Phe Glu Ile Thr Lys Arg Gln Ser
                85                  90                  95

Asp Ser Gln Thr Gly Thr Glu His Tyr Arg Leu Asn Gln Thr Phe Lys
            100                 105                 110

Gly Ile Pro Val Tyr Gly Ala Glu Gln Thr Leu His Phe Asp Lys Ser
        115                 120                 125

Gly Asn Val Ser Leu Tyr Met Gly Gln Val Val Glu Asp Val Ser Ala
    130                 135                 140

Lys Leu Glu Ala Ser Asp Ser Lys Lys Gly Val Thr Glu Asp Val Tyr
145                 150                 155                 160

Ala Ser Asp Thr Lys Asn Asp Leu Val Thr Pro Glu Ile Ser Ala Ser
                165                 170                 175

Gln Ala Ile Ser Ile Ala Glu Lys Asp Ala Ala Ser Lys Ile Gly Ser
            180                 185                 190

Leu Gly Glu Ala Gln Lys Thr Pro Glu Ala Lys Leu Tyr Ile Tyr Ala
```

|   |   |   |   |   | 195 |   |   |   |   | 200 |   |   |   |   | 205 |   |
|---|---|---|---|---|---|---|---|---|---|---|---|---|---|---|---|---|

Pro Glu Asp Gln Ala Ala Arg Leu Ala Tyr Val Thr Glu Val Asn Val
210                 215                 220

Leu Glu Pro Ser Pro Leu Arg Thr Arg Tyr Phe Val Asp Ala Lys Thr
225                 230                 235                 240

Gly Ser Ile Leu Phe Gln Tyr Asp Leu Ile Glu His Ala Thr Gly Thr
            245                 250                 255

Gly Lys Gly Val Leu Gly Asp Thr Lys Ser Phe Thr Val Gly Thr Ser
        260                 265                 270

Gly Ser Ser Tyr Val Met Thr Asp Ser Thr Arg Gly Lys Gly Ile Gln
        275                 280                 285

Thr Tyr Thr Ala Ser Asn Arg Thr Ser Leu Pro Gly Ser Thr Val Thr
    290                 295                 300

Ser Ser Ser Ser Thr Phe Asn Asp Pro Ala Ser Val Asp Ala His Ala
305                 310                 315                 320

Tyr Ala Gln Lys Val Tyr Asp Phe Tyr Lys Ser Asn Phe Asn Arg Asn
                325                 330                 335

Ser Ile Asp Gly Asn Gly Leu Ala Ile Arg Ser Thr Thr His Tyr Ser
            340                 345                 350

Thr Arg Tyr Asn Asn Ala Phe Trp Asn Gly Ser Gln Met Val Tyr Gly
        355                 360                 365

Asp Gly Asp Gly Ser Gln Phe Ile Ala Phe Ser Gly Asp Leu Asp Val
    370                 375                 380

Val Gly His Glu Leu Thr His Gly Val Thr Glu Tyr Thr Ala Asn Leu
385                 390                 395                 400

Glu Tyr Tyr Gly Gln Ser Gly Ala Leu Asn Glu Ser Ile Ser Asp Ile
                405                 410                 415

Phe Gly Asn Thr Ile Glu Gly Lys Asn Trp Met Val Gly Asp Ala Ile
            420                 425                 430

Tyr Thr Pro Gly Val Ser Gly Asp Ala Leu Arg Tyr Met Asp Asp Pro
        435                 440                 445

Thr Lys Gly Gly Gln Pro Ala Arg Met Ala Asp Tyr Asn Asn Thr Ser
    450                 455                 460

Ala Asp Asn Gly Gly Val His Thr Asn Ser Gly Ile Pro Asn Lys Ala
465                 470                 475                 480

Tyr Tyr Leu Leu Ala Gln Gly Gly Thr Phe Gly Gly Val Asn Val Thr
                485                 490                 495

Gly Ile Gly Arg Ser Gln Ala Ile Gln Ile Val Tyr Arg Ala Leu Thr
            500                 505                 510

Tyr Tyr Leu Thr Ser Thr Ser Asn Phe Ser Asn Tyr Arg Ser Ala Met
        515                 520                 525

Val Gln Ala Ser Thr Asp Leu Tyr Gly Ala Asn Ser Thr Gln Thr Thr
    530                 535                 540

Ala Val Lys Asn Ser Leu Ser Ala Val Gly Ile Asn
545                 550                 555

<210> SEQ ID NO 36
<211> LENGTH: 1563
<212> TYPE: DNA
<213> ORGANISM: Paenibacillus amylolyticus
<220> FEATURE:
<221> NAME/KEY: misc_feature
<222> LOCATION: (1)..(1563)
<223> OTHER INFORMATION: nucleotide sequence of the PamPro1 gene
      isolated from Paenibacillus amylolyticus

```
<400> SEQUENCE: 36
atgaaattcg ccaaagttat gccaacaatt cttggaggag ctcttttgct cgcttccgta      60
tcctctgcta ctgcagctcc agtgtctgat caatccattc cacttcaggc cccttatgcc     120
tctgaggggg gtattccatt gaacagtgga acagatgaca ctatctttaa ttatcttgga     180
cagcaggaac aatttctgaa ttccgatgtg aaatcccagc tcaaaattgt caaagaaac      240
acagatacat ctggcgtaag acacttccgc ctgaaacagt atattaaagg tatcccggtt     300
tatggtgcag aacagacggt ccacctggac aaaaccggag ccgtgagctc cgcacttggc     360
gatcttccac cgattgaaga gcaggccatt ccgaatgatg tgtagccga gatcagcgga      420
gaagacgcga tccagattgc aaccgaagaa gcaacctccc ggattggaga gcttggtgcc     480
gcggaaatca cgcctcaagc tgaattgaac atctatcatc atgaagaaga tggtcagaca     540
tatctggttt acattacgga agtaaacgta ctggaacctg cccctctacg gaccaaatat     600
ttcattaacg cagtggatgg cagtatcgta tcccagtttg acctcattaa cttcgctact     660
ggaacaggta caggtgtact cggtgatacc aaaaccctga caaccaccca atccggcagc     720
accttccaac tgaaagacac cactcgtggc aatggcatcc aaacgtatac ggcaaacaat     780
ggctcctcac tgcctggtag cttgcttaca gattcggata atgtatggac cgatcgtgca     840
ggtgtagatg ctcatgctca tgccgctgct acgtatgatt tctacaaaaa caattcaac     900
cgtaacggta ttaatggtaa cggattgttg atcagatcaa ccgtgcacta cggctccaat     960
tacaataacg ccttctggaa cggggcacag attgtctttg gtgacggaga tggaacgatg    1020
ttccgatccc tgtctggtga tctggatgtt gtgggtcatg aattgacgca tggtgttatt    1080
gaatatacag ccaatctgga atatcgcaat gaaccaggtg cactcaatga agcctttgcc    1140
gatattttcg gtaatacgat ccaaagcaaa aactggctgc tcggtgatga tatctacaca    1200
cctaacactc caggagatgc gctgcgctcc ctctccaacc ctacattgta tggtcaacct    1260
gacaaataca gcgatcgcta cacaggctca caggacaacg gcggtgtcca tatcaacagt    1320
ggtatcatca ataaagccta tttccttgct gctcaaggcg aaacacataa tggtgtgact    1380
gttaccggaa tcggccggga taaagcgatc cagattttct acagcacact ggtgaactac    1440
ctgacaccaa cgtccaaatt tgccgctgcc aaaacagcta ccattcaagc agccaaagat    1500
ctgtacggag caacttccgc tgaagctact gctattacca aagcatatca agctgtaggc    1560
ctg                                                                  1563

<210> SEQ ID NO 37
<211> LENGTH: 521
<212> TYPE: PRT
<213> ORGANISM: Paenibacillus amylolyticus
<220> FEATURE:
<221> NAME/KEY: misc_feature
<222> LOCATION: (1)..(521)
<223> OTHER INFORMATION: amino acid sequence of the PamPro1 precursor
      protein

<400> SEQUENCE: 37

Met Lys Phe Ala Lys Val Met Pro Thr Ile Leu Gly Gly Ala Leu Leu
1               5                   10                  15

Leu Ala Ser Val Ser Ser Ala Thr Ala Ala Pro Val Ser Asp Gln Ser
            20                  25                  30

Ile Pro Leu Gln Ala Pro Tyr Ala Ser Glu Gly Gly Ile Pro Leu Asn
        35                  40                  45

Ser Gly Thr Asp Asp Thr Ile Phe Asn Tyr Leu Gly Gln Gln Glu Gln
```

```
                50                  55                  60

Phe Leu Asn Ser Asp Val Lys Ser Gln Leu Lys Ile Val Lys Arg Asn
 65                  70                  75                  80

Thr Asp Thr Ser Gly Val Arg His Phe Arg Leu Lys Gln Tyr Ile Lys
                 85                  90                  95

Gly Ile Pro Val Tyr Gly Ala Glu Gln Thr Val His Leu Asp Lys Thr
                100                 105                 110

Gly Ala Val Ser Ser Ala Leu Gly Asp Leu Pro Pro Ile Glu Glu Gln
                115                 120                 125

Ala Ile Pro Asn Asp Gly Val Ala Glu Ile Ser Gly Glu Asp Ala Ile
130                 135                 140

Gln Ile Ala Thr Glu Glu Ala Thr Ser Arg Ile Gly Glu Leu Gly Ala
145                 150                 155                 160

Ala Glu Ile Thr Pro Gln Ala Glu Leu Asn Ile Tyr His His Glu Glu
                165                 170                 175

Asp Gly Gln Thr Tyr Leu Val Tyr Ile Thr Glu Val Asn Val Leu Glu
                180                 185                 190

Pro Ala Pro Leu Arg Thr Lys Tyr Phe Ile Asn Ala Val Asp Gly Ser
                195                 200                 205

Ile Val Ser Gln Phe Asp Leu Ile Asn Phe Ala Thr Gly Thr Gly Thr
210                 215                 220

Gly Val Leu Gly Asp Thr Lys Thr Leu Thr Thr Thr Gln Ser Gly Ser
225                 230                 235                 240

Thr Phe Gln Leu Lys Asp Thr Thr Arg Gly Asn Gly Ile Gln Thr Tyr
                245                 250                 255

Thr Ala Asn Asn Gly Ser Ser Leu Pro Gly Ser Leu Leu Thr Asp Ser
                260                 265                 270

Asp Asn Val Trp Thr Asp Arg Ala Gly Val Asp Ala His Ala His Ala
                275                 280                 285

Ala Ala Thr Tyr Asp Phe Tyr Lys Asn Lys Phe Asn Arg Asn Gly Ile
290                 295                 300

Asn Gly Asn Gly Leu Leu Ile Arg Ser Thr Val His Tyr Gly Ser Asn
305                 310                 315                 320

Tyr Asn Asn Ala Phe Trp Asn Gly Ala Gln Ile Val Phe Gly Asp Gly
                325                 330                 335

Asp Gly Thr Met Phe Arg Ser Leu Ser Gly Asp Leu Asp Val Val Gly
                340                 345                 350

His Glu Leu Thr His Gly Val Ile Glu Tyr Thr Ala Asn Leu Glu Tyr
                355                 360                 365

Arg Asn Glu Pro Gly Ala Leu Asn Glu Ala Phe Ala Asp Ile Phe Gly
370                 375                 380

Asn Thr Ile Gln Ser Lys Asn Trp Leu Leu Gly Asp Asp Ile Tyr Thr
385                 390                 395                 400

Pro Asn Thr Pro Gly Asp Ala Leu Arg Ser Leu Ser Asn Pro Thr Leu
                405                 410                 415

Tyr Gly Gln Pro Asp Lys Tyr Ser Asp Arg Tyr Thr Gly Ser Gln Asp
                420                 425                 430

Asn Gly Gly Val His Ile Asn Ser Gly Ile Ile Asn Lys Ala Tyr Phe
                435                 440                 445

Leu Ala Ala Gln Gly Gly Thr His Asn Gly Val Thr Val Thr Gly Ile
                450                 455                 460

Gly Arg Asp Lys Ala Ile Gln Ile Phe Tyr Ser Thr Leu Val Asn Tyr
465                 470                 475                 480
```

```
Leu Thr Pro Thr Ser Lys Phe Ala Ala Lys Thr Ala Thr Ile Gln
            485                 490                 495

Ala Ala Lys Asp Leu Tyr Gly Ala Thr Ser Ala Glu Ala Thr Ala Ile
            500                 505                 510

Thr Lys Ala Tyr Gln Ala Val Gly Leu
            515                 520

<210> SEQ ID NO 38
<211> LENGTH: 303
<212> TYPE: PRT
<213> ORGANISM: Paenibacillus amylolyticus
<220> FEATURE:
<221> NAME/KEY: misc_feature
<222> LOCATION: (1)..(303)
<223> OTHER INFORMATION: amino acid sequence of the predicted mature
      form of PamPro1

<400> SEQUENCE: 38

Ala Thr Gly Thr Gly Thr Gly Val Leu Gly Asp Thr Lys Thr Leu Thr
1               5                   10                  15

Thr Thr Gln Ser Gly Ser Thr Phe Gln Leu Lys Asp Thr Thr Arg Gly
            20                  25                  30

Asn Gly Ile Gln Thr Tyr Thr Ala Asn Asn Gly Ser Ser Leu Pro Gly
        35                  40                  45

Ser Leu Leu Thr Asp Ser Asp Asn Val Trp Thr Asp Arg Ala Gly Val
    50                  55                  60

Asp Ala His Ala His Ala Ala Thr Tyr Asp Phe Tyr Lys Asn Lys
65                  70                  75                  80

Phe Asn Arg Asn Gly Ile Asn Gly Asn Gly Leu Leu Ile Arg Ser Thr
                85                  90                  95

Val His Tyr Gly Ser Asn Tyr Asn Asn Ala Phe Trp Asn Gly Ala Gln
            100                 105                 110

Ile Val Phe Gly Asp Gly Asp Gly Thr Met Phe Arg Ser Leu Ser Gly
        115                 120                 125

Asp Leu Asp Val Val Gly His Glu Leu Thr His Gly Val Ile Glu Tyr
    130                 135                 140

Thr Ala Asn Leu Glu Tyr Arg Asn Glu Pro Gly Ala Leu Asn Glu Ala
145                 150                 155                 160

Phe Ala Asp Ile Phe Gly Asn Thr Ile Gln Ser Lys Asn Trp Leu Leu
                165                 170                 175

Gly Asp Asp Ile Tyr Thr Pro Asn Thr Pro Gly Asp Ala Leu Arg Ser
            180                 185                 190

Leu Ser Asn Pro Thr Leu Tyr Gly Gln Pro Asp Lys Tyr Ser Asp Arg
        195                 200                 205

Tyr Thr Gly Ser Gln Asp Asn Gly Gly Val His Ile Asn Ser Gly Ile
    210                 215                 220

Ile Asn Lys Ala Tyr Phe Leu Ala Ala Gln Gly Gly Thr His Asn Gly
225                 230                 235                 240

Val Thr Val Thr Gly Ile Gly Arg Asp Lys Ala Ile Gln Ile Phe Tyr
                245                 250                 255

Ser Thr Leu Val Asn Tyr Leu Thr Pro Thr Ser Lys Phe Ala Ala Ala
            260                 265                 270

Lys Thr Ala Thr Ile Gln Ala Ala Lys Asp Leu Tyr Gly Ala Thr Ser
        275                 280                 285

Ala Glu Ala Thr Ala Ile Thr Lys Ala Tyr Gln Ala Val Gly Leu
    290                 295                 300
```

<210> SEQ ID NO 39
<211> LENGTH: 1587
<212> TYPE: DNA
<213> ORGANISM: Artificial Sequence
<220> FEATURE:
<223> OTHER INFORMATION: Synthetic: nucleotide sequence of the
synthesized PamPro1 gene in plasmid pGX146(AprE- PamPro1)

<400> SEQUENCE: 39

| | | | | | |
|---|---|---|---|---|---|
| gtgagaagca | aaaaattgtg | gatcagcttg | ttgtttgcgt | taacgttaat | ctttacgatg | 60 |
| gcgttcagca | acatgagcgc | gcaggctgct | ggaaaagctc | cggttagcga | ccagtcaatc | 120 |
| cctcttcaag | caccgtatgc | cagcgaagga | ggcattccgc | ttaacagcgg | cacggacgac | 180 |
| acgattttca | attacctggg | ccaacaggag | cagttcctga | cagcgacgt | caagagccag | 240 |
| ctgaagatcg | tcaaaagaaa | cacagacaca | tcaggcgtga | gacacttcag | actgaagcaa | 300 |
| tacatcaagg | gcatcccggt | ttatggcgct | gaacaaacgg | ttcacctgga | caaaacaggc | 360 |
| gcagtttcat | cagcactggg | agatctgccg | ccgattgaag | agcaagcaat | cccgaatgat | 420 |
| ggagttgcgg | aaattagcgg | cgaggatgca | atccaaatcg | cgacggagga | ggctacatca | 480 |
| agaattggag | aacttggcgc | agcggagatt | acaccgcagg | ctgaactgaa | catctatcac | 540 |
| catgaggaag | acggccagac | gtacctggtt | tacattacgg | aagtgaacgt | gctggaaccg | 600 |
| gcacctctga | gaacaaagta | ctttatcaac | gcggttgacg | gcagcatcgt | ctcacagttc | 660 |
| gacctgatta | acttcgccac | gggaacagga | acgggcgttc | ttggagacac | aaagacgctg | 720 |
| acgacgacgc | agtcaggcag | cacattccag | ctgaaggaca | caacaagagg | caacggcatc | 780 |
| caaacgtaca | cggcgaacaa | tggatcatca | ctgccgggct | cactgctgac | ggattcagat | 840 |
| aacgtgtgga | cggatagagc | tggcgttgac | gcgcatgctc | acgctgctgc | gacgtacgac | 900 |
| ttctacaaga | acaagttcaa | cagaaacggc | attaacggaa | atggcctgct | gatcagaagc | 960 |
| acggtgcatt | atggctcaaa | ctacaacaac | gcttttttgga | acggcgcaca | gatcgtgttt | 1020 |
| ggcgacggcg | atggcacaat | gtttagaagc | ctgtcaggag | acctggatgt | ggtgggccac | 1080 |
| gaactgacgc | acgcgtgat | cgagtatacg | gcgaaccttg | aatatagaaa | cgagccggga | 1140 |
| gcactgaatg | aggcgttcgc | ggacattttc | ggcaacacaa | tccagagcaa | aaactggctg | 1200 |
| ctgggcgacg | atatctatac | accgaacaca | ccgggcgatg | cactgagatc | actgtcaaat | 1260 |
| ccgacgctgt | atggccaacc | ggataagtac | tcagacagat | atacgggcag | ccaagacaat | 1320 |
| ggcggcgttc | acatcaactc | aggcatcatc | aacaaggctt | acttccttgc | ggcccaagga | 1380 |
| ggaacacata | acggcgttac | agttacaggc | attggcagag | acaaggcgat | ccagatcttt | 1440 |
| tacagcacgc | tggtgaacta | cctgacacct | acgtcaaagt | ttgccgcagc | gaaaacagca | 1500 |
| acaattcagg | cggctaaaga | cctgtacgga | gcgacatcag | ccgaggccac | agcaattaca | 1560 |
| aaagcatatc | aagcagttgg | ccttttaa | | | | 1587 |

<210> SEQ ID NO 40
<211> LENGTH: 528
<212> TYPE: PRT
<213> ORGANISM: Artificial Sequence
<220> FEATURE:
<223> OTHER INFORMATION: Synthetic: amino acid sequence of the PamPro1
precursor protein expressed from plasmid pGX146(AprE- PamPro1)

<400> SEQUENCE: 40

Met Arg Ser Lys Lys Leu Trp Ile Ser Leu Leu Phe Ala Leu Thr Leu
1               5                   10                  15

```
Ile Phe Thr Met Ala Phe Ser Asn Met Ser Ala Gln Ala Ala Gly Lys
            20                  25                  30

Ala Pro Val Ser Asp Gln Ser Ile Pro Leu Gln Ala Pro Tyr Ala Ser
            35                  40                  45

Glu Gly Gly Ile Pro Leu Asn Ser Gly Thr Asp Thr Ile Phe Asn
 50                  55                  60

Tyr Leu Gly Gln Gln Glu Gln Phe Leu Asn Ser Asp Val Lys Ser Gln
 65                  70                  75                  80

Leu Lys Ile Val Lys Arg Asn Thr Asp Thr Ser Gly Val Arg His Phe
                85                  90                  95

Arg Leu Lys Gln Tyr Ile Lys Gly Ile Pro Val Tyr Gly Ala Glu Gln
            100                 105                 110

Thr Val His Leu Asp Lys Thr Gly Ala Val Ser Ser Ala Leu Gly Asp
            115                 120                 125

Leu Pro Pro Ile Glu Glu Gln Ala Ile Pro Asn Asp Gly Val Ala Glu
130                 135                 140

Ile Ser Gly Glu Asp Ala Ile Gln Ile Ala Thr Glu Glu Ala Thr Ser
145                 150                 155                 160

Arg Ile Gly Glu Leu Gly Ala Ala Glu Ile Thr Pro Gln Ala Glu Leu
                165                 170                 175

Asn Ile Tyr His His Glu Glu Asp Gly Gln Thr Tyr Leu Val Tyr Ile
            180                 185                 190

Thr Glu Val Asn Val Leu Glu Pro Ala Pro Leu Arg Thr Lys Tyr Phe
            195                 200                 205

Ile Asn Ala Val Asp Gly Ser Ile Val Ser Gln Phe Asp Leu Ile Asn
210                 215                 220

Phe Ala Thr Gly Thr Gly Thr Gly Val Leu Gly Asp Thr Lys Thr Leu
225                 230                 235                 240

Thr Thr Thr Gln Ser Gly Ser Thr Phe Gln Leu Lys Asp Thr Thr Arg
                245                 250                 255

Gly Asn Gly Ile Gln Thr Tyr Thr Ala Asn Asn Gly Ser Ser Leu Pro
            260                 265                 270

Gly Ser Leu Leu Thr Asp Ser Asp Asn Val Trp Thr Asp Arg Ala Gly
            275                 280                 285

Val Asp Ala His Ala His Ala Ala Thr Tyr Asp Phe Tyr Lys Asn
290                 295                 300

Lys Phe Asn Arg Asn Gly Ile Asn Gly Asn Gly Leu Leu Ile Arg Ser
305                 310                 315                 320

Thr Val His Tyr Gly Ser Asn Tyr Asn Asn Ala Phe Trp Asn Gly Ala
                325                 330                 335

Gln Ile Val Phe Gly Asp Gly Asp Gly Thr Met Phe Arg Ser Leu Ser
            340                 345                 350

Gly Asp Leu Asp Val Val Gly His Glu Leu Thr His Gly Val Ile Glu
            355                 360                 365

Tyr Thr Ala Asn Leu Glu Tyr Arg Asn Glu Pro Gly Ala Leu Asn Glu
370                 375                 380

Ala Phe Ala Asp Ile Phe Gly Asn Thr Ile Gln Ser Lys Asn Trp Leu
385                 390                 395                 400

Leu Gly Asp Asp Ile Tyr Thr Pro Asn Thr Pro Gly Asp Ala Leu Arg
                405                 410                 415

Ser Leu Ser Asn Pro Thr Leu Tyr Gly Gln Pro Asp Lys Tyr Ser Asp
            420                 425                 430
```

-continued

```
Arg Tyr Thr Gly Ser Gln Asp Asn Gly Gly Val His Ile Asn Ser Gly
            435                 440                 445
Ile Ile Asn Lys Ala Tyr Phe Leu Ala Ala Gln Gly Gly Thr His Asn
        450                 455                 460
Gly Val Thr Val Thr Gly Ile Gly Arg Asp Lys Ala Ile Gln Ile Phe
465                 470                 475                 480
Tyr Ser Thr Leu Val Asn Tyr Leu Thr Pro Thr Ser Lys Phe Ala Ala
                485                 490                 495
Ala Lys Thr Ala Thr Ile Gln Ala Ala Lys Asp Leu Tyr Gly Ala Thr
            500                 505                 510
Ser Ala Glu Ala Thr Ala Ile Thr Lys Ala Tyr Gln Ala Val Gly Leu
        515                 520                 525
```

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 41

His Glu Xaa Xaa His
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 42

His Asp Xaa Xaa His
1               5

<210> SEQ ID NO 43
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Succinyl at 5'-end
<220> FEATURE:
<221> NAME/KEY: MOD_RES
<222> LOCATION: (4)..(4)
<223> OTHER INFORMATION: Para nitroanilide (pNA) at 3'-end

<400> SEQUENCE: 43

Ala Ala Pro Phe
1

<210> SEQ ID NO 44
<211> LENGTH: 306
<212> TYPE: PRT
<213> ORGANISM: Paenibacillus sp.
<220> FEATURE:

<221> NAME/KEY: misc_feature
<222> LOCATION: (1)..(306)
<223> OTHER INFORMATION: Paenibacillus_sp_Aloe-11

<400> SEQUENCE: 44

```
Asn Glu Ala Thr Gly Thr Gly Lys Gly Val Leu Gly Asp Thr Lys Thr
1               5                   10                  15

Phe Asn Thr Thr Ala Ser Gly Ser Ser Tyr Gln Leu Arg Asp Thr Thr
            20                  25                  30

Arg Gly Asn Gly Ile Val Thr Tyr Thr Ala Ser Asn Arg Gln Ser Ile
        35                  40                  45

Pro Gly Thr Ile Leu Thr Asp Ala Asp Asn Val Trp Asn Asp Pro Ala
    50                  55                  60

Gly Val Asp Ala His Ala Tyr Ala Ala Lys Thr Tyr Asp Tyr Lys
65                  70                  75                  80

Glu Lys Phe Asn Arg Asn Ser Ile Asp Gly Arg Gly Leu Gln Leu Arg
                85                  90                  95

Ser Thr Val His Tyr Gly Asn Arg Tyr Asn Asn Ala Phe Trp Asn Gly
            100                 105                 110

Ser Gln Met Thr Tyr Gly Asp Gly Asp Gly Thr Thr Phe Ile Ala Phe
        115                 120                 125

Ser Gly Asp Pro Asp Val Val Gly His Glu Leu Thr His Gly Val Thr
    130                 135                 140

Glu Tyr Thr Ser Asn Leu Glu Tyr Tyr Gly Glu Ser Gly Ala Leu Asn
145                 150                 155                 160

Glu Ala Phe Ser Asp Ile Ile Gly Asn Asp Ile Gln Arg Lys Asn Trp
                165                 170                 175

Leu Val Gly Asp Asp Ile Tyr Thr Pro Arg Ile Ala Gly Asp Ala Leu
            180                 185                 190

Arg Ser Met Ser Asn Pro Thr Leu Tyr Asp Gln Pro Asp His Tyr Ser
        195                 200                 205

Asn Leu Tyr Arg Gly Ser Ser Asp Asn Gly Gly Val His Thr Asn Ser
    210                 215                 220

Gly Ile Ile Asn Lys Ala Tyr Tyr Leu Leu Ala Gln Gly Gly Thr Phe
225                 230                 235                 240

His Gly Val Thr Val Asn Gly Ile Gly Arg Asp Ala Ala Val Gln Ile
                245                 250                 255

Tyr Tyr Ser Ala Phe Thr Asn Tyr Leu Thr Ser Ser Ser Asp Phe Ser
            260                 265                 270

Asn Ala Arg Asp Ala Val Val Gln Ala Ala Lys Asp Leu Tyr Gly Ala
        275                 280                 285

Ser Ser Ala Gln Ala Thr Ala Ala Ala Lys Ser Phe Asp Ala Val Gly
    290                 295                 300

Val Asn
305
```

<210> SEQ ID NO 45
<211> LENGTH: 316
<212> TYPE: PRT
<213> ORGANISM: B. thermoproteolyticus
<220> FEATURE:
<221> NAME/KEY: misc_feature
<222> LOCATION: (1)..(316)
<223> OTHER INFORMATION: B_thermoproteolyticus_P00800

<400> SEQUENCE: 45

Ile Thr Gly Thr Ser Thr Val Gly Val Gly Arg Gly Val Leu Gly Asp

```
            1               5                  10                 15
         Gln Lys Asn Ile Asn Thr Thr Tyr Ser Thr Tyr Tyr Tyr Leu Gln Asp
                         20                 25                 30

Asn Thr Arg Gly Asn Gly Ile Phe Thr Tyr Asp Ala Lys Tyr Arg Thr
                         35                 40                 45

Thr Leu Pro Gly Ser Leu Trp Ala Asp Ala Asp Asn Gln Phe Phe Ala
                  50                 55                 60

Ser Tyr Asp Ala Pro Ala Val Asp Ala His Tyr Tyr Ala Gly Val Thr
         65                 70                 75                 80

Tyr Asp Tyr Tyr Lys Asn Val His Asn Arg Leu Ser Tyr Asp Gly Asn
                         85                 90                 95

Asn Ala Ala Ile Arg Ser Ser Val His Tyr Ser Gln Gly Tyr Asn Asn
                         100                105                110

Ala Phe Trp Asn Gly Ser Gln Met Val Tyr Gly Asp Gly Asp Gly Gln
                         115                120                125

Thr Phe Ile Pro Leu Ser Gly Gly Ile Asp Val Val Ala His Glu Leu
                  130                135                140

Thr His Ala Val Thr Asp Tyr Thr Ala Gly Leu Ile Tyr Gln Asn Glu
         145                150                155                160

Ser Gly Ala Ile Asn Glu Ala Ile Ser Asp Ile Phe Gly Thr Leu Val
                         165                170                175

Glu Phe Tyr Ala Asn Lys Asn Pro Asp Trp Glu Ile Gly Glu Asp Val
                         180                185                190

Tyr Thr Pro Gly Ile Ser Gly Asp Ser Leu Arg Ser Met Ser Asp Pro
                         195                200                205

Ala Lys Tyr Gly Asp Pro Asp His Tyr Ser Lys Arg Tyr Thr Gly Thr
                  210                215                220

Gln Asp Asn Gly Gly Val His Ile Asn Ser Gly Ile Ile Asn Lys Ala
         225                230                235                240

Ala Tyr Leu Ile Ser Gln Gly Gly Thr His Tyr Gly Val Ser Val Val
                         245                250                255

Gly Ile Gly Arg Asp Lys Leu Gly Lys Ile Phe Tyr Arg Ala Leu Thr
                         260                265                270

Gln Tyr Leu Thr Pro Thr Ser Asn Phe Ser Gln Leu Arg Ala Ala Ala
                  275                280                285

Val Gln Ser Ala Thr Asp Leu Tyr Gly Ser Thr Ser Gln Glu Val Ala
         290                295                300

Ser Val Lys Gln Ala Phe Asp Ala Val Gly Val Lys
         305                310                315

<210> SEQ ID NO 46
<211> LENGTH: 306
<212> TYPE: PRT
<213> ORGANISM: Paenibacillus sp. Aloe-11
<220> FEATURE:
<221> NAME/KEY: misc_feature
<222> LOCATION: (1)..(306)
<223> OTHER INFORMATION: ZP_09775365.1_P_sp_Aloe-11

<400> SEQUENCE: 46

Ala Thr Gly Thr Gly Arg Gly Val Asp Gly Lys Thr Lys Ser Phe Thr
         1               5                  10                 15

Thr Thr Ala Ser Gly Asn Arg Tyr Gln Leu Lys Asp Thr Thr Arg Ser
                         20                 25                 30

Asn Gly Ile Val Thr Tyr Thr Ala Gly Asn Arg Gln Thr Thr Pro Gly
                         35                 40                 45
```

```
Thr Ile Leu Thr Asp Thr Asp Asn Val Trp Glu Asp Pro Ala Ala Val
        50                  55                  60

Asp Ala His Ala Tyr Ala Ile Lys Thr Tyr Asp Tyr Tyr Lys Asn Lys
 65                  70                  75                  80

Phe Gly Arg Asp Ser Ile Asp Gly Arg Gly Met Gln Ile Arg Ser Thr
                 85                  90                  95

Val His Tyr Gly Lys Lys Tyr Asn Asn Ala Phe Trp Asn Gly Ser Gln
            100                 105                 110

Met Thr Tyr Gly Asp Gly Asp Gly Ser Thr Phe Thr Phe Phe Ser Gly
            115                 120                 125

Asp Pro Asp Val Val Gly His Glu Leu Thr His Gly Val Thr Glu Phe
        130                 135                 140

Thr Ser Asn Leu Glu Tyr Tyr Gly Glu Ser Gly Ala Leu Asn Glu Ala
145                 150                 155                 160

Phe Ser Asp Ile Ile Gly Asn Asp Ile Asp Gly Thr Ser Trp Leu Leu
                165                 170                 175

Gly Asp Gly Ile Tyr Thr Pro Asn Ile Pro Gly Asp Ala Leu Arg Ser
            180                 185                 190

Leu Ser Asp Pro Thr Arg Phe Gly Gln Pro Asp His Tyr Ser Asn Phe
        195                 200                 205

Tyr Pro Asp Pro Asn Asn Asp Asp Glu Gly Gly Val His Thr Asn Ser
        210                 215                 220

Gly Ile Ile Asn Lys Ala Tyr Tyr Leu Leu Ala Gln Gly Gly Thr Ser
225                 230                 235                 240

His Gly Val Thr Val Thr Gly Ile Gly Arg Glu Ala Ala Val Phe Ile
                245                 250                 255

Tyr Tyr Asn Ala Phe Thr Asn Tyr Leu Thr Ser Thr Ser Asn Phe Ser
            260                 265                 270

Asn Ala Arg Ala Ala Val Ile Gln Ala Ala Lys Asp Phe Tyr Gly Ala
        275                 280                 285

Asp Ser Leu Ala Val Thr Ser Ala Ile Gln Ser Phe Asp Ala Val Gly
        290                 295                 300

Ile Lys
305

<210> SEQ ID NO 47
<211> LENGTH: 304
<212> TYPE: PRT
<213> ORGANISM: P. terrae
<220> FEATURE:
<221> NAME/KEY: misc_feature
<222> LOCATION: (1)..(304)
<223> OTHER INFORMATION: P_terrae_HPL-003_YP_005073223.

<400> SEQUENCE: 47

Ala Thr Gly Thr Gly Lys Gly Val Leu Gly Asp Thr Lys Ser Phe Asn
 1               5                  10                  15

Thr Thr Gln Ser Gly Ser Ser Tyr Gln Leu Lys Asp Thr Thr Arg Gly
             20                  25                  30

Asn Gly Ile Val Thr Tyr Thr Ala Ser Asn Arg Gln Thr Ile Pro Gly
         35                  40                  45

Thr Leu Leu Thr Asp Ala Asp Asn Val Trp Asn Asp Pro Ala Gly Val
        50                  55                  60

Asp Ala His Ala Tyr Ala Ala Lys Thr Tyr Asp Tyr Tyr Lys Asp Lys
 65                  70                  75                  80
```

Phe Gly Arg Asn Ser Ile Asp Gly Arg Gly Leu Gln Leu Arg Ser Thr
                85                  90                  95

Val His Tyr Gly Ser Arg Tyr Asn Asn Ala Phe Trp Asn Gly Ser Gln
            100                 105                 110

Met Thr Tyr Gly Asp Gly Asp Gly Thr Thr Phe Ile Ala Phe Ser Gly
            115                 120                 125

Asp Pro Asp Val Val Gly His Glu Leu Thr His Gly Val Thr Glu Tyr
            130                 135                 140

Thr Ser Asn Leu Asp Tyr Tyr Gly Glu Ser Gly Ala Leu Asn Glu Ser
145                 150                 155                 160

Phe Ser Asp Ile Ile Gly Asn Asp Ile Gln Arg Lys Asn Trp Leu Val
                165                 170                 175

Gly Asp Asp Ile Tyr Thr Pro Ser Ile Ala Gly Asp Ala Leu Arg Ser
            180                 185                 190

Met Ser Asn Pro Thr Leu Tyr Asp Gln Pro Asp His Tyr Ser Asn Leu
            195                 200                 205

Tyr Lys Gly Ser Ser Asp Asn Gly Gly Val His Thr Asn Ser Gly Ile
            210                 215                 220

Ile Asn Lys Ala Tyr Tyr Leu Leu Ala Gln Gly Gly Thr Phe His Asn
225                 230                 235                 240

Val Thr Val Ser Gly Ile Gly Arg Asp Ala Ala Val Gln Ile Tyr Tyr
                245                 250                 255

Ser Ala Phe Thr Asn Tyr Leu Thr Ser Thr Ser Asn Phe Ser Asn Thr
            260                 265                 270

Arg Ala Ala Val Val Gln Ala Ala Lys Asp Leu Tyr Gly Ala Asn Ser
            275                 280                 285

Ala Gln Ala Thr Ala Ala Ala Lys Ser Phe Asp Ala Val Gly Val Asn
            290                 295                 300

<210> SEQ ID NO 48
<211> LENGTH: 301
<212> TYPE: PRT
<213> ORGANISM: Paenibacillus elgii
<220> FEATURE:
<221> NAME/KEY: misc_feature
<222> LOCATION: (1)..(301)
<223> OTHER INFORMATION: Paenibacillus_elgii_B69_ZP_090

<400> SEQUENCE: 48

Ala Thr Gly Thr Gly Lys Gly Val Leu Gly Asp Thr Lys Ser Phe Thr
1               5                   10                  15

Thr Thr Gln Ser Gly Ser Ser Tyr Gln Leu Lys Asp Thr Thr Arg Gly
            20                  25                  30

Gln Gly Ile Val Thr Tyr Ser Ala Gly Asn Arg Thr Ser Leu Pro Gly
            35                  40                  45

Ser Leu Leu Thr Ser Thr Asn Asn Ile Trp Asn Asp Gly Ser Ala Val
50                  55                  60

Asp Ala His Ala Tyr Thr Gly Lys Val Tyr Asp Tyr Tyr Lys Asn Lys
65                  70                  75                  80

Phe Gly Arg Asn Ser Ile Asp Gly Asn Gly Leu Gln Leu Lys Ser Thr
                85                  90                  95

Val His Tyr Ser Thr Arg Tyr Asn Asn Ala Phe Trp Asn Gly Val Gln
            100                 105                 110

Met Val Tyr Gly Asp Gly Asp Gly Val Thr Phe Arg Ser Phe Pro Ala
            115                 120                 125

Asp Pro Asp Val Ile Gly His Glu Leu Thr His Gly Val Thr Glu Ser

```
                130             135             140
Thr Ala Gly Leu Glu Tyr Tyr Gly Glu Ser Gly Ala Leu Asn Glu Ser
145                 150                 155                 160

Ile Ser Asp Ile Phe Gly Asn Ala Ile Glu Gly Lys Asn Trp Leu Ile
                165                 170                 175

Gly Asp Leu Ile Thr Leu Asn Ala Gly Ala Leu Arg Ser Met Glu Asn
                180                 185                 190

Pro Lys Leu Tyr Arg Gln Pro Asp Arg Tyr Gln Asp Arg Tyr Thr Gly
            195                 200                 205

Pro Ser Asp Asn Gly Gly Val His Thr Asn Ser Gly Ile Asn Asn Lys
210                 215                 220

Ala Phe His Leu Ile Ala Gln Gly Gly Thr His Tyr Gly Val Thr Val
225                 230                 235                 240

Asn Gly Ile Gly Arg Ser Ala Ala Glu Gln Ile Phe Tyr Asp Ala Leu
                245                 250                 255

Thr His Tyr Leu Thr Pro Thr Ser Asn Phe Ser Ala Ile Arg Ala Ala
                260                 265                 270

Ala Ile Gln Ala Ala Thr Asp Ser Phe Gly Ala Asn Ser Ser Gln Val
            275                 280                 285

Asp Ala Val Lys Lys Ala Tyr Asn Ala Val Gly Val Asn
290                 295                 300

<210> SEQ ID NO 49
<211> LENGTH: 306
<212> TYPE: PRT
<213> ORGANISM: Paenibacillus polymyxa SC2
<220> FEATURE:
<221> NAME/KEY: misc_feature
<222> LOCATION: (1)..(306)
<223> OTHER INFORMATION: P_polymyxa_SC2

<400> SEQUENCE: 49

Asn Glu Ala Thr Gly Thr Gly Lys Gly Val Leu Gly Asp Ser Lys Ser
1               5                   10                  15

Phe Thr Thr Thr Ala Ser Gly Ser Ser Tyr Gln Leu Lys Asp Thr Thr
                20                  25                  30

Arg Gly Asn Gly Ile Val Thr Tyr Thr Ala Ser Asn Arg Gln Ser Ile
            35                  40                  45

Pro Gly Thr Ile Leu Thr Asp Ala Asp Asn Val Trp Asn Asp Pro Ala
        50                  55                  60

Gly Val Asp Ala His Ala Tyr Ala Ala Lys Thr Tyr Asp Tyr Tyr Lys
65                  70                  75                  80

Ala Lys Phe Gly Arg Asn Ser Ile Asp Gly Arg Gly Leu Gln Leu Arg
                85                  90                  95

Ser Thr Val His Tyr Gly Ser Arg Tyr Asn Asn Ala Phe Trp Asn Gly
                100                 105                 110

Ser Gln Met Thr Tyr Gly Asp Gly Asp Gly Ser Thr Phe Ile Ala Phe
            115                 120                 125

Ser Gly Asp Pro Asp Val Val Gly His Glu Leu Thr His Gly Val Thr
130                 135                 140

Glu Tyr Thr Ser Asn Leu Glu Tyr Tyr Gly Ser Gly Ala Leu Asn
145                 150                 155                 160

Glu Ala Phe Ser Asp Val Ile Gly Asn Asp Ile Gln Arg Lys Asn Trp
                165                 170                 175

Leu Val Gly Asp Asp Ile Tyr Thr Pro Asn Ile Ala Gly Asp Ala Leu
                180                 185                 190
```

```
Arg Ser Met Ser Asn Pro Thr Leu Tyr Asp Gln Pro Asp His Tyr Ser
        195                 200                 205

Asn Leu Tyr Arg Gly Ser Ser Asp Asn Gly Gly Val His Thr Asn Ser
        210                 215                 220

Gly Ile Ile Asn Lys Ala Tyr Tyr Leu Leu Ala Gln Gly Gly Asn Phe
225                 230                 235                 240

His Gly Val Thr Val Asn Gly Ile Gly Arg Asp Ala Ala Val Gln Ile
                245                 250                 255

Tyr Tyr Ser Ala Phe Thr Asn Tyr Leu Thr Ser Ser Ser Asp Phe Ser
            260                 265                 270

Asn Ala Arg Ala Ala Val Ile Gln Ala Ala Lys Asp Leu Tyr Gly Ala
        275                 280                 285

Asn Ser Ala Glu Ala Thr Ala Ala Ala Lys Ser Phe Asp Ala Val Gly
        290                 295                 300

Val Asn
305

<210> SEQ ID NO 50
<211> LENGTH: 306
<212> TYPE: PRT
<213> ORGANISM: Paenibacillus polymyxa SC2
<220> FEATURE:
<221> NAME/KEY: misc_feature
<222> LOCATION: (1)..(306)
<223> OTHER INFORMATION: P_polymyxa_SC2_YP_003948511.1

<400> SEQUENCE: 50

Asn Glu Ala Thr Gly Thr Gly Lys Gly Val Leu Gly Asp Ser Lys Ser
1               5                   10                  15

Phe Thr Thr Thr Ala Ser Gly Ser Ser Tyr Gln Leu Lys Asp Thr Thr
                20                  25                  30

Arg Gly Asn Gly Ile Val Thr Tyr Thr Ala Ser Asn Arg Gln Ser Ile
            35                  40                  45

Pro Gly Thr Ile Leu Thr Asp Ala Asp Asn Val Trp Asn Asp Pro Ala
    50                  55                  60

Gly Val Asp Ala His Ala Tyr Ala Lys Thr Tyr Tyr Tyr Lys
65                  70                  75                  80

Ala Lys Phe Gly Arg Asn Ser Ile Asp Gly Arg Gly Leu Gln Leu Arg
                85                  90                  95

Ser Thr Val His Tyr Gly Ser Arg Tyr Asn Asn Ala Phe Trp Asn Gly
            100                 105                 110

Ser Gln Met Thr Tyr Gly Asp Gly Asp Gly Ser Thr Phe Ile Ala Phe
        115                 120                 125

Ser Gly Asp Pro Asp Val Val Gly His Glu Leu Thr His Gly Val Thr
    130                 135                 140

Glu Tyr Thr Ser Asn Leu Glu Tyr Tyr Gly Glu Ser Gly Ala Leu Asn
145                 150                 155                 160

Glu Ala Phe Ser Asp Val Ile Gly Asn Asp Ile Gln Arg Lys Asn Trp
                165                 170                 175

Leu Val Gly Asp Asp Ile Tyr Thr Pro Asn Ile Ala Gly Asp Ala Leu
            180                 185                 190

Arg Ser Met Ser Asn Pro Thr Leu Tyr Asp Gln Pro Asp His Tyr Ser
        195                 200                 205

Asn Leu Tyr Arg Gly Ser Ser Asp Asn Gly Gly Val His Thr Asn Ser
        210                 215                 220
```

-continued

```
Gly Ile Ile Asn Lys Ala Tyr Tyr Leu Leu Ala Gln Gly Gly Asn Phe
225                 230                 235                 240

His Gly Val Thr Val Asn Gly Ile Gly Arg Asp Ala Ala Val Gln Ile
            245                 250                 255

Tyr Tyr Ser Ala Phe Thr Asn Tyr Leu Thr Ser Ser Asp Phe Ser
        260                 265                 270

Asn Ala Arg Ala Ala Val Ile Gln Ala Ala Lys Asp Leu Tyr Gly Ala
        275                 280                 285

Asn Ser Ala Glu Ala Thr Ala Ala Lys Ser Phe Asp Ala Val Gly
    290                 295                 300

Val Asn
305

<210> SEQ ID NO 51
<211> LENGTH: 304
<212> TYPE: PRT
<213> ORGANISM: P. terrae
<220> FEATURE:
<221> NAME/KEY: misc_feature
<222> LOCATION: (1)..(304)
<223> OTHER INFORMATION: P_terrae_HPL-003_YP_005073223

<400> SEQUENCE: 51

Ala Thr Gly Thr Gly Lys Gly Val Leu Gly Asp Thr Lys Ser Phe Asn
1               5                   10                  15

Thr Thr Gln Ser Gly Ser Ser Tyr Gln Leu Lys Asp Thr Thr Arg Gly
            20                  25                  30

Asn Gly Ile Val Thr Tyr Thr Ala Ser Asn Arg Gln Thr Ile Pro Gly
        35                  40                  45

Thr Leu Leu Thr Asp Ala Asp Asn Val Trp Asn Asp Pro Ala Gly Val
50                  55                  60

Asp Ala His Ala Tyr Ala Ala Lys Thr Tyr Asp Tyr Tyr Lys Asp Lys
65                  70                  75                  80

Phe Gly Arg Asn Ser Ile Asp Gly Arg Gly Leu Gln Leu Arg Ser Thr
                85                  90                  95

Val His Tyr Gly Ser Arg Tyr Asn Asn Ala Phe Trp Asn Gly Ser Gln
            100                 105                 110

Met Thr Tyr Gly Asp Gly Asp Gly Thr Thr Phe Ile Ala Phe Ser Gly
        115                 120                 125

Asp Pro Asp Val Val Gly His Glu Leu Thr His Gly Val Thr Glu Tyr
130                 135                 140

Thr Ser Asn Leu Asp Tyr Tyr Gly Glu Ser Gly Ala Leu Asn Glu Ser
145                 150                 155                 160

Phe Ser Asp Ile Ile Gly Asn Asp Ile Gln Arg Lys Asn Trp Leu Val
                165                 170                 175

Gly Asp Asp Ile Tyr Thr Pro Ser Ile Ala Gly Asp Ala Leu Arg Ser
            180                 185                 190

Met Ser Asn Pro Thr Leu Tyr Asp Gln Pro His Tyr Ser Asn Leu
        195                 200                 205

Tyr Lys Gly Ser Ser Asp Asn Gly Val His Thr Asn Ser Gly Ile
    210                 215                 220

Ile Asn Lys Ala Tyr Tyr Leu Leu Ala Gln Gly Gly Thr Phe His Asn
225                 230                 235                 240

Val Thr Val Ser Gly Ile Gly Arg Asp Ala Ala Val Gln Ile Tyr Tyr
                245                 250                 255

Ser Ala Phe Thr Asn Tyr Leu Thr Ser Thr Ser Asn Phe Ser Asn Thr
```

```
                260                 265                 270
Arg Ala Ala Val Val Gln Ala Ala Lys Asp Leu Tyr Gly Ala Asn Ser
                275                 280                 285

Ala Gln Ala Thr Ala Ala Lys Ser Phe Asp Ala Val Gly Val Asn
                290                 295                 300

<210> SEQ ID NO 52
<211> LENGTH: 309
<212> TYPE: PRT
<213> ORGANISM: P. peoriae
<220> FEATURE:
<221> NAME/KEY: misc_feature
<222> LOCATION: (1)..(309)
<223> OTHER INFORMATION: P_peoriae_KCTC

<400> SEQUENCE: 52

Asp Ile Ile Asn Glu Ala Thr Gly Thr Gly Lys Gly Val Leu Gly Asp
1               5                   10                  15

Thr Lys Ser Phe Thr Thr Thr Ala Ser Gly Ser Ser Tyr Gln Leu Arg
                20                  25                  30

Asp Thr Thr Arg Gly Asn Gly Ile Val Thr Tyr Thr Ala Ser Asn Arg
            35                  40                  45

Gln Ser Ile Pro Gly Thr Ile Leu Thr Asp Ala Asp Asn Val Trp Asn
        50                  55                  60

Asp Pro Ala Gly Val Asp Ala His Ala Tyr Ala Ala Lys Thr Tyr Asp
65                  70                  75                  80

Tyr Tyr Lys Glu Lys Phe Asn Arg Asn Ser Ile Asp Gly Arg Gly Leu
                85                  90                  95

Gln Leu Arg Ser Thr Val His Tyr Gly Asn Arg Tyr Asn Asn Ala Phe
            100                 105                 110

Trp Asn Gly Ser Gln Met Thr Tyr Gly Asp Gly Asp Gly Thr Thr Phe
        115                 120                 125

Ile Ala Phe Ser Gly Asp Pro Asp Val Val Gly His Glu Leu Thr His
130                 135                 140

Gly Val Thr Glu Tyr Thr Ser Asn Leu Glu Tyr Tyr Gly Glu Ser Gly
145                 150                 155                 160

Ala Leu Asn Glu Ser Phe Ser Asp Ile Ile Gly Asn Asp Ile Gln Arg
                165                 170                 175

Lys Asn Trp Leu Val Gly Asp Asp Ile Tyr Thr Pro Arg Ile Ala Gly
            180                 185                 190

Asp Ala Leu Arg Ser Met Ser Asn Pro Thr Leu Tyr Asp Gln Pro Asp
        195                 200                 205

His Tyr Ser Asn Leu Tyr Arg Gly Ser Ser Asp Asn Gly Gly Val His
210                 215                 220

Thr Asn Ser Gly Ile Ile Asn Lys Ala Tyr Tyr Leu Leu Ala Gln Gly
225                 230                 235                 240

Gly Thr Phe His Gly Val Thr Val Asn Gly Ile Gly Arg Asp Ala Ala
                245                 250                 255

Val Gln Ile Tyr Tyr Ser Ala Phe Thr Asn Tyr Leu Thr Ser Ser Ser
            260                 265                 270

Asp Phe Ser Asn Ala Arg Asp Ala Val Val Gln Ala Ala Lys Asp Leu
        275                 280                 285

Tyr Gly Ala Ser Ser Ala Gln Ala Thr Ala Ala Lys Ala Phe Asp
290                 295                 300

Ala Val Gly Val Asn
305
```

<210> SEQ ID NO 53
<211> LENGTH: 316
<212> TYPE: PRT
<213> ORGANISM: Bacillus thermoproteolyticus
<220> FEATURE:
<221> NAME/KEY: misc_feature
<222> LOCATION: (1)..(316)
<223> OTHER INFORMATION: 1KEI.A

<400> SEQUENCE: 53

```
Ile Thr Gly Thr Ser Thr Val Gly Val Gly Arg Gly Val Leu Gly Asp
1               5                   10                  15

Gln Lys Asn Ile Asn Thr Thr Tyr Ser Thr Tyr Tyr Leu Gln Asp
            20                  25                  30

Asn Thr Arg Gly Asn Gly Ile Phe Thr Tyr Asp Ala Lys Tyr Arg Thr
            35                  40                  45

Thr Leu Pro Gly Ser Leu Trp Ala Asp Ala Asn Gln Phe Phe Ala
    50                  55                  60

Ser Tyr Asp Ala Pro Ala Val Asp Ala His Tyr Tyr Ala Gly Val Thr
65                  70                  75                  80

Tyr Asp Tyr Tyr Lys Asn Val His Asn Arg Leu Ser Tyr Asp Gly Asn
                85                  90                  95

Asn Ala Ala Ile Arg Ser Ser Val His Tyr Ser Gln Gly Tyr Asn Asn
            100                 105                 110

Ala Phe Trp Asn Gly Ser Gln Met Val Tyr Gly Asp Gly Asp Gly Gln
        115                 120                 125

Thr Phe Ile Pro Leu Ser Gly Gly Ile Asp Val Val Ala His Glu Leu
130                 135                 140

Thr His Ala Val Thr Asp Tyr Thr Ala Gly Leu Ile Tyr Gln Asn Glu
145                 150                 155                 160

Ser Gly Ala Ile Asn Glu Ala Ile Ser Asp Ile Phe Gly Thr Leu Val
                165                 170                 175

Glu Phe Tyr Ala Asn Lys Asn Pro Asp Trp Glu Ile Gly Glu Asp Val
            180                 185                 190

Tyr Thr Pro Gly Ile Ser Gly Asp Ser Leu Arg Ser Met Ser Asp Pro
        195                 200                 205

Ala Lys Tyr Gly Asp Pro Asp His Tyr Ser Lys Arg Tyr Thr Gly Thr
    210                 215                 220

Gln Asp Asn Gly Gly Val His Ile Asn Ser Gly Ile Ile Asn Lys Ala
225                 230                 235                 240

Ala Tyr Leu Ile Ser Gln Gly Gly Thr His Tyr Gly Val Ser Val Val
                245                 250                 255

Gly Ile Gly Arg Asp Lys Leu Gly Lys Ile Phe Tyr Arg Ala Leu Thr
            260                 265                 270

Gln Tyr Leu Thr Pro Thr Ser Asn Phe Ser Gln Leu Arg Ala Ala Ala
        275                 280                 285

Val Gln Ser Ala Thr Asp Leu Tyr Gly Ser Thr Ser Gln Glu Val Ala
    290                 295                 300

Ser Val Lys Gln Ala Phe Asp Ala Val Gly Val Lys
305                 310                 315
```

<210> SEQ ID NO 54
<211> LENGTH: 316
<212> TYPE: PRT
<213> ORGANISM: B. caldolyticus
<220> FEATURE:

<210> SEQ ID NO 54
<211> LENGTH: 316
<212> TYPE: PRT
<213> ORGANISM: B. caldolyticus
<220> FEATURE:
<221> NAME/KEY: misc_feature
<222> LOCATION: (1)..(316)
<223> OTHER INFORMATION: B_caldolyticus_AAA22623.1

<400> SEQUENCE: 54

```
Thr Ser Thr Val Gly Val Gly Arg Gly Val Leu Gly Asp Gln Lys Tyr
1               5                   10                  15

Ile Asn Thr Thr Tyr Ser Ser Tyr Gly Tyr Tyr Leu Gln Asp
                20                  25                  30

Asn Thr Arg Gly Ser Gly Ile Phe Thr Tyr Asp Gly Asn Arg Thr
                35                  40                  45

Val Leu Pro Gly Ser Leu Trp Ala Asp Gly Asp Asn Gln Phe Phe Ala
50                  55                  60

Ser Tyr Asp Ala Ala Val Asp Ala His Tyr Tyr Ala Gly Val Val
65                  70                  75                  80

Tyr Asp Tyr Tyr Lys Asn Val His Gly Arg Leu Ser Tyr Asp Gly Ser
                85                  90                  95

Asn Ala Ala Ile Arg Ser Thr Val His Tyr Gly Arg Gly Tyr Asn Asn
                100                 105                 110

Ala Phe Trp Asn Gly Ser Gln Met Val Tyr Gly Asp Gly Asp Gly Gln
                115                 120                 125

Thr Phe Leu Pro Phe Ser Gly Gly Ile Asp Val Val Gly His Glu Leu
                130                 135                 140

Thr His Ala Val Thr Asp Tyr Thr Ala Gly Leu Val Tyr Gln Asn Glu
145                 150                 155                 160

Ser Gly Ala Ile Asn Glu Ala Met Ser Asp Ile Phe Gly Thr Leu Val
                165                 170                 175

Glu Phe Tyr Ala Asn Arg Asn Pro Asp Trp Glu Ile Gly Glu Asp Ile
                180                 185                 190

Tyr Thr Pro Gly Val Ala Gly Asp Ala Leu Arg Ser Met Ser Asp Pro
                195                 200                 205

Ala Lys Tyr Gly Asp Pro Asp His Tyr Ser Lys Arg Tyr Thr Gly Thr
                210                 215                 220

Gln Asp Asn Gly Gly Val His Thr Asn Ser Gly Ile Ile Asn Lys Ala
225                 230                 235                 240

Ala Tyr Leu Leu Ser Gln Gly Gly Val His Tyr Gly Val Ser Val Thr
                245                 250                 255

Gly Ile Gly Arg Asp Lys Met Gly Lys Ile Phe Tyr Arg Ala Leu Val
                260                 265                 270

Tyr Tyr Leu Thr Pro Thr Ser Asn Phe Ser Gln Leu Arg Ala Ala Cys
                275                 280                 285

Val Gln Ala Ala Ala Asp Leu Tyr Gly Ser Thr Ser Gln Glu Val Asn
                290                 295                 300

Ser Val Lys Gln Ala Phe Asn Ala Val Gly Val Tyr
305                 310                 315
```

<210> SEQ ID NO 55
<211> LENGTH: 292
<212> TYPE: PRT
<213> ORGANISM: B. anthracis
<220> FEATURE:
<221> NAME/KEY: misc_feature
<222> LOCATION: (1)..(292)
<223> OTHER INFORMATION: B_anthracis_NP843132.1

<400> SEQUENCE: 55

Val Thr Gly Thr Asn Ala Val Gly Thr Gly Lys Gly Val Leu Gly Asp

```
                1               5                   10                  15
            Thr Lys Ser Leu Asn Thr Thr Leu Ser Ala Ser Ser Tyr Tyr Leu Gln
                            20                  25                  30

Asp Asn Thr Arg Gly Ala Thr Ile Phe Thr Tyr Asp Ala Lys Asn Arg
                            35                  40                  45

Ser Thr Leu Pro Gly Thr Leu Trp Val Asp Ala Asp Asn Val Phe Asn
                        50                  55                  60

Ala Ala Tyr Asp Ala Ala Val Asp Ala His Tyr Tyr Ala Gly Arg
             65                 70                  75                  80

Thr Tyr Asp Tyr Tyr Lys Ala Thr Phe Asn Arg Asn Ser Ile Asn Asp
                            85                  90                  95

Ala Gly Ala Pro Leu Lys Ser Thr Val His Tyr Gly Ser Arg Tyr Asn
                            100                 105                 110

Asn Ala Phe Trp Asn Gly Ser Gln Met Val Tyr Gly Asp Gly Asp Gly
                            115                 120                 125

Val Thr Phe Thr Ser Leu Ser Gly Gly Ile Asp Val Ile Gly His Glu
                            130                 135                 140

Leu Thr His Ala Val Thr Glu Tyr Ser Ser Asp Leu Ile Tyr Gln Asn
            145                 150                 155                 160

Glu Ser Gly Ala Leu Asn Glu Ala Ile Ser Asp Val Phe Gly Thr Leu
                            165                 170                 175

Val Glu Tyr Tyr Asp Asn Arg Asn Pro Asp Trp Glu Ile Gly Glu Asp
                            180                 185                 190

Ile Tyr Thr Pro Gly Lys Ala Gly Asp Ala Leu Arg Ser Met Ser Asp
                            195                 200                 205

Pro Thr Lys Tyr Gly Asp Pro Asp His Tyr Ser Lys Arg Tyr Thr Gly
                            210                 215                 220

Thr Gly Asp Asn Gly Gly Val His Thr Asn Ser Gly Ile Ile Asn Lys
            225                 230                 235                 240

Ala Ala Tyr Leu Leu Ala Asn Gly Gly Thr His Tyr Gly Val Thr Val
                            245                 250                 255

Asn Gly Ile Gly Lys Asp Lys Val Gly Ala Ile Tyr Tyr Arg Ala Asn
                            260                 265                 270

Thr Gln Tyr Phe Thr Gln Ser Thr Thr Phe Ser Gln Ala Arg Ala Gly
                            275                 280                 285

Leu Val Gln Ala
                            290

<210> SEQ ID NO 56
<211> LENGTH: 317
<212> TYPE: PRT
<213> ORGANISM: B. thuringiensis
<220> FEATURE:
<221> NAME/KEY: misc_feature
<222>

Ala Ala Tyr Asp Ala Ala Val Asp Ala His Tyr Tyr Ala Gly Lys
65                  70                  75                  80

Thr Tyr Asp Tyr Tyr Lys Ala Thr Phe Asn Arg Asn Ser Ile Asn Asp
                85                  90                  95

Ala Gly Ala Pro Leu Lys Ser Thr Val His Tyr Gly Ser Arg Tyr Asn
            100                 105                 110

Asn Ala Phe Trp Asn Gly Ser Gln Met Val Tyr Gly Asp Gly Asp Gly
        115                 120                 125

Val Thr Phe Thr Ser Leu Ser Gly Gly Ile Asp Val Ile Gly His Glu
    130                 135                 140

Leu Thr His Ala Val Thr Glu Tyr Ser Ser Asp Leu Ile Tyr Gln Asn
145                 150                 155                 160

Glu Ser Gly Ala Leu Asn Glu Ala Ile Ser Asp Val Phe Gly Thr Leu
                165                 170                 175

Val Glu Phe Tyr Asp Asn Arg Asn Pro Asp Trp Glu Ile Gly Glu Asp
            180                 185                 190

Ile Tyr Thr Pro Gly Lys Ala Gly Asp Ala Leu Arg Ser Met Ser Asp
        195                 200                 205

Pro Thr Lys Tyr Gly Asp Pro Asp His Tyr Ser Lys Arg Tyr Thr Gly
    210                 215                 220

Thr Gly Asp Asn Gly Gly Val His Thr Asn Ser Gly Ile Ile Asn Lys
225                 230                 235                 240

Ala Ala Tyr Leu Leu Ala Asn Gly Gly Thr His Tyr Gly Val Thr Val
                245                 250                 255

Asn Gly Ile Gly Lys Asp Lys Val Gly Ala Ile Tyr Tyr Arg Ala Asn
            260                 265                 270

Thr Gln Tyr Phe Thr Gln Ser Thr Thr Phe Ser Gln Ala Arg Ala Gly
        275                 280                 285

Leu Val Gln Ala Ala Thr Asp Leu Tyr Gly Ala Ser Ser Ala Glu Val
    290                 295                 300

Ala Ala Val Lys Gln Ser Tyr Ser Ala Val Gly Val Asn
305                 310                 315

<210> SEQ ID NO 57
<211> LENGTH: 314
<212> TYPE: PRT
<213> ORGANISM: B. cereus
<220> FEATURE:
<221> NAME/KEY: misc_feature
<222> LOCATION: (1)..(314)
<223> OTHER INFORMATION: B_cereus_ZP04310163.1

<400> SEQUENCE: 57

```
Thr Asn Ala Val Gly Thr Gly Lys Gly Val Leu Gly Asp Thr Lys Ser
1               5                   10                  15

Leu Asn Thr Thr Leu Ser Ala Ser Ser Tyr Tyr Leu Gln Asp Asn Thr
            20                  25                  30

Arg Gly Ala Thr Ile Phe Thr Tyr Asp Ala Lys Asn Arg Ser Thr Leu
        35                  40                  45

Pro Gly Thr Leu Trp Val Asp Ala Asp Asn Val Phe Asn Ala Ala Tyr
    50                  55                  60

Asp Ala Ala Ala Val Asp Ala His Tyr Tyr Ala Gly Lys Thr Tyr Asp
65                  70                  75                  80

Tyr Tyr Lys Ala Thr Phe Asn Arg Asn Ser Ile Asn Asp Ala Gly Ala
                85                  90                  95
```

Pro Leu Lys Ser Thr Val His Tyr Gly Ser Arg Tyr Asn Asn Ala Phe
                100                 105                 110

Trp Asn Gly Ser Gln Met Val Tyr Gly Asp Gly Asp Gly Val Thr Phe
            115                 120                 125

Thr Ser Leu Ser Gly Gly Ile Asp Val Ile Gly His Glu Leu Thr His
        130                 135                 140

Ala Val Thr Glu Tyr Ser Ser Asp Leu Ile Tyr Gln Asn Glu Ser Gly
145                 150                 155                 160

Ala Leu Asn Glu Ala Ile Ser Asp Val Phe Gly Thr Leu Val Glu Phe
                165                 170                 175

Tyr Asp Asn Arg Asn Pro Asp Trp Glu Ile Gly Glu Asp Ile Tyr Thr
            180                 185                 190

Pro Gly Lys Ala Gly Asp Ala Leu Arg Ser Met Ser Asp Pro Thr Lys
        195                 200                 205

Tyr Gly Asp Pro Asp His Tyr Ser Lys Arg Tyr Thr Gly Thr Gly Asp
210                 215                 220

Asn Gly Gly Val His Thr Asn Ser Gly Ile Ile Asn Lys Ala Ala Tyr
225                 230                 235                 240

Leu Leu Ala Asn Gly Gly Thr His Tyr Gly Val Thr Val Asn Gly Ile
                245                 250                 255

Gly Lys Asp Lys Val Gly Ala Ile Tyr Tyr Arg Ala Asn Thr Gln Tyr
            260                 265                 270

Phe Thr Gln Ser Thr Thr Phe Ser Gln Ala Arg Ala Gly Leu Val Gln
        275                 280                 285

Ala Ala Ala Asp Leu Tyr Gly Ala Ser Ser Ala Glu Val Ala Ala Val
290                 295                 300

Lys Gln Ser Tyr Ser Ala Val Gly Val Asn
305                 310

<210> SEQ ID NO 58
<211> LENGTH: 317
<212> TYPE: PRT
<213> ORGANISM: Lactobacillus sp.
<220> FEATURE:
<221> NAME/KEY: misc_feature
<222> LOCATION: (1)..(317)
<223> OTHER INFORMATION: Lactobacillus_sp_BAA06144.1

<400> SEQUENCE: 58

Val Thr Gly Thr Asn Ala Val Gly Thr Gly Lys Gly Val Leu Gly Asp
1               5                   10                  15

Thr Lys Ser Leu Asn Thr Thr Leu Ser Ala Ser Ser Tyr Tyr Leu Gln
                20                  25                  30

Asp Asn Thr Arg Gly Ala Thr Ile Phe Thr Tyr Asp Ala Lys Asn Arg
            35                  40                  45

Ser Thr Leu Pro Gly Thr Leu Trp Val Asp Ala Asp Asn Val Phe Asn
        50                  55                  60

Ala Ala Tyr Asp Ala Ala Ala Val Asp Ala His Tyr Tyr Ala Gly Lys
65                  70                  75                  80

Thr Tyr Asp Tyr Tyr Lys Ala Thr Phe Asn Arg Asn Ser Ile Asn Asp
                85                  90                  95

Ala Gly Ala Pro Leu Lys Ser Thr Val His Tyr Gly Ser Lys Tyr Asn
            100                 105                 110

Asn Ala Phe Trp Asn Gly Ser Gln Met Val Tyr Gly Asp Gly Asp Gly
        115                 120                 125

Val Thr Phe Thr Ser Leu Ser Gly Gly Ile Asp Val Ile Gly His Glu

```
                 130                 135                 140

Leu Thr His Ala Val Thr Glu Tyr Ser Ser Asp Leu Ile Tyr Gln Asn
145                 150                 155                 160

Glu Ser Gly Ala Leu Asn Glu Ala Ile Ser Asp Val Phe Gly Thr Leu
                165                 170                 175

Val Glu Tyr Tyr Asp Asn Arg Asn Pro Asp Trp Glu Ile Gly Glu Asp
            180                 185                 190

Ile Tyr Thr Pro Gly Lys Ala Gly Asp Ala Leu Arg Ser Met Ser Asp
        195                 200                 205

Pro Thr Lys Tyr Gly Asp Pro Asp His Tyr Ser Lys Arg Tyr Thr Gly
    210                 215                 220

Thr Ser Asp Asn Gly Gly Val His Thr Asn Ser Gly Ile Ile Asn Lys
225                 230                 235                 240

Ala Ala Tyr Leu Leu Ala Asn Gly Gly Thr His Tyr Gly Val Thr Val
                245                 250                 255

Asn Gly Ile Gly Lys Asp Lys Val Gly Ala Ile Tyr Tyr Arg Ala Asn
            260                 265                 270

Thr Gln Tyr Phe Thr Gln Ser Thr Thr Phe Ser Gln Ala Arg Ala Gly
        275                 280                 285

Leu Val Gln Ala Ala Ala Asp Leu Tyr Gly Ala Ser Ser Ala Glu Val
    290                 295                 300

Ala Ala Val Lys Gln Ser Tyr Ser Ala Val Gly Val Asn
305                 310                 315

<210> SEQ ID NO 59
<211> LENGTH: 317
<212> TYPE: PRT
<213> ORGANISM: Bacillus thermoproteolyticus
<220> FEATURE:
<221> NAME/KEY: misc_feature
<222> LOCATION: (1)..(317)
<223> OTHER INFORMATION: 1NPC.A

<400> SEQUENCE: 59

Val Thr Gly Thr Asn Lys Val Gly Thr Gly Lys Gly Val Leu Gly Asp
1               5                   10                  15

Thr Lys Ser Leu Asn Thr Thr Leu Ser Gly Ser Ser Tyr Tyr Leu Gln
                20                  25                  30

Asp Asn Thr Arg Gly Ala Thr Ile Phe Thr Tyr Asp Ala Lys Asn Arg
            35                  40                  45

Ser Thr Leu Pro Gly Thr Leu Trp Ala Asp Ala Asp Asn Val Phe Asn
        50                  55                  60

Ala Ala Tyr Asp Ala Ala Ala Val Asp Ala His Tyr Tyr Ala Gly Lys
65                  70                  75                  80

Thr Tyr Asp Tyr Tyr Lys Ala Thr Phe Asn Arg Asn Ser Ile Asn Asp
                85                  90                  95

Ala Gly Ala Pro Leu Lys Ser Thr Val His Tyr Gly Ser Asn Tyr Asn
            100                 105                 110

Asn Ala Phe Trp Asn Gly Ser Gln Met Val Tyr Gly Asp Gly Asp Gly
        115                 120                 125

Val Thr Phe Thr Ser Leu Ser Gly Gly Ile Asp Val Ile Gly His Glu
    130                 135                 140

Leu Thr His Ala Val Thr Glu Asn Ser Ser Asn Leu Ile Tyr Gln Asn
145                 150                 155                 160

Glu Ser Gly Ala Leu Asn Glu Ala Ile Ser Asp Ile Phe Gly Thr Leu
                165                 170                 175
```

Val Glu Phe Tyr Asp Asn Arg Asn Pro Asp Trp Glu Ile Gly Glu Asp
            180                 185                 190

Ile Tyr Thr Pro Gly Lys Ala Gly Asp Ala Leu Arg Ser Met Ser Asp
        195                 200                 205

Pro Thr Lys Tyr Gly Asp Pro His Tyr Ser Lys Arg Tyr Thr Gly
    210                 215                 220

Ser Ser Asp Asn Gly Gly Val His Thr Asn Ser Gly Ile Ile Asn Lys
225                 230                 235                 240

Gln Ala Tyr Leu Leu Ala Asn Gly Gly Thr His Tyr Gly Val Thr Val
            245                 250                 255

Thr Gly Ile Gly Lys Asp Lys Leu Gly Ala Ile Tyr Tyr Arg Ala Asn
            260                 265                 270

Thr Gln Tyr Phe Thr Gln Ser Thr Thr Phe Ser Gln Ala Arg Ala Gly
            275                 280                 285

Ala Val Gln Ala Ala Ala Asp Leu Tyr Gly Ala Asn Ser Ala Glu Val
            290                 295                 300

Ala Ala Val Lys Gln Ser Phe Ser Ala Val Gly Val Asn
305                 310                 315

<210> SEQ ID NO 60
<211> LENGTH: 317
<212> TYPE: PRT
<213> ORGANISM: B. cytotoxicus
<220> FEATURE:
<221> NAME/KEY: misc_feature
<222> LOCATION: (1)..(317)
<223> OTHER INFORMATION: B_cytotoxicus_YP001373863.1

<400> SEQUENCE: 60

```
Val Thr Gly Thr Asn Ala Val Gly Thr Gly Thr Gly Val Leu Gly Asp
1               5                   10                  15

Lys Lys Ser Ile Asn Thr Thr Leu Ser Gly Ser Thr Tyr Tyr Leu Gln
            20                  25                  30

Asp Asn Thr Arg Gly Ala Gln Ile Phe Thr Tyr Asp Ala Lys Asn Arg
        35                  40                  45

Ser Ser Leu Pro Gly Thr Leu Trp Ala Asp Val Asp Asn Ala Phe His
    50                  55                  60

Ala Lys Tyr Asp Ala Ala Ala Val Asp Ala His Tyr Tyr Ala Gly Val
65                  70                  75                  80

Thr Tyr Asp Tyr Tyr Lys Asn Thr Phe Asn Arg Asn Ser Ile Asn Asp
                85                  90                  95

Ala Gly Ala Ala Leu Lys Ser Thr Val His Tyr Gly Ser Asn Tyr Asn
            100                 105                 110

Asn Ala Phe Trp Asn Gly Ser Gln Met Val Tyr Gly Asp Gly Asp Gly
        115                 120                 125

Val Thr Phe Thr Ser Leu Ser Gly Gly Ile Asp Val Ile Gly His Glu
    130                 135                 140

Leu Thr His Ala Val Thr Glu Tyr Ser Ser Asn Leu Ile Tyr Gln Tyr
145                 150                 155                 160

Glu Ser Gly Ala Leu Asn Glu Ala Ile Ser Asp Ile Phe Gly Thr Leu
                165                 170                 175

Val Glu Tyr Tyr Asp Asn Arg Asn Pro Asp Trp Glu Ile Gly Glu Asp
            180                 185                 190

Ile Tyr Thr Pro Gly Lys Ala Gly Asp Ala Leu Arg Ser Met Ser Asp
        195                 200                 205
```

```
Pro Thr Lys Tyr Gly Asp Pro Asp His Tyr Ser Lys Arg Tyr Thr Gly
    210             215                 220

Ser Gly Asp Asn Gly Gly Val His Thr Asn Ser Gly Ile Ile Asn Lys
225             230                 235                 240

Ala Ala Tyr Leu Leu Ala Asn Gly Gly Thr His Tyr Gly Val Thr Val
                245                 250                 255

Asn Gly Ile Gly Lys Asp Lys Val Gly Ala Ile Tyr Tyr Arg Ala Asn
                260                 265                 270

Thr Gln Tyr Phe Thr Gln Ser Thr Phe Ser Gln Ala Arg Ala Gly
            275                 280                 285

Leu Val Gln Ala Ala Ala Asp Leu Tyr Gly Ala Asn Ser Ala Glu Val
290                 295                 300

Thr Ala Val Lys Gln Ser Tyr Asp Ala Val Gly Val Lys
305                 310                 315
```

<210> SEQ ID NO 61
<211> LENGTH: 314
<212> TYPE: PRT
<213> ORGANISM: B. megaterium
<220> FEATURE:
<221> NAME/KEY: misc_feature
<222> LOCATION: (1)..(314)
<223> OTHER INFORMATION: B_megaterium_YP005495105.1

<400> SEQUENCE: 61

```
Thr Asn Ala Ile Gly Ser Gly Lys Gly Val Leu Gly Asp Thr Lys Ser
1               5                   10                  15

Leu Lys Thr Thr Leu Ser Gly Ser Ala Tyr Tyr Leu Gln Asp Asn Thr
            20                  25                  30

Arg Gly Ala Thr Ile Tyr Thr Tyr Asp Ala Lys Asn Arg Thr Ser Leu
        35                  40                  45

Pro Gly Thr Leu Trp Ala Asp Thr Asp Asn Thr Tyr Asn Ala Thr Arg
    50                  55                  60

Asp Ala Ala Ala Val Asp Ala His Tyr Tyr Ala Gly Val Thr Tyr Asp
65                  70                  75                  80

Tyr Tyr Lys Asn Lys Phe Asn Arg Asn Ser Tyr Asp Asn Ala Gly Ala
                85                  90                  95

Pro Leu Lys Ser Thr Val His Tyr Ser Ser Gly Tyr Asn Asn Ala Phe
            100                 105                 110

Trp Asn Gly Ser Gln Met Val Tyr Gly Asp Gly Asp Gly Thr Thr Phe
        115                 120                 125

Val Pro Leu Ser Gly Gly Leu Asp Val Ile Gly His Glu Leu Thr His
    130                 135                 140

Ala Val Thr Glu Arg Ser Ser Asn Leu Ile Tyr Gln Tyr Glu Ser Gly
145                 150                 155                 160

Ala Leu Asn Glu Ala Ile Ser Asp Ile Phe Gly Thr Leu Val Glu Tyr
                165                 170                 175

Tyr Asp Asn Arg Asn Pro Asp Trp Glu Ile Gly Glu Asp Ile Tyr Thr
            180                 185                 190

Pro Gly Thr Ser Gly Asp Ala Leu Arg Ser Met Ser Asn Pro Ala Lys
        195                 200                 205

Tyr Gly Asp Pro Asp His Tyr Ser Lys Arg Tyr Thr Gly Ser Ser Asp
    210                 215                 220

Asn Gly Gly Val His Thr Asn Ser Gly Ile Ile Asn Lys Ala Ala Tyr
225                 230                 235                 240

Leu Leu Ala Asn Gly Gly Thr His Tyr Gly Val Thr Val Thr Gly Ile
```

```
                    245                 250                 255
Gly Gly Asp Lys Leu Gly Lys Ile Tyr Tyr Arg Ala Asn Thr Leu Tyr
                260                 265                 270

Phe Thr Gln Ser Thr Thr Phe Ser Gln Ala Arg Ala Gly Leu Val Gln
            275                 280                 285

Ala Ala Ala Asp Leu Tyr Gly Ser Gly Ser Gln Glu Val Ile Ser Val
        290                 295                 300

Gly Lys Ser Phe Asp Ala Val Gly Val Gln
305                 310

<210> SEQ ID NO 62
<211> LENGTH: 322
<212> TYPE: PRT
<213> ORGANISM: Bacillus sp. SG-1
<220> FEATURE:
<221> NAME/KEY: misc_feature
<222> LOCATION: (1)..(322)
<223> OTHER INFORMATION: B_sp_SG-1_ZP01858398.1

<400> SEQUENCE: 62

Val Ser Gly Thr Asp Gln Val Gly Thr Gly Lys Gly Val Leu Gly Asp
1               5                   10                  15

Thr Lys Ser Leu Asn Thr Thr Leu Ser Asn Gly Thr Tyr Tyr Leu Gln
            20                  25                  30

Asp Asn Thr Arg Gly Gly Gly Ile Met Thr Tyr Asp Met Lys Asn Arg
        35                  40                  45

Thr Phe Phe Pro Gln Phe Tyr Leu Pro Gly Ser Leu Trp Ser Asp Ala
    50                  55                  60

Asp Asn Val Tyr Asn Gln Ala Tyr Asp Ala Ala Val Asp Ala His
65                  70                  75                  80

Tyr Phe Ala Gly Ala Thr Phe Asp Tyr Tyr Lys Asp Val Phe Gly Arg
                85                  90                  95

Asn Ser Tyr Asp Asn Lys Gly Thr Thr Ile Gln Ser Ser Val His Tyr
            100                 105                 110

Ser Lys Asn Tyr Asn Asn Ala Phe Trp Asn Gly Ser Gln Met Val Tyr
        115                 120                 125

Gly Asp Gly Asp Gly Thr Thr Phe Ile Pro Leu Ser Gly Gly Leu Asp
    130                 135                 140

Val Val Ala His Glu Leu Thr His Ala Val Thr Asp Thr Ser Ser Asp
145                 150                 155                 160

Leu Val Tyr Gln Asn Glu Ser Gly Ala Leu Asn Glu Ala Ile Ser Asp
                165                 170                 175

Ile Phe Gly Thr Leu Val Glu Tyr His Glu Asn His Asn Pro Asp Phe
            180                 185                 190

Glu Ile Gly Glu Asp Ile Tyr Thr Pro Asn Thr Pro Asn Asp Ala Leu
        195                 200                 205

Arg Ser Met Ser Asp Pro Ala Lys Tyr Gly Asp Pro His Tyr Ser
    210                 215                 220

Val Arg Tyr Thr Gly Thr Gln Asp Asn Gly Gly Val His Ile Asn Ser
225                 230                 235                 240

Gly Ile Ile Asn Lys Gln Ala Tyr Leu Leu Ser Glu Gly Gly Thr His
                245                 250                 255

Tyr Gly Val Asn Val Thr Gly Ile Gly Arg Glu Lys Leu Gly Glu Ile
            260                 265                 270

Tyr Tyr Arg Met Asn Thr Val Tyr Leu Thr Ala Ser Ser Thr Phe Ser
        275                 280                 285
```

```
Gln Ala Arg Ser Ala Ala Val Gln Ala Ser Asp Leu Tyr Gly Ser
        290                 295                 300

Asn Ser Pro Glu Val Gln Ser Val Asn Gln Ser Phe Asp Ala Val Gly
305                 310                 315                 320

Ile Asn
```

<210> SEQ ID NO 63
<211> LENGTH: 306
<212> TYPE: PRT
<213> ORGANISM: Paenibacillus peoriae
<220> FEATURE:
<221> NAME/KEY: misc_feature
<222> LOCATION: (1)..(306)
<223> OTHER INFORMATION: PpePro1

<400> SEQUENCE: 63

```
Ala Thr Gly Thr Gly Arg Gly Val Asp Gly Val Thr Lys Ser Phe Thr
1               5                   10                  15

Thr Thr Ala Ser Gly Asn Gly Tyr Gln Leu Lys Asp Thr Thr Arg Ser
            20                  25                  30

Asn Gly Ile Val Thr Tyr Thr Ala Asn Asn Arg Gln Thr Thr Pro Gly
        35                  40                  45

Thr Ile Met Thr Asp Ala Asp Asn Val Trp Asn Asp Pro Ala Ala Val
    50                  55                  60

Asp Ala His Ala Tyr Ala Ile Lys Thr Tyr Asp Tyr Lys Asn Lys
65                  70                  75                  80

Phe Gly Arg Asp Ser Ile Asp Gly Arg Gly Met Gln Ile Arg Ser Thr
                85                  90                  95

Val His Tyr Gly Lys Lys Tyr Val Asn Ala Phe Trp Asn Gly Ser Gln
            100                 105                 110

Met Thr Tyr Gly Asp Gly Asp Gly Ser Thr Phe Thr Phe Phe Ser Gly
        115                 120                 125

Asp Pro Asp Val Val Gly His Glu Leu Thr His Gly Val Thr Glu Phe
    130                 135                 140

Thr Ser Asn Leu Glu Tyr Tyr Gly Glu Ser Gly Ala Leu Asn Glu Ala
145                 150                 155                 160

Phe Ser Asp Ile Ile Gly Asn Asp Ile Asp Gly Ala Asn Trp Leu Leu
                165                 170                 175

Gly Asp Gly Ile Tyr Thr Pro Gly Ile Pro Gly Asp Ala Leu Arg Ser
            180                 185                 190

Leu Ser Asp Pro Thr Arg Phe Gly Gln Pro Asp His Tyr Ser Asn Phe
        195                 200                 205

Tyr Pro Asp Pro Asn Asn Asp Asp Glu Gly Val His Thr Asn Ser
    210                 215                 220

Gly Ile Ile Asn Lys Ala Tyr Tyr Leu Leu Ala Gln Gly Gly Thr Ser
225                 230                 235                 240

His Gly Val Lys Val Thr Gly Ile Gly Arg Glu Ala Ala Val Phe Ile
                245                 250                 255

Tyr Tyr Asn Ala Phe Thr Asn Tyr Leu Thr Ser Thr Ser Asn Phe Ser
            260                 265                 270

Asn Ala Arg Ala Ala Val Ile Gln Ala Lys Asp Phe Tyr Gly Ala
        275                 280                 285

Asp Ser Leu Ala Val Thr Ser Ala Ile Lys Ser Phe Asp Ala Val Gly
    290                 295                 300

Ile Lys
```

<210> SEQ ID NO 64
<211> LENGTH: 304
<212> TYPE: PRT
<213> ORGANISM: Paenibacillus polymyxa
<220> FEATURE:
<221> NAME/KEY: misc_feature
<222> LOCATION: (1)..(304)
<223> OTHER INFORMATION: PpoPro2

<400> SEQUENCE: 64

| Ala | Thr | Gly | Thr | Gly | Lys | Gly | Val | Leu | Gly | Asp | Thr | Lys | Ser | Phe | Thr |
|---|---|---|---|---|---|---|---|---|---|---|---|---|---|---|---|
| 1 | | | | 5 | | | | | 10 | | | | | 15 | |

| Thr | Thr | Ala | Ser | Gly | Ser | Ser | Tyr | Gln | Leu | Lys | Asp | Thr | Thr | Arg | Gly |
|---|---|---|---|---|---|---|---|---|---|---|---|---|---|---|---|
| | | | 20 | | | | | 25 | | | | | 30 | | |

| Asn | Gly | Ile | Val | Thr | Tyr | Thr | Ala | Ser | Asn | Arg | Gln | Ser | Ile | Pro | Gly |
|---|---|---|---|---|---|---|---|---|---|---|---|---|---|---|---|
| | | 35 | | | | | 40 | | | | | 45 | | | |

| Thr | Leu | Leu | Thr | Asp | Ala | Asp | Asn | Val | Trp | Asn | Asp | Pro | Ala | Gly | Val |
|---|---|---|---|---|---|---|---|---|---|---|---|---|---|---|---|
| 50 | | | | | 55 | | | | | 60 | | | | | |

| Asp | Ala | His | Ala | Tyr | Ala | Ala | Lys | Thr | Tyr | Asp | Tyr | Tyr | Lys | Ser | Lys |
|---|---|---|---|---|---|---|---|---|---|---|---|---|---|---|---|
| 65 | | | | | 70 | | | | | 75 | | | | | 80 |

| Phe | Gly | Arg | Asp | Ser | Val | Asp | Gly | Arg | Gly | Leu | Gln | Leu | Arg | Ser | Thr |
|---|---|---|---|---|---|---|---|---|---|---|---|---|---|---|---|
| | | | | 85 | | | | | 90 | | | | | 95 | |

| Val | His | Tyr | Gly | Ser | Arg | Tyr | Asn | Asn | Ala | Phe | Trp | Asn | Gly | Ser | Gln |
|---|---|---|---|---|---|---|---|---|---|---|---|---|---|---|---|
| | | | 100 | | | | | 105 | | | | | 110 | | |

| Met | Thr | Tyr | Gly | Asp | Gly | Asp | Gly | Ser | Thr | Phe | Ile | Ala | Phe | Ser | Gly |
|---|---|---|---|---|---|---|---|---|---|---|---|---|---|---|---|
| | | 115 | | | | | 120 | | | | | 125 | | | |

| Asp | Pro | Asp | Val | Val | Gly | His | Glu | Leu | Thr | His | Gly | Val | Thr | Glu | Tyr |
|---|---|---|---|---|---|---|---|---|---|---|---|---|---|---|---|
| 130 | | | | | 135 | | | | | 140 | | | | | |

| Thr | Ser | Asn | Leu | Glu | Tyr | Tyr | Gly | Glu | Ser | Gly | Ala | Leu | Asn | Glu | Ala |
|---|---|---|---|---|---|---|---|---|---|---|---|---|---|---|---|
| 145 | | | | | 150 | | | | | 155 | | | | | 160 |

| Phe | Ser | Asp | Val | Ile | Gly | Asn | Asp | Ile | Gln | Arg | Lys | Asn | Trp | Leu | Val |
|---|---|---|---|---|---|---|---|---|---|---|---|---|---|---|---|
| | | | | 165 | | | | | 170 | | | | | 175 | |

| Gly | Asp | Asp | Ile | Tyr | Thr | Pro | Asn | Ile | Ala | Gly | Asp | Ala | Leu | Arg | Ser |
|---|---|---|---|---|---|---|---|---|---|---|---|---|---|---|---|
| | | | 180 | | | | | 185 | | | | | 190 | | |

| Met | Ser | Asn | Pro | Thr | Leu | Tyr | Asp | Gln | Pro | Asp | His | Tyr | Ser | Asn | Leu |
|---|---|---|---|---|---|---|---|---|---|---|---|---|---|---|---|
| | 195 | | | | | 200 | | | | | 205 | | | | |

| Tyr | Lys | Gly | Ser | Ser | Asp | Asn | Gly | Gly | Val | His | Thr | Asn | Ser | Gly | Ile |
|---|---|---|---|---|---|---|---|---|---|---|---|---|---|---|---|
| 210 | | | | | 215 | | | | | 220 | | | | | |

| Ile | Asn | Lys | Ala | Tyr | Tyr | Leu | Leu | Ala | Gln | Gly | Gly | Thr | Phe | His | Gly |
|---|---|---|---|---|---|---|---|---|---|---|---|---|---|---|---|
| 225 | | | | | 230 | | | | | 235 | | | | | 240 |

| Val | Ala | Val | Asn | Gly | Ile | Gly | Arg | Asp | Ala | Ala | Val | Gln | Ile | Tyr | Tyr |
|---|---|---|---|---|---|---|---|---|---|---|---|---|---|---|---|
| | | | | 245 | | | | | 250 | | | | | 255 | |

| Ser | Ala | Phe | Thr | Asn | Tyr | Leu | Thr | Ser | Ser | Asp | Phe | Ser | Asn | Ala | |
|---|---|---|---|---|---|---|---|---|---|---|---|---|---|---|---|
| | | | 260 | | | | | 265 | | | | | 270 | | |

| Arg | Ala | Ala | Val | Ile | Gln | Ala | Ala | Lys | Asp | Leu | Tyr | Gly | Ala | Asn | Ser |
|---|---|---|---|---|---|---|---|---|---|---|---|---|---|---|---|
| | | 275 | | | | | 280 | | | | | 285 | | | |

| Ala | Glu | Ala | Thr | Ala | Ala | Lys | Ser | Phe | Asp | Ala | Val | Gly | Val | Asn | |
|---|---|---|---|---|---|---|---|---|---|---|---|---|---|---|---|
| | 290 | | | | | 295 | | | | | 300 | | | | |

<210> SEQ ID NO 65
<211> LENGTH: 303
<212> TYPE: PRT
<213> ORGANISM: Paenibacillus terrae
<220> FEATURE:
<221> NAME/KEY: misc_feature
<222> LOCATION: (1)..(303)

<223> OTHER INFORMATION: PtePro1

<400> SEQUENCE: 65

Ala Thr Gly Thr Gly Val Gly Val Leu Gly Asp Thr Lys Thr Phe Thr
1               5                   10                  15

Thr Thr Gln Ser Gly Thr Gln Tyr Val Met Gln Asp Thr Thr Arg Gly
            20                  25                  30

Gly Gly Ile Val Thr Tyr Ser Ala Gly Asn Thr Gln Ser Leu Pro Gly
        35                  40                  45

Thr Leu Met Arg Asp Thr Asp Asn Val Trp Thr Asp Pro Ala Ala Val
    50                  55                  60

Asp Ala His Ala Tyr Ala Val Val Tyr Asp Tyr Phe Lys Asn Asn
65                  70                  75                  80

Phe Asn Arg Asp Ser Leu Asp Gly Arg Gly Met Ala Ile Lys Ser Thr
                85                  90                  95

Val His Tyr Gly Ser Arg Tyr Asn Asn Ala Phe Trp Asn Gly Thr Gln
            100                 105                 110

Ile Ala Tyr Gly Asp Gly Asp Thr Thr Phe Arg Ala Phe Ser Gly
            115                 120                 125

Asp Leu Asp Val Ile Gly His Glu Leu Thr His Gly Ile Thr Glu Lys
    130                 135                 140

Thr Ala Gly Leu Ile Tyr Gln Gly Glu Ser Gly Ala Leu Asn Glu Ser
145                 150                 155                 160

Ile Ser Asp Val Phe Gly Asn Thr Ile Gln Gly Lys Asn Trp Leu Ile
                165                 170                 175

Gly Asp Asp Ile Tyr Thr Pro Ser Ile Pro Gly Asp Ala Leu Arg Ser
            180                 185                 190

Met Glu Asn Pro Thr Leu Phe Asn Gln Pro Asp His Tyr Ser Asn Ile
            195                 200                 205

Tyr Arg Gly Ser Asp Asp Asn Gly Gly Val His Thr Asn Ser Gly Ile
    210                 215                 220

Pro Asn Lys Ala Phe Tyr Leu Leu Ala Gln Gly Gly Thr His Arg Gly
225                 230                 235                 240

Val Ser Val Thr Gly Ile Gly Arg Gly Asp Ala Ala Lys Ile Val Tyr
                245                 250                 255

Lys Ala Leu Thr Tyr Tyr Leu Thr Ser Thr Ser Asn Phe Ala Ala Met
            260                 265                 270

Arg Gln Ala Ala Ile Ser Ser Ala Thr Asp Leu Phe Gly Ala Asn Ser
        275                 280                 285

Ala Gln Val Asn Ser Val Lys Ala Ala Tyr Ala Ala Val Gly Ile
    290                 295                 300

<210> SEQ ID NO 66
<211> LENGTH: 304
<212> TYPE: PRT
<213> ORGANISM: Brevibacillus brevis
<220> FEATURE:
<221> NAME/KEY: misc_feature
<222> LOCATION: (1)..(304)
<223> OTHER INFORMATION: BbrPro1

<400> SEQUENCE: 66

Val Thr Ala Thr Gly Lys Gly Val Leu Gly Asp Thr Lys Gln Phe Glu
1               5                   10                  15

Thr Thr Lys Gln Gly Ser Thr Tyr Met Leu Lys Asp Thr Thr Arg Gly
            20                  25                  30

```
Lys Gly Ile Glu Thr Tyr Thr Ala Asn Asn Arg Thr Ser Leu Pro Gly
             35                  40                  45

Thr Leu Met Thr Asp Ser Asp Asn Tyr Trp Thr Asp Gly Ala Ala Val
 50                  55                  60

Asp Ala His Ala His Ala Gln Lys Thr Tyr Asp Tyr Phe Arg Asn Val
 65                  70                  75                  80

His Asn Arg Asn Ser Tyr Asp Gly Asn Gly Ala Val Ile Arg Ser Thr
                 85                  90                  95

Val His Tyr Ser Thr Arg Tyr Asn Asn Ala Phe Trp Asn Gly Ser Gln
                100                 105                 110

Met Val Tyr Gly Asp Gly Asp Gly Thr Thr Phe Leu Pro Leu Ser Gly
            115                 120                 125

Gly Leu Asp Val Val Ala His Glu Leu Thr His Ala Val Thr Glu Arg
130                 135                 140

Thr Ala Gly Leu Val Tyr Gln Asn Glu Ser Gly Ala Leu Asn Glu Ser
145                 150                 155                 160

Met Ser Asp Ile Phe Gly Ala Met Val Asp Asn Asp Asp Trp Leu Met
                165                 170                 175

Gly Glu Asp Ile Tyr Thr Pro Gly Arg Ser Gly Asp Ala Leu Arg Ser
            180                 185                 190

Leu Gln Asp Pro Ala Ala Tyr Gly Asp Pro Asp His Tyr Ser Lys Arg
        195                 200                 205

Tyr Thr Gly Ser Gln Asp Asn Gly Gly Val His Thr Asn Ser Gly Ile
    210                 215                 220

Asn Asn Lys Ala Ala Tyr Leu Leu Ala Glu Gly Gly Thr His Tyr Gly
225                 230                 235                 240

Val Arg Val Asn Gly Ile Gly Arg Thr Asp Thr Ala Lys Ile Tyr Tyr
                245                 250                 255

His Ala Leu Thr His Tyr Leu Thr Pro Tyr Ser Asn Phe Ser Ala Met
            260                 265                 270

Arg Arg Ala Ala Val Leu Ser Ala Thr Asp Leu Phe Gly Ala Asn Ser
        275                 280                 285

Arg Gln Val Gln Ala Val Asn Ala Ala Tyr Asp Ala Val Gly Val Lys
    290                 295                 300

<210> SEQ ID NO 67
<211> LENGTH: 300
<212> TYPE: PRT
<213> ORGANISM: Bacillus subtilis
<220> FEATURE:
<221> NAME/KEY: misc_feature
<222> LOCATION: (1)..(300)
<223> OTHER INFORMATION: NprE

<400> SEQUENCE: 67

Ala Ala Thr Thr Gly Thr Gly Thr Thr Leu Lys Gly Lys Thr Val Ser
 1               5                  10                  15

Leu Asn Ile Ser Ser Glu Ser Gly Lys Tyr Val Leu Arg Asp Leu Ser
                 20                  25                  30

Lys Pro Thr Gly Thr Gln Ile Ile Thr Tyr Asp Leu Gln Asn Arg Glu
             35                  40                  45

Tyr Asn Leu Pro Gly Thr Leu Val Ser Ser Thr Thr Asn Gln Phe Thr
 50                  55                  60

Thr Ser Ser Gln Arg Ala Ala Val Asp Ala His Tyr Asn Leu Gly Lys
 65                  70                  75                  80

Val Tyr Asp Tyr Phe Tyr Gln Lys Phe Asn Arg Asn Ser Tyr Asp Asn
```

-continued

```
                85                  90                  95
Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ser Phe Phe Ser Pro Leu Ser Gly Ser Met Asp Val Thr Ala His Glu
    130                 135                 140

Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
                165                 170                 175

Asn Asp Thr Glu Asp Trp Asp Ile Gly Glu Asp Ile Thr Val Ser Gln
            180                 185                 190

Pro Ala Leu Arg Ser Leu Ser Asn Pro Thr Lys Tyr Gly Gln Pro Asp
        195                 200                 205

Asn Phe Lys Asn Tyr Lys Asn Leu Pro Asn Thr Asp Ala Gly Asp Tyr
    210                 215                 220

Gly Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
                245                 250                 255

Ala Leu Thr Val Tyr Leu Thr Pro Ser Ser Thr Phe Lys Asp Ala Lys
            260                 265                 270

Ala Ala Leu Ile Gln Ser Ala Arg Asp Leu Tyr Gly Ser Gln Asp Ala
        275                 280                 285

Ala Ser Val Glu Ala Ala Trp Asn Ala Val Gly Leu
    290                 295                 300

<210> SEQ ID NO 68
<211> LENGTH: 300
<212> TYPE: PRT
<213> ORGANISM: Bacillus subtilis
<220> FEATURE:
<221> NAME/KEY: misc_feature
<222> LOCATION: (1)..(300)
<223> OTHER INFORMATION: NprE_variant

<400> SEQUENCE: 68

Ala Ala Thr Thr Gly Thr Gly Thr Thr Leu Lys Gly Lys Thr Val Ser
1               5                   10                  15

Leu Asn Ile Ser Ser Glu Ser Gly Lys Tyr Val Leu Arg Asp Leu Ser
            20                  25                  30

Lys Pro Thr Gly Thr Gln Ile Ile Thr Tyr Asp Leu Gln Asn Arg Glu
        35                  40                  45

Tyr Asn Leu Pro Gly Thr Leu Val Ser Ser Thr Asn Gln Phe Thr
    50                  55                  60

Thr Ser Ser Gln Arg Ala Ala Val Asp Ala His Tyr Asn Leu Gly Lys
65                  70                  75                  80

Val Tyr Asp Tyr Phe Tyr Gln Lys Phe Asn Arg Asn Ser Tyr Asp Asn
                85                  90                  95

Lys Gly Gly Lys Ile Val Ser Ser Val His Tyr Gly Ser Arg Tyr Asn
            100                 105                 110

Asn Ala Ala Trp Ile Gly Asp Gln Met Ile Tyr Gly Asp Gly Asp Gly
        115                 120                 125

Ile Leu Phe Ser Pro Leu Ser Gly Ser Leu Asp Val Thr Ala His Glu
    130                 135                 140
```

```
Met Thr His Gly Val Thr Gln Glu Thr Ala Asn Leu Asn Tyr Glu Asn
145                 150                 155                 160

Gln Pro Gly Ala Leu Asn Glu Ser Phe Ser Asp Val Phe Gly Tyr Phe
            165                 170                 175

Asn Asp Thr Glu Asp Trp Asp Ile Gly Glu Asp Ile Thr Ile Ser Gln
        180                 185                 190

Pro Ala Leu Arg Ser Leu Ser Asn Pro Thr Lys Tyr Gly Gln Pro Asp
            195                 200                 205

Asn Phe Lys Asn Tyr Lys Asn Leu Pro Asn Thr Pro Ala Gly Asp Tyr
        210                 215                 220

Gly Gly Val His Thr Asn Ser Gly Ile Pro Asn Lys Ala Ala Tyr Asn
225                 230                 235                 240

Thr Ile Thr Lys Ile Gly Val Asn Lys Ala Glu Gln Ile Tyr Tyr Arg
            245                 250                 255

Ala Leu Thr Val Tyr Leu Thr Pro Ser Ser Thr Phe Lys Asp Ala Lys
        260                 265                 270

Ala Ala Leu Ile Gln Ser Ala Arg Asp Leu Tyr Gly Ser Gln Asp Ala
            275                 280                 285

Ala Ser Val Glu Ala Ala Trp Asn Ala Val Gly Leu
        290                 295                 300
```

METALLOPROTEASES

CROSS REFERENCE TO RELATED APPLICATIONS

This application is a Continuation of U.S. Ser. No. 14/893,473, filed Nov. 23, 2015, which is a 371 of International Patent Application No. PCT/US2014/039928, filed May 29, 2014, which claims benefit of priority from International patent applications Serial No. PCT/CN2013/076419; Serial No. PCT/CN2013/076387; Serial No. PCT/CN2013/076401; Serial No. PCT/CN2013/076406; Serial No. PCT/CN2013/076414; Serial No. PCT/CN2013/076384; Serial No. PCT/CN2013/076398; and Serial No. PCT/CN2013/076415; all filed on 29 May 2013, the contents of which are incorporated herein by reference in their entirety.

SEQUENCE LISTING

The sequence listing submitted via EFS, in compliance with 37 C.F.R. § 1.52(e), is incorporated herein by reference. The sequence listing text file submitted via EFS contains the file "20171207_NB40167USCNT2_SeqLst.txt", created on Dec. 7, 2017, which is 207 kilo bytes in size.

FIELD OF THE INVENTION

The present disclosure relates to proteases and variants thereof. Compositions containing the proteases are suitable for use in cleaning, food and feed as well as in a variety of other industrial applications.

BACKGROUND

Metalloproteases (MPs) are among the hydrolases that mediate nucleophilic attack on peptide bonds using a water molecule coordinated in the active site. In their case, a divalent ion, such as zinc, activates the water molecule. This metal ion is held in place by amino acid ligands, usually 3 in number. The clan MA consists of zinc-dependent MPs in which two of the zinc ligands are the histidines in the motif: HisGluXXHis (SEQ ID NO: 41). This Glu is the catalytic residue. These are two domain proteases with the active site between the domains. In subclan MA(E), also known as Glu-zincins, the $3^{rd}$ ligand is a Glu located C-terminal to the HDXXH (SEQ ID NO: 42) motif. Members of the families: M1, 3, 4, 13, 27 and 34 are all secreted proteases, almost exclusively from bacteria (Rawlings and Salvessen (2013) Handbook of Proteolytic Enzymes, Elsevier Press). They are generally active at elevated temperatures and this stability is attributed to calcium binding. Thermolysin-like proteases are found in the M4 family as defined by MEROPS (Rawlings et al., (2012) Nucleic Acids Res 40:D343-D350). Although proteases have long been known in the art of industrial enzymes, there remains a need for novel proteases that are suitable for particular conditions and uses.

SUMMARY

The present disclosure provides novel metalloprotease enzymes, nucleic acids encoding the same, and compositions and methods related to the production and use thereof.

In some embodiments, the invention is a polypeptide comprising an amino acid sequence having at least 60%, at least 80%, or at least 95% sequence identity to the amino acid sequence of SEQ ID NO: 3. In some embodiments, the invention is any of the above, wherein said polypeptide is derived from a member of the order Bacillales; family Bacillaceae, Paenibacillaceae, Alicyclobacillaceae, Lactobacillaceae, or a *Bacillus, Alicyclobacillus, Geobacillus, Exiguobacterium, Lactobacillus,* or *Paenibacillus* spp., such as *Paenibacillus polymyxa*. In some embodiments, the invention is any of the above, wherein said polypeptide is derived from a member of the Pseudococcidae, or a *Planococcus* spp., such as *Planococcus donghaensis*. In various embodiments of the invention, any of the above polypeptides has protease activity, such as azo-casein hydrolysis. In various embodiments of the invention, any of the above polypeptides retains at least 50% of its maximal activity between pH 5 and 9.5. In various embodiments of the invention, any of the above polypeptides retains at least 50% of its maximal activity between 30° C. and 70° C. In various embodiments of the invention, any of the above polypeptides has cleaning activity in a detergent composition, such as an ADW, laundry, liquid laundry, or powder laundry detergent composition.

In some embodiments, the invention is a polypeptide comprising an amino acid sequence having at least 60%, at least 80%, or at least 95% sequence identity to the amino acid sequence of SEQ ID NO: 8. In some embodiments, the invention is any of the above, wherein said polypeptide is derived from a member of the order Bacillales; family Bacillaceae, Paenibacillaceae, or Brevibacillaceae, or a *Bacillus, Brevibacillus,* or *Paenibacillus* spp., such as *Paenibacillus* sp. In some embodiments, the invention is any of the above, wherein said polypeptide is derived from *Brevibacillus* sp. In various embodiments of the invention, any of the above polypeptides has protease activity, such as azo-casein hydrolysis. In various embodiments of the invention, any of the above polypeptides retains at least 50% of its maximal activity between pH 5 and 10. In various embodiments of the invention, any of the above polypeptides retains at least 50% of its maximal activity between 35° C. and 70° C. In various embodiments of the invention, any of the above polypeptides has cleaning activity in a detergent composition, such as an ADW, laundry, liquid laundry, or powder laundry detergent composition.

In some embodiments, the invention is a polypeptide comprising an amino acid sequence having at least 60%, at least 80%, or at least 95% sequence identity to the amino acid sequence of SEQ ID NO: 13. In some embodiments, the invention is any of the above, wherein said polypeptide is derived from a member of the order Bacillales; family Bacillaceae, Paenibacillaceae, or Brevibacillaceae, or a *Bacillus, Geobacillus, Brevibacillus,* or *Paenibacillus* spp., such as *Paenibacillus humicus*. In some embodiments, the invention is any of the above, wherein said polypeptide is derived from *Bacillus polymyxa*. In various embodiments of the invention, any of the above polypeptides has protease activity, such as azo-casein hydrolysis. In various embodiments of the invention, any of the above polypeptides retains at least 50% of its maximal activity between pH 5 and 9.5. In various embodiments of the invention, any of the above polypeptides retains at least 50% of its maximal activity between 35° C. and 70° C. In various embodiments of the invention, any of the above polypeptides has cleaning activity in a detergent composition, such as an ADW, laundry, liquid laundry, or powder laundry detergent composition.

In some embodiments, the invention is a polypeptide comprising an amino acid sequence having at least 60%, at least 80%, or at least 95% sequence identity to the amino acid sequence of SEQ ID NO: 18. In some embodiments, the invention is any of the above, wherein said polypeptide is derived from a member of the order Bacillales; family Bacillaceae, Paenibacillaceae, or Brevibacillaceae, or a *Bacillus, Geobacillus, Brevibacillus*, or *Paenibacillus* spp., such as *Paenibacillus ehimensis*. In some embodiments, the invention is any of the above, wherein said polypeptide is derived from *Brevibacillus* sp. In various embodiments of the invention, any of the above polypeptides has protease activity, such as azo-casein hydrolysis. In various embodiments of the invention, any of the above polypeptides retains at least 50% of its maximal activity between pH 5 and 10.5. In various embodiments of the invention, any of the above polypeptides retains at least 50% of its maximal activity between 45° C. and 75° C. In various embodiments of the invention, any of the above polypeptides has cleaning activity in a detergent composition, such as an ADW, laundry, liquid laundry, or powder laundry detergent composition.

In some embodiments, the invention is a polypeptide comprising an amino acid sequence having at least 60%, at least 80%, or at least 95% sequence identity to the amino acid sequence of SEQ ID NO: 23. In some embodiments, the invention is any of the above, wherein said polypeptide is derived from a member of the order Bacillales; family Bacillaceae, Paenibacillaceae, Alicyclobacillaceae, Lactobacillaceae, or a *Bacillus, Geobacillus, Alicyclobacillus, Brevibacillus, Paenibacillus*, or *Lactobacillus* spp., such as *Paenibacillus barcinonensis*. In some embodiments, the invention is any of the above, wherein said polypeptide is derived from a member of the family Pseudococcidae, or a *Planococcus* spp., such as *Planococcus donghaensis*. In various embodiments of the invention, any of the above polypeptides has protease activity, such as azo-casein hydrolysis. In various embodiments of the invention, any of the above polypeptides retains at least 50% of its maximal activity between pH 5 and 10. In various embodiments of the invention, any of the above polypeptides retains at least 50% of its maximal activity between 35° C. and 65° C. In various embodiments of the invention, any of the above polypeptides has cleaning activity in a detergent composition, such as an ADW, laundry, liquid laundry, or powder laundry detergent composition.

In some embodiments, the invention is a polypeptide comprising an amino acid sequence having at least 60%, at least 80%, or at least 95% sequence identity to the amino acid sequence of SEQ ID NO: 28. In some embodiments, the invention is any of the above, wherein said polypeptide is derived from a member of the order Bacillales; family Bacillaceae, Paenibacillaceae, or a *Bacillus, Brevibacillus, Paenibacillus*, or *Lactobacillus* spp., such as *Paenibacillus polymyxa*. In some embodiments, the invention is any of the above, wherein said polypeptide is derived from a member of the family Pseudococcidae, or a *Planococcus* spp., such as *Planococcus donghaensis*. In various embodiments of the invention, any of the above polypeptides has protease activity, such as azo-casein hydrolysis. In various embodiments of the invention, any of the above polypeptides retains at least 50% of its maximal activity between pH 5 and 9.5. In various embodiments of the invention, any of the above polypeptides retains at least 50% of its maximal activity between 30° C. and 65° C. In various embodiments of the invention, any of the above polypeptides has cleaning activity in a detergent composition, such as an ADW, laundry, liquid laundry, or powder laundry detergent composition.

In some embodiments, the invention is a polypeptide comprising an amino acid sequence having at least 60%, at least 80%, or at least 95% sequence identity to the amino acid sequence of SEQ ID NO: 33. In some embodiments, the invention is any of the above, wherein said polypeptide is derived from a member of the order Bacillales; family Bacillaceae, Paenibacillaceae, or a *Bacillus, Geobacillus, Brevibacillus*, or *Paenibacillus* spp., such as *Paenibacillus hunanensis*. In some embodiments, the invention is any of the above, wherein said polypeptide is derived from *Bacillus polymyxa*. In various embodiments of the invention, any of the above polypeptides has protease activity, such as azo-casein hydrolysis. In various embodiments of the invention, any of the above polypeptides retains at least 50% of its maximal activity between pH 4.5 and 9.0. In various embodiments of the invention, any of the above polypeptides retains at least 50% of its maximal activity between 35° C. and 70° C. In various embodiments of the invention, any of the above polypeptides has cleaning activity in a detergent composition, such as an ADW, laundry, liquid laundry, or powder laundry detergent composition.

In some embodiments, the invention is a polypeptide comprising an amino acid sequence having at least 60%, at least 80%, or at least 95% sequence identity to the amino acid sequence of SEQ ID NO: 38. In some embodiments, the invention is any of the above, wherein said polypeptide is derived from a member of the order Bacillales; family Bacillaceae, Paenibacillaceae, Lactobacillaceae, or a *Bacillus, Brevibacillus, Lactobacillus, Paenibacillus*, or *Geobacillus* spp., such as *Paenibacillus amylolyticus*. In various embodiments of the invention, any of the above polypeptides has protease activity, such as azo-casein hydrolysis. In various embodiments of the invention, any of the above polypeptides retains at least 50% of its maximal activity between pH 5.5 and 10. In various embodiments of the invention, any of the above polypeptides retains at least 50% of its maximal activity between 35° C. and 65° C. In various embodiments of the invention, any of the above polypeptides has cleaning activity in a detergent composition, such as an ADW, laundry, liquid laundry, or powder laundry detergent composition.

In some embodiments, the invention is a composition comprising any of the above, such as a cleaning or detergent composition. In some embodiments, the composition further comprises a surfactant, at least one calcium ion and/or zinc ion, at least one stabilizer, at least one bleaching agent, and can contain phosphate, or be phosphate-free. In some embodiments, the composition further comprises one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and combinations thereof. In some embodiments, the composition is formulated at a pH of from about 5.5 to about 8.5. In some embodiments, the invention is a method of cleaning using any of the above polypeptides or compositions. In some embodiments, the invention is a textile processing composition, animal feed composition, leather processing composition, or feather processing composition.

BRIEF DESCRIPTION OF THE DRAWINGS

FIG. 1.1 provides a plasmid map of pGX085 (aprE-PspPro3), described in Example 1.2.

FIG. 1.2 provides a dose response curve of PspPro3 in the azo-casein assay.

FIG. 1.3 provides the pH profile of PspPro3.

FIG. 1.4 provides the temperature profile of PspPro3.

FIG. 1.5A shows dose response for cleaning of PA-S-38 microswatches by PspPro3 protein in ADW detergent at pH 6 and 8.

FIG. 1.5B shows dose response for cleaning of PA-S-38 microswatches shows by PspPro3 protein in ADW detergent at pH 6 and 8 in the presence of bleach.

FIG. 1.6 shows cleaning performance of PspPro3 protein in liquid laundry detergent.

FIG. 1.7 (SEQ ID NOS: 3, 44, and 45, respectively) shows alignment of PspPro3 with other protein homologs.

FIG. 1.8 provides the phylogenetic tree for PspPro3 and its homologs.

FIG. 2.1 provides a plasmid map of pGX084 (aprE-PspPro2), described in Example 2.2.

FIG. 2.2 provides a dose response curve of PspPro2 in the azo-casein assay.

FIG. 2.3 provides the pH profile of purified PspPro2.

FIG. 2.4 provides the temperature profile of purified PspPro2.

FIG. 2.5A shows dose response for cleaning performance of PspPro2 at pH 6 in AT dish detergent with bleach.

FIG. 2.5B shows dose response for cleaning performance of purified PspPro2 at pH 8 in AT detergent with bleach.

FIG. 2.6A shows cleaning performance of PspPro2 protein in liquid laundry detergent.

FIG. 2.6B shows cleaning performance of PspPro2 protein in powder laundry detergent.

FIG. 2.7 (SEQ ID NOS: 8, 46, and 45, respectively) shows alignment of PspPro2 with other protein homologs.

FIG. 2.8 provides the phylogenetic tree for PspPro2 and its homologs.

FIG. 3.1 provides a plasmid map of pGX150 (aprE-PhuPro2), described in Example 3.2.

FIG. 3.2 provides a dose response curve of PhuPro2 in the azo-casein assay.

FIG. 3.3 provides the pH profile of purified PhuPro2.

FIG. 3.4 provides the temperature profile of purified PhuPro2.

FIG. 3.5A shows dose response for c leaning performance of PhuPro2 in AT dish detergent at pH 6.

FIG. 3.5B shows dose response for cleaning performance of PhuPro2 in AT dish detergent at pH 8.

FIG. 3.6 (SEQ ID NOS: 13, 47 and 45, respectively) shows alignment of PhuPro2 with other protein homologs.

FIG. 3.7 provides the phylogenetic tree for PhuPro2 and its homologs.

FIG. 4.1 provides a plasmid map of pGX148 (aprE-PehPro1), described in Example 4.2.

FIG. 4.2 provides a dose response curve of PehPro1 in the azo-casein assay.

FIG. 4.3 provides the pH profile of purified PehPro1.

FIG. 4.4 provides the temperature profile of purified PehPro1.

FIG. 4.5A shows dose response for cleaning performance of PehPro1 at pH 6 in AT dish detergent with bleach.

FIG. 4.5B shows dose response for cleaning performance of purified PehPro1 at pH 8 in AT detergent with bleach.

FIG. 4.6 (SEQ ID NOS: 18, 48, and 45, respectively) shows alignment of PehPro1 with other protein homologs.

FIG. 4.7 provides the phylogenetic tree for PehPro1 and its homologs.

FIG. 5.1 provides a plasmid map of pGX147 (aprE-PbaPro1), described in Example 5.2.

FIG. 5.2 provides a dose response curve of PbaPro1 in the azo-casein assay.

FIG. 5.3 provides the pH profile of purified PbaPro1.

FIG. 5.4 provides the temperature profile of purified PbaPro1.

FIG. 5.5A shows dose response for cleaning of PA-S-38 microswatches by PbaPro1 protein in ADW detergent at pH 6.

FIG. 5.5B shows dose response for cleaning of PA-S-38 microswatches shows by PbaPro1 protein in ADW detergent at pH 8.

FIG. 5.6 (SEQ ID NOS: 23, 49, and 45, respectively) shows the alignment of PbaPro1 with protease homologs.

FIG. 5.7 provides the phylogenetic tree for PbaPro1 and its homologs.

FIG. 6.1 provides a plasmid map of pGX138 (aprE-PpoPro1), described in Example 6.2.

FIG. 6.2 provides a dose response curve of PpoPro1 in the azo-casein assay.

FIG. 6.3 provides the pH profile of purified PpoPro1.

FIG. 6.4 provides the temperature profile of purified PpoPro1.

FIG. 6.5A shows dose response for cleaning of PA-S-38 microswatches by PpoPro1 protein in ADW detergent at pH 6 in the presence of bleach.

FIG. 6.5B shows dose response for cleaning of PA-S-38 microswatches shows by PpoPro1 protein in ADW detergent at pH 8 in the presence of bleach.

FIG. 6.6 (SEQ ID NOS: 28, 50, and 45, respectively) shows the alignment of PpoPro1 with protease homologs.

FIG. 6.7 provides the phylogenetic tree for PpoPro1 and its homologs.

FIG. 7.1 provides a plasmid map of pGX149 (aprE-PhuPro1), described in Example 7.2.

FIG. 7.2 provides a dose response curve of PhuPro1 in the azo-casein assay.

FIG. 7.3 provides the pH profile of purified PhuPro1.

FIG. 7.4 provides the temperature profile of purified PhuPro1.

FIG. 7.5A shows dose response for cleaning of PA-S-38 microswatches by PhuPro1 protein in ADW detergent at pH 6.

FIG. 7.5B shows dose response for cleaning of PA-S-38 microswatches shows by Phu Pro1 protein in ADW detergent at pH 8.

FIG. 7.6 (SEQ ID NOS: 33, 51, and 45, respectively) shows alignment of PhuPro1 with other protein homologs.

FIG. 7.7 provides the phylogenetic tree for PhuPro1 and its homologs.

FIGS. 7.8A and 7.8B show cleaning performances of PhuPro1 and Purafect® Prime HA proteases.

FIG. 8.1 provides a plasmid map of pGX146 (aprE-PamPro1), described in Example 8.2.

FIG. 8.2 provides a dose response curve of PamPro1 in the azo-casein assay.

FIG. 8.3 provides the pH profile of purified PamPro1.

FIG. 8.4 provides the temperature profile of purified PamPro1.

FIG. 8.5A shows dose response for cleaning of PA-S-38 microswatches by PamPro1 protein in ADW detergent at pH 6.

FIG. 8.5B shows dose response for cleaning of PA-S-38 microswatches shows by PamPro1 protein in ADW detergent at pH 8.

FIG. 8.6 (SEQ ID NOS: 38, 52, and 45, respectively) shows the alignment of PamPro1 with protease homologs.

FIG. 8.7 provides the phylogenetic tree for PamPro1 and its homologs.

FIGS. 9.1A thru 9.1D (SEQ ID NOS: 53-62, 38, 23, 13, 63, 8, 28, 64, 3, 18, 33, 65-68, respectively) show the alignment of the various *Paenibacillus* metalloproteases with other bacterial metalloprotease homologs.

FIG. 9.2 provides the phylogenetic tree of the various *Paenibacillus* metalloproteases with other bacterial metalloprotease homologs.

DETAILED DESCRIPTION

The present invention provides novel metalloprotease enzymes, especially enzymes useful for detergent compositions cloned from various *Paenibacillus* sp. The compositions and methods are based, in part, on the observation that the novel metalloproteases of the present invention have proteolytic activity in the presence of detergent compositions. This feature makes metalloproteases of the present invention particularly well suited to and useful in a variety of cleaning applications where the enzyme can hydrolyze polypeptides in the presence of surfactants and other components found in detergent compositions. The invention includes compositions comprising at least one of the novel metalloprotease enzymes set forth herein. Some such compositions comprise detergent compositions. The metalloprotease enzymes of the present invention can be combined with other enzymes useful in detergent compositions. The invention also provides methods of cleaning using metalloprotease enzymes of the present invention.

Definitions and Abbreviations

Unless otherwise indicated, the practice of the present invention involves conventional techniques commonly used in molecular biology, protein engineering, microbiology, and recombinant DNA technology, which are within the skill of the art. Such techniques are known to those of skill in the art and are described in numerous texts and reference works well known to those of skill in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Many technical dictionaries are known to those of skill in the art. Although any methods and materials similar or equivalent to those described herein find use in the practice of the present invention, some suitable methods and materials are described herein. Accordingly, the terms defined immediately below are more fully described by reference to the Specification as a whole. Also, as used herein, the singular "a", "an" and "the" includes the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Furthermore, the headings provided herein are not limitations of the various aspects or embodiments of the invention.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well known procedures exist for measuring proteolytic activity (See e.g., Kalisz, "Microbial Proteinases," In: Fiechter (ed.), *Advances in Biochemical Engineering/Biotechnology*, (1988)). For example, proteolytic activity may be ascertained by comparative assays which analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011 and U.S. Pat. No. 6,376,450, both of which are incorporated herein by reference). The pNA peptidyl assay (See e.g., Del Mar et al., Anal. Biochem. 99:316-320 [1979]) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA)(SEQ ID NO: 43). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

As used herein, the term "variant polypeptide" refers to a polypeptide comprising an amino acid sequence that differs in at least one amino acid residue from the amino acid sequence of a parent or reference polypeptide (including but not limited to wild-type polypeptides).

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores under stressful environmental conditions is considered the defining feature of the genus *Bacillus*, although this characteristic also applies to the recently named *Alicyclobacillus*, *Amphibacillus*, *Aneurinibacillus*, *Paenibacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

The terms "polynucleotide" and "nucleic acid," which are used interchangeably herein, refer to a polymer of any length of nucleotide monomers covalently bonded in a chain. DNA (deoxyribonucleic acid), a polynucleotide comprising deoxyribonucleotides, and RNA (ribonucleic acid), a polymer of ribonucleotides, are examples of polynucleotides or nucleic acids having distinct biological function. Polynucleotides or nucleic acids include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, expressed sequence tag(s) (EST(s)), exons, introns, messenger RNA (mRNA), transfer RNA (tRNA), ribosomal RNA (rRNA), ribozymes, complementary DNA (cDNA), recombinant polynucleotides, branched polynucleotides, plasmids, vectors, isolated DNA of any sequence, isolated RNA of any sequence, nucleic acid probes, and primers.

As used herein, the term "mutation" refers to changes made to a reference amino acid or nucleic acid sequence. It is intended that the term encompass substitutions, insertions and deletions.

As used herein, the term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multi-cloning site, and a selectable marker. The process of inserting a vector into a target cell is typically referred to as transformation. The present invention includes, in some embodiments, a vector that comprises a DNA sequence encoding a metalloprotease polypeptide (e.g., precursor or mature metalloprotease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein, the term "expression cassette," "expression plasmid" or "expression vector" refers to a nucleic acid construct or vector generated recombinantly or synthetically for the expression of a nucleic acid of interest in a target cell. An expression vector or expression cassette typically comprises a promoter nucleotide sequence that drives expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Many prokaryotic and eukaryotic expression vectors are commercially available.

In some embodiments, the ends of the sequence are closed such that the DNA construct forms a closed circle. The nucleic acid sequence of interest, which is incorporated into the DNA construct, using techniques well known in the art, may be a wild-type, mutant, or modified nucleic acid. In some embodiments, the DNA construct comprises one or more nucleic acid sequences homologous to the host cell chromosome. In other embodiments, the DNA construct comprises one or more non-homologous nucleotide sequences. Once the DNA construct is assembled in vitro, it may be used, for example, to: 1) insert heterologous sequences into a desired target sequence of a host cell; and/or 2) mutagenize a region of the host cell chromosome (i.e., replace an endogenous sequence with a heterologous sequence); 3) delete target genes; and/or 4) introduce a replicating plasmid into the host. "DNA construct" is used interchangeably herein with "expression cassette."

As used herein, a "plasmid" refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction (See e.g., Ferrari et al., "Genetics," in Hardwood et al. (eds.), *Bacillus*, Plenum Publishing Corp., pp. 57-72 [1989]). Transformation refers to the genetic alteration of a cell which results from the uptake, optional genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) but which has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination," "recombining," and "recombined" of polynucleotides or nucleic acids refer generally to the assembly or combining of two or more nucleic acid or polynucleotide strands or fragments to generate a new polynucleotide or nucleic acid. The recombinant polynucleotide or nucleic acid is sometimes referred to as a chimera. A nucleic acid or polypeptide is "recombinant" when it is artificial or engineered.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

"Host strain" or "host cell" refers to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used through out this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". Mutations can also be named by using the three letter code for an amino acid followed by its position in the polypeptide chain as counted from the N-terminus; for example, Ala10 for alanine at position 10. Multiple mutations are indicated by inserting a "-" between the mutations. Mutations at positions 87 and 90 are represented as either "G087S-A090Y" or "G87S-A90Y" or "G87S+A90Y" or "G087S+A090Y". For deletions, the one letter code "Z" is used. For an insertion relative to the parent sequence, the one letter code "Z" is on the left side of the position number. For a deletion, the one letter code "Z" is on the right side of the position number. For insertions, the position number is the position number before the inserted amino acid(s), plus 0.01 for each amino acid. For example, an insertion of three amino acids alanine (A), serine (S) and tyrosine (Y) between position 87 and 88 is shown as "Z087.01A-Z087.02S-Z087.03Y." Thus, combining all the mutations above plus a deletion at position 100 is: "G087S-Z087.01A-Z087.02S-Z087.03Y-A090Y-A100Z." When describing modifications, a position followed by amino acids listed in parentheses indicates a list of substitutions at that position by any of the listed amino acids. For example, 6(L,I) means position 6 can be substituted with a leucine or isoleucine.

A "prosequence" or "propetide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial metalloproteases are often expressed as pro-enzymes.

The term "signal sequence" or "signal peptide" refers to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is native or naturally occurring sequence. As used herein, the term "naturally-occurring" refers to anything (e.g., proteins, amino acids, or nucleic acid sequences) that are found in nature.

As used herein, the term "non-naturally occurring" refers to anything that is not found in nature (e.g., recombinant nucleic acids and protein sequences produced in the laboratory), as modification of the wild-type sequence.

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity which are naturally produced by *Bacillus*, as well as to serine proteases like those produced by *Bacillus* sources but which through the use of genetic engineering techniques are produced by non-*Bacillus* organisms transformed with a nucleic acid encoding the serine proteases.

The term "identical" in the context of two nucleic acids or polypeptide sequences refers to the residues in the two sequences that are the same when aligned for maximum correspondence, as measured using one of the following sequence comparison or analysis algorithms.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "% identity or percent identity" refers to sequence similarity. Percent identity may be determined using standard techniques known in the art (See e.g., Smith and Waterman, Adv. Appl. Math. 2:482 [1981]; Needleman and Wunsch, J. Mol. Biol. 48:443 [1970]; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (See, Feng and Doolittle, J. Mol. Evol. 35:351-360 [1987]). The method is similar to that described by Higgins and Sharp (See, Higgins and Sharp, CABIOS 5:151-153 [1989]). Useful PILEUP parameters include a default gap weight of 3.00, a default gap length weight of 0.10, and weighted end gaps. Other useful algorithm is the BLAST algorithms described by Altschul et al., (See, Altschul et al., J. Mol. Biol. 215:403-410 [1990]; and Karlin and Altschul, Proc. Natl. Acad. Sci. USA 90:5873-5787 [1993]). The BLAST program uses several search parameters, most of which are set to the default values.

The NCBI BLAST algorithm finds the most relevant sequences in terms of biological similarity but is not recommended for query sequences of less than 20 residues (Altschul, S F et al. (1997) Nucleic Acids Res. 25:3389-3402 and Schaffer, A A et al. (2001) Nucleic Acids Res. 29:2994-3005). Example default BLAST parameters for a nucleic acid sequence searches are:

Neighboring words threshold: 11
E-value cutoff: 10
Scoring Matrix: NUC.3.1 (match=1, mismatch=−3)
Gap Opening: 5
Gap Extension: 2 and the following parameters for amino acid sequence searches:

Word size: 3
E-value cutoff: 10
Scoring Matrix: BLOSUM62
Gap Opening: 11
Gap extension: 1

A percent (%) amino acid sequence identity value is determined by the number of matching identical residues divided by the total number of residues of the "reference" sequence including any gaps created by the program for optimal/maximum alignment. If a sequence is 90% identical to SEQ ID NO: A, SEQ ID NO: A is the "reference" sequence. BLAST algorithms refer the "reference" sequence as "query" sequence.

The CLUSTAL W algorithm is another example of a sequence alignment algorithm. See Thompson et al. (1994) Nucleic Acids Res. 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF. |

In CLUSTAL algorithms, deletions occurring at either terminus are included. For example, a variant with five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A polypeptide of interest may be said to be "substantially identical" to a reference polypeptide if the polypeptide of interest comprises an amino acid sequence having at least about 60%, least about 65%, least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having least about 60%, least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

"Hybridization" refers to the process by which one strand of nucleic acid forms a duplex with, i.e., base pairs with, a complementary strand. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm–5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions can be used to identify sequences having strict identity or near-strict identity with the hybridization probe; while intermediate or low stringency hybridization can be used to identify or detect polynucleotide sequence homologs.

Moderate and high stringency hybridization conditions are well known in the art. Stringent hybridization conditions are exemplified by hybridization under the following conditions: 65° C. and 0.1×SSC (where 1×SSC=0.15 M NaCl, 0.015 M $Na_3$ citrate, pH 7.0). Hybridized, duplex nucleic acids are characterized by a melting temperature (Tm), where one half of the hybridized nucleic acids are unpaired with the complementary strand. Mismatched nucleic acids within the duplex lower the Tm. Very stringent hybridization conditions involve 68° C. and 0.1×SSC. A nucleic acid encoding a variant metalloprotease can have a Tm reduced by 1° C.-3° C. or more compared to a duplex formed between the nucleic acid and its identical complement.

Another example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. to accommodate factors such as probe length and the like.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 9'7%, about 98%, about 99%, about 99.5%, about 99.6%, about 99.'7%, about 99.8% or more pure (e.g., percent by weight on a molar basis). In a related sense, the invention provides methods of enriching compositions for one or more molecules of the invention, such as one or more polypeptides or polynucleotides of the invention. A composition is enriched for a molecule when there is a substantial increase in the concentration of the molecule after application of a purification or enrichment technique. A substantially pure polypeptide or polynucleotide of the invention (e.g., substantially pure metalloprotease polypeptide or polynucleotide encoding a metalloprotease polypeptide of the invention, respectively) will typically comprise at least about 55%, about 60%, about 65%, about 70%, about 75%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

The term "enriched" refers to a compound, polypeptide, cell, nucleic acid, amino acid, or other specified material or component that is present in a composition at a relative or absolute concentration that is higher than a starting composition.

In a related sense, the invention provides methods of enriching compositions for one or more molecules of the invention, such as one or more polypeptides of the invention (e.g., one or more metalloprotease polypeptides of the invention) or one or more nucleic acids of the invention (e.g., one or more nucleic acids encoding one or more metalloprotease polypeptides of the invention). A composition is enriched for a molecule when there is a substantial increase in the concentration of the molecule after application of a purification or enrichment technique. A substantially pure polypeptide or polynucleotide will typically comprise at least about 55%, about 60%, about 65%, about 70%, about 75%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The terms "modified nucleic acid sequence" and "modified gene" are used interchangeably herein to refer to a nucleic acid sequence that includes a deletion, insertion or interruption of naturally occurring (i.e., wild-type) nucleic acid sequence. In some embodiments, the expression product of the modified nucleic acid sequence is a truncated protein (e.g., if the modification is a deletion or interruption of the sequence). In some embodiments, the truncated protein retains biological activity. In alternative embodiments, the expression product of the modified nucleic acid sequence is an elongated protein (e.g., modifications comprising an insertion into the nucleic acid sequence). In some embodiments, a nucleotide insertion in the nucleic acid sequence leads to a truncated protein (e.g., when the insertion results in the formation of a stop codon). Thus, an insertion may result in either a truncated protein or an elongated protein as an expression product.

A "mutant" nucleic acid sequence typically refers to a nucleic acid sequence that has an alteration in at least one codon occurring in a host cell's wild-type sequence such that the expression product of the mutant nucleic acid sequence is a protein with an altered amino acid sequence relative to the wild-type protein. The expression product may have an altered functional capacity (e.g., enhanced enzymatic activity).

As used herein, the phrase "alteration in substrate specificity" refers to changes in the substrate specificity of an enzyme. In some embodiments, a change in substrate specificity is defined as a change in $k_{cat}$ and/or $K_m$ for a particular substrate, resulting from mutations of the enzyme or alteration of reaction conditions. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios of $k_{cat}/K_m$ for substrates of interest. However, it is not intended that the present invention be limited to any particular substrate composition or substrate specificity.

As used herein, "surface property" is used in reference to electrostatic charge, as well as properties such as the hydrophobicity and hydrophilicity exhibited by the surface of a protein. As used herein, the term "net charge" is defined as the sum of all charges present in a molecule. "Net charge changes" are made to a parent protein molecule to provide a variant that has a net charge that differs from that of the parent molecule (i.e., the variant has a net charge that is not the same as that of the parent molecule). For example, substitution of a neutral amino acid with a negatively charged amino acid or a positively charged amino acid with a neutral amino acid results in net charge of −1 with respect to the parent molecule. Substitution of a positively charged amino acid with a negatively charged amino acid results in a net charge of −2 with respect to the parent. Substitution of a neutral amino acid with a positively charged amino acid or a negatively charged amino acid with a neutral amino acid results in net charge of +1 with respect to the parent. Substitution of a negatively charged amino acid with a positively charged amino acid results in a net charge of +2 with respect to the parent. The net charge of a parent protein can also be altered by deletion and/or insertion of charged amino acids. A net change change applies to changes in charge of a variant versus a parent when measured at the same pH conditions.

The terms "thermally stable" and "thermostable" and "thermostability" refer to proteases that retain a specified amount of enzymatic activity after exposure to identified temperatures over a given period of time under conditions prevailing during the proteolytic, hydrolyzing, cleaning or other process of the invention, while being exposed to altered temperatures. "Altered temperatures" encompass increased or decreased temperatures. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to altered temperatures over a given time period, for example, at least about 60 minutes, about 120 minutes, about 180 minutes, about 240 minutes, about 300 minutes, etc.

The term "enhanced stability" in the context of an oxidation, chelator, thermal, chemical, autolytic and/or pH stable protease refers to a higher retained proteolytic activity over time as compared to other proteases (e.g., thermolysin proteases) and/or wild-type enzymes.

The term "diminished stability" in the context of an oxidation, chelator, thermal and/or pH stable protease refers to a lower retained proteolytic activity over time as compared to other proteases (e.g., thermolysin proteases) and/or wild-type enzymes.

The term "cleaning activity" refers to a cleaning performance achieved by a metalloprotease polypeptide or reference protease under conditions prevailing during the proteolytic, hydrolyzing, cleaning, or other process of the invention. In some embodiments, cleaning performance of a metalloprotease polypeptide or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO 99/34011 and U.S. Pat. No. 6,605,458, both of which are herein incorporated by reference, as well as those cleaning assays and methods included in the Examples provided below.

The term "cleaning effective amount" of a metalloprotease polypeptide or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a metalloprotease polypeptide of the invention. In some embodiments, the cleaning compositions of the present invention include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

The term "enhanced performance" in the context of cleaning activity refers to an increased or greater cleaning activity by an enzyme with respect to a parent or reference protein as measured on certain enzyme sensitive stains such as egg, milk, grass, ink, oil, and/or blood, as determined by usual evaluation after a standard wash cycle and/or multiple wash cycles.

The term "diminished performance" in the context of cleaning activity refers to a decreased or lesser cleaning activity by an enzyme on certain enzyme sensitive stains such as egg, milk, grass or blood, as determined by usual evaluation after a standard wash cycle and/or multiple wash cycles.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwash compositions (e.g., "hand" or "manual" dishwashing detergents) and automatic dishwashing compositions (e.g., "automatic dishwashing detergents").

Cleaning composition or cleaning formulations, as used herein, include, unless otherwise indicated, granular or powder-form all-purpose or heavy-duty washing agents, especially cleaning detergents; liquid, granular, gel, solid, tablet, or paste-form all-purpose washing agents, especially the so-called heavy-duty liquid (HDL) detergent or heavy-duty powder detergent (HDD) types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, and personal cleansing compositions.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners including toilet bowl cleaners; fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets. All of such products which are applicable may be in standard, concentrated or even highly concentrated form even to the extent that such products may in certain aspect be non-aqueous.

As used herein, the term "detergent composition" or "detergent formulation" is used in reference to a composition intended for use in a wash medium for the cleaning of soiled or dirty objects, including particular fabric and/or non-fabric objects or items. Such compositions of the present invention are not limited to any particular detergent composition or formulation. Indeed, in some embodiments, the detergents of the invention comprise at least one metalloprotease polypeptide of the invention and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the invention, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a metalloprotease polypeptide of the invention) refers to the contribution of a metalloprotease polypeptide to washing that provides additional cleaning performance to the detergent as compared to the detergent without the addition of the metalloprotease polypeptide to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

The term "improved wash performance" is used to indicate that a better end result is obtained in stain removal under relevant washing conditions, or that less metalloprotease polypeptide, on weight basis, is needed to obtain the same end result relative to the corresponding wild-type or starting parent protease.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

The position of an amino acid residue in a given amino acid sequence is typically numbered herein using the numbering of the position of the corresponding amino acid residue of the wild type *Paenibacillus* metalloprotease amino acid sequences shown in SEQ ID NOs: 3, 8, 13, 18, 23, 28, 33 or 38. The *Paenibacillus* sp. metalloprotease amino acid sequences, thus serves as a reference parent sequence. A given amino acid sequence, such as a metalloprotease enzyme amino acid sequence and variants thereof described herein, can be aligned with the wild type metalloprotease sequence (e.g., SEQ ID NO: 3) using an alignment algorithm as described herein, and an amino acid residue in the given amino acid sequence that aligns (preferably optimally aligns) with an amino acid residue in the wild type sequence can be conveniently numbered by reference to the corresponding amino acid residue in the metalloprotease sequence.

Oligonucleotide synthesis and purification steps are typically performed according to specifications. Techniques and procedures are generally performed according to conventional methods well known in the art and various general references that are provided throughout this document. Procedures therein are believed to be well known to those of ordinary skill in the art and are provided for the convenience of the reader.

Metalloprotease Polypeptides of the Present Invention

The present invention provides novel metalloprotease enzyme polypeptides, which may be collectively referred to as "enzymes of the invention" or "polypeptides of the invention." Polypeptides of the invention include isolated, recombinant, substantially pure, or non-naturally occurring polypeptides. In some embodiments, polypeptides of the invention are useful in cleaning applications and can be incorporated into cleaning compositions that are useful in methods of cleaning an item or a surface in need of cleaning.

In some embodiments, the enzyme of the present invention has 50, 60, 65, 70, 75, 80, 85, 90, 91, 92, 93, 94, 95, 96, 97, 98, 99 or 100% identity to SEQ ID NOs: 3, 8, 13, 18, 23, 28, 33 or 38. In various embodiments, the enzyme of the present invention has 50, 60, 65, 70, 75, 80, 85, 90, 91, 92, 93, 94, 95, 96, 97, 98, 99 or 100% identity to a metalloprotease enzyme from any genus in Tables 1.2, 2.2, 3.2, 4.2, 5.2, 6.2, 7.2 or 8.2.

In some embodiments, the enzyme of the present invention, including all embodiments supra, can be derived from a member of the order Bacillales or family Bacillaceae, Paenibacillaceae, Alicyclobacillaceae, or Lactobacillaceae. In some embodiments, the enzyme of the present invention, including all embodiments supra, can be derived from a *Bacillus, Alicyclobacillus, Geobacillus, Exiguobacterium, Lactobacillus,* or *Paenibacillus* species. In some embodiments, the enzyme of the present invention, including all embodiments supra, can be derived from a member of the Pseudococcidae family. In some embodiments, the enzyme of the present invention, including all embodiments supra, can be derived from a *Planococcus* species. Various enzyme metalloproteases have been found that have a high identity to each other and to the *Paenibacillus* enzymes as shown in SEQ ID NOs: 3, 8, 13, 18, 23, 28, 33 or 38.

In a particular embodiment, the invention is an enzyme derived from the genus *Paenibacillus*. In a particular embodiment, the invention is an enzyme derived from the genus *Paenibacillus* and from the species *Paenibacillus* sp., *Paenibacillus ehimensis, Paenibacillus hunanensis, Paenibacillus barcinonensis, Paenibacillus amylolyticus, Paenibacillus humicus* and *Paenibacillus polymyxa*.

Described are compositions and methods relating to enzymes cloned from *Paenibacillus*. The compositions and methods are based, in part, on the observation that cloned and expressed enzymes of the present invention have proteolytic activity in the presence of a detergent composition. Enzymes of the present invention also demonstrate excellent stability in detergent compositions. These features makes enzymes of the present invention well suited for use in a variety of cleaning applications, where the enzyme can hydrolyze proteins in the presence of surfactants and other components found in detergent compositions.

In some embodiments, the invention includes an isolated, recombinant, substantially pure, or non-naturally occurring enzyme having protease activity, which polypeptide comprises a polypeptide sequence having at least about 60%, 65%, 70%, 75%, 80%, 85%, 86%, 87%, 88%, 89%, 90%, 91%, 92%, 93%, 94%, 95%, 96%, 97%, 98%, 99% or 100% sequence identity to a parent enzyme as provided herein.

In some embodiments, the polypeptide of the present invention, is a polypeptide having a specified degree of amino acid sequence homology to the exemplified polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% sequence homology to the amino acid sequences of SEQ ID NOs: 3, 8, 13, 18, 23, 28, 33 or 38. Homology can be determined by amino acid sequence alignment, e.g., using a program such as BLAST, ALIGN, or CLUSTAL, as described herein.

Also provided are polypeptide enzymes of the present invention, having protease activity, said enzymes comprising an amino acid sequence which differs from the amino acid sequence of SEQ ID NOs: 3, 8, 13, 18, 23, 28, 33 or 38 by no more than 50, no more than 40, no more than 30, no more than 35, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 amino acid residue(s), when aligned using any of the previously described alignment methods.

As noted above, the variant enzyme polypeptides of the invention have enzymatic activities (e.g., protease activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant metalloprotease enzyme polypeptides of the invention are described infra. The enzymatic activity (e.g., protease enzyme activity) of an enzyme polypeptide of the invention can be determined readily using procedures well known to those of ordinary skill in the art. The Examples presented infra describe methods for evaluating the enzymatic activity and cleaning performance. The performance of polypeptide enzymes of the invention in removing stains (e.g., a protein stain such as blood/milk/ink or egg yolk), cleaning hard surfaces, or cleaning laundry, dishware or tableware item(s) can be readily determined using procedures well known in the art and/or by using procedures set forth in the Examples.

The metalloprotease polypeptides of the invention have protease activity such that they are useful in casein hydrolysis, collagen hydrolysis, elastin hydrolysis, keratin hydrolysis, soy protein hydrolysis or corn meal protein hydrolysis. Thus, the polypeptides of the invention find use in other applications such as pretreatments for food, feed, or protein degradation.

The polypeptides of the invention are also useful in pretreatment of animal feed products, such as soy protein, corn meal, and other protein rich components. Pretreatment of these animal feed products with a polypeptide of the invention may help in the breakdown of complex proteins into their hydrolysates which are easily digestible by animals.

In yet other embodiments, the disclosed metalloprotease polypeptides find use in hydrolysis of corn soy protein. The disclosed metalloprotease polypeptides may be used alone or in combination with other proteases, amylases or lipases to produce peptides and free amino acids from the corn or soy protein. In some embodiments, the recovered proteins, peptides or amino acids can be subsequently used in animal feed or human food products.

The polypeptides of the invention are also useful in treatment of wounds, particularly in wound debridement. Wound debridement is the removal of dead, damaged or infected tissue to improve the healing potential of the remaining healthy tissue. Debridement is an important part of the healing process for burns and other serious wounds. The wounds or burns may be treated with a composition comprising a polypeptide of the invention which would result in removal of unwanted damaged tissue and improving the healthy tissue.

The metalloprotease polypeptides of the present invention can have protease activity over a broad range of pH conditions. In some embodiments, the metalloprotease polypeptides have protease activity on azo-casein as a substrate, as demonstrated in Examples 3.1 to 3.8. In some embodiments, the metalloprotease polypeptides have protease activity at a pH of from about 3.0 to about 12.0. In some embodiments, the metalloprotease polypeptides have protease activity at a pH of from about 4.0 to about 10.5. In some embodiments, the metalloprotease polypeptides have at least 70% of maximal protease activity at a pH of from about 5.5 to about 9.0. In some embodiments, the metalloprotease polypeptides have at least 80% of maximal protease activity at a pH of from about 6.0 to about 8.5. In some embodiments, the metalloprotease polypeptides have maximal protease activity at a pH of about 7.5.

In some embodiments, the metalloprotease polypeptides of the present invention have protease activity at a temperature range of from about 10° C. to about 100° C. In some embodiments, the metalloprotease polypeptides of the present invention have protease activity at a temperature range of from about 20° C. to about 90° C. In some embodiments, the metalloprotease polypeptides have at least 70% of maximal protease activity at a temperature of from about 45° C. to about 60° C. In some embodiments, the metalloprotease polypeptides have maximal protease activity at a temperature of 50° C.

In some embodiments, the metalloprotease polypeptides of the present invention demonstrate cleaning performance in a cleaning composition. Cleaning compositions often include ingredients harmful to the stability and performance of enzymes, making cleaning compositions a harsh environment for enzymes, e.g. metalloproteases, to retain function. Thus, it is not trivial for an enzyme to be put in a cleaning composition and expect enzymatic function (e.g. metalloprotease activity, such as demonstrated by cleaning performance). In some embodiments, the metalloprotease polypeptides of the present invention demonstrate cleaning performance in automatic dishwashing (ADW) detergent compositions. In some embodiments, the cleaning performance in automatic dishwashing (ADW) detergent compositions includes cleaning of egg yolk stains. In some embodiments, the metalloprotease polypeptides of the present invention demonstrate cleaning performance in laundry detergent compositions. In some embodiments, the cleaning performance in laundry detergent compositions includes cleaning of blood/milk/ink stains. In each of the cleaning compositions, the metalloprotease polypeptides of the present invention demonstrate cleaning performance with or without a bleach component.

The metalloprotease polypeptides of the invention have protease activity such that they are useful in casein hydrolysis, collagen hydrolysis, elastin hydrolysis, keratin hydrolysis, soy protein hydrolysis or corn meal protein hydrolysis. Thus, the polypeptides of the invention find use in other applications such as pretreatments for food, feed, or protein degradation.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleotides in one or more codons such that a particular codon encodes the same or a different amino acid, resulting in either a silent variation (e.g., when the encoded amino acid is not altered by the nucleotide mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence of the invention can also be modified to include one or more codons that provide for optimum expression in an expression system (e.g., bacterial expression system), while, if desired, said one or more codons still encode the same amino acid(s).

In some embodiments, the present invention provides a genus of enzyme polypeptides having the desired enzymatic activity (e.g., protease enzyme activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., proteolytic activity, as reflected in the cleaning activity or performance of the polypeptide enzymes of SEQ ID NOs: 3, 8, 13, 18, 23, 28, 33 and 38). Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (conservative amino acid residues are considered functionally homologous or conserved in calculating percent functional homology). A conservative amino acid substitution typically involves the substitution of an amino acid in an amino acid sequence with a functionally similar amino acid. For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine.

Conservatively substituted variations of a polypeptide sequence of the invention (e.g., variant metalloproteases of the invention) include substitutions of a small percentage, sometimes less than 25%, 20%, 15%, 14%, 13%, 12%, 11%, 10%, 9%, 8%, 7%, or 6% of the amino acids of the polypeptide sequence, or less than 5%, 4%, 3%, 2%, or 1%, or less than 10, 9, 8, 7, 6, 5, 4, 3, 2, or 1 amino acid substitution of the amino acids of the polypeptide sequence, with a conservatively selected amino acid of the same conservative substitution group.

As described elsewhere herein in greater detail and in the Examples provided herein, polypeptides of the invention may have cleaning abilities that may be compared to known proteases, including known metalloproteases.

Nucleic Acids of the Invention

The invention provides isolated, non-naturally occurring, or recombinant nucleic acids which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include metalloprotease polypeptides having enzymatic activity (e.g., proteolytic activity) which are useful in cleaning applications and cleaning compositions for cleaning an item or a surface (e.g., surface of an item) in need of cleaning.

In some embodiments, the invention provides an isolated, recombinant, substantially pure, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, or non-naturally-occurring nucleic acid comprising a nucleotide sequence encoding a combination of two or more of any polypeptides of the invention described above and elsewhere herein. In some embodiments, the nucleic acids of the present invention has 50, 60, 65, 70, 75, 80, 85, 90, 91, 92, 93, 94, 95, 96, 97, 98, 99 or 100% identity to SEQ ID NO: 4, 9, 14, 19, 24, 29, 34 and 39.

The present invention provides nucleic acids encoding a metalloprotease polypeptide of the present invention, wherein the metalloprotease polypeptide is a mature form having proteolytic activity, wherein the amino acid positions of the variant are numbered by correspondence with the amino acid sequence of *Paenibacillus* metalloprotease polypeptides set forth as SEQ ID NOs: 3, 8, 13, 18, 23, 28, 33 or 38.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the nucleic acids of the invention can be also facilitated by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984], as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries using one or more oligonucleotide probes that can hybridize to or PCR-amplify polynucleotides which encode a metalloprotease polypeptide polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination).

Methods for Making Modified Metalloprotease Polypeptides of the Invention

A variety of methods are known in the art that are suitable for generating modified polynucleotides of the invention that encode metalloprotease polypeptides of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified polynucleotides and proteins (e.g., metalloprotease polypeptides) include DNA shuffling methodologies, methods based on non-homologous recombination of genes, such as ITCHY (See, Ostermeier et al., 7:2139-44 [1999]), SCRACHY (See, Lutz et al. 98:11248-53 [2001]), SHIPREC (See, Sieber et al., 19:456-60 [2001]), and NRR (See, Bittker et al., 20:1024-9 [2001]; Bittker et al., 101: 7011-6 [2004]), and methods that rely on the use of oligonucleotides to insert random and targeted mutations, deletions and/or insertions (See, Ness et al., 20:1251-5 [2002]; Coco et al., 20:1246-50 [2002]; Zha et al., 4:34-9 [2003]; Glaser et al., 149:3903-13 [1992]).

Vectors, Cells, and Methods for Producing Metalloprotease Polypeptides of the Invention The present invention provides vectors comprising at least one metalloprotease polynucleotide of the invention described herein (e.g., a polynucleotide encoding a metalloprotease polypeptide of the invention described herein), expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector. Such cells are typically referred to as host cells. Some such cells comprise bacterial cells, including, but are not limited to *Bacillus* sp. cells, such as *B. subtilis* cells. The invention also provides recombinant cells (e.g., recombinant host cells) comprising at least one metalloprotease polypeptide of the invention.

In some embodiments, the invention provides a vector comprising a nucleic acid or polynucleotide of the invention. In some embodiments, the vector is an expression vector or expression cassette in which a polynucleotide sequence of the invention which encodes a metalloprotease polypeptide of the invention is operably linked to one or additional nucleic acid segments required for efficient gene expression (e.g., a promoter operably linked to the polynucleotide of the invention which encodes a metalloprotease polypeptide of the invention). A vector may include a transcription terminator and/or a selection gene, such as an antibiotic resistance gene, that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for *Bacillus*, John Wiley & Sons [1990]; suitable replicating plasmids for *B. subtilis* include those listed on p. 92) See also, Perego, Integrational Vectors for Genetic Manipulations in *Bacillus subtilis*, in Sonenshein et al., [eds.] *Bacillus subtilis* and Other Gram-Positive Bacteria: Biochemistry, Physiology and Molecular Genetics, American Society for Microbiology, Washington, D.C. [1993], pp. 615-624), and p2JM103BBI.

For expression and production of a protein of interest (e.g., metalloprotease polypeptide) in a cell, at least one expression vector comprising at least one copy of a polynucleotide encoding the metalloprotease polypeptide, and in some instances comprising multiple copies, is transformed into the cell under conditions suitable for expression of the metalloprotease. In some embodiments of the present invention, a polynucleotide sequence encoding the metalloprotease polypeptide (as well as other sequences included in the vector) is integrated into the genome of the host cell, while in other embodiments, a plasmid vector comprising a polynucleotide sequence encoding the metalloprotease polypeptide remains as autonomous extra-chromosomal element within the cell. The invention provides both extrachromosomal nucleic acid elements as well as incoming nucleotide sequences that are integrated into the host cell genome. The vectors described herein are useful for production of the metalloprotease polypeptides of the invention. In some embodiments, a polynucleotide construct encoding the metalloprotease polypeptide is present on an integrating vector that enables the integration and optionally the amplification of the polynucleotide encoding the metalloprotease polypeptide into the host chromosome. Examples of sites for integration are well known to those skilled in the art. In some embodiments, transcription of a polynucleotide encoding a metalloprotease polypeptide of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the amyE, amyQ, amyL, pstS, sacB, pSPAC, pAprE, pVeg, pHpall promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. Additional promoters include, but are not limited to the A4 promoter, as well as phage Lambda PR or PL promoters, and the *E. coli* lac, trp or tac promoters.

Metalloprotease polypeptides of the present invention can be produced in host cells of any suitable microorganism, including bacteria and fungi. In some embodiments, metalloprotease polypeptides of the present invention can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, the metalloprotease polypeptides are produced by *Bacillus* sp. host cells. Examples of *Bacillus* sp. host cells that find use in the production of the metalloprotease polypeptides of the invention include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii,* and *B. megaterium,* as well as other organisms within the genus *Bacillus*. In some embodiments, *B. subtilis* host cells are used for production of metalloprotease polypeptides. U.S. Pat. Nos. 5,264,366 and 4,760,025 (RE 34,606) describe various *Bacillus* host strains that can be used for producing metalloprotease polypeptide of the invention, although other suitable strains can be used.

Several bacterial strains that can be used to produce metalloprotease polypeptides of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *Bacillus subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT110, and PEP 211strain (See e.g., Hoch et al., Genetics 73:215-228 [1973]; See also, U.S. Pat. Nos. 4,450,235 and 4,302,544, and EP 0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. In some embodiments, the mutation is in a degU gene, and in some embodiments the mutation is degU(Hy)32 (See e.g., Msadek et al., J. Bacteriol. 172:824-834 [1990]; and Olmos et al., Mol. Gen. Genet. 253:562-567 [1997]). In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a metalloprotease polypeptide of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., U.S. Pat. Appln. Pub. No. 2005/0202535, incorporated herein by reference).

Host cells are transformed with at least one nucleic acid encoding at least one metalloprotease polypeptide of the invention using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and transfection, transduction, and protoplast fusion are well known and suited for use in the present invention. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087 [1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a metalloprotease polypeptide of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one metalloprotease polypeptide or at least one nucleic acid of the invention.

In some embodiments, host cells transformed with at least one polynucleotide sequence encoding at least one metalloprotease polypeptide of the invention are cultured in a suitable nutrient medium under conditions permitting the expression of the present protease, after which the resulting protease is recovered from the culture. In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.).

In some embodiments, a metalloprotease polypeptide produced by a recombinant host cell is secreted into the culture medium. A nucleic acid sequence that encodes a purification facilitating domain may be used to facilitate purification of proteins. A vector or DNA construct comprising a polynucleotide sequence encoding a metalloprotease polypeptide may further comprise a nucleic acid sequence encoding a purification facilitating domain to facilitate purification of the metalloprotease polypeptide (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as a metalloprotease polypeptide of the invention, are well known. Various assays for detecting and measuring activity of proteases (e.g., metalloprotease polypeptides of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.)., Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) (SEQ ID NO: 43) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature metalloprotease polypeptides of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (MA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature metalloprotease polypeptide of the invention. A mature metalloprotease polypeptide does not include a signal peptide or a propeptide sequence. Some methods comprise making or producing a metalloprotease polypeptide of the invention in a recombinant bacterial host cell, such as for example, a Bacillus sp. cell (e.g., a B. subtilis cell). In some embodiments, the invention provides a method of producing a metalloprotease polypeptide of the invention, the method comprising cultivating a recombinant host cell comprising a recombinant expression vector comprising a nucleic acid encoding a metalloprotease polypeptide of the invention under conditions conducive to the production of the metalloprotease polypeptide. Some such methods further comprise recovering the metalloprotease polypeptide from the culture.

In some embodiments the invention provides methods of producing a metalloprotease polypeptide of the invention, the methods comprising: (a) introducing a recombinant expression vector comprising a nucleic acid encoding a metalloprotease polypeptide of the invention into a population of cells (e.g., bacterial cells, such as B. subtilis cells); and (b) culturing the cells in a culture medium under conditions conducive to produce the metalloprotease polypeptide encoded by the expression vector. Some such methods further comprise: (c) isolating the metalloprotease polypeptide from the cells or from the culture medium.

Fabric and Home Care Products

In some embodiments, the metalloprotease polypeptides of the present invention can be used in compositions comprising an adjunct material and a metalloprotease polypeptide, wherein the composition is a fabric and home care product.

In some embodiments, the fabric and home care product compositions comprising at least one metalloprotease polypeptide comprise one or more of the following ingredients (based on total composition weight): from about 0.0005 wt % to about 0.1 wt %, from about 0.001 wt % to about 0.05 wt %, or even from about 0.002 wt % to about 0.03 wt % of said metalloprotease polypeptide; and one or more of the following: from about 0.00003 wt % to about 0.1 wt % fabric hueing agent; from about 0.001 wt % to about 5 wt %, perfume capsules; from about 0.001 wt % to about 1 wt %, cold-water soluble brighteners; from about 0.00003 wt % to about 0.1 wt % bleach catalysts; from about 0.00003 wt % to about 0.1 wt % first wash lipases; from about 0.00003 wt % to about 0.1 wt % bacterial cleaning cellulases; and/or from about 0.05 wt % to about 20 wt % Guerbet nonionic surfactants.

In some embodiments, the fabric and home care product composition is a liquid laundry detergent or a dishwashing detergent, such as an automatic dishwashing (ADW) detergent or hand dishwashing detergent.

It is intended that the fabric and home care product is provided in any suitable form, including a fluid or solid, or granular, powder, solid, bar, liquid, tablet, gel, or paste form. The fabric and home care product may be in the form of a unit dose pouch, especially when in the form of a liquid, and typically the fabric and home care product is at least partially, or even completely, enclosed by a water-soluble pouch. In addition, in some embodiments of the fabric and home care products comprising at least one metalloprotease polypeptide, the fabric and home care product may have any combination of parameters and/or characteristics detailed above.

Compositions Having the Metalloprotease Polypeptide of the Present Invention

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

As indicated herein, in some embodiments, the cleaning compositions of the present invention further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705, 464, 5,710,115, 5,698,504, 5,695,679, 5,686,014 and 5,646, 101, all of which are incorporated herein by reference). Embodiments of specific cleaning composition materials are exemplified in detail below. In embodiments in which the cleaning adjunct materials are not compatible with the metalloprotease polypeptides of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

The cleaning compositions of the present invention are advantageously employed for example, in laundry applications, hard surface cleaning, dishwashing applications, including automatic dishwashing and hand dishwashing, as well as cosmetic applications such as dentures, teeth, hair and skin. In addition, due to the unique advantages of increased effectiveness in lower temperature solutions, the enzymes of the present invention are ideally suited for laundry applications. Furthermore, the enzymes of the present invention find use in granular and liquid compositions.

The metalloprotease polypeptides of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the metalloprotease polypeptides provided herein, alone or in combination with other proteases and/or additional enzymes. The required level of enzyme is achieved by the addition of one or more metalloprotease polypeptides of the present invention. Typically the present cleaning compositions comprise at least about 0.0001 weight percent, from about 0.0001 to about 10, from about 0.001 to about 1, or from about 0.01 to about 0.1 weight percent of at least one of the metalloprotease polypeptides of the present invention.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. Techniques for controlling pH at recommended usage levels include the use of buffers, alkalis, acids, etc., and are well known to those skilled in the art.

Suitable "low pH cleaning compositions" typically have a pH of from about 3 to about 5, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a pH of from about 3 to about 5. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the metalloprotease polypeptide(s) is/are employed in a granular composition or liquid, it is desirable for the metalloprotease polypeptide to be in the form of an encapsulated particle to protect the metalloprotease polypeptide from other components of the granular composition during storage. In addition, encapsulation is also a means of controlling the availability of the metalloprotease polypeptide during the cleaning process. In some embodiments, encapsulation enhances the performance of the metalloprotease polypeptide (s) and/or additional enzymes. In this regard, the metalloprotease polypeptides of the present invention are encapsulated with any suitable encapsulating material known in the art. In some embodiments, the encapsulating material typically encapsulates at least part of the metalloprotease polypeptide (s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the metalloprotease polypeptides of the present invention find particular use in the cleaning industry, including, but not limited to laundry and dish detergents. These applications place enzymes under various environmental stresses. The metalloprotease polypeptides of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, European detergents typically have about 4500-5000 ppm of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of the detergent components are present in the wash water. North American detergents are generally considered to be medium detergent concentration systems as they have approximately 975 ppm of detergent components present in the wash water. Brazil typically has approximately 1500 ppm of detergent components in the wash water.

A high detergent concentration system includes detergents where greater than about 2000 ppm of the detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent to about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 40° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present invention provides metalloprotease polypeptides that show surprising wash performance in at least one set of wash conditions (e.g., water temperature, water hardness, and/or detergent concentration). In some embodiments, the metalloprotease polypeptides of the present invention are comparable in wash performance to other metalloprotease polypeptide proteases. In some embodiments of the present invention, the metalloprotease polypeptides provided herein exhibit enhanced oxidative stability, enhanced thermal stability, enhanced cleaning capabilities under various conditions, and/or enhanced chelator stability. In addition, the metalloprotease polypeptides of the present invention find use in cleaning compositions that do not include detergents, again either alone or in combination with builders and stabilizers.

In some embodiments of the present invention, the cleaning compositions comprise at least one metalloprotease polypeptide of the present invention at a level from about 0.00001% to about 10% by weight of the composition and the balance (e.g., about 99.999% to about 90.0%) comprising cleaning adjunct materials by weight of composition. In some other embodiments of the present invention, the cleaning compositions of the present invention comprises at least one metalloprotease polypeptide at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, or any combinations or mixtures thereof. In some embodiments, a combination of enzymes is used (i.e., a "cocktail") comprising conventional applicable enzymes like protease, lipase, cutinase and/or cellulase in conjunction with amylase is used.

In addition to the metalloprotease polypeptides provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the *Fusarium* protease described in WO 89/06270. In some embodiments, commercially available protease enzymes that find use in the present invention include, but are not limited to MAXATASE® protease, MAXACAL™ protease, MAXAPEM™ protease, OPTICLEAN® protease, OPTIMASE® protease, PROPERASE® protease, PURAFECT® protease, PURAFECT® OXP protease, PURAIVIAX™ protease, EXCEL-LASE™ protease, and PURAFAST™ protease (Genencor); ALCALASE® protease, SAVINASE® protease, PRIMASE® protease, DURAZYIVI™ protease, POLARZYME® protease, OVOZYME® protease, KANNASE® protease, LIQUANASE® protease, NEUTRASE® protease, RELASE® protease and ESPERASE® protease (Novozymes); BLAP™ protease and BLAP™ protease variants (Henkel Kommanditgesellschaft auf Aktien, Duesseldorf, Germany), and KAP protease (*B. alkalophilus* subtilisin; Kao Corp., Tokyo, Japan). Various proteases are described in WO95/23221, WO 92/21760, WO 09/149200, WO 09/149144, WO 09/149145, WO 11/072099, WO 10/056640, WO 10/056653, WO 11/140364, WO 12/151534, U.S. Pat. Publ. No. 2008/0090747, and U.S. Pat. Nos. 5,801,039, 5,340,735, 5,500,364, 5,855,625, US RE 34,606, 5,955,340, 5,700,676, 6,312,936, and 6,482,628, and various other patents. In some further embodiments, metalloproteases find use in the present invention, including but not limited to the neutral metalloprotease described in WO 07/044993.

In addition, any suitable lipase finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), *Pseudomonas* lipases such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipase polypeptide enzymes such as cutinases also find use in some embodiments of the present invention, including but not limited to the cutinase derived from *Pseudomonas mendocina* (See, WO 88/09367), and the cutinase derived from *Fusarium solani pisi* (See, WO 90/09446).

Additional suitable lipases include commercially available lipases such as M1 LIPASE™ lipase, LUMA FAST™ lipase, and LIPOMAX™ lipase (Genencor); LIPEX® lipase, LIPOLASE® lipase and LIPOLASE® ULTRA lipase (Novozymes); and LIPASE P™ "Amano" lipase (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In some other embodiments of the present invention, the cleaning compositions of the present invention also comprise lipases at a level of about 0.0001% to about 10%, about 0.001% to about 5%, about 0.001% to about 2%, about 0.005% to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Additional suitable amylases include those found in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021. Commercially available amylases that find use in the present invention include, but are not limited to DURAMYL® amylase, TERMAMYL® amylase, FUNGAMYL® amylase, STAINZYME® amylase, STAINZYME PLUS® amylase, STAINZYME ULTRA® amylase, and BAN™ amylase (Novozymes), as well as POWERASE™ amylase, RAPIDASE® amylase and MAXAMYL® P amylase (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In some other embodiments of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME cellulase, CELLUCLEAN cellulase, CAREZYME cellulase (Novozymes), PURADEX cellulase AND REVITALENZ cellulase (Danisco US Inc.), and KAC-500(B) cellulase (Kao Corporation). In some embodiments, cellulases are incorporated as portions or fragments of mature wild-type or variant cellulases, wherein a portion of the N-terminus is deleted (See e.g., U.S. Pat. No. 5,874, 276). Additional suitable cellulases include those found in WO2005054475, WO2005056787, U.S. Pat. Nos. 7,449, 318, and 7,833,773. In some embodiments, the cleaning compositions of the present invention further comprise cellulases at a level from about 0.00001% to about 10% of additional cellulase by weight of the composition and the balance of cleaning adjunct materials by weight of composition. In some other embodiments of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114; 6,602,842; 5,476,775 and 6,440,991, and U.S. Prov. App. Ser. No. 61/739,267; all of which are incorporated herein by reference). Commercially available mannanases that find use in the present invention include, but are not limited to MANNASTAR mannanase, PURABRITE mannanase, and MANNAWAY mannanase. In some embodiments, the cleaning compositions of the present invention further comprise mannanases at a level from about 0.00001% to about 10% of additional mannanase by weight of the composition and the balance of cleaning adjunct materials by weight of composition. In some embodiments of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In some other embodiments of the present invention, the cleaning compositions of the present invention also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the metalloprotease polypeptide (s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracids, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642; 6,605,458; 5,705,464; 5,710,115; 5,698,504; 5,695,679; 5,686,014 and 5,646,101, all of which are incorporated herein by reference). Embodiments of specific cleaning composition materials are exemplified in detail below. In embodiments in which the cleaning adjunct materials are not compatible with the metalloprotease polypeptides of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

In some embodiments, an effective amount of one or more metalloprotease polypeptide (s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the metalloprotease polypeptides of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use in detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the metalloprotease polypeptides of the present invention. Thus, in some embodiments, the compositions comprising at least one metalloprotease polypeptide of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one metalloprotease polypeptide of the present invention are fabric cleaning compositions such as those described in U.S. Pat. Nos. 6,610,642 and 6,376,450. In addition, the metalloprotease polypeptides of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one metalloprotease polypeptide provided herein. Thus, in some embodiments, the compositions comprising at least one metalloprotease polypeptide of the present invention is a hard surface cleaning composition such as those described in U.S. Pat. Nos. 6,610,642; 6,376,450, and 6,376,450.

In yet further embodiments, the present invention provides dishwashing compositions comprising at least one metalloprotease polypeptide provided herein. Thus, in some embodiments, the compositions comprising at least one metalloprotease polypeptide of the present invention is a hard surface cleaning composition such as those in U.S. Pat. Nos. 6,610,642 and 6,376,450. In some still further embodiments, the present invention provides dishwashing compositions comprising at least one metalloprotease polypeptide provided herein. In some further embodiments, the compositions comprising at least one metalloprotease polypeptide of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450; 6,605,458; 6,605,458, and 6,610,642, find use with the metalloprotease polypeptides provided herein.

The cleaning compositions of the present invention are formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392, and 5,486,303, all of which are incorporated herein by reference. When a low pH cleaning composition is desired, the pH of such composition is adjusted via the addition of a material such as monoethanolamine or an acidic material such as HCl.

In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the metalloprotease polypeptides of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, incorporated by reference. The aforementioned adjunct ingredients may constitute the balance of the cleaning compositions of the present invention.

In some embodiments, the cleaning compositions according to the present invention comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N(CH$_2$COOM)$_2$ where R is C$_{1-12}$ alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,Ndiacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400µ to about 1200µ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle of the invention is a highly active particle comprising a high level of amino carboxylic builder. Sulphuric acid has been found to further contribute to the stability of the final particle.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

In some embodiments, builders for use herein include phosphate builders and non-phosphate builders. In some embodiments, the builder is a phosphate builder. In some embodiments, the builder is a non-phosphate builder. If present, builders are used in a level of from 0.1% to 80%, or from 5 to 60%, or from 10 to 50% by weight of the composition. In some embodiments the product comprises a mixture of phosphate and non-phosphate builders. Suitable phosphate builders include mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition of the invention. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2 100 949). In some embodiments, the non-ionic surfactant can be ethoxylated nonionic surfactants, epoxy-capped poly(oxyalkylated) alcohols and amine oxides surfactants.

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some embodiments, silicates are present at a level of from about 5% to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts, such as calcium formate. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810410, WO 99/06521, and EP 2 100 949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO 2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

In some embodiments, the cleaning composition is a high density liquid (HDL) composition having a variant metalloprotease polypeptide protease. The HDL liquid laundry detergent can comprise a detersive surfactant (10%-40%) comprising anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof); and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), optionally wherein the weight ratio of anionic detersive surfactant (with a hydrophilic index (HIc) of from 6.0 to 9) to non-ionic detersive surfactant is greater than 1:1.

The composition can comprise optionally, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated C-$C_6$ mono-carboxylic acid, $C_1$-$C_6$ alkyl ester of acrylic or methacrylic acid, and mixtures thereof.

The composition can comprise additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition can further comprise saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydroxyethyl cellulose, cationic starch, cationic polyacrylamides, and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The composition can further comprise enzymes (0.01 wt % active enzyme to 0.03 wt % active enzyme) selected from a group of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof. The composition may comprise an enzyme stabilizer (examples of which include polyols such as propylene glycol or glycerol, sugar or sugar alcohol, lactic acid, reversible protease inhibitor, boric acid, a boric acid derivative, e.g., an aromatic borate ester, or a phenyl boronic acid derivative such as 4-formylphenyl boronic acid, peptides or formate).

The composition can further comprise silicone or fatty-acid based suds suppressors; heuing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition can be any liquid form, for example a liquid or gel form, or any combination thereof. The composition may be in any unit dose form, for example a pouch.

In some embodiments, the cleaning composition is a high density powder (HDD) composition having a variant metalloprotease polypeptide protease. The HDD powder laundry detergent can comprise a detersive surfactant including anionic detersive surfactants (selected from a group of linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from a group of linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from a group of alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (selected from a group of alkanolamine sulpho-betaines); ampholytic surfactants; semi-polar non-ionic surfactants and mixtures thereof builders (phosphate free builders [for example zeolite builders examples of which include zeolite A, zeolite $\chi$, zeolite P and zeolite MAP in the range of 0 wt % to less than 10 wt %]; phosphate builders [examples of which include sodium tri-polyphosphate in the range of 0 wt % to less than 10 wt %]; citric acid, citrate salts and nitrilotriacetic acid or salt thereof in the range of less than 15 wt %); silicate salt (sodium or potassium silicate or sodium meta-silicate in the range of 0 wt % to less than 10 wt %, or layered silicate (SKS-6)); carbonate salt (sodium carbonate and/or sodium bicarbonate in the range of 0 wt % to less than 10 wt %); and bleaching agents (photobleaches, examples of which include sulfonated zinc phthalocyanines, sulfonated aluminum phthalocyanines, xanthenes dyes, and mixtures thereof; hydrophobic or hydrophilic bleach activators (examples of which include dodecanoyl oxybenzene sulfonate, decanoyl oxybenzene sulfonate, decanoyl oxybenzoic acid or salts thereof, 3,5,5-trimethyl hexanoyl oxybenzene sulfonate, tetraacetyl ethylene diamine-TAED, and nonanoyloxybenzene sulfonate-NOBS, nitrile quats, and mixtures thereof; hydrogen peroxide; sources of hydrogen peroxide (inorganic perhydrate salts examples of which include mono or tetra hydrate sodium salt of perborate, percarbonate, persulfate, perphosphate, or persilicate); preformed hydrophilic and/or hydrophobic peracids (selected from a group consisting of percarboxylic acids and salts, percarbonic acids and salts, perimidic acids and salts, peroxymonosulfuric acids and salts) & mixtures thereof and/or bleach catalyst (such as imine bleach boosters examples of which include iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; metal-containing bleach catalyst for example copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephos-phonic acid) and water-soluble salts thereof).

The composition can further comprise enzymes selected from a group of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases and any mixture thereof.

The composition can further comprise additional detergent ingredients including perfume microcapsules, starch encapsulated perfume accord, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic dishwashing (ADW) detergent composition having a metalloprotease of the present invention. The ADW detergent composition can comprise two or more non-ionic surfactants selected from a group of ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% comprising either phosphate (mono-phosphates, di-phosphates, tri-polyphosphates or oligomeric-poylphosphates, preferred sodium tripolyphosphate-STPP or phosphate-free builders [amino acid based compounds, examples of which include MGDA (methyl-glycine-diacetic acid), and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), B-alaninediacetic acid (B-ADA) and their salts], homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers (provide dimensional stability to the product) in the range of about 0.1% to about 50% by weight; drying aids in the range of about 0.1% to about 10% by weight (selected from polyesters, especially anionic polyesters optionally together with further monomers with 3 to 6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1% to about 20% by weight (sodium or potassium silicates for example sodium disilicate, sodium meta-silicate and crystalline phyllosilicates); bleach-inorganic (for example perhydrate salts such as perborate, percarbonate, perphosphate, persulfate and persilicate salts) and organic (for example organic peroxyacids including diacyl and tetraacylperoxides, especially diperoxydodecanedioc acid, diperoxytetradecanedioc acid, and diperoxyhexadecanedioc acid); bleach activators-organic peracid precursors in the range from about 0.1% to about 10% by weight; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1% to 5% by weight (selected from benzatriazoles, metal salts and complexes, and/or silicates); enzymes in the range from about 0.01 to 5.0 mg of active enzyme per gram of automatic dishwashing detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof); and enzyme stabilizer components (selected from oligosaccharides, polysaccharides and inorganic divalent metal salts).

The metalloproteases are normally incorporated into the detergent composition at a level of from 0.000001% to 5% of enzyme protein by weight of the composition, or from 0.00001% to 2%, or from 0.0001% to 1%, or from 0.001% to 0.75% of enzyme protein by weight of the composition.

Metalloprotease Polypeptides of the Present Invention for Use in Animal Feed

In a further aspect of the invention, the metalloprotease polypeptides of the present invention can be used as a component of an animal feed composition, animal feed additive and/or pet food comprising a metalloprotease and variants thereof. The present invention further relates to a method for preparing such an animal feed composition, animal feed additive composition and/or pet food comprising mixing the metalloprotease polypeptide with one or more animal feed ingredients and/or animal feed additive ingredients and/or pet food ingredients. Furthermore, the present invention relates to the use of the metalloprotease polypeptide in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

Metalloprotease Polypeptides of the Present Invention for Use in Textile Desizing Also contemplated are compositions and methods of treating fabrics (e.g., to desize a textile) using a metalloprotease polypeptide of the present invention. Fabric-treating methods are well known in the art (see, e.g., U.S. Pat. No. 6,077,316). For example, the feel and appearance of a fabric can be improved by a method comprising contacting the fabric with a metalloprotease in a solution. The fabric can be treated with the solution under pressure.

A metalloprotease of the present invention can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A metalloprotease of the present invention can be applied during or after the weaving to remove these sizing starch or starch derivatives. After weaving, the metalloprotease can be used to remove the size coating before further processing the fabric to ensure a homogeneous and wash-proof result.

A metalloprotease of the present invention can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. The metalloprotease can be used in methods of finishing denim garments (e.g., a "bio-stoning process"), enzymatic desizing and providing softness to fabrics, and/or finishing process.

Metalloprotease Polypeptides of the Present Invention for Use in Paper Pulp Bleaching The metalloprotease polypeptides described herein find further use in the enzyme aided bleaching of paper pulps such as chemical pulps, semi-chemical pulps, kraft pulps, mechanical pulps or pulps prepared by the sulfite method. In general terms, paper pulps are incubated with a metalloprotease polypeptide of the present invention under conditions suitable for bleaching the paper pulp.

In some embodiments, the pulps are chlorine free pulps bleached with oxygen, ozone, peroxide or peroxyacids. In some embodiments, the metalloprotease polypeptides are used in enzyme aided bleaching of pulps produced by modified or continuous pulping methods that exhibit low lignin contents. In some other embodiments, the metalloprotease polypeptides are applied alone or preferably in combination with xylanase and/or endoglucanase and/or alpha-galactosidase and/or cellobiohydrolase enzymes.

Metalloprotease Polypeptides of the Present Invention for Use in Protein Degradation The metalloprotease polypeptides described herein find further use in the enzyme aided removal of proteins from animals and their subsequent degradation or disposal, such as feathers, skin, hair, hide, and the like. In some instances, immersion of the animal carcass in a solution comprising a metalloprotease polypeptide of the present invention can act to protect the skin from damage in comparison to the traditional immersion in scalding water or the defeathering process. In one embodiment, feathers can be sprayed with an isolated metalloprotease polypeptide of the present invention under conditions suitable for digesting or initiating degradation of the plumage. In some embodiments, a metalloprotease of the present invention can be used, as above, in combination with an oxidizing agent.

In some embodiments, removal of the oil or fat associated with raw feathers is assisted by using a metalloprotease polypeptide of the present invention. In some embodiments, the metalloprotease polypeptides are used in compositions for cleaning the feathers as well as to sanitize and partially dehydrate the fibers. In some other embodiments, the metalloprotease polypeptides are applied in a wash solution in combination with 95% ethanol or other polar organic solvent with or without a surfactant at about 0.5% (v/v).

In yet other embodiments, the disclosed metalloprotease polypeptides find use in recovering protein from plumage. The disclosed metalloprotease polypeptides may be used alone or in combination in suitable feather processing and proteolytic methods, such as those disclosed in PCT/EP2013/065362, PCT/EP2013/065363, and PCT/EP2013/065364, which are hereby incorporated by reference. In some embodiments, the recovered protein can be subsequently used in animal or fish feed.

EXPERIMENTAL

The claimed invention is described in further detail in the following examples which are not in any way intended to limit the scope of the invention as claimed.

Example 1.1

Cloning of *Paenibacillus* sp. Metalloprotease PspPro3

A strain of *Paenibacillus* sp. was selected as a potential source for enzymes which may be useful for various industrial applications. Genomic DNA for sequencing was obtained by first growing the strain on Heart Infusion agar plates (Difco) at 37° C. for 24 hours. Cell material was scraped from the plates and used to prepare genomic DNA with the ZF Fungal/Bacterial DNA miniprep kit from Zymo (Cat No. D6005). The genomic DNA was used for genome sequencing. The entire genome of the *Paenibacillus* sp. strain was sequenced by BaseClear (Leiden, The Netherlands) using the Illumina's next generation sequencing technology. After assembly of the data, contigs were annotated by BioXpr (Namur, Belgium). One of the genes identified after annotation in *Paenibacillus* sp. encodes a metalloprotease and the sequence of this gene, called PspPro3, is provided in SEQ ID NO: 1. The corresponding protein encoded by the PspPro3 gene is shown in SEQ ID NO: 2. At the N-terminus, the protein has a signal peptide with a length of 26 amino acids as predicted by SignalP version 4.0 (Nordahl Petersen et al. (2011) Nature Methods, 8:785-786). The presence of a signal sequence suggests that PspPro3 is a secreted enzyme. The propeptide region was predicted based on protein sequence alignment with the *Paenibacillus polymyxa* Npr protein (Takekawa et al. (1991) Journal of Bacteriology, 173 (21): 6820-6825). The predicted mature region of PspPro3 protein is shown on SEQ ID NO: 3.

The nucleotide sequence of the PspPro3 gene isolated from *Paenibacillus* sp. is set forth as SEQ ID NO: 1. The sequence encoding the predicted native signal peptide is shown in italics:

```
ATGTTAATGAAAAAAGTATGGGTTTCGCTTCTTGGAGGAGCGATGTTATT

AGGGTCTGTAGCGTCTGGTGCATCAGCAGCGGAGAGTTCCGTTTCGGGGC

CGGCTCAGCTTACGCCAACCTTCCATGCCGAACAATGGAAAGCACCTTCA

TCGGTATCGGGTGATGACATCGTATGGAGCTATTTAAATCGGCAAAAGAA

AACGTTGCTGGGTACGGACAGCACCAGTGTCCGTGATCAATTCCGTATCG

TAGATCGCACAAGCGACAAATCCGGCGTGAGCCATTATCGGCTGAAGCAA

TATGTAAACGGAATTCCCGTATATGGAGCTGAACAGACCATTCATGTGGG

CAAATCCGGTGAAGTGACCTCTTATCTGGGAGCCGTGATTACTGAGGATC

AGCAAGAAGAAGCTACGCAAGGTACAACTCCGAAAATCAGCGCTTCTGAA

GCGGTCCATACCGCATATCAGGAGGCAGCTACACGGGTTCAAGCCCTCCC

TACCTCCGATGATACGATTTCTAAAGATGCGGAGGAGCCAAGCAGTGTAA

GCAAAGACACTTACTCCGAAGCAGCTAACAACGGAAAAACGAGTTCTGTT

GAAAAGGACAAGCTCAGCCTTGAGAAAGCGGCTGACCTGAAAGATAGCAA

AATTGAAGCGGTGGAGGCAGAGCCAAACTCCATTGCCAAAATCGCCAACC

TGCAGCCTGAGGTAGATCCTAAAGCCGAACTATATTTCTATGCGAAGGGC

GATGCATTGCAGCTGGTTTATGTGACTGAGGTTAATATTTTGCAGCCTGC

GCCGCTGCGTACACGCTACATCATTGACGCCAATGATGGCAAAATCGTAT

CCCAGTATGACATCATTAATGAAGCGACAGGCACAGGCAAAGGTGTACTC

GGTGATACCAAAACATTCAACACTACTGCTTCCGGCAGCAGCTACCAGTT

AAGAGATACGACTCGCGGGAATGGAATCGTGACTTACACGGCCTCCAACC

GTCAAAGCATCCCAGGTACGATCCTGACCGATGCCGATAACGTATGGAAT

GATCCAGCCGGCGTGGATGCCCACGCTTATGCAGCCAAAACCTATGATTA

TTATAAGGAAAAGTTCAATCGCAACAGCATTGACGGACGAGGCCTGCAGC

TCCGTTCGACAGTTCATTACGGCAATCGTTACAACAACGCCTTCTGGAAC

GGCTCCCAAATGACTTATGGAGACGGAGACGGCACCACATTTATCGCTTT

TAGCGGTGATCCGGATGTAGTTGGTCATGAACTCACACACGGTGTTACGG

AGTATACTTCCAATTTGGAATATTACGGAGAATCCGGTGCGTTGAACGAG

GCCTTCTCGGACATCATCGGCAATGACATCCAGCGTAAAAACTGGCTTGT

AGGCGATGATATTTACACGCCACGCATTGCGGGTGATGCACTTCGTTCTA

TGTCCAATCCTACGCTGTACGATCAACCGGATCACTATTCGAACTTGTAC

AGAGGCAGCTCCGATAACGGCGGCGTTCATACGAACAGCGGTATTATAAA

TAAAGCCTATTATCTGTTGGCACAAGGCGGCACCTTCCATGGTGTAACTG

TCAATGGGATTGGCCGCGATGCAGCGGTTCAAATTTACTACAGCGCCTTT

ACGAACTACCTGACTTCTTCTTCTGACTTCTCCAATGCACGTGATGCCGT

TGTACAAGCGGCAAAAGATCTCTACGGCGCGAGCTCGGCACAAGCTACCG

CAGCAGCCAAATCTTTTGATGCTGTAGGCGTTAAC
```

The amino acid sequence of the PspPro3 precursor protein is set forth as SEQ ID NO: 2. The predicted signal peptide is shown in italics, and the predicted pro-peptide is shown in underlined text:

```
MLMKKVWVSLLGGAMLLGSVASGASAAESSVSGPAQLTPTFHAEQWKAPS

SVSGDDIVWSYLNRQKKTLLGTDSTSVRDQFRIVDRTSDKSGVSHYRLKQ

YVNGIPVYGAEQTIHVGKSGEVTSYLGAVITEDQQEEATQGTTPKISASE

AVHTAYQEAATRVQALPTSDDTISKDAEEPSSVSKDTYSEAANNGKTSSV

EKDKLSLEKAADLKDSKIEAVEAEPNSIAKIANLQPEVDPKAELYFYAKG

DALQLVYVTEVNILQPAPLRTRYIIDANDGKIVSQYDIINEATGTGKGVL

GDTKTFNTTASGSSYQLRDTTRGNGIVTYTASNRQSIPGTILTDADNVWN

DPAGVDAHAYAAKTYDYYKEKFNRNSIDGRGLQLRSTVHYGNRYNNAFWN

GSQMTYGDGDGTTFIAFSGDPDVVGHELTHGVTEYTSNLEYYGESGALNE

AFSDIIGNDIQRKNWLVGDDIYTPRIAGDALRSMSNPTLYDQPDHYSNLY

RGSSDNGGVHTNSGIINKAYYLLAQGGTFHGVTVNGIGRDAAVQIYYSAF

TNYLTSSSDFSNARDAVVQAAKDLYGASSAQATAAAKSFDAVGVN
```

The amino acid sequence of the predicted mature form of PspPro3 is set forth as SEQ ID NO: 3:

```
ATGTGKGVLGDTKTFNTTASGSSYQLRDTTRGNGIVTYTASNRQSIPGTI

LTDADNVWNDPAGVDAHAYAAKTYDYYKEKFNRNSIDGRGLQLRSTVHYG

NRYNNAFWNGSQMTYGDGDGTTFIAFSGDPDVVGHELTHGVTEYTSNLEY

YGESGALNEAFSDIIGNDIQRKNWLVGDDIYTPRIAGDALRSMSNPTLYD

QPDHYSNLYRGSSDNGGVHTNSGIINKAYYLLAQGGTFHGVTVNGIGRDA

AVQIYYSAFTNYLTSSSDFSNARDAVVQAAKDLYGASSAQATAAAKSFDA

VGVN
```

Example 1.2

Expression of *Paenibacillus* sp. Metalloprotease PspPro3

The DNA sequence of the propeptide-mature form of PspPro3 was synthesized and inserted into the *Bacillus subtilis* expression vector p2JM103BBI (Vogtentanz, *Protein Expr Purif*, 55:40-52, 2007) by Generay (Shanghai, China), resulting in plasmid pGX085 (AprE-PspPro3) (FIG. 1.1). Ligation of the gene encoding the PspPro3 protein into the digested vector resulted in the addition of three codons (Ala-Gly-Lys) between the 3' end of the *Bacillus subtilis* AprE signal sequence and the 5' end of the predicted PspPro3 native propeptide. The gene has an alternative start codon (GTG). As shown in FIG. 1.1, pGX085(AprE-PspPro3) contains an AprE promoter, an AprE signal sequence used to direct target protein secretion in *B. subtilis*, and the synthetic nucleotide sequence encoding the predicted propeptide and mature region of PspPro3 (SEQ ID NO: 4). The translation product of the synthetic AprE-PspPro3 gene is shown in SEQ ID NO: 5.

*B. subtilis* cells (degU$^{Hy}$ 32, ΔscoC) were transformed with the pGX085(AprE-PspPro3) plasmid and the transformed cells were spread on Luria Agar plates supplemented with 5 ppm Chloramphenicol and 1.2% skim milk (Cat

232100, Difco). Colonies with the largest clear halos on the plates were selected and subjected to fermentation in a 250 ml shake flask with MBD medium (a MOPS based defined medium, supplemented with additional 5 mM CaCl$_2$). The broth from the shake flasks was concentrated and buffer-exchanged into the loading buffer containing 20 mM Tris-HCl (pH 8.5), 1 mM CaCl$_2$ and 10% propylene glycol using a VivaFlow 200 ultra filtration device (Sartorius Stedim). After filtering, this sample was applied to a 150 mL Q Sepharose High Performance column pre-equilibrated with the loading buffer above and PspPro3 was then eluted from the column via the loading buffer supplemented with a linear NaCl gradient from 0 to 0.7 M. The corresponding active purified protein fractions were further pooled and concentrated via 10K Amicon Ultra for further analyses.

The nucleotide sequence of the synthesized PspPro3 gene in plasmid pGX085(AprE-PspPro3) is depicted in SEQ ID NO: 4. The sequence encoding the predicted native signal peptide is shown in italics and the region encoding the three residue addition (AGK) is shown in bold:

*GTGAGAAGCAAAAAATTGTGGATCAGCTTGTTGTTTGCGTTAACGTTAAT*

*CTTTACGATGGCGTTCAGCAACATGAGCGCGCAGGCT*GCTGGAAAAGCAG

AATCATCAGTGTCAGGACCGGCTCAGCTTACGCCGACGTTTCATGCAGAG

CAGTGGAAAGCACCGAGCAGCGTTAGCGGAGATGACATCGTGTGGAGCTA

CCTGAACAGACAGAAGAAAACGCTTCTTGGCACGGACAGCACGAGCGTCA

GAGACCAGTTCAGAATCGTGGATAGAACAAGCGACAAAAGCGGCGTCAGC

CATTATAGACTGAAGCAGTATGTGAACGGAATCCCGGTTTATGGCGCAGA

ACAAACAATCCATGTCGGAAAGAGCGGCGAAGTTACGAGCTATCTGGGCG

CGGTTATTACAGAGGACCAGCAAGAGGAGGCTACACAAGGCACGACACCG

AAAATTTCAGCATCAGAGGCAGTTCATACGGCCTACCAAGAAGCTGCAAC

GAGAGTTCAAGCCCTGCCTACGTCAGATGATACAATCAGCAAAGACGCTG

AGGAACCTAGCTCAGTTAGCAAGGACACGTATAGCGAAGCCGCGAACAAT

GGCAAGACGTCAAGCGTGGAAAAAGACAAGCTTTCACTGGAGAAGGCCGC

TGATCTGAAAGACTCAAAGATCGAGGCTGTGGAAGCGGAACCGAATAGCA

TTGCAAAGATTGCCAACCTGCAACCGGAGGTGGACCCGAAGGCGGAGCTG

TATTTCTACGCTAAAGGCGATGCACTGCAACTGGTTTACGTCACGGAGGT

TAACATCCTGCAGCCGGCACCGCTTAGAACGAGATACATCATTGACGCGA

ACGACGGCAAGATCGTGAGCCAGTACGACATTATCAACGAGGCCACGGGA

ACGGGCAAGGGAGTCCTTGGCGACACGAAGACATTCAATACAACGGCCTC

AGGCTCATCATACCAGCTGAGAGACACGACGAGAGGCAACGGAATCGTCA

CGTACACGGCTAGCAATAGACAGAGCATTCCGGGCACAATCCTTACGGAC

GCAGACAATGTGTGGAATGACCCGGCAGGCGTGGACGCACATGCCTACGC

AGCGAAGACGTACGACTACTACAAGGAGAAGTTCAACAGAAACAGCATCG

ACGGAAGAGGACTGCAACTTAGAAGCACGGTGCATTACGGCAACAGATAC

AACAACGCTTTCTGGAACGGCAGCCAAATGACGTATGGAGACGGCGATGG

AACAACGTTTATCGCATTCTCAGGCGACCCTGACGTTGTGGGACATGAAC

TGACGCATGGAGTCACAGAATACACGAGCAATCTGGAGTATTACGGAGAA

TCAGGCGCACTTAATGAGGCCTTCAGCGACATCATCGGAAACGACATCCA

GAGAAAGAACTGGCTGGTTGGCGATGATATCTACACGCCGAGAATTGCGG

GCGACGCGCTGAGATCAATGAGCAACCCTACGCTGTACGATCAGCCGGAT

CATTACAGCAACCTGTATAGAGGCTCAAGCGATAATGGCGGCGTGCATAC

AAACAGCGGCATCATCAACAAAGCCTATTATCTGCTGGCGCAAGGCGGCA

CATTCCATGGCGTTACAGTTAATGGCATTGGCAGAGACGCAGCCGTGCAG

ATCTACTACAGCGCATTCACGAATTACCTGACATCAAGCAGCGACTTTTC

AAATGCAAGAGATGCAGTGGTGCAGGCGGCTAAAGACCTTTATGGAGCTT

CAAGCGCTCAGGCCACAGCTGCGGCAAAAAGCTTCGACGCGGTTGGAGTG

AAT

The amino acid sequence of the PspPro3 precursor protein expressed from plasmid pGX085(AprE-PspPro3) is depicted in SEQ ID NO: 5. The predicted signal sequence is shown in italics, the three residue addition (AGK) shown in bold and the predicted pro-peptide is shown in underlined text:

*MRSKKLWISLLFALTLIFTMAFSNMSAQA*AGK<u>AESSVSGPAQLTPTFHAE</u>

<u>QWKAPSSVSGDDIVWSYLNRQKKTLLGTDSTSVRDQFRIVDRTSDKSGVS</u>

<u>HYRLKQYVNGIPVYGAEQTIHVGKSGEVTSYLGAVITEDQQEEATQGTTP</u>

<u>KISASEAVHTAYQEAATRVQALPTSDDTISKDAEEPSSVSKDTYSEAANN</u>

<u>GKTSSVEKDKLSLEKAADLKDSKIEAVEAEPNSIAKIANLQPEVDPKAEL</u>

<u>YFYAKGDALQLVYVTEVNILQPAPLRTRYIIDANDGKIVSQYDIINEATG</u>

TGKGVLGDTKTFNTTASGSSYQLRDTTRGNGIVTYTASNRQSIPGTILTD

ADNVWNDPAGVDAHAYAAKTYDYYKEKFNRNSIDGRGLQLRSTVHYGNRY

NNAFWNGSQMTYGDGDGTTFIAFSGDPDVVGHELTHGVTEYTSNLEYYGE

SGALNEAFSDIIGNDIQRKNWLVGDDIYTPRIAGDALRSMSNPTLYDQPD

HYSNLYRGSSDNGGVHTNSGIINKAYYLLAQGGTFHGVTVNGIGRDAAVQ

IYYSAFTNYLTSSSDFSNARDAVVQAAKDLYGASSAQATAAAKSFDAVGV

N

The amino acid sequence of the PspPro3 recombinant protein isolated from *Bacillus subtilis* culture was determined by tandem mass spectrometry, and shown below. It is the same as predicted and depicted in SEQ ID NO: 3.

ATGTGKGVLGDTKTFNTTASGSSYQLRDTTRGNGIVTYTASNRQSIPGTI

LTDADNVWNDPAGVDAHAYAAKTYDYYKEKFNRNSIDGRGLQLRSTVHYG

NRYNNAFWNGSQMTYGDGDGTTFIAFSGDPDVVGHELTHGVTEYTSNLEY

YGESGALNEAFSDIIGNDIQRKNWLVGDDIYTPRIAGDALRSMSNPTLYD

QPDHYSNLYRGSSDNGGVHTNSGIINKAYYLLAQGGTFHGVTVNGIGRDA

AVQIYYSAFTNYLTSSSDFSNARDAVVQAAKDLYGASSAQATAAAKSFDA

VGVN

Example 1.3

Proteolytic Activity of Metalloprotease PspPro3

The proteolytic activity of purified PspPro3 was measured in 50 mM Tris (pH 7), using azo-casein (Cat #74H7165, Megazyme) as a substrate. Prior to the reaction, the enzyme was diluted with Milli-Q water (Millipore) to specific concentrations. The azo-casein was dissolved in 100 mM Tris buffer (pH 7) to a final concentration of 1.5% (w/v). To initiate the reaction, 50 µL of the diluted enzyme (or Milli-Q $H_2O$ alone as the blank control) was added to the non-binding 96-well microtiter Plate (96-MTP) (Corning Life Sciences, #3641) placed on ice, followed by the addition of 50 µL of 1.5% azo-casein. After sealing the 96-MTP, the reaction was carried out in a Thermomixer (Eppendorf) at 40° C. and 650 rpm for 10 min. The reaction was terminated by adding 100 µL of 5% Trichloroacetic Acid (TCA). Following equilibration (5 min at the room temperature) and subsequent centrifugation (2000 g for 10 min at 4° C.), 120 µL supernatant was transferred to a new 96-MTP, and absorbance of the supernatant was measured at 440 nm ($A_{440}$) using a SpectraMax 190. Net $A_{440}$ was calculated by subtracting the $A_{440}$ of the blank control from that of enzyme, and then plotted against different protein concentrations (from 1.25 ppm to 40 ppm). Each value was the mean of duplicate assays, and the value varies no more than 5%. The proteolytic activity is shown as Net $A_{440}$. The proteolytic assay with azo-casein as the substrate (FIG. 1.2) indicates that PspPro3 is an active protease.

Example 1.4 pH Profile of Metalloprotease PspPro3

With azo-casein as the substrate, the pH profile of PspPro3 was studied in 12.5 mM acetate/Bis-Tris/HEPES/CHES buffer with different pH values (ranging from pH 4 to 11). To initiate the assay, 50 µL of 25 mM acetate/Bis-Tris/HEPES/CHES buffer with a specific pH was first mixed with 2 µL diluted enzyme (250 ppm in Milli-Q $H_2O$) in a 96-MTP placed on ice, followed by the addition of 48 µL of 1.5% (w/v) azo-casein prepared in $H_2O$. The reaction was performed and analyzed as described in Example 1.3. Enzyme activity at each pH was reported as relative activity where the activity at the optimal pH was set to be 100%. The pH values tested were 4, 5, 5.5, 6, 6.5, 7, 7.5, 8, 8.5, 9, 10 and 11. Each value was the mean of triplicate assays. As shown in FIG. 1.3, the optimal pH of PspPro3 is 7.5, with greater than 70% of maximal activity retained between pH 5.5 and 9.

Example 1.5

Temperature Profile of Metalloprotease PspPro3

The temperature profiles of PspPro3 were analyzed in 50 mM Tris buffer (pH 7) using the azo-casein assay. The enzyme sample and azo-casein substrate were prepared as in Example 3. Prior to the reaction, 50 µL of 1.5% azo-casein and 45 µl Milli-Q $H_2O$ were mixed in a 200 µL PCR tube, which was then subsequently incubated in a Peltier Thermal Cycler (BioRad) at desired temperatures (i.e. 20-90° C.) for 5 min. After the incubation, 5 µL of diluted PspPro3 (100 ppm) or $H_2O$ (the blank control) was added to the substrate mixture, and the reaction was carried out in the Peltier Thermal Cycle for 10 min at different temperatures. To terminate the reaction, each assay mixture was transferred to a 96-MTP containing 100 µL of 5% TCA per well. Subsequent centrifugation and absorbance measurement were performed as described in Example 1.3. The activity was reported as relative activity where the activity at the optimal temperature was set to be 100%. The tested temperatures were 20, 30, 40, 50, 60, 70, 80, and 90° C. Each value was the mean of triplicate assays. The data in FIG. 1.4 suggest that PspPro3 showed an optimal temperature at 50° C., and retained greater than 70% of its maximal activity between 45° C. and 60° C.

Example 1.6

Cleaning Performance of Metalloprotease PspPro3 in Automatic Dishwashing (ADW) Conditions The cleaning performance of PspPro3 in automatic dishwashing (ADW) conditions was tested using PA-S-38 (egg yolk, with pigment, aged by heating) microswatches (CFT-Vlaardingen, The Netherlands) at pH 6 or 8 using a model automatic dishwashing (ADW) detergent. Prior to the reaction, purified PspPro3 were diluted with a dilution solution containing 10 mM NaCl, 0.1 mM $CaCl_2$, 0.005% TWEEN® 80 and 10% propylene glycol to the desired concentrations. The reactions were performed in AT detergent (composition shown in Table 1.1) with 100 ppm water hardness ($Ca^{2+}$: $Mg^{2+}$=3:1), in the absence or presence of a bleach component (Peracid N,N-phthaloylaminoperoxycaproic acid-PAP). To initiate the reaction, 180 µL of AT detergent buffered at pH 6 or 8 was added to a 96-MTP placed with PA-S-38 microswatches, followed by the addition of 20 µL of diluted enzymes (or the dilution solution as the blank control). The 96-MTP was sealed and incubated in an incubator/shaker for 30 min at 50° C. and 1150 rpm. After incubation, 1004, of wash liquid from each well was transferred to a new 96-MTP, and its absorbance was measured at 405 nm ($A_{405}$) (referred here as the "Initial performance") using a spectrophotometer. The remaining wash liquid in the 96-MTP was discarded and the microswatches were rinsed once with 200 µL water. Following the addition of 180 µL of 0.1 M CAPS buffer (pH 10), the second incubation was carried out in the incubator/shaker at 50° C. and 1150 rpm for 10 min. One hundred microliter of the resulting wash liquid was transferred to a new 96-MTP, and its absorbance measured at 405 nm (referred here as "Wash-off"). The sum of two absorbance measurements ("Initial performance" plus "Wash-off") gives the "Total performance", which measures the protease activity on the model stain. Dose response in cleaning the PA-S-38 microswatches at pH 6 and pH 8 for PspPro3 in AT detergent, in the absence or presence of bleach, is shown in FIGS. 5A and 5B, respectively.

TABLE 1.1

Composition of AT dish detergent formula with bleach

| Ingredient | Concentration (mg/ml) |
| --- | --- |
| MGDA (methylglycinediacetic acid) | 0.143 |
| Sodium citrate | 1.86 |
| Citric acid* | varies |
| PAP (peracid N,N-phthaloylaminoperoxycaproic acid) | 0.057 |
| Plurafac ® LF 18B (a non-ionic surfactant) | 0.029 |
| Bismuthcitrate | 0.006 |
| Bayhibit ® S (Phosphonobutantricarboxylic acid sodium salt) | 0.006 |

TABLE 1.1-continued

Composition of AT dish detergent formula with bleach

| Ingredient | Concentration (mg/ml) |
|---|---|
| Acusol ™ 587 (a calcium polyphosphate inhibitor) | 0.029 |
| PEG 6000 | 0.043 |
| PEG 1500 | 0.1 |

*The pH of the AT detergent is adjusted to the desired value (pH 6 or 8) by the addition of 0.9M citric acid.

Example 1.7

Cleaning Performance of Metalloprotease PspPro3 in Laundry Conditions

The cleaning performance of PspPro3 protein in liquid laundry detergent was tested using EMPA-116 (cotton soiled with blood/milk/ink) microswatches (obtained from CFT Vlaardingen, The Netherlands) at pH 8.2 using a commercial detergent. Prior to the reaction, purified PspPro3 protein samples were diluted with a dilution solution (10 mM NaCl, 0.1 mM $CaCl_2$), 0.005% TWEEN® 80 surfactant and 10% propylene glycol) to the desired concentrations; and the commercial detergent (Tide®, Clean Breeze® detergent, Proctor & Gamble, USA, purchased September 2011) was incubated at 95° C. for 1 hour to inactivate the enzymes present in the detergent. Proteolytic assays were subsequently performed to confirm the inactivation of proteases in the commercial detergent. The heat treated detergent was further diluted with 5 mM HEPES (pH 8.2) to a final concentration of 0.788 g/L. Meanwhile, the water hardness of the buffered liquid detergent was adjusted to 103 ppm ($Ca^{2+}$: $Mg^{2+}$=3:1). The specific conductivity of the buffered detergent was adjusted to either 0.62 mS/cm (low conductivity) or 3.5 mS/cm (high conductivity) by adjusting the NaCl concentration in the buffered detergent. To initiate the reaction, 190 µl of either the high or low conductivity buffered detergent was added to a 96-MTP containing the EMPA-116 microswatches, followed by the addition of 10 µl of diluted enzyme (or the dilution solution as blank control). The 96-MTP was sealed and incubated in an incubator/shaker for 20 min at 32° C. and 1150 rpm. After incubation, 150 µl of wash liquid from each well was transferred to a new 96-MTP, and its absorbance was measured at 600 nm using a spectrophotometer, which indicates the protease activity on the model stain; and Net A600 was subsequently calculated by subtracting the A600 of the blank control from that of the enzyme. Dose response for the cleaning of EMPA-116 microswatches in liquid laundry detergent at high or low conductivity is shown in FIG. 1.6.

Example 1.8

Comparison of PspPro3 to Other Metalloproteases

A. Identification of Homologous Proteases

Homologs were identified by a BLAST search (Altschul et al., Nucleic Acids Res, 25:3389-402, 1997) against the NCBI non-redundant protein database and the Genome Quest Patent database with search parameters set to default values. The mature protein amino acid sequence for PspPro3 (SEQ ID NO: 3) was used as the query sequence. Percent identity (PID) for both search sets is defined as the number of identical residues divided by the number of aligned residues in the pairwise alignment. Tables 1.2A and 1.2B provide a list of sequences with the percent identity to PspPro3. The length in Table 1.2 refers to the entire sequence length of the homologous proteases.

TABLE 1.2A

List of sequences with percent identity to PspPro3 protein identified from the NCBI non-redundant protein database

| Accession # | PID to PspPro3 | Organism | Length |
|---|---|---|---|
| ZP_10321515.1 | 55 | Bacillus macauensis ZFHKF-1 | 552 |
| AAC43402.1 | 57 | Alicyclobacillus acidocaldarius | 546 |
| P00800 | 57 | Bacillus thermoproteolyticus | 548 |
| AAA22621.1 | 58 | Geobacillus stearothermophilus | 548 |
| ZP_01862236.1 | 59 | Bacillus sp. SG-1 | 560 |
| YP_002884504.1 | 59 | Exiguobacterium sp. AT1b | 509 |
| AEI46285.1 | 60 | Paenibacillus mucilaginosus KNP414 | 525 |
| ZP_08093424 | 60 | Planococcus donghaensis MPA1U2 | 553 |
| ZP_10324092.1 | 61 | Bacillus macauensis ZFHKF-1 | 533 |
| YP_006792441.1 | 61 | Exiguobacterium antarcticum B7 | 498 |
| AAK69076.1 | 63 | Bacillus thuringiensis serovar finitimus | 566 |
| NP_976992.1 | 64 | Bacillus cereus ATCC 10987 | 566 |
| ZP_04321694 | 64 | Bacillus cereus | 566 |
| BAA06144 | 64 | Lactobacillus sp. | 566 |
| ZP_10241029.1 | 78 | Paenibacillus peoriae KCTC 3763 | 599 |
| YP_005073223 | 93 | Paenibacillus terrae HPL-003 | 591 |
| YP_003872179 | 94 | Paenibacillus polymyxa E681 | 592 |
| ZP_09775364 | 100 | Paenibacillus sp. Aloe-11 | 593 |

TABLE 1.2B

List of sequences with percent identity to PspPro3 protein identified from the Genome Quest Patent database

| Patent # | PID to PspPro3 | Organism | Length |
|---|---|---|---|
| US20120107907-0184 | 57.88 | Bacillus caldoyticus | 319 |
| US20120107907-0177 | 57.88 | Bacillus caldolyticus | 544 |
| WO2012110563-0002 | 58.2 | Bacillus caldolyticus | 319 |
| EP2390321-0176 | 58.52 | Bacillus stearothermophilus | 548 |
| U.S. Pat. No. 6,518,054-0002 | 59.22 | Bacillus sp. | 316 |
| WO2004011619-0044 | 60.6 | Empty | 507 |
| WO2004011619-0047 | 62.14 | Empty | 532 |
| WO2004011619-0046 | 62.26 | Empty | 536 |
| WO2012110563-0004 | 63.02 | Bacillus megaterium | 320 |
| JP2002272453-0003 | 63.67 | Empty | 562 |
| U.S. Pat. No. 8,114,656-0186 | 64.24 | Bacillus brevis | 304 |
| WO2012110562-0005 | 64.52 | Bacillus cereus | 320 |
| WO2007044993-0178 | 64.74 | Bacillus thuringiensis | 566 |
| EP2178896-0184 | 65.38 | Bacillus anthracis | 566 |
| WO2012110563-0005 | 65.48 | Bacillus cereus | 320 |
| JP1995184649-0001 | 65.71 | Lactobacillus sp. | 566 |
| U.S. Pat. No. 5,962,264-0004 | 65.81 | Empty | 566 |
| US20120107907-0185 | 66.13 | Bacillus cereus | 317 |
| U.S. Pat. No. 8,114,656-0187 | 93.36 | Bacillus polymyxa | 302 |
| JP2005229807-0019 | 93.38 | Paenibacillus polymyxa | 566 |

B. Alignment of Homologous Protease Sequences

The amino acid sequence for mature PspPro3 (SEQ ID NO: 3) was aligned with thermolysin (P00800, Bacillus thermoproteolyticus) and protease from Paenibacillus sp. Aloe-11 (ZP_09775364) using CLUSTALW software (Thompson et al., Nucleic Acids Research, 22:4673-4680, 1994) with the default parameters. FIG. 1.7 shows the alignment of PspPro3 with these protease sequences.

C. Phylogenetic Tree

A phylogenetic tree for full length sequence of PspPro3 (SEQ ID NO: 2) was built using sequences of representative homologs from Tables 2A and the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 1.8.

Example 1.9

Terg-o-Tometer Performance Evaluation of PspPro3

The wash performance of PspPro3 was tested in a laundry detergent application using a Terg-o-Tometer (Instrument Marketing Services, Inc, Fairfield, N.J.). The performance evaluation was conducted at 32° C. and 16° C. The soil load consisted of two of each of the following stain swatches: EMPA116 Blood, Milk, Ink on cotton (Test materials AG, St. Gallen, Switzerland), EMPA117 Blood, Milk, Ink on polycotton (Test materials AG, St. Gallen, Switzerland), EMPA112 Cocoa on cotton (Test materials AG, St. Gallen, Switzerland), and CFT C-10 Pigment, Oil, and Milk content on cotton (Center for Testmaterials BV, Vlaardingen, Netherlands), plus extra white interlock knit fabric to bring the total fabric load to 40 g per beaker of the Terg-o-Tometer, which was filled with 1 L of deionized water. The water hardness was adjusted to 6 grains per gallon, and the pH in the beaker was buffered with 5 mM HEPES, pH 8.2. Heat inactivated Tide Regular HDL (Procter & Gamble), a commercial liquid detergent purchased in a local US supermarket, was used at 0.8 g/L. The detergent was inactivated before use by treatment at 92° C. in a water bath for 2-3 hours followed by cooling to room temperature. Heat inactivation of commercial detergents serves to destroy the activity of enzymatic components while retaining the properties of the non-enzymatic components. Enzyme activity in the heat inactivated detergent was measured using the Suc-AAPF-pNA assay for measuring protease activity. The Purafect® Prime HA, (Genencor Int'l) and PspPro3 proteases were each added to final concentrations of 0, 0.2, 0.5, 1, and 1.5 ppm. The wash time was 12 minutes. After the wash treatment, all swatches were rinsed for 3 minutes and machine-dried at low heat.

Four of each types of swatch were measured before and after treatment by optical reflectance using a Tristimulus Minolta Meter CR-400. The difference in the L, a, b values was converted to total color difference (dE), as defined by the CIE-LAB color space. Cleaning of the stains is expressed as percent stain removal index (% SRI) by taking a ratio between the color difference before and after washing, and comparing it to the difference of unwashed soils (before wash) to unsoiled fabric, and averaging the eight values obtained by reading two different regions of each washed swatch and is reported in Tables 1.9A and 1.9B as Average % SRI (dE)±95CI. Table 1.9A summarizes the cleaning performance of PspPro3 at 32° C. and Table 1.9B at 16° C.

TABLE 1.9A

Cleaning performance of PspPro3 at 32° C.

| | EMPA-116 | | | | EMPA-117 | | | |
|---|---|---|---|---|---|---|---|---|
| | Purafect Prime HA | | PspPro3 | | Purafect Prime HA | | SprPro3 | |
| ppm enzyme | Average % SRI (dE) | 95CI [% SRI (dE)] | Average % SRI (dE) | 95CI [% SRI (dE)] | Average % SRI (dE) | 95CI [% SRI (dE)] | Average % SRI (dE) | 95CI [% SRI (dE)] |
| 0 | 0.19 | 0.01 | 0.19 | 0.01 | 0.17 | 0.01 | 0.17 | 0.01 |
| 0.2 | 0.27 | 0.02 | 0.27 | 0.02 | 0.25 | 0.03 | 0.30 | 0.02 |
| 0.5 | 0.28 | 0.03 | 0.31 | 0.01 | 0.30 | 0.03 | 0.31 | 0.02 |
| 1 | 0.30 | 0.01 | 0.32 | 0.02 | 0.35 | 0.02 | 0.34 | 0.03 |
| 1.5 | 0.31 | 0.02 | 0.31 | 0.01 | 0.37 | 0.01 | 0.37 | 0.03 |

| | EMPA-112 | | | | CFT C-10 | | | |
|---|---|---|---|---|---|---|---|---|
| | Purafect Prime HA | | PspPro3 | | Purafect Prime HA | | PspPro3 | |
| ppm enzyme | Average % SRI (dE) | 95CI [% SRI (dE)] | Average % SRI (dE) | 95CI [% SRI (dE)] | Average % SRI (dE) | 95CI [% SRI (dE)] | Average % SRI (dE) | 95CI [% SRI (dE)] |
| 0 | 0.11 | 0.03 | 0.11 | 0.03 | 0.07 | 0.01 | 0.07 | 0.01 |
| 0.2 | 0.11 | 0.05 | 0.18 | 0.04 | 0.12 | 0.01 | 0.11 | 0.01 |
| 0.5 | 0.13 | 0.04 | 0.17 | 0.03 | 0.15 | 0.01 | 0.16 | 0.01 |
| 1 | 0.18 | 0.03 | 0.19 | 0.04 | 0.17 | 0.01 | 0.21 | 0.01 |
| 1.5 | 0.19 | 0.03 | 0.18 | 0.04 | 0.18 | 0.01 | 0.23 | 0.01 |

TABLE 1.9B

Cleaning performance of PspPro3 at 16° C.

| ppm enzyme | Purafect Prime HA Average % SRI (dE) | Purafect Prime HA 95CI [% SRI (dE)] | PspPro3 Average % SRI (dE) | PspPro3 95CI [% SRI (dE)] | Purafect Prime HA Average % SRI (dE) | Purafect Prime HA 95CI [% SRI (dE)] | PspPro3 Average % SRI (dE) | PspPro3 95CI [% SRI (dE)] |
|---|---|---|---|---|---|---|---|---|
| | EMPA-116 | | | | EMPA-117 | | | |
| 0 | 0.15 | 0.02 | 0.15 | 0.02 | 0.13 | 0.01 | 0.13 | 0.01 |
| 0.2 | 0.19 | 0.02 | 0.20 | 0.03 | 0.15 | 0.02 | 0.15 | 0.02 |
| 0.5 | 0.20 | 0.02 | 0.19 | 0.02 | 0.21 | 0.02 | 0.20 | 0.02 |
| 1 | 0.24 | 0.04 | 0.21 | 0.02 | 0.22 | 0.02 | 0.20 | 0.01 |
| 1.5 | 0.19 | 0.02 | 0.25 | 0.04 | 0.23 | 0.03 | 0.20 | 0.01 |
| | EMPA-112 | | | | CFT C-10 | | | |
| 0 | 0.08 | 0.03 | 0.08 | 0.03 | 0.04 | 0.08 | 0.04 | 0.08 |
| 0.2 | 0.12 | 0.02 | 0.09 | 0.01 | 0.06 | 0.12 | 0.06 | 0.09 |
| 0.5 | 0.08 | 0.02 | 0.11 | 0.02 | 0.08 | 0.08 | 0.08 | 0.11 |
| 1 | 0.11 | 0.02 | 0.10 | 0.03 | 0.08 | 0.11 | 0.09 | 0.10 |
| 1.5 | 0.13 | 0.02 | 0.11 | 0.03 | 0.11 | 0.13 | 0.10 | 0.11 |

Example 2.1

Cloning of Metalloprotease PspPro2 from *Paenibacillus* sp

A strain of *Paenibacillus* sp. was selected as a potential source for enzymes which may be useful for various industrial applications. Genomic DNA for sequencing was obtained by first growing the strain on Heart Infusion agar plates (Difco) at 37° C. for 24 hr. Cell material was scraped from the plates and used to prepare genomic DNA with the ZF Fungal/Bacterial DNA miniprep kit from Zymo (Cat No. D6005). The genomic DNA was used for genome sequencing. The entire genome of the *Paenibacillus* sp. strain was sequenced by BaseClear (Leiden, The Netherlands) using the Illumina's next generation sequencing technology. After assembly of the data, contigs were annotated by BioXpr (Namur, Belgium). One of the genes identified after annotation in *Paenibacillus* sp. encodes a metalloprotease and the sequence of this gene, called PspPro2, is provided in SEQ ID NO: 6. The corresponding protein encoded by the PspPro2 gene is shown in SEQ ID NO: 7. At the N-terminus, the protein has a signal peptide with a length of 24 amino acids as predicted by SignalP version 4.0 (Nordahl Petersen et al. (2011) Nature Methods, 8:785-786). The presence of a signal sequence suggests that PspPro2 is a secreted enzyme. The propeptide region of PspPro2 was predicted based on protein sequence alignment with the *Paenibacillus polymyxa* Npr protein (Takekawa et al. (1991) Journal of Bacteriology, 173 (21): 6820-6825). The predicted mature region of PspPro2 is shown in SEQ ID NO: 8.

The nucleotide sequence of the PspPro2 gene isolated from *Paenibacillus* sp. is set forth as SEQ ID NO: 6. The sequence encoding the predicted native signal peptide is shown in italics:

*ATGAAAAAAGTATGGGTTTCACTTCTTGGAGGAGCGATGTTATTAGGGGC*

*TGTAGCACCAGGTGCATCAGCAGCAGAGCATTCTGTTCCTGATCCTACTC*

*AGCTAACACCGACCTTTCACGCCGAGCAATGGAAGGCTCCTTCCACGGTA*

*ACCGGCGACAATATTGTATGGAGCTATTTGAATCGACAAAAGAAAACCTT*

-continued

ATTGAATACAGACAGCACCAGTGTGCGTGATCAGTTCCGCATCATTGATC

GTACAAGCGACAAATCCGGTGCAAGCCATTATCGGCTCAAGCAATATGTA

AACGGGATCCCCGTATATGGGGCTGAACAGACCATTCATGTGAACAACGC

CGGTAAAGTAACCTCTTATTTGGGTGCTGTCATTTCAGAGGATCAGCAGC

AAGACGCGACCGAAGATACCACTCCAAAAATCAGCGCGACTGAAGCCGTT

TATACCGCATATGCAGAAGCCGCTGCCCGGATTCAATCCTTCCCTTCCAT

CAATGATAGTCTTTCTGAGGCTAGTGAGGAACAAGGGAGTGAGAATCAAG

GCAATGAGATTCAAAACATTGGGATTAAAAGCAGTGTAAGTAATGACACT

TACGCAGAGGCGCATAACAACGTACTTTTAACCCCCGTTGACCAAGCAGA

GCAAAGTTACATTGCCAAAATTGCTAATCTGGAGCCAAGTGTAGAGCCCA

AAGCAGAATTATACATCTATCCAGATGGTGAGACTACACGACTGGTTTAT

GTAACAGAGGTTAATATTCTTGAACCTGCGCCTCTGCGCACACGCTACTT

CATTGATGCGAAAACCGGCAAAATCGTATTCCAGTATGACATCCTCAACC

ACGCAACAGGCACCGGCCGCGGCGTGGATGGCAAAACAAAATCATTTACG

ACTACAGCTTCAGGCAACCGGTATCAGTTGAAAGACACGACTCGCAGCAA

TGGAATCGTGACTTACACCGCTGGCAATCGCCAGACGACGCCAGGTACGA

TTTTGACCGATACAGATAATGTATGGGAGGACCCTGCGGCTGTTGATGCC

CATGCCTACGCCATTAAAACCTATGACTATTATAAGAATAAATTCGGTCG

CGACAGTATTGATGGACGTGGCATGCAAATTCGTTCGACAGTCCATTACG

GCAAAAAATATAACAATGCCTTCTGGAACGGCTCGCAAATGACCTACGGA

GACGGAGACGGGTCCACATTTACCTTCTTCAGCGGCGATCCCGATGTCGT

GGGGCATGAGCTCACCCACGGCGTCACCGAGTTCACCTCCAATTTGGAGT

ATTATGGTGAGTCCGGTGCATTGAACGAAGCCTTCTCGGATATTATCGGT

AATGATATAGATGGCACCAGTTGGCTTCTTGGCGACGGCATTTATACGCC

TAATATTCCAGGCGACGCTCTGCGTTCCCTGTCCGATCCTACACGATTCG

GCCAGCCGGATCACTACTCCAATTTCTATCCGGACCCCAACAATGATGAT

```
GAAGGCGGAGTCCATACGAACAGCGGTATTATCAACAAAGCCTATTATTT

GCTGGCACAAGGCGGTACGTCCCATGGTGTAACGGTAACTGGTATCGGAC

GCGAAGCGGCTGTATTCATTTACTACAATGCCTTTACCAACTATTTGACC

TCTACCTCCAACTTCTCTAACGCACGCGCTGCTGTTATACAGGCAGCCAA

GGATTTTTATGGTGCTGATTCGCTGGCAGTAACCAGTGCTATTCAATCCT

TTGATGCGGTAGGAATCAAA
```

The amino acid sequence of the PspPro2 precursor protein is set forth as SEQ ID NO: 7. The predicted signal peptide is shown in italics, and the predicted pro-peptide is shown in underlined text:

```
MKKVWVSLLGGAMLLGAVAPGASAAEHSVPDPTQLTPTFHAEQWKAPSTV

TGDNIVWSYLNRQKKTLLNTDSTSVRDQFRIIDRTSDKSGASHYRLKQYV

NGIPVYGAEQTIHVNNAGKVTSYLGAVISEDQQQDATEDTTPKISATEAV

YTAYAEAAARIQSFPSINDSLSEASEEQGSENQGNEIQNIGIKSSVSNDT

YAEAHNNVLLTPVDQAEQSYIAKIANLEPSVEPKAELYIYPDGETTRLVY

VTEVNILEPAPLRTRYFIDAKTGKIVFQYDILNHATGTGRGVDGKTKSFT

TTASGNRYQLKDTTRSNGIVTYTAGNRQTTPGTILTDTDNVWEDPAAVDA

HAYAIKTYDYYKNKFGRDSIDRGRGMQIRSTVHYGKKYNNAFWNGSQMTYG

DGDGSTFTFFSGDPDVVGHELTHGVTEFTSNLEYYGESGALNEAFSDIIG

NDIDGTSWLLGDGIYTPNIPGDALRSLSDPTRFGQPDHYSNFYPDPNNDD

EGGVHTNSGIINKAYYLLAQGGTSHGVTVTGIGREAAVFIYYNAFTNYLT

STSNFSNARAAVIQAAKDFYGADSLAVTSAIQSFDAVGIK
```

The amino acid sequence of the predicted mature form of PspPro2 is set forth as SEQ ID NO: 8.

```
ATGTGRGVDGKTKSFTTTASGNRYQLKDTTRSNGIVTYTAGNRQTTPGTI

LTDTDNVWEDPAAVDAHAYAIKTYDYYKNKFGRDSIDRGRGMQIRSTVHYG

KKYNNAFWNGSQMTYGDGDGSTFTFFSGDPDVVGHELTHGVTEFTSNLEY

YGESGALNEAFSDIIGNDIDGTSWLLGDGIYTPNIPGDALRSLSDPTRFG

QPDHYSNFYPDPNNDDEGGVHTNSGIINKAYYLLAQGGTSHGVTVTGIGR

EAAVFIYYNAFTNYLTSTSNFSNARAAVIQAAKDFYGADSLAVTSAIQSF

DAVGIK
```

Example 2.2

Expression of *Paenibacillus* sp. Metalloprotease PspPro2

The DNA sequence of the propeptide-mature form of PspPro2 was synthesized and inserted into the *Bacillus subtilis* expression vector p2JM103BBI (Vogtentanz, *Protein Expr Purif,* 55:40-52, 2007) by Generay (Shanghai, China), resulting in plasmid pGX084 (AprE-PspPro2) (FIG. 2.1). Ligation of this gene encoding the PspPro2 protein into the digested vector resulted in the addition of three codons (Ala-Gly-Lys) between the 3' end of the *Bacillus subtilis* AprE signal sequence and the 5' end of the predicted PspPro2 native propeptide. The gene has an alternative start codon (GTG). As shown in FIG. 2.1, pGX084(AprE-PspPro2) contains an AprE promoter, an AprE signal sequence used to direct target protein secretion in *B. subtilis*, and the synthetic nucleotide sequence encoding the predicted propeptide and mature regions of PspPro2, (SEQ ID NO: 9). The translation product of the synthetic AprE-PspPro2 gene is shown in SEQ ID NO: 10.

The pGX084(AprE-PspPro2) plasmid was transformed into *B. subtilis* cells (degU$^{Hy}$32, ΔscoC) and the transformed cells were spread on Luria Agar plates supplemented with 5 ppm chloramphenicol and 1.2% skim milk (Cat #232100, Difco). Colonies with the largest clear halos on the plates were selected and subjected to fermentation in a 250 ml shake flask with MBD medium (a MOPS based defined medium, supplemented with additional 5 mM CaCl$_2$).

The broth from the shake flasks was concentrated and buffer-exchanged into the loading buffer containing 20 mM Tris-HCl (pH 8.5) and 1 mM CaCl$_2$ using a VivaFlow 200 ultra filtration device (Sartorius Stedim). After filtering, this sample was applied to a 150 ml Q Sepharose High Performance column pre-equilibrated with the loading buffer above, PspPro2 was eluted from the column with a linear salt gradient from 0 to 0.5 M NaCl in the loading buffer. The corresponding active fractions were collected, concentrated and buffer-exchanged again into the loading buffer described above. The sample was loaded onto a 20 ml DEAE Fast Flow column pre-equilibrated with the same loading buffer. PspPro2 was eluted from the column with a linear salt gradient from 0 to 0.3 M NaCl in the loading buffer. The corresponding active purified protein fractions were further pooled and concentrated via 10K Amicon Ultra for further analyses. The nucleotide sequence of the synthesized PspPro2 gene in plasmid pGX084 (AprE-PspPro2) is depicted in SEQ ID NO: 9. The sequence encoding the predicted native signal peptide is shown in italics and the oligonucleotide encoding the three residue addition (AGK) is shown in bold:

```
GTGAGAAGCAAAAAATTGTGGATCAGCTTGTTGTTTGCGTTAACGTTAAT

CTTTACGATGGCGTTCAGCAACATGAGCGCGCAGGCTGCTGGAAAAGCAG

AGCATTCAGTTCCTGACCCGACGCAACTTACACCGACATTTCATGCTGAG

CAGTGGAAGGCACCGAGCACGGTCACGGGCGACAACATCGTGTGGAGCTA

CCTGAACAGACAGAAAAAGACGCTGCTGAACACGGACTCAACGAGCGTGA

GAGACCAGTTCAGAATCATCGACAGAACGAGCGACAAGTCAGGCGCGTCA

CATTATAGACTGAAGCAGTACGTGAACGGCATCCCGGTCTACGGAGCCGA

GCAAACGATCCATGTGAATAATGCGGGCAAAGTTACATCATACCTGGGCG

CCGTCATCTCAGAAGACCAGCAGCAAGATGCAACGGAGGATACAACACCG

AAGATCAGCGCCACAGAAGCGGTCTATACGGCTTACGCCGAAGCGGCTGC

AAGAATCCAGAGCTTCCCGTCAATTAATGACAGCCTGAGCGAAGCATCAG

AGGAACAAGGCAGCGAGAACCAGGGCAATGAAATCCAAAACATCGGCATC

AAGAGCAGCGTGTCAAACGACACGTATGCGGAGGCTCATAACAACGTTCT

GCTGACACCGGTCGATCAGGCCGAACAGAGCTATATTGCAAAGATCGCGA

ATCTGGAGCCGTCAGTCGAGCCGAAGGCCGAGCTGTATATCTATCCGGAC

GGCGAGACGACGAGACTGGTGTACGTTACGGAGGTCAACATCCTTGAGCC

TGCGCCGCTGAGAACAAGATACTTTATCGACGCCAAGACGGGCAAGATCG
```

-continued

```
TGTTTCAGTACGATATCCTGAACCATGCGACGGGAACAGGCAGAGGCGTG

GACGGCAAAACAAAATCATTCACGACAACGGCAAGCGGCAACAGATACCA

GCTGAAGGACACAACAAGATCAAATGGCATCGTCACATACACGGCCGGAA

ATAGACAGACGACGCCGGGAACGATTCTGACGGATACAGATAACGTGTGG

GAAGATCCGGCAGCAGTTGATGCACATGCATACGCGATCAAGACGTACGA

CTACTACAAGAACAAATTCGGAAGAGATTCAATCGATGGAAGAGGCATGC

AAATCAGATCAACGGTTCATTATGGCAAAAAGTACAACAATGCCTTCTGG

AACGGCAGCCAAATGACATACGGCGATGGAGACGGCTCAACGTTTACATT

CTTTTCAGGCGACCCGGACGTCGTCGGCCATGAACTGACGCATGGCGTTA

CAGAGTTCACGAGCAACCTGGAGTATTACGGCGAATCAGGCGCACTGAAT

GAGGCTTTCAGCGACATCATTGGCAACGACATTGATGGCACATCATGGCT

GCTTGGCGACGGCATTTACACACCTAACATTCCGGGCGATGCACTGAGAA

GCCTGTCAGACCCTACGAGATTCGGCCAACCTGACCATTACAGCAACTTC

TACCCGGATCCTAATAACGATGATGAGGGCGGAGTGCATACGAACAGCGG

CATTATCAACAAAGCGTACTATCTGCTGGCACAAGGCGGAACGTCACATG

GAGTGACGGTGACAGGAATCGGCAGAGAGGCGGCAGTGTTTATCTACTAC

AACGCCTTCACAAACTACCTGACGAGCACGTCAAATTTCAGCAACGCTAG

AGCGGCGGTCATCCAGGCAGCAAAGGACTTTTATGGAGCAGACTCACTGG

CAGTTACGTCAGCAATTCAGTCATTCGACGCAGTTGGAATTAAG
```

The amino acid sequence of the PspPro2 precursor protein expressed from plasmid pGX084(AprE-PspPro2) is depicted in SEQ ID NO: 10. The predicted signal sequence is shown in italics, the three residue addition (AGK) is shown in bold, and the predicted pro-peptide is shown in underlined text:

*MRSKKLWISLLFALTLIFTMAFSNMSAQA*AGK<u>AEHSVPDPTQLTPTFHAE</u>

<u>QWKAPSTVTGDNIVWSYLNRQKKTLLNTDSTSVRDQFRIIDRTSDKSGAS</u>

<u>HYRLKQYVNGIPVYGAEQTIHVNNAGKVTSYLGAVISEDQQQDATEDTTP</u>

<u>KISATEAVYTAYAEAAARIQSFPSINDSLSEASEEQGSENQGNEIQNIGI</u>

<u>KSSVSNDTYAEAHNNVLLTPVDQAEQSYIAKIANLEPSVEPKAELYIYPD</u>

<u>GETTRLVYVTEVNILEPAPLRTRYFIDAKTGKIVFQYDILNH</u>ATGTGRGV

DGKTKSFTTTASGNRYQLKDTTRSNGIVTYTAGNRQTTPGTILTDTDNVW

EDPAAVDAHAYAIKTYDYYKNKFGRDSIDGRGMQIRSTVHYGKKYNNAFW

NGSQMTYGDGDGSTFTFFSGDPDVVGHELTHGVTEFTSNLEYYGESGALN

EAFSDIIGNDIDGTSWLLGDGIYTPNIPGDALRSLSDPTRFGQPDHYSNF

YPDPNNDDEGGVHTNSGIINKAYYLLAQGGTSHGVTVTGIGREAAVFIYY

NAFTNYLTSTSNFSNARAAVIQAAKDFYGADSLAVTSAIQSFDAVGIK

The amino acid sequence of the recombinant PspPro2 protein isolated from *Bacillus subtilis* culture was determined by tandem mass spectrometry, and shown below. It is the same as predicted and depicted in SEQ ID NO: 8.

ATGTGRGVDGKTKSFTTTASGNRYQLKDTTRSNGIVTYTAGNRQTTPGTI

LTDTDNVWEDPAAVDAHAYAIKTYDYYKNKFGRDSIDGRGMQIRSTVHYG

KKYNNAFWNGSQMTYGDGDGSTFTFFSGDPDVVGHELTHGVTEFTSNLEY

YGESGALNEAFSDIIGNDIDGTSWLLGDGIYTPNIPGDALRSLSDPTRFG

QPDHYSNFYPDPNNDDEGGVHTNSGIINKAYYLLAQGGTSHGVTVTGIGR

EAAVFIYYNAFTNYLTSTSNFSNARAAVIQAAKDFYGADSLAVTSAIQSF

DAVGIK

Example 2.3

Proteolytic Activity of Metalloprotease PspPro2

The proteolytic activity of purified PspPro2 was measured in 50 mM Tris (pH 7), using azo-casein (Cat #74H7165, Megazyme) as a substrate. Prior to the reaction, the enzyme was diluted with Milli-Q water (Millipore) to specific concentrations. The azo-casein was dissolved in 100 mM Tris buffer (pH 7) to a final concentration of 1.5% (w/v). To initiate the reaction, 50 µl of the diluted enzyme (or Milli-Q $H_2O$ alone as the blank control) was added to the non-binding 96-well Microtiter Plate (96-MTP) (Corning Life Sciences, #3641) placed on ice, followed by the addition of 50 µl of 1.5% azo-casein. After sealing the 96-MTP, the reaction was carried out in a Thermomixer (Eppendorf) at 40° C. and 650 rpm for 10 min. The reaction was terminated by adding 100 µl of 5% Trichloroacetic Acid (TCA). Following equilibration (5 min at the room temperature) and subsequent centrifugation (2000 g for 10 min at 4° C.), 120 µl supernatant was transferred to a new 96-MTP, and absorbance of the supernatant was measured at 440 nm ($A_{440}$) using a SpectraMax 190. Net $A_{440}$ was calculated by subtracting the $A_{440}$ of the blank control from that of enzyme, and then plotted against different protein concentrations (from 1.25 ppm to 40 ppm). Each value was the mean of duplicate assays, and the value varies no more than 5%. The proteolytic activity is shown as Net $A_{440}$. The proteolytic assays with azo-casein as the substrate (FIG. 2.2) indicate that PspPro2 is an active protease.

Example 2.4 pH Profile of Metalloprotease PspPro2

With azo-casein as the substrate, the pH profile of PspPro2 was studied in 12.5 mM acetate/Bis-Tris/HEPES/CHES buffer with different pH values (ranging from pH 4 to 11). To initiate the assay, 50 µl of 25 mM acetate/Bis-Tris/HEPES/CHES buffer with a specific pH was first mixed with 2 µl diluted enzyme (500 ppm in Milli-Q $H_2O$) in a 96-MTP placed on ice, followed by the addition of 48 µl of 1.5% (w/v) azo-casein prepared in $H_2O$. The reaction was performed and analyzed as described in Example 2.3. Enzyme activity at each pH was reported as the relative activity, where the activity at the optimal pH was set to be 100%. The pH values tested were 4, 5, 5.5, 6, 6.5, 7, 7.5, 8, 8.5, 9, 10 and 11. Each result was the mean of triplicate assays. As shown in FIG. 2.3, the optimal pH of PspPro2 is 7.5 with greater than 70% of its maximal activity retained between pH 5.5 and 9.5.

Example 2.5

Temperature Profile of Metalloprotease PspPro2

The temperature profile of PspPro2 was analyzed in 50 mM Tris buffer (pH 7) using the azo-casein assay. The enzyme sample and azo-casein substrate were prepared as in Example 2.3. Prior to the reaction, 50 µl of 1.5% azo-casein and 45 µl Milli-Q H$_2$O were mixed in a 200 µl PCR tube, which was then subsequently incubated in a Peltier Thermal Cycler (BioRad) at desired temperatures (i.e. 20-90° C.) for 5 min. After the incubation, 5 µl of diluted PspPro2 (200 ppm) or H$_2$O (the blank control) was added to the substrate mixture, and the reaction was carried out in the Peltier Thermal Cycle for 10 min at different temperatures. To terminate the reaction, each assay mixture was transferred to a 96-MTP containing 100 µl of 5% TCA per well. Subsequent centrifugation and absorbance measurement were performed as described in Example 3. The activity was reported as the relative activity, where the activity at the optimal temperature was set to be 100%. The tested temperatures are 20, 30, 40, 50, 60, 70, 80 and 90° C. Each result was the mean of triplicate assays. The data in FIG. 2.4 suggest that PspPro2 showed an optimal temperature at 50° C., and retained greater than 70% of its maximal activity between 40 and 65° C.

Example 2.6

Cleaning Performance of Metalloprotease PspPro2 in Automatic Dishwashing (ADW) Conditions The cleaning performance of PspPro2 protein in automatic dishwashing (ADW) conditions was tested using PA-S-38 (egg yolk, with pigment, aged by heating) microswatches (CFT-Vlaardingen, The Netherlands) at pH 6 and 8 using a model automatic dishwashing (ADW) detergent. Prior to the reaction, purified PspPro2 protein samples were diluted with the dilution solution containing 10 mM NaCl, 0.1 mM CaCl$_2$, 0.005% TWEEN® 80 and 10% propylene glycol to the desired concentrations. The reactions were performed in AT detergent with 100 ppm water hardness (Ca$^{2+}$: Mg$^{2+}$=3:1), in the presence of a bleach component (Peracid N,N-phthaloylaminoperoxycaproic acid-PAP) (AT detergent composition shown in Table 1). To initiate the reaction, 180 µl of the AT detergent solution at pH 6 or pH 8 was added to a 96-MTP placed with PA-S-38 microswatches, followed by the addition of 20 µl of diluted enzymes (or the dilution solution as the blank control). The 96-MTP was sealed and incubated in an incubator/shaker for 30 min at 50° C. and 1150 rpm. After incubation, 100 µl of wash liquid from each well was transferred to a new 96-MTP, and its absorbance was measured at 405 nm (referred here as the "Initial performance") using a spectrophotometer. The remaining wash liquid in the 96-MTP was discarded and the microswatches were rinsed once with 200 µl water. Following the addition of 180 µl of 0.1 M CAPS buffer (pH 10), the second incubation was carried out in the incubator/shaker at 50° C. and 1150 rpm for 10 min. One hundred microliters of the resulting wash liquid was transferred to a new 96-MTP, and its absorbance was measured at 405 nm (referred here as "Wash-off"). The sum of two absorbance measurements ("Initial performance" plus "Wash-off") gives the "Total performance", which measures the protease activity on the model stain. Dose response for cleaning of PA-S-38 microswatches at pH 6 and pH 8 for PspPro2 in AT detergent in the presence of bleach, is shown in FIGS. 2.5A and 2.5B, respectively.

TABLE 2.1

Composition of AT dish detergent with bleach

| Ingredient | Concentration (mg/ml) |
|---|---|
| MGDA (methylglycinediacetic acid) | 0.143 |
| Sodium citrate | 1.86 |
| Citric acid* | varies |
| PAP (peracid N,N-phthaloylaminoperoxycaproic acid) | 0.057 |
| Plurafac ® LF 18B (a non-ionic surfactant) | 0.029 |
| Bismuthcitrate | 0.006 |
| Bayhibit ® S (Phosphonobutantricarboxylic acid sodium salt) | 0.006 |
| Acusol ™ 587 (a calcium polyphosphate inhibitor) | 0.029 |
| PEG 6000 | 0.043 |
| PEG 1500 | 0.1 |

*The pH of the AT formula detergent is adjusted to the desired pH value (pH 6 or 8) by the addition of 0.9M citric acid.

Example 2.7

Cleaning Performance of Metalloprotease PspPro2 in Laundry Conditions

A. Cleaning Performance in Liquid Laundry Detergent

The cleaning performance of PspPro2 protein in liquid laundry detergent was tested using EMPA-116 (cotton soiled with blood/milk/ink) microswatches (obtained from CFT Vlaardingen, The Netherlands) at pH 8.2 using a commercial detergent. Prior to the reaction, purified PspPro2 protein samples were diluted with a dilution solution (10 mM NaCl, 0.1 mM CaCl$_2$, 0.005% TWEEN® 80 and 10% propylene glycol) to the desired concentrations; and the commercial detergent (Tide®, Clean Breeze®, Proctor & Gamble, USA, purchased September 2011) was incubated at 95° C. for 1 hour to inactivate the enzymes present in the detergent. Proteolytic assays were subsequently performed to confirm the inactivation of proteases in the commercial detergent. The heat treated detergent was further diluted with 5 mM HEPES (pH 8.2) to a final concentration of 0.788 g/L. Meanwhile, the water hardness of the buffered liquid detergent was adjusted to 103 ppm (Ca$^{2+}$: Mg$^{2+}$=3:1). The specific conductivity of the buffered detergent was adjusted to either 0.62 mS/cm (low conductivity) or 3.5 mS/cm (high conductivity) by adjusting the NaCl concentration in the buffered detergent. To initiate the reaction, 190 µl of either the high or low conductivity buffered detergent was added to a 96-MTP containing the EMPA-116 microswatches, followed by the addition of 10 µl of diluted enzyme (or the dilution solution as blank control). The 96-MTP was sealed and incubated in an incubator/shaker for 20 min at 32° C. and 1150 rpm. After incubation, 150 µl of wash liquid from each well was transferred to a new 96-MTP, and its absorbance was measured at 600 nm using a spectrophotometer, which indicates the protease activity on the model stain; and Net A$_{600}$ was subsequently calculated by subtracting the A$_{600}$ of the blank control from that of the enzyme. Dose response for the cleaning of EMPA-116 microswatches in liquid laundry detergent at high or low conductivity is shown in FIG. 2.6A.

B. Cleaning Performance in Powder Laundry Detergent

The cleaning performance of PspPro2 protein in powder laundry detergent was tested using PA-S-38 (egg yolk, with pigment, aged by heating) microswatches (CFT-Vlaardingen, The Netherlands) using a commercial detergent. Prior to the reaction, purified PspPro2 protein samples were diluted with a dilution solution (10 mM NaCl, 0.1 mM CaCl$_2$, 0.005% TWEEN® 80 and 10% propylene glycol) to the desired concentrations. The powder laundry detergent (Tide®, Bleach Free, Proctor & Gamble, China, purchased in December 2011) was dissolved in water with 103 ppm water hardness (Ca$^{2+}$: Mg$^{2+}$=3:1) to a final concentration of 2 g/L (with conductivity of 2.3 mS/cm-low conductivity) or 5 g/L (with conductivity of 5.5 mS/cm-high conductivity). The detergents of different conductivities were subsequently heated in a microwave to near boiling in order to inactivate the enzymes present in the detergent. Proteolytic activity was measured following treatment to ensure that proteases in the commercial detergent had been inactivated. To initiate the reaction, 190 µl of either the high or low conductivity heat-treated detergent was added to a 96-MTP containing the PA-S-38 microswatches, followed by the addition of 10 µl of diluted enzyme (or the dilution solution as blank control). The 96-MTP was sealed and incubated in an incubator/shaker for 15 minutes at 32° C. and 1150 rpm. After incubation, 150 µl of wash liquid from each well was transferred to a new 96-MTP, and its absorbance was measured at 405 nm using a spectrophotometer, which indicates the protease activity on the model stain; and Net A$_{405}$ was subsequently calculated by subtracting the A$_{405}$ of the blank control from that of the enzyme. Dose response for the cleaning of PA-S-38 microswatches in powder laundry detergent at high or low conductivity is shown in FIG. 2.6B.

Example 2.8

Comparison of PspPro2 to Other Metalloproteases

Identification of Homologous Proteases

Homologs were identified by a BLAST search (Altschul et al., Nucleic Acids Res, 25:3389-402, 1997) against the NCBI non-redundant protein database and the Genome Quest Patent database with search parameters set to default values. The mature protein amino acid sequence for PspPro2 (SEQ ID NO: 8) is used as query sequence. Percent identity (PID) for both search sets is defined as the number of identical residues divided by the number of aligned residues in the pairwise alignment. Tables 2.2A and 2.2B provide a list of sequences with the percent identity to PspPro2. The length in Table 2.2 refers to the entire sequence length of the homologous proteases.

TABLE 2.2A

List of sequences with percent identity to PspPro2 protein identified from the NCBI non-redundant protein database

| Accession # | PID to PspPro2 | Organism | Length |
|---|---|---|---|
| AAB02774.1 | 55 | Geobacillus stearothermophilus | 552 |
| AAA22623.1 | 56 | Bacillus caldolyticus | 544 |
| P00800 | 56 | Bacillus thermoproteolyticus | 548 |
| YP_003670279.1 | 57 | Geobacillus sp. C56-T3 | 546 |
| BAD60997.1 | 57 | Bacillus megaterium | 562 |
| ZP_02326503.1 | 58 | Paenibacillus larvae subsp. larvae BRL-230010 | 520 |
| ZP_08640523.1 | 58 | Brevibacillus laterosporus LMG 15441 | 564 |
| YP_003597483.1 | 58 | Bacillus megaterium DSM 319 | 562 |
| ZP_09069025.1 | 59 | Paenibacillus larvae subsp. larvae B-3650 | 520 |
| YP_001373863.1 | 59 | Bacillus cytotoxicus NVH 391-98 | 565 |
| ZP_04149724.1 | 59 | Bacillus pseudomycoides DSM 12442 | 566 |
| CAA43589.1 | 60 | Brevibacillus brevis | 527 |
| ZP_10738945.1 | 60 | Brevibacillus sp. CF112 | 528 |
| ZP_04216147.1 | 60 | Bacillus cereus Rock3-44 | 566 |

TABLE 2.2A-continued

List of sequences with percent identity to PspPro2 protein identified from the NCBI non-redundant protein database

| Accession # | PID to PspPro2 | Organism | Length |
|---|---|---|---|
| ZP_10575942.1 | 61 | Brevibacillus sp. BC25 | 528 |
| YP_002770810.1 | 62 | Brevibacillus brevis NBRC 100599 | 528 |
| ZP_08511445.1 | 63 | Paenibacillus sp. HGF7 | 525 |
| ZP_09077634.1 | 64 | Paenibacillus elgii B69 | 524 |
| ZP_09071078.1 | 67 | Paenibacillus larvae subsp. larvae B-3650 | 529 |
| YP_003872180.1 | 73 | Paenibacillus polymyxa E681 | 587 |
| YP_005073223.1 | 78 | Paenibacillus terrae HPL-003 | 591 |
| ZP_09775364.1 | 78 | Paenibacillus sp. Aloe-11 | 593 |
| YP_003948511.1 | 80 | Paenibacillus polymyxa SC2 | 592 |
| YP_005073224.1 | 94 | Paenibacillus terrae HPL-003 | 595 |
| ZP_10241029.1 | 96 | Paenibacillus peoriae KCTC 3763 | 599 |
| ZP_09775365.1 | 100 | Paenibacillus sp. Aloe-11 | 580 |

TABLE 2.2B

List of sequences with percent identity to PspPro2 protein identified from the Genome Quest database

| Patent # | PID to PspPro2 | Organism | Length |
|---|---|---|---|
| JP2002272453-0002 | 57.01 | Bacillus megaterium | 562 |
| U.S. Pat. No. 6,518,054-0001 | 57.19 | Bacillus sp. | 319 |
| EP2390321-0177 | 57.19 | Bacillus caldolyticus | 544 |
| US20120107907-0176 | 57.19 | Bacillus stearothermophilis | 548 |
| WO9520663-0003 | 57.51 | empty | 319 |
| WO2012110562-0003 | 57.51 | Geobacillus stearothermophilus | 319 |
| WO2012110563-0002 | 57.51 | Bacillus caldolyticus | 319 |
| WO2004011619-0056 | 57.51 | empty | 546 |
| WO2004011619-0003 | 57.51 | empty | 546 |
| JP2002272453-0003 | 57.64 | empty | 562 |
| U.S. Pat. No. 6,518,054-0002 | 57.88 | Bacillus sp. | 316 |
| EP2178896-0184 | 58.15 | Bacillus anthracis | 566 |
| WO2012110563-0004 | 58.28 | Bacillus megaterium | 320 |
| JP1995184649-0001 | 58.79 | Lactobacillus sp. | 566 |
| JP1994014788-0003 | 58.84 | empty | 317 |
| U.S. Pat. No. 8,114,656-0178 | 59.42 | Bacillus thuringiensis | 566 |
| WO2012110562-0005 | 59.49 | Bacillus cereus | 320 |
| U.S. Pat. No. 5,962,264-0004 | 59.81 | empty | 566 |
| US20120107907-0185 | 59.81 | Bacillus cereus | 317 |
| US20120107907-0179 | 59.81 | Bacillus cereus | 566 |
| WO2012110563-0005 | 60.13 | Bacillus cereus | 320 |
| EP2390321-0186 | 60.33 | Bacillus brevis | 304 |
| JP2005229807-0018 | 78.62 | Paenibacillus polymyxa | 566 |
| EP2390321-0187 | 79.21 | Bacillus polymyxa | 302 |

B. Alignment of Homologous Protease Sequences

The amino acid sequence of mature PspPro2 (SEQ ID NO: 8) was aligned with thermolysin (P00800, Bacillus thermoproteolyticus) and protease from Paenibacillus sp. Aloe-11 (ZP_09775365.1) sequences using CLUSTALW software (Thompson et al., Nucleic Acids Research, 22:4673-4680, 1994) with the default parameters. FIG. 2.7 shows the alignment of PspPro2 with these protease sequences.

C. Phylogenetic Tree

A phylogenetic tree for precursor PspPro2 protein sequence (SEQ ID NO: 7) was built using sequences of representative homologs from Table 2A and the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 2.8.

Example 3.1

Cloning of *Paenibacillus* Humicus Metalloprotease PhuPro2

A strain (DSM18784) of *Paenibacillus* humicus was selected as a potential source of enzymes which may be useful in various industrial applications. Genomic DNA for sequencing was obtained by first growing the strain on Heart Infusion agar plates (Difco) at 37° C. for 24 hr. Cell material was scraped from the plates and used to prepare genomic DNA with the ZF Fungal/Bacterial DNA miniprep kit from Zymo (Cat No. D6005). The genomic DNA was used for genome sequencing. The entire genome of the *Paenibacillus* humicus strain was sequenced by BaseClear (Leiden, The Netherlands) using the Illumina's next generation sequencing technology. After assembly of the data, contigs were annotated by BioXpr (Namur, Belgium). One of the genes identified after annotation in *Paenibacillus* humicus encodes a metalloprotease and the sequence of this gene, called PhuPro2, is provided in SEQ ID NO: 11. The corresponding protein encoded by the PhuPro2 gene is shown in SEQ ID NO: 12. At the N-terminus, the protein has a signal peptide with a length of 23 amino acids as predicted by SignalP version 4.0 (Nordahl Petersen et al. (2011) Nature Methods, 8:785-786). The presence of a signal sequence suggests that PhuPro2 is a secreted enzyme. The propeptide region was predicted based on its protein sequence alignment with the *Paenibacillus polymyxa* Npr protein (Takekawa et al. (1991) Journal of Bacteriology, 173 (21): 6820-6825). The predicted mature region of PhuPro2 protein in shown in SEQ ID NO: 13. The nucleotide sequence of the PhuPro2 gene isolated from *Paenibacillus* humicus is set forth as SEQ ID NO: 11. The sequence encoding the predicted native signal peptide is shown in italics:

*ATGAAAAAAATGATTCCTACTCTGCTCGGTACCGTATTGCTGCTTTCTTC*

*CGCTTCCGCTGTCGCTGCTGAATCGCCAAGCCTCGGAGCGGCCGGAACTC*

CCGGGGTCAGCGTCGTGAACAATCAGCTCGTGACTCAATTCATCGAGGCT

TCCAAGGATGCCAAGATTGTCCCGGGCTCTTCCGAGGATAAAATCTGGGC

TTTCCTTGAAGGCCAGCAAGCAAAGCTGGGTGTATCCGCAGCGGATGTAA

AAACCTCGTTCCTGATCCAGAAGAAGGAAGTCGATCCGACTTCGGGCGTC

GAGCATTTCCGCCTGCAGCAATATGTGAATGGCATCCCGGTATATGGCGG

TGACCAAACCATTCACATCGACAAGGCCGGCCAGGTTACGTCGTTCGTAG

GAGCTGTTCTGCCGGCTCAAAATCAAATCACGGCAAAATCCAGCGTACCA

GCCATAAGCGCATCCGACGCTCTGGCTATCGCGGCGAAGGAAGCCAGTTC

CCGCATCGGCGAGCTGGGAGCACAGGAGAAGACTCCGTCGGCTCAGCTGT

ACGTATATCCGGAAGGCAACGGGTCGCGTCTCGTCTACCAGACGGAAGTG

AATGTGCTTGAGCCGCAGCCTCTGCGCACCCGCTATCTTATCGATGCGGC

CGACGGCCATATCGTGCAGCAGTACGATCTGATCGAGACGGCGACCGGTT

CGGGCACGGGCGTGCTGGGCGACAATAAGACGTTCCAGACGACTCTTTCC

GGCAGCACGTACCAGCTGAAAGACACCACTCGCGGCAACGGCATCTACAC

CTACACAGCCAGCAATCGGACCACGATTCCGGGCACGCTGCTGACGGACG

CCGACAACGTATGGACGGATGGAGCCGCCGTCGATGCCCATACTTATGCC

GGAAAAGTATATGATTTCTACAAAACGAAGTTCGGACGCAACAGCCTCGA

CGGCAACGGCCTGCTGATCCGTTCCTCGGTCCACTACAGCAGCAGGTACA

ACAATGCCTTCTGGAACGGCACCCAGATTGTATTCGGCGACGGCGACGGC

TCGACGTTCATTCCGCTGTCGGGCGATCTCGACGTGGTCGGCCATGAGCT

GTCCCACGGAGTCATCGAGTACACGTCCAACCTTCAATACCTCAATGAAT

CCGGCGCGCTGAACGAGTCCTATGCCGACGTCCTCGGCAACTCGATCCAG

GCGAAAAACTGGCTTATCGGCGACGATGTCTATACGCCTGGCATCTCCGG

AGATGCTCTCCGTTCCATGTCCAACCCGACGCTTTACGGGCAGCCGGACA

ACTATGCCAACCGCTATACGGGATCTTCCGACAACGGCGGCGTTCATACG

AACAGCGGCATCACGAACAAAGCGTTCTACCTGCTCGCCCAAGGCGGCAC

CCAGAACGGCGTTACCGTCGCCGGCATCGGGCGCGACGCAGCCGTGAACA

TTTTCTACAACACAGTGGCCTATTACCTTACTTCCACTTCCAACTTCGCC

GCGGCGAAGAACGCCTCGATCCAGGCAGCCAAAGACCTGTACGGAACGGG

CTCCTCTTATGTCACCTCGGTGACCAATGCATTCAGAGCCGTAGGCCTG

The amino acid sequence of the PhuPro2 precursor protein is set forth as SEQ ID NO: 12. The predicted signal sequence is shown in italics, and the predicted propeptide is shown in underlined text:

*MKKMIPTLLGTVLLLSSASAVAA*<u>ESPSLGAAGTPGVSVVNNQLVTQFIEA</u>

<u>SKDAKIVPGSSEDKIWAFLEGQQAKLGVSAADVKTSFLIQKKEVDPTSGV</u>

<u>EHFRLQQYVNGIPVYGGDQTIHIDKAGQVTSFVGAVLPAQNQITAKSSVP</u>

<u>AISASDALAIAAKEASSRIGELGAQEKTPSAQLYVYPEGNGSRLVYQTEV</u>

<u>NVLEPQPLRTRYLIDAADGHIVQQYDLIETATGSGTGVLGDNKTFQTTLS</u>

GSTYQLKDTTRGNGIYTYTASNRTTIPGTLLTDADNVWTDGAAVDAHTYA

GKVYDFYKTKFGRNSLDGNGLLIRSSVHYSSRYNNAFWNGTQIVFGDGDG

STFIPLSGDLDVVGHELSHGVIEYTSNLQYLNESGALNESYADVLGNSIQ

AKNWLIGDDVYTPGISGDALRSMSNPTLYGQPDNYANRYTGSSDNGGVHT

NSGITNKAFYLLAQGGTQNGVTVAGIGRDAAVNIFYNTVAYYLTSTSNFA

AAKNASIQAAKDLYGTGSSYVTSVTNAFRAVGL

The amino acid sequence of the predicted mature form of PhuPro2 is set forth as SEQ ID NO: 13:

ATGSGTGVLGDNKTFQTTLSGSTYQLKDTTRGNGIYTYTASNRTTIPGTL

LTDADNVWTDGAAVDAHTYAGKVYDFYKTKFGRNSLDGNGLLIRSSVHYS

SRYNNAFWNGTQIVFGDGDGSTFIPLSGDLDVVGHELSHGVIEYTSNLQY

LNESGALNESYADVLGNSIQAKNWLIGDDVYTPGISGDALRSMSNPTLYG

QPDNYANRYTGSSDNGGVHTNSGITNKAFYLLAQGGTQNGVTVAGIGRDA

-continued
AVNIFYNTVAYYLTSTSNFAAAKNASIQAAKDLYGTGSSYVTSVTNAFRA

VGL

Example 3.2

Expression of *Paenibacillus Humicus* s Metalloprotease PhuPro2

The DNA sequence of the propeptide-mature form of PhuPro2 was synthesized and inserted into the *Bacillus subtilis* expression vector p2JM103BBI (Vogtentanz, *Protein Expr Purif*, 55:40-52, 2007) by Generay (Shanghai, China), resulting in plasmid pGX150(AprE-PhuPro2) (FIG. 1). Ligation of this gene encoding the PhuPro2 protein into the digested vector resulted in the addition of three codons (Ala-Gly-Lys) between the 3' end of the *B. subtilis* AprE signal sequence and the 5' end of the predicted PhuPro2 native propeptide. The gene has an alternative start codon (GTG). The resulting plasmid shown in FIG. 1 was labeled pGX150(AprE-PhuPro2). As shown in FIG. 3.1, pGX150 (AprE-PhuPro2) contains an AprE promoter, an AprE signal sequence used to direct target protein secretion in *B. subtilis*, and the synthetic nucleotide sequence encoding the predicted propeptide and mature regions of PhuPro2 (SEQ ID NO: 14). The translation product of the synthetic AprE-PhuPro2 gene is shown in SEQ ID NO: 15.

The pGX150 (AprE-PhuPro2) plasmid was then transformed into *B. subtilis* cells (degU$^{Hy}$ 32, ΔscoC) and the transformed cells were spread on Luria Agar plates supplemented with 5 ppm Chloramphenicol and 1.2% skim milk (Cat #232100, Difco). Colonies with the largest clear halos on the plates were selected and subjected to fermentation in a 250 ml shake flask with MBD medium (a MOPS based defined medium, supplemented with additional 5 mM CaCl$_2$).

The broth from the shake flasks was concentrated and buffer-exchanged into the loading buffer containing 20 mM Tris-HCl (pH 8.5), 1 mM CaCl$_2$ and 10% propylene glycol using a VivaFlow 200 ultra filtration device (Sartorius Stedim). After filtering, this sample was applied to an 80 ml Q Sepharose High Performance column pre-equilibrated with the loading buffer above; and the active flow-through fractions were collected and concentrated. The sample was loaded onto a 320 ml Superdex 75 gel filtration column pre-equilibrated with the loading buffer described above containing 0.15 M NaCl. The corresponding active purified protein fractions were further pooled and concentrated via 10K Amicon Ultra for further analyses.

The nucleotide sequence of the synthesized PhuPro2 gene in plasmid pGX150(AprE-PhuPro2) is depicted in SEQ ID NO: 14. The sequence encoding the three residue addition (AGK) is shown in bold:

GTGAGAAGCAAAAAATTGTGGATCAGCTTGTTGTTTGCGTTAACGTTAAT

CTTTACGATGGCGTTCAGCAACATGAGCGCGCAGGCTGCTGGAAAAGAAT

CACCGAGCCTTGGCGCTGCAGGAACACCGGGCGTTAGCGTTGTGAATAAC

CAACTGGTCACGCAGTTCATCGAAGCATCAAAAGACGCGAAAATTGTCCC

TGGATCAAGCGAAGATAAGATTTGGGCATTTCTGGAAGGCCAGCAAGCAA

AGCTTGGCGTCTCAGCTGCCGACGTGAAGACGAGCTTCCTGATCCAGAAG

AAGGAGGTTGACCCGACATCAGGCGTTGAGCACTTTAGACTGCAACAGTA

CGTCAACGGCATCCCGGTTTATGGAGGCGATCAAACAATCCATATTGATA

AGGCAGGCCAGGTCACATCATTCGTCGGAGCTGTCCTGCCGGCTCAGAAC

CAAATTACAGCAAAATCATCAGTTCCGGCAATTTCAGCCTCAGACGCTCT

GGCAATCGCTGCCAAGGAGGCAAGCTCAAGAATTGGCGAACTGGGCGCAC

AAGAAAAGACACCGAGCGCCCAACTTTATGTCTATCCGGAGGGCAACGGA

AGCAGACTGGTGTACCAGACAGAGGTCAATGTTCTGGAGCCGCAACCGCT

GAGAACGAGATACCTTATCGATGCTGCGGATGGCCACATTGTTCAGCAAT

ACGACCTGATTGAGACAGCAACAGGAAGCGGAACGGGCGTGCTGGGCGAC

AACAAGACGTTTCAGACAACACTTAGCGGCAGCACGTACCAACTTAAGGA

CACGACGAGAGGCAATGGCATTTACACGTACACGGCCTCAAACAGAACGA

CAATCCCAGGCACACTGCTGACGGATGCAGACAATGTTTGGACGGACGGC

GCAGCAGTTGACGCACACACGTACGCCGGCAAGGTGTACGACTTTTACAA

GACGAAGTTCGGCAGAAACAGCCTTGATGGAAATGGACTGCTGATCAGAA

GCAGCGTCCACTACAGCAGCAGATACAATAACGCCTTCTGGAACGGCACA

CAAATCGTCTTTGGCGATGGAGACGGATCAACATTCATCCCGCTGTCAGG

CGACCTGGACGTTGTGGGCCACGAGCTGAGCCACGGCGTCATCGAGTACA

CGAGCAACCTGCAGTACCTGAATGAAAGCGGCGCACTGAACGAGTCATAT

GCTGATGTGCTTGGCAATAGCATCCAGGCCAAGAACTGGCTTATCGGAGA

CGACGTCTACACACCTGGCATCAGCGGCGATGCTCTGAGAAGCATGAGCA

ATCCTACACTTTACGGCCAACCGGACAACTACGCGAATAGATATACGGGC

AGCAGCGACAATGGCGGCGTTCATACAAACTCAGGCATCACGAACAAGGC

GTTCTACCTGCTGGCACAGGGAGGCACGCAAAACGGCGTTACAGTTGCGG

GCATTGGCAGAGATGCGGCCGTCAACATCTTCTACAACACAGTCGCCTAC

TACCTGACGAGCACGTCAAACTTCGCAGCGGCAAAGAACGCATCAATTCA

AGCAGCAAAGGATCTGTACGGAACAGGCAGCTCATATGTCACGTCAGTTA

CGAATGCGTTTAGAGCCGTCGGCCTTTAA

The amino acid sequence of the PhuPro2 precursor protein expressed from plasmid pGX150(AprE-PhuPro2) is depicted in SEQ ID NO: 15. The predicted signal sequence is shown in italics, the three residue addition (AGK) is shown in bold, and the predicted propeptide is shown in underlined text.

(SEQ ID NO: 15)
*MRSKKLWISLLFALTLIFTMAFSNMSAQA*AGKESPSLGAAGTPGVSVVNN

QLVTQFIEASKDAKIVPGSSEDKIWAFLEGQQAKLGVSAADVKTSFLIQK

KEVDPTSGVEHFRLQQYVNGIPVYGGDQTIHIDKAGQVTSFVGAVLPAQN

QITAKSSVPAISASDALAIAAKEASSRIGELGAQEKTPSAQLYVYPEGNG

SRLVYQTEVNVLEPQPLRTRYLIDAADGHIVQQYDLIETATGSGTGVLGD

NKTFQTTLSGSTYQLKDTTRGNGIYTYTASNRTTIPGTLLTDADNVWTDG

AAVDAHTYAGKVYDFYKTKFGRNSLDGNGLLIRSSVHYSSRYNNAFWNGT

QIVFGDGDGSTFIPLSGDLDVVGHELSHGVIEYTSNLQYLNESGALNESY

-continued
ADVLGNSIQAKNWLIGDDVYTPGISGDALRSMSNPTLYGQPDNYANRYTG

SSDNGGVHTNSGITNKAFYLLAQGGTQNGVTVAGIGRDAAVNIFYNTVAY

YLTSTSNFAAAKNASIQAAKDLYGTGSSYVTSVTNAFRAVGL.

Example 3.3

Proteolytic Activity of Metalloprotease PhuPro2

The proteolytic activity of purified metalloprotease PhuPro2 was measured in 50 mM Tris (pH 7), using azo-casein (Cat #74H7165, Megazyme) as a substrate. Prior to the reaction, the enzyme was diluted with Milli-Q water (Millipore) to specific concentrations. The azo-casein was dissolved in 100 mM Tris buffer (pH 7) to a final concentration of 1.5% (w/v). To initiate the reaction, 50 µl of the diluted enzyme (or Milli-Q $H_2O$ alone as the blank control) was added to the non-binding 96-well Microtiter Plate (96-MTP) (Corning Life Sciences, #3641) placed on ice, followed by the addition of 50 µl of 1.5% azo-casein. After sealing the 96-MTP, the reaction was carried out in a Thermomixer (Eppendorf) at 40° C. and 650 rpm for 10 min. The reaction was terminated by adding 100 µl of 5% Trichloroacetic Acid (TCA). Following equilibration (5 min at the room temperature) and subsequent centrifugation (2000 g for 10 min at 4° C.), 120 µl supernatant was transferred to a new 96-MTP, and absorbance of the supernatant was measured at 440 nm ($A_{440}$) using a SpectraMax 190. Net $A_{440}$ was calculated by subtracting the $A_{440}$ of the blank control from that of enzyme, and then plotted against different protein concentrations (from 1.25 ppm to 40 ppm). Each value was the mean of triplicate assays.

The proteolytic activity is shown as Net $A_{440}$. The proteolytic assay with azo-casein as the substrate (shown in FIG. 3.2) indicates that PhuPro2 is an active protease.

Example 3.4 pH Profile of Metalloprotease PhuPro2

With azo-casein as the substrate, the pH profile of metalloprotease PhuPro2 was studied in 12.5 mM acetate/Bis-Tris/HEPES/CHES buffer with different pH values (ranging from pH 4 to 11). To initiate the assay, 50 µl of 25 mM acetate/Bis-Tris/HEPES/CHES buffer with a specific pH was first mixed with 2 µl Milli-Q $H_2O$ diluted enzyme (125 ppm) in a 96-MTP placed on ice, followed by the addition of 48 µl of 1.5% (w/v) azo-casein prepared in $H_2O$. The reaction was performed and analyzed as described in Example 3.3. Enzyme activity at each pH was reported as the relative activity, where the activity at the optimal pH was set to be 100%. The pH values tested were 4, 5, 6, 7, 8, 9, 10 and 11. Each value was the mean of triplicate assays. As shown in FIG. 3.3, the optimal pH of PhuPro2 is 6, with greater than 70% of maximal activity retained between 5.5 and 8.5.

Example 3.5

Temperature Profile of Metalloprotease PhuPro2

The temperature profile of metalloprotease PhuPro2 was analyzed in 50 mM Tris buffer (pH 7) using the azo-casein assays. The enzyme sample and azo-casein substrate were prepared as in Example 3.3. Prior to the reaction, 50 µl of 1.5% azo-casein and 45 µl Milli-Q $H_2O$ were mixed in a 200 µl PCR tube, which was then subsequently incubated in a Peltier Thermal Cycler (BioRad) at desired temperatures (i.e. 20-90° C.) for 5 min. After the incubation, 5 µl of diluted enzyme (50 ppm) or $H_2O$ (the blank control) was added to the substrate mixture, and the reaction was carried out in the Peltier Thermal Cycle for 10 min at different temperatures. To terminate the reaction, each assay mixture was transferred to a 96-MTP containing 100 µl of 5% TCA per well. Subsequent centrifugation and absorbance measurement were performed as described in Example 3.3. The activity was reported as the relative activity, where the activity at the optimal temperature was set to be 100%. The tested temperatures are 20, 30, 40, 50, 60, 70, 80, and 90° C. Each value was the mean of duplicate assays (the value varies no more than 5%). The data in FIG. 3.4 suggests that PhuPro2 showed an optimal temperature at 50° C., and retained greater than 70% of its maximum activity between 45 and 65° C.

Example 3.6

Cleaning Performance of Metalloprotease PhuPro2

The cleaning performance of PhuPro2 was tested using PA-S-38 (egg yolk, with pigment, aged by heating) microswatches (CFT-Vlaardingen, The Netherlands) at pH 6 and 8 using a model automatic dishwashing (ADW) detergent. Prior to the reaction, purified protease samples were diluted with a dilution solution containing 10 mM NaCl, 0.1 mM $CaCl_2$, 0.005% TWEEN® 80 and 10% propylene glycol to the desired concentrations. The reactions were performed in AT detergent with 100 ppm water hardness ($Ca^{2+}:Mg^{2+}$=3:1) (detergent composition shown in Table 3.1). To initiate the reaction, 180 µl of the AT detergent buffered at pH 6 or pH 8 was added to a 96-MTP placed with PA-S-38 microswatches, followed by the addition of 20 µl of diluted enzymes (or the dilution solution as the blank control). The 96-MTP was sealed and incubated in an incubator/shaker for 30 min at 50° C. and 1150 rpm. After incubation, 100 µl of wash liquid from each well was transferred to a new 96-MTP, and its absorbance was measured at 405 nm (referred here as the "Initial performance") using a spectrophotometer. The remaining wash liquid in the 96-MTP was discarded and the microswatches were rinsed once with 200 µl water. Following the addition of 180 µl of 0.1 M CAPS buffer (pH 10), the second incubation was carried out in the incubator/shaker at 50° C. and 1150 rpm for 10 min. One hundred microliters of the resulting wash liquid was transferred to a new 96-MTP, and its absorbance measured at 405 nm (referred here as the "Wash-off"). The sum of two absorbance measurements ("Initial performance" plus "Wash-off") gives the "Total performance", which measures the protease activity on the model stain; and Net $A_{405}$ was subsequently calculated by subtracting the $A_{405}$ of the "Total performance" of the blank control from that of the enzyme. Dose response in cleaning the PA-S-38 microswatches at pH 6 and pH 8 in AT dish detergent for PhuPro2 is shown in FIGS. 3.5A and 3.5B.

TABLE 3.1

Composition of AT dish detergent

| Ingredient | Concentration (mg/ml) |
|---|---|
| MGDA (methylglycinediacetic acid) | 0.143 |
| Sodium citrate | 1.86 |
| Citric acid* | varies |
| Plurafac ® LF 18B (a non-ionic surfactant) | 0.029 |
| Bismuthcitrate | 0.006 |
| Bayhibit ® S (Phosphonobutantricarboxylic acid sodium salt) | 0.006 |
| Acusol ™ 587 (a calcium polyphosphate inhibitor) | 0.029 |
| PEG 6000 | 0.043 |
| PEG 1500 | 0.1 |

*The pH of the AT formula detergent is adjusted to the desired value (pH 6 or 8) by the addition of 0.9M citric acid.

Example 3.7

Comparison of PhuPro2 to Other Proteases

A. Identification of Homologous Proteases

Homologs were identified by a BLAST search (Altschul et al., Nucleic Acids Res, 25:3389-402, 1997) against the NCBI non-redundant protein database and the Genome Quest Patent database with search parameters set to default values. The predicted mature protein amino acid sequence for PhuPro2 (SEQ ID NO: 13) is used as the query sequences. Percent identity (PID) for both search sets is defined as the number of identical residues divided by the number of aligned residues in the pairwise alignment. Tables 3.2A and 3.2B provide a list of sequences with the percent identity to PhuPro2. The length in Table 3.2 refers to the entire sequence length of the homologous proteases.

TABLE 3.2A

List of sequences with percent identity to PhuPro2 protein identified from the NCBI non-redundant protein database

| Accession # | PID to PhuPro2 | Organism | Length |
|---|---|---|---|
| P00800 | 59 | Bacillus thermoproteolyticus | 548 |
| YP_003872180.1 | 59 | Paenibacillus polymyxa E681 | 587 |
| ZP_10575942.1 | 59 | Brevibacillus sp. BC25 | 528 |
| ZP_02326602.1 | 60 | Paenibacillus larvae subsp. larvae BRL-230010 | 520 |
| ADM87306.1 | 61 | Bacillus megaterium | 562 |
| ZP_09069025.1 | 61 | Paenibacillus larvae subsp. larvae B-3650 | 520 |
| ZP_09069194.1 | 62 | Paenibacillus larvae subsp. Larvae B-3650 | 502 |
| ZP_10738945.1 | 63 | Brevibacillus sp. CF112 | 528 |
| ZP_08511445.1 | 64 | Paenibacillus sp. HGF7 | 525 |
| ZP_09077634.1 | 65 | Paenibacillus elgii B69 | 524 |
| ZP_09775365.1 | 65 | Paenibacillus sp. Aloe-11 | 580 |
| ZP_09775364.1 | 70 | Paenibacillus sp. Aloe-11 | 593 |
| P29148 | 71 | Paenibacillus polymyxa | 590 |
| ZP_10241030.1 | 71 | Paenibacillus peoriae KCTC 3763 | 593 |
| ZP_09071078.1 | 71 | Paenibacillus larvae subsp. larvae B-3650 | 529 |
| YP_003872179.1 | 72 | Paenibacillus polymyxa E681 | 592 |
| YP_005073223.1 | 72 | Paenibacillus terrae HPL-003 | 591 |

TABLE 3.2B

List of sequences with percent identity to PhuPro2 protein identified from the Genome Quest Patent database

| Patent ID # | PID to PhuPro2 | Organism | Length |
|---|---|---|---|
| US20090208474-0030 | 59.22 | Bacillus thermoproteolyticus | 316 |
| JP2002272453-0002 | 59.42 | Bacillus megaterium | 562 |
| JP2006124323-0003 | 59.55 | Bacillus thermoproteolyticus | 316 |
| U.S. Pat. No. 8,114,656-0183 | 59.87 | Bacillus stearothermophilus | 316 |
| JP1989027475-0001 | 59.87 | Bacillus subtilis | 316 |
| US20120009651-0002 | 59.87 | Geobacillus caldoproteolyticus | 548 |
| JP2002272453-0003 | 60.45 | empty | |
| WO2012110563-0004 | 60.77 | Bacillus megaterium | 320 |
| EP2390321-0186 | 62.25 | Bacillus brevis | 304 |
| JP2005229807-0018 | 71.85 | Paenibacillus polymyxa | 566 |
| U.S. Pat. No. 8,114,656-0187 | 72.09 | Bacillus polymyxa | 302 |

B. Alignment of Homologous Protease Sequences

The amino acid sequence of predicted mature PhuPro2 (SEQ ID NO: 13) protein was aligned with thermolysin (P00800, Bacillus thermoproteolyticus), and protease from Paenibacillus terrae HPL-003 (YP 005073223.1) sequences using CLUSTALW software (Thompson et al., Nucleic Acids Research, 22:4673-4680, 1994) with the default parameters. FIG. 3.6 shows the alignment of PhuPro2 with these protease sequences.

C. Phylogenetic Tree

A phylogenetic tree for full length sequence of PhuPro2 (SEQ ID NO: 12) was built using sequences of representative homologs from Table 2A and the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 3.7.

Example 4.1

Cloning of *Paenibacillus ehimensis* Metalloprotease PehPro1

A strain (DSM11029) of *Paenibacillus ehimensis* was selected as a potential source of enzymes which may be useful in various industrial applications. Genomic DNA for sequencing was obtained by first growing the strain on Heart Infusion agar plates (Difco) at 37° C. for 24 hr. Cell material was scraped from the plates and used to prepare genomic DNA with the ZF Fungal/Bacterial DNA miniprep kit from Zymo (Cat No. D6005). The genomic DNA was used for genome sequencing. The entire genome of the *Paenibacillus ehimensis* strain was sequenced by BaseClear (Leiden, The Netherlands) using the Illumina's next generation sequencing technology. After assembly of the data, contigs were annotated by BioXpr (Namur, Belgium). One of the genes identified after annotation in *Paenibacillus ehimensis* encodes a metalloprotease and the sequence of this gene, called PehPro1, is provided in SEQ ID NO: 16. The corresponding protein encoded by the PehPro1 gene is shown in SEQ ID NO: 17. At the N-terminus, the protein has a signal peptide with a length of 23 amino acids as predicted by SignalP version 4.0 (Nordahl Petersen et al. (2011) Nature Methods, 8:785-786). The presence of a signal sequence suggests that PehPro1 is a secreted enzyme. The propeptide region was predicted based on protein sequence alignment with the *Paenibacillus polymyxa* Npr protein (Takekawa et al. (1991) Journal of Bacteriology, 173 (21): 6820-6825). The predicted mature region of PehPro1 protein is shown in SEQ ID NO: 18.

The nucleotide sequence of the PehPro1 gene isolated from *Paenibacillus ehimensis* is set forth as SEQ ID NO: 16. The sequence encoding the predicted native signal peptide is shown in italics:

```
ATGTTAAAAGTATGGGCATCGATTATTACAGGAGCATTTTTGCTCGGGAG
CGTGCAAGGGGTGCAAGCTGCTCCACAAGATCAAGCTGCTCCCTTCGGAG
GATTCACCCCTCAATTGATTACCGGGGAAAGCTGGAGTGCGCCGCAAGGA
GTATCGGGAGAGGAAAAAATCTGGAAGTATCTCGAATCCAAGCAGGAAAG
CTTCCAAATCGGCCAAACCGTTGATCTGAAAAAGCAATTGAAAATTATCG
GCCAAACGACCGACGAGAAAACGGGAACCACGCATTACCGTCTACAGCAG
TATGTGGGAGGCGTCCCCGTATACGGCGGCGTACAAACGATCCATGTCAA
CAAAGAAGGACAAGTTACCTCGCTGATCGGCAGCCTGCTTCCCGACCAGC
AGCAGCAAGTTTCGAAAAGCTTGAATTCGCAAATCAGCGAAGCGCAAGCC
ATCGCCGTGGCCCAGAAAGATACCGAGGCCGCCGTCGGCAAGCTGGGTGA
ACCGCAAAAGACACCGGAAGCGGATCTGTACGTTTATTTACACAACGGAC
AACCGGTCCTCGCTTATGTGACCGAGGTTAACGTTCTCGAACCGGAGGCA
ATCCGGACGCGCTACTTCATCAGCGCCGAAGACGGCAGCATTTTATTCAA
GTACGACATCCTCGCTCACGCTACAGGTACCGGAAAAGGCGTGCTCGGAG
ATACGAAATCGTTCACGACCACGCAATCCGGCTCCACTTATCAATTGAAG
GATACGACGCGCGGGCAAGGTATCGTCACTTACAGCGCTGGCAACCGGTC
CTCTCTGCCGGGAACGCTGCTCACCAGCTCCAGCAATATTTGGAACGACG
GCGCGGCGGTCGATGCGCATGCCTATACCGCCAAAGTGTACGATTACTAT
AAAAACAAATTTGGCCGCAACAGCATTGACGGCAACGGCTTCCAGCTTAA
ATCGACCGTGCACTATTCCTCCAGATACAACAACGCCTTCTGGAACGGTG
TGCAAATGGTGTACGGCGACGGCGACGGCGTAACCTTCATTCCGTTCTCC
GCCGATCCGGACGTCATCGGCCACGAATTGACCCACGGCGTTACGGAACA
TACGGCCGGCCTGGAATACTACGGCGAATCCGGAGCGCTGAACGAATCGA
TCTCCGATATTATCGGCAACGCGATCGACGGCAAAAACTGGCTGATCGGC
GACTTGATTTATACGCCGAATACTCCCGGGACGCCCTCCGCTCTATGGA
GAACCCCAAGCTGTATAACCAACCCGACCGCTATCAAGACCGCTATACGG
GACCTTCCGATAACGGCGGCGTGCATATTAACAGCGGTATCAACAACAAA
GCCTTCTACCTGATCGCCCAAGGCGGCACGCACTATGGCGTCACCGTGAA
CGGGATCGGACGCGATGCGGCTGTGCAAATTTTCTATGACGCCCTCATCA
ATTACCTGACTCCAACTTCGAACTTCTCGGCGATGCGCGCAGCAGCCATT
CAAGCGGCAACCGACCTGTACGGAGCGAATTCTTCTCAAGTAAACGCTGT
CAAAAAAGCGTATACTGCCGTCGGCGTGAAC
```

The amino acid sequence of the PehPro1 precursor protein is set forth as SEQ ID NO: 17. The predicted signal sequence is shown in italics, and the predicted propeptide is shown in underlined text:

```
MLKVWASIITGAFLLGSVQGVQAAPQDQAAPFGGFTPQLITGESWSAPQG
VSGEEKIWKYLESKQESFQIGQTVDLKKQLKIIGQTTDEKTGTTHYRLQQ
YVGGVPVYGGVQTIHVNKEGQVTSLIGSLLPDQQQQVSKSLNSQISEAQA
IAVAQKDTEAAVGKLGEPQKTPEADLYVYLHNGQPVLAYVTEVNVLEPEA
IRTRYFISAEDGSILFKYDILAHATGTGKGVLGDTKSFTTTQSGSTYQLK
DTTRGQGIVTYSAGNRSSLPGTLLTSSSNIWNDGAAVDAHAYTAKVYDYY
KNKFGRNSIDGNGFQLKSTVHYSSRYNNAFWNGVQMVYGDGDGVTFIPFS
ADPDVIGHELTHGVTEHTAGLEYYGESGALNESISDIIGNAIDGKNWLIG
DLIYTPNTPGDALRSMENPKLYNQPDRYQDRYTGPSDNGGVHINSGINNK
AFYLIAQGGTHYGVTVNGIGRDAAVQIFYDALINYLTPTSNFSAMRAAAI
QAATDLYGANSSQVNAVKKAYTAVGVN
```

The amino acid sequence of the predicted mature form of PehPro1 is set forth as SEQ ID NO: 18:

```
ATGTGKGVLGDTKSFTTTQSGSTYQLKDTTRGQGIVTYSAGNRSSLPGTL
LTSSSNIWNDGAAVDAHAYTAKVYDYYKNKFGRNSIDGNGFQLKSTVHYS
SRYNNAFWNGVQMVYGDGDGVTFIPFSADPDVIGHELTHGVTEHTAGLEY
YGESGALNESISDIIGNAIDGKNWLIGDLIYTPNTPGDALRSMENPKLYN
QPDRYQDRYTGPSDNGGVHINSGINNKAFYLIAQGGTHYGVTVNGIGRDA
AVQIFYDALINYLTPTSNFSAMRAAAIQAATDLYGANSSQVNAVKKAYTA
VGVN
```

Example 4.2

Expression of *Paenibacillus ehimensis* Metalloprotease PehPro1

The DNA sequence of the propeptide-mature form of PehPro1 was synthesized and inserted into the *Bacillus subtilis* expression vector p2JM103BBI (Vogtentanz, *Protein Expr Purif,* 55:40-52, 2007) by Generay (Shanghai, China), resulting in plasmid pGX148(AprE-PehPro1) (FIG. 4.1). Ligation of this gene encoding the PehPro1 protein into the digested vector resulted in the addition of three codons (Ala-Gly-Lys) between the 3' end of the *B. subtilis* AprE signal sequence and the 5' end of the predicted PehPro1 native propeptide. The gene has an alternative start codon (GTG). The resulting plasmid shown in FIG. 1 was labeled pGX148(AprE-PehPro1). As shown in FIG. 1, pGX148 (AprE-PehPro1) contains an AprE promoter, an AprE signal sequence used to direct target protein secretion in *B. subtilis*, and the synthetic nucleotide sequence encoding the predicted propeptide and mature regions of PehPro1 (SEQ ID NO: 19). The translation product of the synthetic AprE-PehPro1 gene is shown in SEQ ID NO: 20.

The pGX148(AprE-PehPro1) plasmid was then transformed into *B. subtilis* cells (degU$^{Hy}$32, ΔscoC) and the transformed cells were spread on Luria Agar plates supplemented with 5 ppm Chloramphenicol and 1.2% skim milk (Cat #232100, Difco). Colonies with the largest clear halos on the plates were selected and subjected to fermentation in a 250 ml shake flask with MBD medium (a MOPS based defined medium, supplemented with additional 5 mM CaCl$_2$).

The broth from the shake flasks was concentrated and buffer-exchanged into the loading buffer containing 20 mM Tris-HCl (pH 8.5), 1 mM CaCl$_2$ and 10% propylene glycol using a VivaFlow 200 ultra filtration device (Sartorius Stedim). After filtering, this sample was applied to an 80 ml Q Sepharose High Performance column pre-equilibrated with the loading buffer above, PehPro1 was eluted from the column with a linear salt gradient from 0 to 0.3 M NaCl in the loading buffer. The corresponding active fractions were collected, concentrated and buffer-exchanged again into the loading buffer described above. The sample was loaded onto a 40 ml DEAE Fast Flow column pre-equilibrated with the same loading buffer. PehPro1 was eluted from the column with a linear salt gradient from 0 to 0.15 M NaCl in the loading buffer. The corresponding active purified protein fractions were further pooled and concentrated via 10K Amicon Ultra for further analyses.

The nucleotide sequence of the synthesized PehPro1 gene in plasmid pGX148(AprE-PehPro1) is depicted in SEQ ID NO: 19. The sequence encoding the three residue addition (AGK) is shown in bold:

```
GTGAGAAGCAAAAAATTGTGGATCAGCTTGTTGTTTGCGTTAACGTTAAT
CTTTACGATGGCGTTCAGCAACATGAGCGCGCAGGCTGCTGGAAAAGCAC
CTCAAGATCAGGCAGCACCTTTTGGAGGCTTTACACCGCAACTTATCACA
GGCGAATCATGGTCAGCACCGCAGGGCGTTTCAGGCGAGGAAAAGATCTG
GAAGTACCTTGAGAGCAAGCAGGAGTCATTTCAAATCGGCCAGACAGTCG
ACCTGAAAAAGCAACTGAAGATCATCGGCCAAACAACGGACGAAAAGACG
GGCACGACGCATTATAGACTGCAACAATATGTTGGCGGCGTGCCGGTTTA
TGGAGGCGTGCAAACAATCCACGTGAACAAGGAAGGACAGGTCACGTCAC
TGATCGGCAGCCTGCTGCCGGATCAGCAGCAACAAGTCTCAAAGAGCCTG
AACTCACAAATTAGCGAGGCACAAGCGATTGCAGTTGCACAAAAGGACAC
GGAAGCAGCTGTCGGCAAGCTGGGCGAACCGCAAAAAACACCTGAGGCTG
ACCTTTACGTCTACCTGCATAACGGCCAGCCGGTCCTTGCGTACGTTACG
GAAGTTAACGTGCTGGAGCCGGAGGCCATCAGAACGAGATACTTCATTAG
CGCGGAGGATGGAAGCATTCTGTTTAAGTACGATATTCTTGCTCACGCGA
CAGGCACAGGCAAGGGCGTCCTTGGCGACACAAAAAGCTTCACGACAACG
CAGAGCGGATCAACGTACCAGCTGAAAGATACAACAAGAGGACAAGGCAT
CGTTACGTATTCAGCGGGCAATAGATCAAGCCTGCCGGGCACACTGCTGA
CATCAAGCTCAAACATTTGGAATGACGGCGCAGCAGTTGATGCCCATGCG
TACACAGCCAAGGTGTACGACTACTATAAGAACAAGTTTGGCAGAAATAG
CATCGACGGAAATGGATTTCAACTTAAATCAACGGTGCACTACTCATCAA
GATATAACAATGCGTTTTGGAACGGAGTGCAGATGGTCTACGGAGACGGC
GACGGCGTGACATTTATTCCGTTTAGCGCCGACCCGGACGTGATTGGACA
TGAACTGACACATGGAGTGACAGAGCATACGGCGGGACTGGAATATTACG
GCGAAAGCGGCGCACTGAACGAAAGCATCTCAGACATTATTGGAAACGCA
ATCGATGGCAAAAACTGGCTGATTGGCGATCTGATTTATACGCCGAATAC
ACCGGGCGATGCACTGAGATCAATGGAGAATCCGAAGCTGTACAACCAAC
CGGACAGATACCAAGATAGATACACAGGACCGTCAGACAACGGCGGAGTC
CATATCAACAGCGGAATCAATAACAAAGCCTTTTACCTGATCGCCCAAGG
CGGAACGCACTATGGCGTTACAGTCAATGGCATCGGAAGAGATGCCGCAG
TTCAGATTTTCTATGACGCGCTGATCAACTATCTGACGCCTACAAGCAAT
TTCTCAGCAATGAGAGCCGCAGCAATCCAAGCAGCCACGGATCTGTATGG
AGCCAATTCATCACAAGTTAATGCTGTTAAGAAGGCTTATACGGCAGTGG
GAGTTAACTAA
```

The amino acid sequence of the PehPro1 precursor protein expressed from plasmid pGX148(AprE-PehPro1) is depicted in SEQ ID NO: 20. The predicted signal sequence is shown in italics, the three residue addition (AGK) is shown in bold, and the predicted pro-peptide is shown in underlined text.

*MRSKKLWISLLFALTLIFTMAFSNMSAQA*AGKAPQDQAAPFGGFTPQLIT
<u>GESWSAPQGVSGEEKIWKYLESKQESFQIGQTVDLKKQLKIIGQTTDEKT</u>
<u>GTTHYRLQQYVGGVPVYGGVQTIHVNKEGQVTSLIGSLLPDQQQQVSKSL</u>
<u>NSQISEAQAIAVAQKDTEAAVGKLGEPQKTPEADLYVYLHNGQPVLAYVT</u>
EVNVLEPEAIRTRYFISAEDGSILFKYDILAHATGTGKGVLGDTKSFTTT
QSGSTYQLKDTTRGQGIVTYSAGNRSSLPGTLLTSSSNIWNDGAAVDAHA
YTAKVYDYYKNKFGRNSIDGNGFQLKSTVHYSSRYNNAFWNGVQMVYGDG
DGVTFIPFSADPDVIGHELTHGVTEHTAGLEYYGESGALNESISDIIGNA
IDGKNWLIGDLIYTPNTPGDALRSMENPKLYNQPDRYQDRYTGPSDNGGV
HINSGINNKAFYLIAQGGTHYGVTVNGIGRDAAVQIFYDALINYLTPTSN
FSAMRAAAIQAATDLYGANSSQVNAVKKAYTAVGVN.

Example 4.3

Proteolytic Activity of Metalloprotease PehPro1

The proteolytic activity of purified metalloprotease PehPro1 was measured in 50 mM Tris (pH 7), using azo-casein (Cat #74H7165, Megazyme) as a substrate. Prior to the reaction, the enzyme was diluted with Milli-Q water (Millipore) to specific concentrations. The azo-casein was dissolved in 100 mM Tris buffer (pH 7) to a final concentration of 1.5% (w/v). To initiate the reaction, 50 µl of the diluted enzyme (or Milli-Q H$_2$O alone as the blank control) was added to the non-binding 96-well Microtiter Plate (96-MTP) (Corning Life Sciences, #3641) placed on ice, followed by the addition of 50 µl of 1.5% azo-casein. After sealing the 96-MTP, the reaction was carried out in a Thermomixer (Eppendorf) at 40° C. and 650 rpm for 10 min. The reaction was terminated by adding 100 µl of 5% Trichloroacetic Acid (TCA). Following equilibration (5 min at the room temperature) and subsequent centrifugation (2000 g for 10 min at 4° C.), 120 µl supernatant was transferred to a new 96-MTP, and absorbance of the supernatant was measured at 440 nm ($A_{440}$) using a SpectraMax 190. Net $A_{440}$ was calculated by subtracting the $A_{440}$ of the blank control from that of enzyme, and then plotted against different protein concentrations (from 1.25 ppm to 40 ppm). Each value was the mean of triplicate assays. The proteolytic activity is shown as Net $A_{440}$. The proteolytic assay with azo-casein as the substrate (shown in FIG. 4.2) indicates that PehPro1 is an active protease.

Example 4.4 pH Profile of Metalloprotease PehPro1

With azo-casein as the substrate, the pH profile of metalloprotease PehPro1 was studied in 12.5 mM acetate/Bis-Tris/HEPES/CHES buffer with different pH values (ranging from pH 4 to 11). To initiate the assay, 50 µl of 25 mM acetate/Bis-Tris/HEPES/CHES buffer with a specific pH was first mixed with 2 µl Milli-Q $H_2O$ diluted enzyme (250 ppm) in a 96-MTP placed on ice, followed by the addition of 48 µl of 1.5% (w/v) azo-casein prepared in $H_2O$. The reaction was performed and analyzed as described in Example 4.3. Enzyme activity at each pH was reported as the relative activity, where the activity at the optimal pH was set to be 100%. The pH values tested were 4, 5, 6, 7, 8, 9, 10 and 11. Each value was the mean of triplicate assays. As shown in FIG. 4.3, the optimal pH of PehPro1 is 7, with greater than 70% of maximal activity retained between 5.5 and 9.5.

Example 4.5

Temperature Profile of Metalloprotease PehPro1

The temperature profile of metalloprotease PehPro1 was analyzed in 50 mM Tris buffer (pH 7) using the azo-casein assays. The enzyme sample and azo-casein substrate were prepared as in Example 4.3. Prior to the reaction, 50 µl of 1.5% azo-casein and 45 µl Milli-Q $H_2O$ were mixed in a 200 µl PCR tube, which was then subsequently incubated in a Peltier Thermal Cycler (BioRad) at desired temperatures (i.e. 20-90° C.) for 5 min. After the incubation, 5 µl of diluted enzyme (100 ppm) or $H_2O$ (the blank control) was added to the substrate mixture, and the reaction was carried out in the Peltier Thermal Cycle for 10 min at different temperatures. To terminate the reaction, each assay mixture was transferred to a 96-MTP containing 100 µl of 5% TCA per well. Subsequent centrifugation and absorbance measurement were performed as described in Example 4.3. The activity was reported as the relative activity, where the activity at the optimal temperature was set to be 100%. The tested temperatures are 20, 30, 40, 50, 60, 70, 80, and 90° C. Each value was the mean of duplicate assays (the value varies no more than 5%). The data in FIG. 4.4 suggest that PehPro1 showed an optimal temperature at 70° C., and retained greater than 70% of its maximum activity between 60 and 75° C.

Example 4.6

Cleaning Performance of Metalloprotease PehPro1

The cleaning performance of PehPro1 was tested using PA-S-38 (egg yolk, with pigment, aged by heating) microswatches (CFT-Vlaardingen, The Netherlands) at pH 6 and 8 using a model automatic dishwashing (ADW) detergent. Prior to the reaction, purified protease samples were diluted with a dilution solution containing 10 mM NaCl, 0.1 mM $CaCl_2$, 0.005% TWEEN® 80 and 10% propylene glycol to the desired concentrations. The reactions were performed in AT detergent with 100 ppm water hardness ($Ca^{2+}$: $Mg^{2+}$=3:1) (detergent composition shown in Table 4.1). To initiate the reaction, 180 µl of the AT detergent buffered at pH 6 or pH 8 was added to a 96-MTP placed with PA-S-38 microswatches, followed by the addition of 20 µl of diluted enzymes (or the dilution solution as the blank control). The 96-MTP was sealed and incubated in an incubator/shaker for 30 min at 50° C. and 1150 rpm. After incubation, 100 µl of wash liquid from each well was transferred to a new 96-MTP, and its absorbance was measured at 405 nm (referred here as the "Initial performance") using a spectrophotometer. The remaining wash liquid in the 96-MTP was discarded and the microswatches were rinsed once with 200 µl water. Following the addition of 180 µl of 0.1 M CAPS buffer (pH 10), the second incubation was carried out in the incubator/shaker at 50° C. and 1150 rpm for 10 min. One hundred microliters of the resulting wash liquid was transferred to a new 96-MTP, and its absorbance measured at 405 nm (referred here as the "Wash-off"). The sum of two absorbance measurements ("Initial performance" plus "Wash-off") gives the "Total performance", which measures the protease activity on the model stain; and Net $A_{405}$ was subsequently calculated by subtracting the $A_{405}$ of the "Total performance" of the blank control from that of the enzyme. Dose response in cleaning the PA-S-38 microswatches at pH 6 and pH 8 for PehPro1 in AT detergent is shown in FIGS. 4.5A and 4.5B.

TABLE 4.1

Composition of AT dish detergent

| Ingredient | Concentration (mg/ml) |
| --- | --- |
| MGDA (methylglycinediacetic acid) | 0.143 |
| Sodium citrate | 1.86 |
| Citric acid* | varies |
| Plurafac ® LF 18B (a non-ionic surfactant) | 0.029 |
| Bismuthcitrate | 0.006 |
| Bayhibit ® S (Phosphonobutantricarboxylic acid sodium salt) | 0.006 |
| Acusol ™ 587 (a calcium polyphosphate inhibitor) | 0.029 |
| PEG 6000 | 0.043 |
| PEG 1500 | 0.1 |

*The pH of the AT formula detergent is adjusted to the desired value (pH 6 or 8) by the addition of 0.9M citric acid.

Example 4.7

Comparison of PehPro1 to Other Proteases

A. Identification of Homologous Proteases

Homologs were identified by a BLAST search (Altschul et al., Nucleic Acids Res, 25:3389-402, 1997) against the NCBI non-redundant protein database and the Genome Quest Patent database with search parameters set to default values. The mature protein amino acid sequence for PehPro1 (SEQ ID NO: 18) was used as the query sequence. Percent identity (PID) for both search sets is defined as the number of identical residues divided by the number of aligned residues in the pairwise alignment. Tables 4.2A and 4.2B provide a list of sequences with the percent identity to PehPro1. The length in Table 4.2 refers to the entire sequence length of the homologous proteases.

TABLE 4.2A

List of sequences with percent identity to PehPro1 protein identified from the NCBI non-redundant protein database

| Accession # | PID to PehPro1 | Organism | Length |
|---|---|---|---|
| ZP_09077634.1 | 88 | *Paenibacillus elgii* B69 | 524 |
| ZP_09071078.1 | 74 | *Paenibacillus larvae* subsp. *larvae* B-3650 | 529 |
| YP_003872179.1 | 74 | *Paenibacillus polymyxa* E681 | 592 |
| P29148 | 73 | *Paenibacillus polymyxa* | 590 |
| P43263 | 68 | *Brevibacillus brevis* | 527 |
| ZP_09775365.1 | 68 | *Paenibacillus* sp. Aloe-11 | 580 |
| ZP_10241029.1 | 67 | *Paenibacillus peoriae* KCTC 3763 | 599 |
| ZP_10575942.1 | 66 | *Brevibacillus* sp. BC25 | 528 |
| YP_002770810.1 | 67 | *Brevibacillus brevis* NBRC 100599 | 528 |
| ZP_08640523.1 | 64 | *Brevibacillus laterosporus* LMG 15441 | 564 |
| YP_004646155.1 | 63 | *Paenibacillus mucilaginosus* KNP414 | 525 |
| ZP_08093424.1 | 60 | *Planococcus donghaensis* MPA1U2 | 553 |
| YP_003670279.1 | 59 | *Geobacillus* sp. C56-T3 | 546 |
| P00800 | 59 | *Bacillus thermoproteolyticus* | 548 |

TABLE 4.2B

List of sequences with percent identity to PehPro1 protein identified from the Genome Quest Patent database

| Patent ID # | PID to PehPro1 | Organism | Length |
|---|---|---|---|
| JP2005229807-0019 | 74.5 | *Paenibacillus polymyxa* | 566 |
| US20120107907-0187 | 74.09 | *Bacillus polymyxa* | 302 |
| US8114656-0186 | 68.21 | *Bacillus brevis* | 304 |
| WO2004011619-0044 | 63.25 | empty | 507 |
| EP2390321-0185 | 62.9 | *Bacillus cereus* | 317 |
| WO2012110563-0004 | 62.7 | *Bacillus megaterium* | 320 |
| WO2012110563-0005 | 62.58 | *Bacillus cereus* | 320 |
| JP1995184649-0001 | 62.5 | *Lactobacillus* sp. | 566 |
| JP2005333991-0002 | 62.38 | empty | 562 |
| EP2178896-0184 | 62.18 | *Bacillus anthracis* | 566 |
| JP1994014788-0003 | 61.94 | empty | 317 |
| EP2390321-0178 | 61.86 | *Bacillus thuringiensis* | 566 |
| US6518054-0002 | 60.84 | *Bacillus* sp. | 316 |
| US8114656-0176 | 60.13 | *Bacillus stearothermophilus* | 548 |
| US6103512-0003 | 59.81 | empty | 319 |
| US20120107907-0184 | 59.49 | *Bacillus caldoyticus* | 319 |

B. Alignment of Homologous Protease Sequences

The amino acid sequence of predicted mature PehPro1 (SEQ ID NO: 18) was aligned with thermolysin (P00800, *Bacillus thermoproteolyticus*) and protease from *Paenibacillus elgii* B69 (ZP 09077634.1) using CLUSTALW software (Thompson et al., Nucleic Acids Research, 22:4673-4680, 1994) with the default parameters. FIG. 4.6 shows the alignment of PehPro1 with these protease sequences.

C. Phylogenetic Tree

A phylogenetic tree for precursor protein PehPro1 (SEQ ID NO: 17) was built using sequences of representative homologs from Table 2A and the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 4.7.

Example 5.1

Cloning of *Paenibacillus barcinonensis* Metalloprotease PbaPro1

A strain (DSM15478) of *Paenibacillus barcinonensis* was selected as a potential source of enzymes which may be useful in various industrial applications. Genomic DNA for sequencing was obtained by first growing the strain on Heart Infusion agar plates (Difco) at 37° C. for 24 hr. Cell material was scraped from the plates and used to prepare genomic DNA with the ZF Fungal/Bacterial DNA miniprep kit from Zymo (Cat No. D6005). The genomic DNA was used for genome sequencing. The entire genome of the *Paenibacillus barcinonensis* strain was sequenced by BaseClear (Leiden, The Netherlands) using the Illumina's next generation sequencing technology. After assembly of the data, contigs were annotated by BioXpr (Namur, Belgium). One of the genes identified after annotation in *Paenibacillus barcinonensis* encodes a metalloprotease and the sequence of this gene, called PbaPro1, is provided in SEQ ID NO: 21. The corresponding protein encoded by the PbaPro1 gene is shown in SEQ ID NO: 22. At the N-terminus, the protein has a signal peptide with a length of 25 amino acids as predicted by SignalP version 4.0 (Nordahl Petersen et al. (2011) Nature Methods, 8:785-786). The presence of a signal sequence suggests that PbaPro1 is a secreted enzyme. The propeptide region was predicted based on protein sequence alignment with the *Paenibacillus polymyxa* Npr protein (Takekawa et al. (1991) Journal of Bacteriology, 173 (21): 6820-6825). The predicted mature region of PbaPro1 protein is shown in SEQ ID NO: 23.

The nucleotide sequence of the PbaPro1 gene isolated from *Paenibacillus barcinonensis* is set forth as SEQ ID NO: 21. The sequence encoding the predicted native signal peptide is shown in italics:

*ATGAAATTGACCAAAATTATGCCAACAATTCTTGCAGGAGCTCTTTTGCT*

*CACATCCCTGTCCTCTGCAGCAGCAATGCCGTTATCTGACTCATCCATTC*

CATTTGAGGGCCCCTACACCTCCGAGGAGAGTATTCTGTTGAACAACAAC

CCGGACGAAATGATTTATAATTTTCTTGCACAACAAGAGCAATTTCTGAA

TGCCGACGTCAAAGGACAGCTCAAAATCATTAAACGCAACACAGACACTT

```
CCGGCATCAGACACTTTCGTCTGAAGCAATACATCAAAGGTGTTCCGGTT

TACGGCGCAGAACAAACGATCCATCTGGACAAGAACGGAGCTGTAACTTC

CGCACTCGGCGATCTTCCGCCAATTGAAGAACAGGCTGTTCCGAATGATG

GCGTTCCCGCAATCAGTGCAGACGATGCCATCCGTGCCGCCGAGAATGAA

GCCACCTCCCGTCTTGGAGAGCTTGGCGCACCAGAGCTTGAGCCAAAGGC

CGAATTAAACATTTATCATCATGAAGATGACGGACAAACCTACCTCGTTT

ACATTACGGAAGTTAACGTGCTTGAGCCTTCCCCGCTACGGACCAAATAT

TTTATTAACGCCCTTGATGGAAGCATCGTATCTCAATACGATATTATCAA

CTTTGCCACAGGCACCGGTACAGGCGTGCATGGTGATACCAAAACACTGA

CGACAACTCAATCCGGCAGCACCTATCAGCTGAAAGATACAACTCGTGGA

AAAGGCATTCAAACCTATACTGCGAACAATCGCTCCTCGCTTCCAGGCAG

CTTGTCTACCAGTTCCAATAACGTATGGACAGACCGTGCAGCTGTAGATG

CGCACGCCTATGCTGCCGCCACATATGACTTCTACAAAAACAAATTCAAT

CGCAACGGCATTGACGGAAACGGGCTGTTGATTCGCTCTACAGTGCATTA

TGGCTCCAACTATAAAAACGCCTTCTGGAACGGAGCACAGATTGTCTATG

GAGATGGCGATGGCATCGAGTTCGGTCCCTTCTCCGGTGATCTCGATGTT

GTCGGACATGAATTGACACACGGGGTGATTGAATATACAGCCAATCTCGA

ATATCGCAATGAGCCGGGTGCTTTAAACGAAGCTTTTGCCGACATTATGG

GGAACACCATCGAAAGCAAAAACTGGCTGCTTGGCGACGGAATCTATACT

CCAAACATTCCAGGTGATGCCCTGCGCTCGTTATCCGACCCTACGCTGTA

TAACCAGCCTGACAAATACAGTGATCGCTACACTGGCTCTCAGGATAATG

GCGGTGTGCATATCAACAGCGGGATCATTAACAAAGCATATTATCTTGCA

GCCCAAGGCGGTACTCATAACGGGGTAACCGTTAGCGGCATCGGCCGGGA

TAAAGCAGTACGTATTTTCTATAGCACGCTGGTGAACTACCTGACGCCAA

CCTCCAAATTTGCAGCAGCCAAAACAGCGACAATTCAGGCAGCCAAGGAC

CTGTACGGTGCCAATTCCGCTGAAGCTACGGCAATCACCAAAGCTTATCA

AGCGGTAGGTTTG
```

The amino acid sequence of the PbaPro1 precursor protein is set forth as SEQ ID NO: 22. The predicted signal sequence is shown in italics, and the predicted pro-peptide is shown in underlined text:

```
MKLTKIMPTILAGALLLTSLSSAAAMPLSDSSIPFEGPYTSEESILLNNN

PDEMIYNFLAQQEQFLNADVKGQLKIIKRNTDTSGIRHFRLKQYIKGVPV

YGAEQTIHLDKNGAVTSALGDLPPIEEQAVPNDGVPAISADDAIRAAENE

ATSRLGELGAPELEPKAELNIYHHEDDGQTYLVYITEVNVLEPSPLRTKY

FINALDGSIVSQYDIINFATGTGVHGDTKTLTTTQSGSTYQLKDTTRG

KGIQTYTANNRSSLPGSLSTSSNNVWTDRAAVDAHAYAAATYDFYKNKFN

RNGIDGNGLLIRSTVHYGSNYKNAFWNGAQIVYGDGDGIEFGPFSGDLDV

VGHELTHGVIEYTANLEYRNEPGALNEAFADIMGNTIESKNWLLGDGIYT

PNIPGDALRSLSDPTLYNQPDKYSDRYTGSQDNGGVHINSGIINKAYYLA

AQGGTHNGVTVSGIGRDKAVRIFYSTLVNYLTPTSKFAAAKTATIQAAKD

LYGANSAEATAITKAYQAVGL
```

The amino acid sequence of the predicted mature form of PbaPro1 is set forth as SEQ ID NO: 23:

```
ATGTGTGVHGDTKTLTTTQSGSTYQLKDTTRGKGIQTYTANNRSSLPGSL

STSSNNVWTDRAAVDAHAYAAATYDFYKNKFNRNGIDGNGLLIRSTVHYG

SNYKNAFWNGAQIVYGDGDGIEFGPFSGDLDVVGHELTHGVIEYTANLEY

RNEPGALNEAFADIMGNTIESKNWLLGDGIYTPNIPGDALRSLSDPTLYN

QPDKYSDRYTGSQDNGGVHINSGIINKAYYLAAQGGTHNGVTVSGIGRDK

AVRIFYSTLVNYLTPTSKFAAAKTATIQAAKDLYGANSAEATAITKAYQA

VGL
```

Example 5.2

Expression of *Paenibacillus barcinonensis* Metalloprotease PbaPro1

The DNA sequence of the propeptide-mature form of PbaPro1 was synthesized and inserted into the *Bacillus subtilis* expression vector p2JM103BBI (Vogtentanz, *Protein Expr Purif*, 55:40-52, 2007) by Generay (Shanghai, China), resulting in plasmid pGX147(AprE-PbaPro1) (FIG. 5.1). Ligation of this gene encoding the PbaPro1 protein into the digested vector resulted in the addition of three codons (Ala-Gly-Lys) between the 3' end of the *B. subtilis* AprE signal sequence and the 5' end of the predicted PbaPro1 native propeptide. The gene has an alternative start codon (GTG). The resulting plasmid shown in FIG. 1 was labeled pGX147(AprE-PbaPro1). As shown in FIG. 5.1, pGX147 (AprE-PbaPro1) contains an AprE promoter, an AprE signal sequence used to direct target protein secretion in *B. subtilis*, and the synthetic nucleotide sequence encoding the predicted propeptide and mature regions of PbaPro1 (SEQ ID NO: 24). The translation product of the synthetic AprE-PbaPro1 gene is shown in SEQ ID NO: 25.

The pGX147(AprE-PbaPro1) plasmid was then transformed into *B. subtilis* cells (degU$^{Hy}$ 32, ΔscoC) and the transformed cells were spread on Luria Agar plates supplemented with 5 ppm Chloramphenicol and 1.2% skim milk (Cat #232100, Difco). Colonies with the largest clear halos on the plates were selected and subjected to fermentation in a 250 ml shake flask with MBD medium (a MOPS based defined medium, supplemented with additional 5 mM CaCl$_2$).

The broth from the shake flasks was concentrated and buffer-exchanged into the loading buffer containing 20 mM Tris-HCl (pH 8.5), 1 mM CaCl$_2$ and 10% propylene glycol using a VivaFlow 200 ultra filtration device (Sartorius Stedim). After filtering, this sample was applied to an 80 ml Q Sepharose High Performance column pre-equilibrated with the loading buffer above; and the active flow-through fractions were collected and concentrated. The sample was loaded onto a 320 ml Superdex 75 gel filtration column pre-equilibrated with the loading buffer described above containing 0.15 M NaCl. The corresponding active purified protein fractions were further pooled and concentrated via 10K Amicon Ultra for further analyses.

The nucleotide sequence of the synthesized PbaPro1 gene in plasmid pGX147(AprE-PbaPro1) is depicted in SEQ ID NO: 24. The sequence encoding the three residue addition (AGK) is shown in bold:

```
GTGAGAAGCAAAAAATTGTGGATCAGCTTGTTGTTTGCGTTAACGTTAAT

CTTTACGATGGCGTTCAGCAACATGAGCGCGCAGGCTGCTGGAAAAATGC

CTCTGTCAGACAGCAGCATTCCGTTTGAGGGCCCGTACACATCAGAAGAA

AGCATCCTGCTGAACAACAACCCGGACGAGATGATCTACAATTTCCTGGC

ACAGCAGGAGCAGTTCCTGAACGCAGACGTGAAGGGCCAGCTGAAAATCA

TCAAAAGAAACACAGACACGAGCGGCATCAGACACTTCAGACTGAAGCAG

TACATCAAGGGCGTCCCGGTTTACGGCGCTGAGCAGACAATCCACCTGGA

CAAAAATGGCGCAGTGACGAGCGCACTTGGAGATCTGCCGCCGATTGAAG

AGCAAGCAGTCCCGAACGATGGCGTTCCGGCGATTAGCGCTGATGACGCT

ATCAGAGCCGCGGAAAACGAAGCGACGTCAAGACTGGGAGAACTTGGCGC

ACCGGAACTTGAACCGAAGGCGGAACTGAACATCTATCACCACGAAGACG

ATGGACAGACGTACCTGGTGTACATCACGGAGGTGAATGTGCTGGAGCCG

TCACCGCTGAGAACAAAATACTTCATCAATGCGCTGGATGGCAGCATCGT

TAGCCAATACGACATCATTAACTTCGCCACAGGCACGGGCACAGGCGTTC

ATGGCGACACAAAAACGCTTACGACAACACAGTCAGGCTCAACGTACCAG

CTGAAAGACACAACAAGAGGCAAGGGCATCCAGACGTATACAGCCAATAA

CAGAAGCTCACTTCCGGGCTCACTGTCAACAAGCAGCAATAATGTCTGGA

CGGACAGAGCTGCAGTGGACGCGCACGCGTATGCTGCGGCCACGTACGAC

TTCTACAAGAACAAGTTCAACAGAAACGGCATTGATGGCAACGGCCTGCT

TATTAGAAGCACGGTCCACTACGGCTCAAACTACAAGAATGCGTTTTGGA

ACGGCGCCCAAATTGTTTATGGCGATGGAGACGGCATCGAGTTCGGACCT

TTTAGCGGCGACCTGGATGTGGTCGGACATGAACTGACGCACGGCGTTAT

CGAGTATACGGCGAATCTGGAATACAGAAATGAACCGGGCGCTCTGAATG

AGGCCTTCGCGGATATCATGGGCAACACAATTGAGAGCAAAAACTGGCTT

CTGGGCGACGGAATCTACACGCCGAACATTCCGGGAGATGCACTGAGATC

ACTGAGCGACCCTACGCTGTACAACCAGCCGGACAAATACAGCGACAGAT

ACACGGGATCACAGGACAATGGCGGCGTCCATATTAACTCAGGCATCATC

AACAAAGCGTATTATCTGGCAGCTCAAGGCGGCACGCATAATGGCGTCAC

AGTTAGCGGAATCGGCAGAGACAAGGCCGTCAGAATTTTCTACTCAACGC

TGGTGAACTACCTGACACCGACAAGCAAGTTTGCAGCCGCCAAAACAGCC

ACGATTCAGGCAGCAAAGGACCTGTACGGAGCGAACTCAGCAGAGGCCAC

AGCGATTACGAAGGCTTATCAAGCCGTGGGACTGTAA
```

The amino acid sequence of the PbaPro1 precursor protein expressed from plasmid pGX147(AprE-PbaPro1) is depicted in SEQ ID NO: 25. The predicted signal sequence is shown in italics, the three residue addition (AGK) is shown in bold, and the predicted pro-peptide is shown in underlined text.

*MRSKKLWISLLFALTLIFTMAFSNMSAQA*AGK<u>MPLSDSSIPFEGPYTSEE</u>

<u>SILLNNNPDEMIYNFLAQQEQFLNADVKGQLKIIKRNTDTSGIRHFRLKQ</u>

<u>YIKGVPVYGAEQTIHLDKNGAVTSALGDLPPIEEQAVPNDGVPAISADDA</u>

<u>IRAAENEATSRLGELGAPELEPKAELNIYHHEDDGQTYLVYITEVNVLEP</u>

<u>SPLRTKYFINALDGSIVSQYDIINFATGTGTGVHGDTKTLTTTQSGSTYQ</u>

<u>LKDTTRGKGIQTYTANNRSSLPGSLSTSSNNVWTDRAAVDAHAYAAATYD</u>

<u>FYKNKFNRNGIDGNGLLIRSTVHYGSNYKNAFWNGAQIVYGDGDGIEFGP</u>

<u>FSGDLDVVGHELTHGVIEYTANLEYRNEPGALNEAFADIMGNTIESKNWL</u>

<u>LGDGIYTPNIPGDALRSLSDPTLYNQPDKYSDRYTGSQDNGGVHINSGII</u>

<u>NKAYYLAAQGGTHNGVTVSGIGRDKAVRIFYSTLVNYLTPTSKFAAAKTA</u>

<u>TIQAAKDLYGANSAEATAITKAYQAVGL</u>

Example 5.3

Proteolytic Activity of Metalloprotease PbaPro1

The proteolytic activity of purified metalloprotease PbaPro1 was measured in 50 mM Tris (pH 7), using azo-casein (Cat #74H7165, Megazyme) as a substrate. Prior to the reaction, the enzyme was diluted with Milli-Q water (Millipore) to specific concentrations. The azo-casein was dissolved in 100 mM Tris buffer (pH 7) to a final concentration of 1.5% (w/v). To initiate the reaction, 50 μl of the diluted enzyme (or Milli-Q H$_2$O alone as the blank control) was added to the non-binding 96-well Microtiter Plate (96-MTP) (Corning Life Sciences, #3641) placed on ice, followed by the addition of 50 μl of 1.5% azo-casein. After sealing the 96-MTP, the reaction was carried out in a Thermomixer (Eppendorf) at 40° C. and 650 rpm for 10 min. The reaction was terminated by adding 100 μl of 5% Trichloroacetic Acid (TCA). Following equilibration (5 min at the room temperature) and subsequent centrifugation (2000 g for 10 min at 4° C.), 120 μl supernatant was transferred to a new 96-MTP, and absorbance of the supernatant was measured at 440 nm ($A_{440}$) using a SpectraMax 190. Net $A_{440}$ was calculated by subtracting the $A_{440}$ of the blank control from that of enzyme, and then plotted against different protein concentrations (from 1.25 ppm to 40 ppm). Each value was the mean of triplicate assays.

The proteolytic activities are shown as Net $A_{440}$. The proteolytic assay with azo-casein as the substrate (shown in FIG. 5.2) indicates that PbaPro1 is an active protease.

Example 5.4 pH Profile of Metalloprotease PbaPro1

With azo-casein as the substrate, the pH profile of metalloprotease PbaPro1 was studied in 12.5 mM acetate/Bis-Tris/HEPES/CHES buffer with different pH values (ranging from pH 5 to 11). To initiate the assay, 50 μl of 25 mM acetate/Bis-Tris/HEPES/CHES buffer with a specific pH was first mixed with 2 μl Milli-Q H$_2$O diluted enzyme (125 ppm) in a 96-MTP placed on ice, followed by the addition of 48 μl of 1.5% (w/v) azo-casein prepared in H$_2$O. The reaction was performed and analyzed as described in Example 5.3. Enzyme activity at each pH was reported as the relative activity, where the activity at the optimal pH was set to be 100%. The pH values tested were 5, 6, 7, 8, 9, 10 and 11. Each value was the mean of triplicate assays. As shown in FIG. 5.3, the optimal pH of PbaPro1 is 8, with greater than 70% of maximal activity retained between 7 and 9.

Example 5.5

Temperature Profile of Metalloprotease PbaPro1

The temperature profiles of metalloprotease PbaPro1 was analyzed in 50 mM Tris buffer (pH 7) using the azo-casein assays. The enzyme sample and azo-casein substrate were prepared as in Example 5.3. Prior to the reaction, 50 µl of 1.5% azo-casein and 45 µl Milli-Q $H_2O$ were mixed in a 200 µl PCR tube, which was then subsequently incubated in a Peltier Thermal Cycler (BioRad) at desired temperatures (i.e. 20-90° C.) for 5 min. After the incubation, 5 µl of diluted enzyme (50 ppm) or $H_2O$ (the blank control) was added to the substrate mixture, and the reaction was carried out in the Peltier Thermal Cycle for 10 min at different temperatures. To terminate the reaction, each assay mixture was transferred to a 96-MTP containing 100 µl of 5% TCA per well. Subsequent centrifugation and absorbance measurement were performed as described in Example 5.3. The activity was reported as the relative activity, where the activity at the optimal temperature was set to be 100%. The tested temperatures are 20, 30, 40, 50, 60, 70, 80, and 90° C. Each value was the mean of duplicate assays (the value varies no more than 5%). The data in FIG. 5.4 suggest that PbaPro1 showed an optimal temperature at 50° C., and retained greater than 70% of its maximum activity between 45 and 55° C.

Example 5.6

Cleaning Performance of Metalloprotease PbaPro1

The cleaning performance of PbaPro1 was tested using PA-S-38 (egg yolk, with pigment, aged by heating) microswatches (CFT-Vlaardingen, The Netherlands) at pH 6 and 8 using a model automatic dishwashing (ADW) detergent. Prior to the reaction, purified protease samples were diluted with a dilution solution containing 10 mM NaCl, 0.1 mM $CaCl_2$, 0.005% TWEEN® 80 and 10% propylene glycol to the desired concentrations. The reactions were performed in AT detergent with 100 ppm water hardness ($Ca^{2+}$: $Mg^{2+}$=3:1) (detergent composition shown in Table 5.1). To initiate the reaction, 180 µl of the AT detergent buffered at pH 6 or pH 8 was added to a 96-MTP placed with PA-S-38 microswatches, followed by the addition of 20 µl of diluted enzymes (or the dilution solution as the blank control). The 96-MTP was sealed and incubated in an incubator/shaker for 30 min at 50° C. and 1150 rpm. After incubation, 100 µl of wash liquid from each well was transferred to a new 96-MTP, and its absorbance was measured at 405 nm (referred here as the "Initial performance") using a spectrophotometer. The remaining wash liquid in the 96-MTP was discarded and the microswatches were rinsed once with 200 µl water. Following the addition of 180 µl of 0.1 M CAPS buffer (pH 10), the second incubation was carried out in the incubator/shaker at 50° C. and 1150 rpm for 10 min. One hundred microliters of the resulting wash liquid was transferred to a new 96-MTP, and its absorbance measured at 405 nm (referred here as the "Wash-off"). The sum of two absorbance measurements ("Initial performance" plus "Wash-off") gives the "Total performance", which measures the protease activity on the model stain; and Net $A_{405}$ was subsequently calculated by subtracting the $A_{405}$ of the "Total performance" of the blank control from that of the enzyme. Dose response in cleaning the PA-S-38 microswatches at pH 6 and pH 8 in AT detergent for PbaPro1 is shown in FIGS. 5.5A and 5.5B.

TABLE 5.1

Composition of AT dish detergent formula with bleach

| Ingredient | Concentration (mg/ml) |
|---|---|
| MGDA (methylglycinediacetic acid) | 0.143 |
| Sodium citrate | 1.86 |
| Citric acid* | varies |
| PAP (peracid N,N-phthaloylaminoperoxycaproic acid) | 0.057 |
| Plurafac ® LF 18B (a non-ionic surfactant) | 0.029 |
| Bismuthcitrate | 0.006 |
| Bayhibit ® S (Phosphonobutantricarboxylic acid sodium salt) | 0.006 |
| Acusol ™ 587 (a calcium polyphosphate inhibitor) | 0.029 |
| PEG 6000 | 0.043 |
| PEG 1500 | 0.1 |

*The pH of the AT formula detergent is adjusted to the desired value (pH 6 or 8) by the addition of 0.9M citric acid.

Example 5.7

Comparison of PbaPro1 to Other Proteases

A. Identification of Homologous Proteases

Homologs were identified by a BLAST search (Altschul et al., Nucleic Acids Res, 25:3389-402, 1997) against the NCBI non-redundant protein database and the Genome Quest Patent database with search parameters set to default values. The predicted mature protein amino acid sequence for PbaPro1 (SEQ ID NO: 23) was used as the query sequence. Percent identity (PID) for both search sets is defined as the number of identical residues divided by the number of aligned residues in the pairwise alignment. Tables 5.2A and 5.2B provide a list of sequences with the percent identity to PbaPro1. The length in Table 5.2 refers to the entire sequence length of the homologous proteases.

TABLE 5.2A

List of sequences with percent identity to PbaPro1 protein identified from the NCBI non-redundant protein database

| Accession # | PID to PbaPro1 | Organism | Length |
|---|---|---|---|
| AAB02774.1 | 56 | Geobacillus stearothermophilus | 552 |
| P00800 | 56 | Bacillus stermoproteolyticus | 548 |
| AAA22623.1 | 57 | Bacillus caldolyticus | 544 |
| YP_003670279.1 | 57 | Geobacillus sp. C56-T3 | 546 |
| AAC43402.1 | 57 | Alicyclobacillus acidocaldarius | 546 |
| YP_003597483.1 | 57 | Bacillus megaterium DSM 319 | 562 |
| ZP_08093424.1 | 57 | Planococcus donghaensis MPA1U2 | 553 |
| ZP_08640523.1 | 59 | Brevibacillus laterosporus LMG 15441 | 564 |
| ZP_04216147.1 | 59 | Bacillus cereus Rock3-44 | 566 |
| YP_001373863.1 | 60 | Bacillus cytotoxicus NVH 391-98 | 565 |
| YP_004646155.1 | 60 | Paenibacillus mucilaginosus KNP414 | 525 |
| ZP_10738945.1 | 61 | Brevibacillus sp. CF112 | 528 |
| CAA43589.1 | 63 | Brevibacillus brevis | 527 |
| ZP_02326602.1 | 64 | Paenibacillus larvae subsp. larvae BRL-230010 | 520 |
| ZP_02326503.1 | 65 | Paenibacillus larvae subsp. larvae B-3650 | 520 |
| ZP_09077634.1 | 66 | Paenibacillus elgii B69 | 524 |
| ZP_08511445.1 | 68 | [Paenibacillus sp. HGF7 | 525 |
| ZP_09775364.1 | 70 | Paenibacillus sp. Aloe-11 | 593 |
| YP_005073223.1 | 70 | Paenibacillus terrae HPL-003 | 591 |
| ZP_10241030.1 | 70 | Paenibacillus peoriae KCTC 3763 | 593 |
| YP_003948511.1 | 71 | Paenibacillus polymyxa SC2 | 592 |

TABLE 5.2B

List of sequences with percent identity to PbaPro1 protein identified from the Genome Quest Patent database

| Patent # | PID to PbaPro1 | Organism | Length |
|---|---|---|---|
| JP2005333991-0002 | 56.91 | | 562 |
| WO2012110562-0007 | 56.96 | Bacillus cereus | 320 |
| WO2012110562-0006 | 57.23 | Bacillus megaterium | 320 |
| EP2390321-0178 | 57.23 | Bacillus thuringiensis | 566 |
| EP2390321-0184 | 57.56 | Bacillus caldoyticus | 319 |
| WO2007044993-0184 | 57.56 | Bacillus sp. | 319 |
| US20120107907-0177 | 57.56 | Bacillus caldolyticus | 544 |
| CN102168095-0002 | 57.88 | | 319 |
| WO2012110562-0004 | 57.88 | Bacillus caldolyticus | 319 |
| WO2012110562-0003 | 57.88 | Geobacillus stearothermophilus | 319 |
| WO2004011619-0056 | 57.88 | | 546 |
| JP1995184649-0001 | 57.88 | Lactobacillus sp. | 566 |
| JP2010535248-0240 | 57.88 | Bacillus anthracis | 566 |
| US6518054-0001 | 58.2 | Bacillus sp. | 319 |
| US6103512-0003 | 58.2 | | 319 |
| WO2011163237-0001 | 58.2 | Geobacillus stearothermophilus | 548 |
| JP1994014788-0003 | 58.25 | | 317 |
| US8114656-0185 | 58.9 | Bacillus cereus | 317 |
| US20120107907-0179 | 58.9 | Bacillus cereus | 566 |
| WO2012110563-0005 | 59.22 | Bacillus cereus | 320 |
| WO2004011619-0044 | 59.6 | | 507 |
| US20120107907-0186 | 63.25 | Bacillus brevis | 304 |
| JP2005229807-0018 | 70.86 | Paenibacillus polymyxa | 566 |
| EP2390321-0187 | 71.1 | Bacillus polymyxa | 302 |
| JP2009511072-0203 | 71.1 | Paenibacillus polymyxa | 302 |

B. Alignment of Homologous Protease Sequences

The amino acid sequence of the predicted mature PbaPro1 (SEQ ID NO: 23) was aligned with Thermolysin (P00800, Bacillus thermoproteolyticus), and protease from Paenibacillus polymyxa SC2 (YP 003948511.1) using CLUSTALW software (Thompson et al., Nucleic Acids Research, 22:4673-4680, 1994) with the default parameters. FIG. 5.6 shows the alignment of PbaPro1 with these protease sequences.

C. Phylogenetic Tree

A phylogenetic tree for full length sequence of PbaPro1 (SEQ ID NO: 22) was built using sequences of representative homologs from Table 2A and the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 5.7.

Example 6.1

Cloning of Paenibacillus polymyxa SC2 Metalloprotease PpoPro1

The nucleic acid sequence for the PpoPro1 gene was identified in the NCBI database (NCBI Reference Sequence: NC 014622.1 from 4536397-4538175) and is provided in SEQ ID NO: 26. The corresponding protein encoded by the PpoPro1 gene is shown in SEQ ID NO: 27. At the N-terminus, the protein has a signal peptide with a length of 24 amino acids as predicted by SignalP version 4.0 (Nordahl Petersen et al. (2011) Nature Methods, 8:785-786). The presence of a signal sequence suggests that PpoPro1 is a secreted enzyme. The propeptide region was predicted based on protein sequence alignment with the Paenibacillus polymyxa Npr protein (Takekawa et al. (1991) Journal of Bacteriology, 173 (21): 6820-6825). The predicted mature region of PpoPro1 protein is shown in SEQ ID NO: 28.

The nucleotide sequence of the PpoPro1 gene identified from NCBI database is set forth as SEQ ID NO: 26. The sequence encoding the predicted native signal peptide is shown in italics:

*ATGAAAAAAGTATGGGTTTCGCTTCTTGGAGGAGCTATGTTATTAGGGTC*

*TGTCGCGTCTGGTGCATCTGCGGAGAGTTCCGTTTCGGGGCCAGCTCAGC*

TTACACCGACCTTCCACGCCGAGCAATGGAAAGCACCTACCTCGGTATCG

GGGGATGACATTGTATGGAGCTATTTAAATCGACAAAAGAAATCGTTGCT

GGGTGTGGATAGCTCCAGTGTACGTGAACAATTCCGAATCGTTGATCGCA

CAAGCGACAAATCCGGTGTAAGCCATTATCGACTGAAGCAGTATGTAAAC

GGAATTCCCGTGTATGGAGCTGAACAAACTATTCATGTGGGCAAATCTGG

TGAGGTCACCTCTTACTTAGGAGCGGTGGTTAATGAGGATCAGCAGGCAG

AAGCTACGCAAGGTACAACTCCAAAAATCAGCGCTTCTGAAGCGGTCTAC

ACCGCATATAAAGAAGCAGCTGCACGGATTGAAGCCCTCCCTACCTCCGA

CGATACTATTTCTAAAGACGCTGAGGAGCCAAGCAGTGTAAGTAAAGATA

CTTACGCCGAAGCAGCTAACAACGAAAAAACGCTTTCTGTTGATAAGGAC

GAGCTGAGTCTTGATCAGGCATCTGTCCTGAAAGATAGCAAAATTGAAGC

AGTGGAACCAGAAAAAAGTTCCATTGCCAAAATCGCTAATCTGCAGCCTG

AAGTAGATCCTAAAGCAGAACTCTACTACTACCCTAAGGGGGATGACCTG

CTGCTGGTTTATGTAACAGAAGTTAATGTTTTAGAACCTGCCCCACTGCG

TACCCGCTACATTATTGATGCCAATGACGGCAGCATCGTATTCCAGTATG

ACATCATTAATGAAGCGACAGGCACAGGTAAAGGTGTGCTTGGTGATTCC

AAATCGTTCACTACTACCGCTTCCGGCAGTAGCTACCAGTTAAAAGATAC

AACACGCGGTAACGGAATCGTGACTTACACGGCCTCCAACCGTCAAAGCA

TCCCAGGTACCATTTTGACAGATGCCGATAATGTATGGAATGATCCAGCT

GGTGTGGACGCCCATGCGTATGCTGCTAAAACCTATGATTACTATAAAGC

CAAATTTGGACGCAACAGCATTGACGGACGCGGTCTGCAACTTCGTTCGA

CGGTCCATTACGGTAGTCGCTACAACAATGCCTTCTGGAACGGCTCCCAA

ATGACTTATGGAGATGGAGATGGTAGCACATTTATCGCCTTCAGCGGGGA

CCCCGATGTAGTAGGACATGAACTTACGCATGGTGTCACAGAGTATACTT

CGAATTTGGAATATTACGGAGAGTCCGGCGCATTGAATGAAGCTTTCTCA

GACGTTATCGGGAATGACATTCAGCGCAAAAACTGGCTTGTAGGCGATGA

TATTTACACGCCAAACATTGCAGGCGATGCCCTTCGCTCAATGTCCAATC

CAACCCTGTACGATCAACCAGATCACTATTCCAACCTGTACAGAGGCAGC

TCCGATAACGGCGGTGTTCACACCAACAGCGGTATTATCAATAAAGCTTA

CTACTTGTTAGCACAAGGTGGTAATTTCCATGGCGTAACTGTAAATGGAA

TTGGCCGTGATGCAGCGGTGCAAATTTACTACAGTGCCTTTACGAACTAC

CTGACTTCTTCTTCCGACTTCTCCAACGCACGTGCTGCTGTGATCCAAGC

CGCAAAAGATCTGTACGGGGCGAACTCAGCAGAAGCAACTCAGCTGCCA

AGTCTTTTGACGCTGTAGGCGTAAACTAA

The amino acid sequence of the PpoPro1 precursor protein is set forth as SEQ ID NO: 27. The predicted signal sequence is shown in italics, and the predicted propeptide is shown in underlined text:

*MKKVWVSLLGGAMLLGSVASGASA*<u>ESSVSGPAQLTPTFHAEQWKAPTSVS</u>
<u>GDDIVWSYLNRQKKSLLGVDSSSVREQFRIVDRTSDKSGVSHYRLKQYVN</u>
<u>GIPVYGAEQTIHVGKSGEVTSYLGAVVNEDQQAEATQGTTPKISASEAVY</u>
<u>TAYKEAAARIEALPTSDDTISKDAEEPSSVSKDTYAEAANNEKTLSVDKD</u>
<u>ELSLDQASVLKDSKIEAVEPEKSSIAKIANLQPEVDPKAELYYYPKGDDL</u>
<u>LLVYVTEVNVLEPAPLRTRYIIDANDGSIVFQYDIINEATGTGKGVLGDS</u>
KSFTTTASGSSYQLKDTTRGNGIVTYTASNRQSIPGTILTDADNVWNDPA
GVDAHAYAAKTYDYYKAKFGRNSIDGRGLQLRSTVHYGSRYNNAFWNGSQ
MTYGDGDGSTFIAFSGDPDVVGHELTHGVTEYTSNLEYYGESGALNEAFS
DVIGNDIQRKNWLVGDDIYTPNIAGDALRSMSNPTLYDQPDHYSNLYRGS
SDNGGVHTNSGIINKAYYLLAQGGNFHGVTVNGIGRDAAVQIYYSAFTNY
LTSSSDFSNARAAVIQAAKDLYGANSAEATAAAKSFDAVGVN

The amino acid sequence of the predicted mature form of PpoPro1 is set forth as SEQ ID NO: 28:

ATGTGKGVLGDSKSFTTTASGSSYQLKDTTRGNGIVTYTASNRQSIPGTI
LTDADNVWNDPAGVDAHAYAAKTYDYYKAKFGRNSIDGRGLQLRSTVHYG
SRYNNAFWNGSQMTYGDGDGSTFIAFSGDPDVVGHELTHGVTEYTSNLEY
YGESGALNEAFSDVIGNDIQRKNWLVGDDIYTPNIAGDALRSMSNPTLYD
QPDHYSNLYRGSSDNGGVHTNSGIINKAYYLLAQGGNFHGVTVNGIGRDA
AVQIYYSAFTNYLTSSSDFSNARAAVIQAAKDLYGANSAEATAAAKSFDA
VGVN

Example 6.2

Expression of *Paenibacillus polymyxa* SC2 Metalloprotease PpoPro1

The DNA sequence of the propeptide-mature form of PpoPro1 was synthesized and inserted into the *Bacillus subtilis* expression vector p2JM103BBI (Vogtentanz, *Protein Expr Purif*, 55:40-52, 2007) by Generay (Shanghai, China), resulting in plasmid pGX138(AprE-PpoPro1) (FIG. 1). Ligation of this gene encoding the PpoPro1 protein into the digested vector resulted in the addition of three codons (Ala-Gly-Lys) between the 3' end of the *B. subtilis* AprE signal sequence and the 5' end of the predicted PpoPro1 native propeptide. The gene has an alternative start codon (GTG). The resulting plasmid shown in FIG. 6.1, labeled pGX138(AprE-PpoPro1 contains an AprE promoter, an AprE signal sequence used to direct target protein secretion in *B. subtilis*, and the synthetic nucleotide sequence encoding the predicted propeptide and mature regions of PpoPro1 (SEQ ID NO: 29). The translation product of the synthetic AprE-PpoPro1 gene is shown in SEQ ID NO: 30.

The pGX138(AprE-PpoPro1) plasmid was then transformed into *B. subtilis* cells (degU$^{Hy}$ 32, ΔscoC) and the transformed cells were spread on Luria Agar plates supplemented with 5 ppm Chloramphenicol and 1.2% skim milk (Cat #232100, Difco). Colonies with the largest clear halos on the plates were selected and subjected to fermentation in a 250 ml shake flask with MBD medium (a MOPS based defined medium, supplemented with additional 5 mM CaCl$_2$).

The broth from the shake flasks was concentrated and buffer-exchanged into the loading buffer containing 20 mM Tris-HCl (pH 8.5), 1 mM CaCl$_2$ and 10% propylene glycol using a VivaFlow 200 ultra filtration device (Sartorius Stedim). After filtering, this sample was applied to an 80 ml Q Sepharose High Performance column pre-equilibrated with the loading buffer above, PpoPro1 was eluted from the column with a linear salt gradient from 0 to 0.25 M NaCl in the loading buffer. The corresponding active fractions were collected and concentrated. The sample was loaded onto a 320 ml Superdex 75 gel filtration column pre-equilibrated with the loading buffer described above containing 0.15 M NaCl. The corresponding active purified protein fractions were further pooled and concentrated via 10K Amicon Ultra for further analyses.

The nucleotide sequence of the synthesized PpoPro1 gene in plasmid pGX138(AprE-PpoPro1) is depicted in SEQ ID NO: 29. The sequence encoding the three residue addition (AGK) is shown in bold:

GTGAGAAGCAAAAAATTGTGGATCAGCTTGTTGTTTGCGTTAACGTTAAT
CTTTACGATGGCGTTCAGCAACATGAGCGCGCAGGCTGCTGGAAAAGAAT
CATCAGTGTCAGGACCGGCTCAGCTTACACCGACATTTCACGCAGAACAA
TGGAAGGCTCCGACGTCAGTTTCAGGAGACGACATCGTGTGGAGCTACCT
GAATAGACAGAAGAAAGCCTGCTGGGAGTGGATAGCAGCAGCGTCAGAG
AGCAGTTCAGAATCGTTGACAGAACGAGCGACAAAAGCGGAGTCAGCCAT
TATAGACTGAAGCAGTACGTGAATGGCATCCCGGTTTATGGCGCAGAGCA
GACAATTCATGTTGGCAAGAGCGGAGAAGTCACAAGCTATCTGGGCGCTG
TGGTCAATGAAGATCAACAAGCCGAGGCTACACAGGGAACAACGCCGAAA
ATTAGCGCCTCAGAGGCAGTCTACACGGCGTACAAAGAAGCGGCTGCAAG
AATCGAAGCCCTGCCGACATCAGACGATACAATTTCAAAAGATGCGGAGG
AGCCGAGCTCAGTTAGCAAGGATACATACGCGGAAGCCGCAAACAATGAG
AAAACACTGAGCGTGGACAAGGACGAGCTGTCACTTGATCAGGCTAGCGT
CCTTAAAGACAGCAAGATCGAGGCCGTTGAGCCTGAAAAGTCATCAATTG
CGAAAATCGCCAATCTGCAACCTGAAGTCGACCCGAAGGCGGAACTGTAC
TACTACCCGAAAGGCGATGACCTGCTTCTGGTGTACGTCACGGAAGTGAA
CGTCCTGGAACCGGCACCGCTGAGAACAAGATACATCATCGACGCGAACG
ACGGAAGCATCGTCTTCCAGTATGACATTATCAACGAAGCAACGGGAACG
GGCAAAGGCGTTCTTGGAGACTCAAAGAGCTTCACGACAACGGCTTCAGG
AAGCAGCTACCAGCTGAAAGACACGACGAGAGGAAACGGAATCGTCACAT
ATACGGCGTCAAACAGACAAAGCATCCCTGGCACAATCCTGACGGATGCT
GACAACGTTTGGAATGATCCGGCTGGCGTGGATGCCCATGCTTATGCGGC
AAAAACGTATGACTATTACAAGGCGAAGTTCGGCAGAAATTCAATCGATG
GCAGAGGACTGCAGCTTAGAAGCACGGTGCACTACGGATCAAGATATAAC
AATGCCTTCTGGAACGGCAGCCAGATGACATACGGAGACGGAGATGGAAG

```
                    -continued
CACATTTATTGCATTCAGCGGCGACCCTGATGTGGTTGGCCATGAGCTGA

CGCATGGCGTTACAGAATATACGAGCAATCTTGAATACTACGGCGAGTCA

GGCGCTCTGAACGAGGCATTTAGCGATGTTATCGGCAATGACATCCAGAG

AAAAAACTGGCTGGTGGGCGACGATATTTACACGCCTAATATCGCTGGCG

ATGCCCTTAGATCAATGTCAAACCCGACGCTGTATGATCAGCCTGACCAC

TACTCAAACCTGTATAGAGGCTCATCAGATAACGGAGGCGTCCATACGAA

TAGCGGCATCATTAACAAGGCATATTATCTTCTGGCCCAGGGCGGCAATT

TTCATGGAGTGACGGTTAATGGAATTGGAAGAGACGCAGCCGTCCAAATC

TACTACAGCGCTTTCACGAACTACCTTACATCAAGCTCAGACTTTAGCAA

TGCCAGAGCTGCTGTTATCCAGGCAGCGAAGGATCTTTACGGCGCCAACT

CAGCCGAAGCTACGGCCGCAGCTAAATCATTTGATGCAGTGGGCGTTAAT
```

The amino acid sequence of the PpoPro1 precursor protein expressed from plasmid pGX138(AprE-PpoPro1) is depicted in SEQ ID NO: 30. The predicted signal sequence is shown in italics, the three residue addition (AGK) is shown in bold, and the predicted pro-peptide is shown in underlined text.

*MRSKKLWISLLFALTLIFTMAFSNMSAQA*AGKESSVSGPAQLTPTFHAEQ

WKAPTSVSGDDIVWSYLNRQKKSLLGVDSSSVREQFRIVDRTSDKSGVSH

YRLKQYVNGIPVYGAEQTIHVGKSGEVTSYLGAVVNEDQQAEATQGTTPK

ISASEAVYTAYKEAAARIEALPTSDDTISKDAEEPSSVSKDTYAEAANNE

KTLSVDKDELSLDQASVLKDSKIEAVEPEKSSIAKIANLQPEVDPKAELY

YYPKGDDLLLVYVTEVNVLEPAPLRTRYIIDANDGSIVFQYDIINEATGT

GKGVLGDSKSFTTTASGSSYQLKDTTRGNGIVTYTASNRQSIPGTILTDA

DNVWNDPAGVDAHAYAAKTYDYYKAKFGRNSIDGRGLQLRSTVHYGSRYN

NAFWNGSQMTYGDGDGSTFIAFSGDPDVVGHELTHGVTEYTSNLEYYGES

GALNEAFSDVIGNDIQRKNWLVGDDIYTPNIAGDALRSMSNPTLYDQPDH

YSNLYRGSSDNGGVHTNSGIINKAYYLLAQGGNFHGVTVNGIGRDAAVQI

YYSAFTNYLTSSSDFSNARAAVIQAAKDLYGANSAEATAAAKSFDAVGVN

Example 6.3

Proteolytic Activity of Metalloprotease PpoPro1

The proteolytic activity of purified PpoPro1 was measured in 50 mM Tris (pH 7), using azo-casein (Cat #74H7165, Megazyme) as a substrate. Prior to the reaction, the enzyme was diluted with Milli-Q water (Millipore) to specific concentrations. The azo-casein was dissolved in 100 mM Tris buffer (pH 7) to a final concentration of 1.5% (w/v). To initiate the reaction, 50 μL of the diluted enzyme (or Milli-Q H$_2$O alone as the blank control) was added to the non-binding 96-well microtiter Plate (96-MTP) (Corning Life Sciences, #3641) placed on ice, followed by the addition of 50 μL of 1.5% azo-casein. After sealing the 96-MTP, the reaction was carried out in a Thermomixer (Eppendorf) at 40° C. and 650 rpm for 10 min. The reaction was terminated by adding 100 μL of 5% Trichloroacetic Acid (TCA). Following equilibration (5 min at the room temperature) and subsequent centrifugation (2000 g for 10 min at 4° C.), 120 μL supernatant was transferred to a new 96-MTP, and absorbance of the supernatant was measured at 440 nm (A$_{440}$) using a SpectraMax 190. Net A$_{440}$ was calculated by subtracting the A$_{440}$ of the blank control from that of enzyme, and then plotted against different protein concentrations (from 1.25 ppm to 40 ppm). Each value was the mean of duplicate assays, and the value varies no more than 5%. The proteolytic activity is shown as Net A$_{440}$. The proteolytic assay with azo-casein as the substrate (FIG. 6.2) indicates PpoPro1 is an active protease.

Example 4 pH Profile of Metalloprotease PpoPro1

With azo-casein as the substrate, the pH profile of PpoPro1 was studied in 12.5 mM acetate/Bis-Tris/HEPES/CHES buffer with different pH values (ranging from pH 4 to 11). To initiate the assay, 50 μL of 25 mM acetate/Bis-Tris/HEPES/CHES buffer with a specific pH was first mixed with 2 μL diluted enzyme (250 ppm in Milli-Q H$_2$O) in a 96-MTP placed on ice, followed by the addition of 48 μL of 1.5% (w/v) azo-casein prepared in H$_2$O. The reaction was performed and analyzed as described in Example 6.3. Enzyme activity at each pH was reported as relative activity where the activity at the optimal pH was set to be 100%. The pH values tested were 4, 5, 6, 7, 8, 9, 10 and 11. Each value was the mean of triplicate assays. As shown in FIG. 6.3, the optimal pH of PpoPro1 is about 7, with greater than 70% of maximal activity retained between 5.5 and 8.5.

Example 6.5

Temperature Profile of Metalloprotease PpoPro1

The temperature profile of PpoPro1 was analyzed in 50 mM Tris buffer (pH 7) using the azo-casein assay. The enzyme sample and azo-casein substrate were prepared as in Example 6.3. Prior to the reaction, 50 μL of 1.5% azo-casein and 45 μl Milli-Q H$_2$O were mixed in a 200 μL PCR tube, which was then subsequently incubated in a Peltier Thermal Cycler (BioRad) at desired temperatures (i.e. 20-90° C.) for 5 min. After the incubation, 5 μL of diluted PpoPro1 (100 ppm) or H$_2$O (the blank control) was added to the substrate mixture, and the reaction was carried out in the Peltier Thermal Cycle for 10 min at different temperatures. To terminate the reaction, each assay mixture was transferred to a 96-MTP containing 100 μL of 5% TCA per well. Subsequent centrifugation and absorbance measurement were performed as described in Example 6.3. The activity was reported as relative activity where the activity at the optimal temperature was set to be 100%. The tested temperatures were 20, 30, 40, 50, 60, 70, 80, and 90° C. Each value was the mean of duplicate assays (the value varies no more than 5%). The data in FIG. 6.4 suggests that PpoPro1 showed an optimal temperature at 50° C., and retained greater than 70% of its maximum activity between 40 and 55° C.

Example 6.6

Cleaning Performance of Metalloprotease PpoPro1

The cleaning performance of PpoPro1 was tested using PA-S-38 (egg yolk, with pigment, aged by heating) microswatches (CFT-Vlaardingen, The Netherlands) at pH 6 or 8 using a model automatic dishwashing (ADW) detergent (AT detergent). Prior to the reaction, purified PpoPro1 was diluted with a dilution solution containing 10 mM NaCl, 0.1 mM $CaCl_2$, 0.005% TWEEN® 80 and 10% propylene glycol to the desired concentrations. The reactions were performed in AT detergent (composition shown in Table 6.1) with 100 ppm water hardness ($Ca^{2+}$: $Mg^{2+}$=3:1), in the presence of a bleach component ((Peracid NN-phthaloylaminoperoxycaproic acid-PAP). To initiate the reaction, 180 μL of AT detergent buffered at pH 6 or 8 was added to a 96-MTP placed with PA-S-38 microswatches, followed by the addition of 20 μL of diluted enzymes (or the dilution solution as the blank control). The 96-MTP was sealed and incubated in an incubator/shaker for 30 min at 50° C. and 1150 rpm. After incubation, 100 μL of wash liquid from each well was transferred to a new 96-MTP, and its absorbance was measured at 405 nm (referred here as the "Initial performance") using a spectrophotometer. The remaining wash liquid in the 96-MTP was discarded and the microswatches were rinsed once with 200 μL water. Following the addition of 180 μL of 0.1 M CAPS buffer (pH 10), the second incubation was carried out in the incubator/shaker at 50° C. and 1150 rpm for 10 min. One hundred microliter of the resulting wash liquid was transferred to a new 96-MTP, and its absorbance measured at 405 nm (referred here as "Wash-off"). The sum of two absorbance measurements ("Initial performance" plus "Wash-off") gives the "Total performance", which measures the protease activity on the model stain; and Net $A_{405}$ was subsequently calculated by subtracting the $A_{405}$ of the "Total performance" of the blank control from that of the enzyme. Dose response in cleaning the PA-S-38 microswatches at pH 6 and pH 8 for PpoPro1 in AT dish detergent, in the presence of bleach, is shown in FIGS. 6.5A and 6.5B.

TABLE 6.1

Composition of AT dish detergent formula with bleach

| Ingredient | Concentration (mg/ml) |
|---|---|
| MGDA (methylglycinediacetic acid) | 0.143 |
| Sodium citrate | 1.86 |
| Citric acid* | varies |
| PAP (peracid N,N-phthaloylaminoperoxycaproic acid) | 0.057 |
| Plurafac ® LF 18B (a non-ionic surfactant) | 0.029 |
| Bismuthcitrate | 0.006 |
| Bayhibit ® S (Phosphonobutantricarboxylic acid sodium salt) | 0.006 |
| Acusol ™ 587 (a calcium polyphosphate inhibitor) | 0.029 |
| PEG 6000 | 0.043 |
| PEG 1500 | 0.1 |

*The pH of the AT formula detergent is adjusted to the desired value (pH 6 or 8) by the addition of 0.9M citric acid.

Example 6.7

Comparison of PpoPro1 to Other Metalloproteases

Identification of Homologous Proteases

Homologs were identified by a BLAST search (Altschul et al., Nucleic Acids Res, 25:3389-402, 1997) against the NCBI non-redundant protein database and the Genome Quest Patent database with search parameters set to default values. The predicted mature protein amino acid sequence for PpoPro1 (SEQ ID NO: 28) was used as the query sequence. Percent identity (PID) for both search sets is defined as the number of identical residues divided by the number of aligned residues in the pairwise alignment. Tables 6.2A and 6.2B provide a list of sequences with the percent identity to PpoPro1. The length in Table 6.2 refers to the entire sequence length of the homologous proteases.

TABLE 6.2A

List of sequences with percent identity to PpoPro1 protein identified from the NCBI non-redundant protein database

| Accession | PID to PpoPro1 | Organism | Length |
|---|---|---|---|
| P00800 | 56 | Bacillus thermoproteolyticus | 548 |
| ZP_08640523.1 | 57 | Brevibacillus laterosporus LMG 15441 | 564 |
| AAA22623.1 | 57 | Bacillus caldolyticus | 544 |
| ZP_08093424.1 | 59 | Planococcus donghaensis MPA1U2 | 553 |
| ZP_10738945.1 | 60 | Brevibacillus sp. CF112 | 528 |
| CAA43589.1 | 62 | Brevibacillus brevis | 527 |
| ZP_02326503.1 | 62 | Paenibacillus larvae subsp. larvae BRL-230010 | 520 |
| YP_005495105.1 | 63 | Bacillus megaterium WSH-002 | 562 |
| YP_001373863.1 | 64 | Bacillus cytotoxicus NVH 391-98 | 565 |
| ZP_04310163.1 | 64 | Bacillus cereus BGSC 6E1 | 581 |
| BAA06144.1 | 64 | Lactobacillus sp. | 566 |
| ZP_08511445.1 | 65 | Paenibacillus sp. HGF7 | 525 |
| ZP_04216147.1 | 65 | Bacillus cereus Rock3-44 | 566 |
| ZP_09071078.1 | 68 | Paenibacillus larvae subsp. larvae B-3650 | |
| ZP_09077634.1 | 69 | Paenibacillus elgii B69 | 524 |
| YP_005073224.1 | 79 | Paenibacillus terrae HPL-003 | 595 |
| ZP_10241029.1 | 80 | Paenibacillus peoriae KCTC 3763 | 599 |
| YP_005073223.1 | 93 | Paenibacillus terrae HPL-003 | 591 |
| ZP_10241030.1 | 95 | Paenibacillus peoriae KCTC 3763 | 593 |
| ZP_09775364.1 | 95 | Paenibacillus sp. Aloe-11 | 593 |
| YP_003872179.1 | 97 | Paenibacillus polymyxa E681 | 592 |
| YP_003948511.1 | 100 | Paenibacillus polymyxa SC2 | 592 |

TABLE 6.2B

List of sequences with percent identity to PpoPro1 protein identified from the Genome Quest Patent database

| Patent # | PID to PpoPro1 | Organism | Length |
|---|---|---|---|
| US20120107907-0187 | 97.34 | Bacillus polymyxa | 302 |
| US5962264-0004 | 65.48 | empty | 566 |
| WO2012110563-0005 | 65.16 | Bacillus cereus | 320 |
| JP1994070791-0002 | 64.52 | empty | 317 |
| WO2012110562-0005 | 64.19 | Bacillus cereus | 320 |
| WO2012110563-0004 | 63.34 | Bacillus megaterium | 320 |
| JP2002272453-0002 | 61.98 | Bacillus megaterium | 562 |
| WO2004011619-0047 | 61.49 | empty | 532 |
| EP2390321-0186 | 62.58 | Bacillus brevis | 304 |
| US6518054-0002 | 59.22 | Bacillus sp. | 316 |
| US6518054-0001 | 58.52 | Bacillus sp. | 319 |
| US20120107907-0176 | 58.52 | Bacillus stearothermophilis | 548 |
| JP2005229807-0019 | 93.05 | Paenibacillus polymyxa | 566 |
| WO2012110562-0003 | 58.2 | Geobacillus stearothermophilus | 319 |
| WO2004011619-0044 | 59.27 | empty | 507 |
| EP2390321-0185 | 66.13 | Bacillus cereus | 317 |
| JP1995184649-0001 | 65.71 | Lactobacillus sp. | 566 |
| EP2178896-0184 | 65.38 | Bacillus anthracis | 566 |

Alignment of Homologous Protease Sequences

The amino acid sequence of predicted mature PpoPro1 (SEQ ID NO: 28) was aligned with thermolysin (P00800, Bacillus thermoproteolyticus) and protease from Paenibacillus polymyxa SC2 (YP_003948511.1) using CLUSTALW software (Thompson et al., Nucleic Acids Research, 22:4673-4680, 1994) with the default parameters. FIG. 6.6 shows the alignment of PpoPro1 with these protease sequences.

Phylogenetic Tree

A phylogenetic tree for precursor PpoPro1 (SEQ ID NO: 27) was built using sequences of representative homologs from Tables 6.2A and the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 6.7.

Example 7.1

Cloning of *Paenibacillus* Hunanensis Metalloprotease PhuPro1

A strain (DSM22170) of *Paenibacillus* hunanensis was selected as a potential source of enzymes which may be useful in various industrial applications. Genomic DNA for sequencing was obtained by first growing the strain on Heart Infusion agar plates (Difco) at 37° C. for 24 hr. Cell material was scraped from the plates and used to prepare genomic DNA with the ZF Fungal/Bacterial DNA miniprep kit from Zymo (Cat No. D6005). The genomic DNA was used for genome sequencing. The entire genome of the *Paenibacillus* hunanensis strain was sequenced by BaseClear (Leiden, The Netherlands) using the Illumina's next generation sequencing technology. After assembly of the data, contigs were annotated by BioXpr (Namur, Belgium). One of the genes identified after annotation in *Paenibacillus* hunanensis encodes a metalloprotease and the sequence of this gene, called PhuPro1, is provided in SEQ ID NO: 31. This gene has an alternative start codon (TTG). The corresponding protein encoded by the PhuPro1 gene is shown in SEQ ID NO: 32. At the N-terminus, the protein has a signal peptide with a length of 23 amino acids as predicted by SignalP version 4.0 (Nordahl Petersen et al. (2011) Nature Methods, 8:785-786). The presence of a signal sequence suggests that PhuPro1 is a secreted enzyme. The propeptide region was predicted based on protein sequence alignment with the *Paenibacillus polymyxa* Npr protein (Takekawa et al. (1991) Journal of Bacteriology, 173 (21): 6820-6825). The predicted mature region of PhuPro1 protein is shown in SEQ ID NO: 33.

The nucleotide sequence of the PhuPro1 gene isolated from *Paenibacillus hunanensis* is set forth as SEQ ID NO: 31. The sequence encoding the predicted native signal peptide is shown in italics:

*TTGAAAAAAACAGTTGGTCTTTTACTTGCAGGTAGCTTGCTCGTTGGTGC*

*TACAACGTCCGCTTTCGCAGCAGAAGCAAATGATCTGGCACCACTCGGTG*

ATTACACGCCAAAATTGATTACGCAAGCAACAGGCATCACTGGCGCTAGT

GGCGATGCTAAAGTATGGAAGTTCCTGGAGAAGCAAAAACGTACCATCGT

AACCGATGATGCAGCTTCTGCTGATGTGAAGGAATTGTTTGAGATCACAA

AACGTCAATCCGATTCTCAAACCGGTACAGAGCACTATCGCCTGAACCAA

ACCTTTAAAGGCATCCCAGTCTATGGCGCAGAGCAAACACTGCACTTTGA

CAAATCCGGCAATGTATCTCTGTACATGGGTCAGGTTGTTGAGGATGTGT

CCGCTAAACTGGAAGCTTCCGATTCCAAAAAAGGCGTAACTGAGGATGTA

TACGCTTCGGATACGAAAAATGATCTGGTAACACCAGAAATCAGCGCTTC

TCAAGCCATCTCGATTGCTGAAAAGGATGCAGCTTCCAAAATCGGCTCCC

TCGGCGAAGCACAAAAAACGCCAGAAGCGAAGCTGTATATCTACGCTCCT

GAGGATCAAGCAGCACGTCTGGCTTATGTGACAGAAGTAAACGTACTGGA

GCCATCTCCGCTGCGTACTCGCTATTTTGTAGATGCAAAAACAGGTTCGA

TCCTGTTCCAATATGATCTGATTGAGCATGCAACAGGTACAGGTAAAGGG

GTACTGGGTGATACCAAGTCCTTCACTGTAGGTACTTCCGGTTCTTCCTA

TGTGATGACTGATAGCACGCGTGGAAAAGGTATCCAAACCTACACGGCGT

CTAACCGCACATCACTGCCAGGTAGCACTGTAACGAGCAGCAGCAGCACA

TTTAACGATCCAGCATCTGTCGATGCCCATGCGTATGCACAAAAAGTATA

TGATTTCTACAAATCCAACTTTAACCGCAACAGCATCGACGGTAATGGTC

TGGCTATCCGCTCCACTACGCACTATTCCACACGTTATAACAATGCGTTC

TGGAATGGTTCCCAAATGGTATACGGTGATGGCGATGGTTCGCAATTCAT

CGCATTCTCCGGCGACCTTGACGTAGTAGGTCACGAGCTGACACACGGTG

TAACCGAGTACACAGCGAACCTGGAATACTATGGTCAATCCGGTGCACTG

AACGAATCCATTTCGGATATCTTTGGTAACACAATCGAAGGTAAAAACTG

GATGGTAGGCGATGCGATCTACACACCAGGCGTATCCGGCGATGCTCTTC

GCTACATGGATGATCCAACAAAAGGTGGACAACCAGCGCGTATGGCAGAT

TACAACAACACAAGCGCTGATAATGGCGGTGTACACACAAACAGTGGTAT

CCCGAATAAAGCATACTACTTGCTGGCACAGGGTGGCACATTTGGCGGTG

TAAATGTAACAGGTATCGGTCGCTCGCAAGCGATCCAGATCGTTTACCGT

GCACTAACATACTACCTGACATCCACATCTAACTTCTCGAACTACCGTTC

TGCAATGGTGCAAGCATCTACAGACCTGTACGGTGCAAACTCTACACAA

CAACAGCGGTGAAAAACTCGCTGAGCGCAGTAGGCATTAAC

The amino acid sequence of the PhuPro1 precursor protein is set forth as SEQ ID NO: 32. The predicted signal sequence is shown in italics, and the predicted pro-peptide is shown in underlined text:

*MKKTVGLLLAGSLLVGATTSAFA*<u>AEANDLAPLGDYTPKLITQATGITGAS</u>

<u>GDAKVWKFLEKQKRTIVTDDAASADVKELFEITKRQSDSQTGTEHYRLNQ</u>

<u>TFKGIPVYGAEQTLHFDKSGNVSLYMGQVVEDVSAKLEASDSKKGVTEDV</u>

<u>YASDTKNDLVTPEISASQAISIAEKDAASKIGSLGEAQKTPEAKLYIYAP</u>

<u>EDQAARLAYVTEVNVLEPSPLRTRYFVDAKTGSILFQYDLIEHATGTGKG</u>

VLGDTKSFTVGTSGSSYVMTDSTRGKGIQTYTASNRTSLPGSTVTSSSST

FNDPASVDAHAYAQKVYDFYKSNFNRNSIDGNGLAIRSTTHYSTRYNNAF

WNGSQMVYGDGDGSQFIAFSGDLDVVGHELTHGVTEYTANLEYYGQSGAL

NESISDIFGNTIEGKNWMVGDAIYTPGVSGDALRYMDDPTKGGQPARMAD

YNNTSADNGGVHTNSGIPNKAYYLLAQGGTFGGVNVTGIGRSQAIQIVYR

ALTYYLTSTSNFSNYRSAMVQASTDLYGANSTQTTAVKNSLSAVGIN

The amino acid sequence of the predicted mature form of PhuPro1 is set forth as SEQ ID NO: 33:

ATGTGKGVLGDTKSFTVGTSGSSYVMTDSTRGKGIQTYTASNRTSLPGST
VTSSSSTFNDPASVDAHAYAQKVYDFYKSNFNRNSIDGNGLAIRSTTHYS
TRYNNAFWNGSQMVYGDGDGSQFIAFSGDLDVVGHELTHGVTEYTANLEY
YGQSGALNESISDIFGNTIEGKNWMVGDAIYTPGVSGDALRYMDDPTKGG
QPARMADYNNTSADNGGVHTNSGIPNKAYYLLAQGGTFGGVNVTGIGRSQ
AIQIVYRALTYYLTSTSNFSNYRSAMVQASTDLYGANSTQTTAVKNSLSA
VGIN

Example 7.2

Expression of *Paenibacillus* Hunanensis Metalloprotease PhuPro1

The DNA sequence of the propeptide-mature form of PhuPro1 was synthesized and inserted into the *Bacillus subtilis* expression vector p2JM103BBI (Vogtentanz, *Protein Expr Purif*, 55:40-52, 2007) by Generay (Shanghai, China), resulting in plasmid pGX149(AprE-PhuPro1) (FIG. 7.1). Ligation of this gene encoding the PhuPro1 protein into the digested vector resulted in the addition of three codons (Ala-Gly-Lys) between the 3' end of the *B. subtilis* AprE signal sequence and the 5' end of the predicted PhuPro1 native propeptide. The gene has an alternative start codon (GTG). The resulting plasmid shown in FIG. 1, labeled pGX149(AprE-PhuPro1) contains an AprE promoter, an AprE signal sequence used to direct target protein secretion in *B. subtilis*, and the synthetic nucleotide sequence encoding the predicted propeptide and mature regions of PhuPro1 (SEQ ID NO: 34). The translation product of the synthetic AprE-PhuPro1 gene is shown in SEQ ID NO: 35.

The pGX149(AprE-PhuPro1) plasmid was then transformed into *B. subtilis* cells (degU$^{Hy}$ 32, ΔscoC) and the transformed cells were spread on Luria Agar plates supplemented with 5 ppm Chloramphenicol and 1.2% skim milk (Cat #232100, Difco). Colonies with the largest clear halos on the plates were selected and subjected to fermentation in a 250 ml shake flask with MBD medium (a MOPS based defined medium, supplemented with additional 5 mM CaCl$_2$).

The broth from the shake flasks was concentrated and buffer-exchanged into the loading buffer containing 20 mM Tris-HCl (pH 8.5), 1 mM CaCl$_2$ and 10% propylene glycol using a VivaFlow 200 ultra filtration device (Sartorius Stedim). After filtering, this sample was applied to a 80 ml Q Sepharose High Performance column pre-equilibrated with the loading buffer above; and the active flow-through fractions were collected and concentrated via 10K Amicon Ultra for further analyses.

The nucleotide sequence of the synthesized PhuPro1 gene in plasmid pGX149(AprE-PhuPro1) is depicted in SEQ ID NO: 34. The sequence encoding the three residue addition (AGK) is shown in bold:

GTGAGAAGCAAAAAATTGTGGATCAGCTTGTTGTTTGCGTTAACGTTAAT
CTTTACGATGGCGTTCAGCAACATGAGCGCGCAGGCTGCTGGAAAAGCAG
AAGCTAATGATCTTGCCCCGCTTGGCGATTATACACCGAAGCTTATTACA
CAGGCAACGGGAATTACAGGCGCATCAGGCGATGCGAAGGTGTGGAAGTT
CCTGGAGAAGCAGAAGAGAACGATTGTCACGGACGACGCCGCAAGCGCGG
ATGTCAAGGAGCTGTTCGAGATCACGAAGAGACAGAGCGATAGCCAGACG
GGAACGGAGCATTACAGACTGAACCAGACGTTCAAGGGCATTCCGGTCTA
CGGGAGCTGAACAAACGCTGCATTTTGATAAAAGCGGCAACGTCTCACTGT
ACATGGGCCAAGTCGTTGAGGACGTTAGCGCCAAACTTGAGGCTAGCGAC
AGCAAGAAAGGCGTCACAGAAGATGTCTACGCGTCAGACACGAAAAACGA
CCTGGTTACACCGGAAATCTCAGCTTCACAGGCCATCTCAATTGCAGAGA
AAGACGCAGCGTCAAAAATCGGCTCACTGGGCGAGGCTCAGAAAACGCCG
GAGGCGAAACTTTACATCTACGCCCCTGAGGACCAGGCTGCGAGACTGGC
TTACGTGACAGAAGTTAATGTGCTGGAGCCGTCACCGCTTAGAACGAGAT
ATTTCGTGGACGCAAAGCAGGGCAGCATTCTGTTTCAGTACGATCTTATC
GAACACGCGACAGGCACAGGAAAGGGAGTTCTGGGAGACACAAAAAGCTT
CACGGTTGGCACGTCAGGCAGCAGCTACGTGATGACAGACAGCACGAGAG
GCAAGGGCATTCAAACGTATACAGCGAGCAACAGAACAAGCCTGCCGGGA
AGCACAGTCACGAGCTCATCATCAACGTTTAATGACCCGGCCTCAGTGGA
TGCTCACGCATACGCGCAGAAAGTGTACGACTTCTACAAAAGCAACTTCA
ATAGAAACAGCATCGACGGAAACGGCCTTGCGATCAGAAGCACGACGCAC
TACAGCACAAGATACAACAACGCCTTCTGGAACGGCAGCCAAATGGTTTA
CGGCGATGGCGACGGATCACAGTTTATCGCATTTAGCGGAGACCTGGACG
TCGTTGGCCATGAGCTGACACATGGCGTTACGGAGTACACAGCAAACCTG
GAATACTATGGCCAGTCAGGCGCCCTTAACGAGAGCATCAGCGACATTTT
TGGCAATACGATCGAAGGAAAGAACTGGATGGTCGGCGACGCAATCTACA
CACCCGGGCGTTTCAGGCGATGCACTGAGATATATGGACGACCCGACAAAG
GGCGGACAGCCGGCCAGAATGGCGGATTACAATAATACGTCAGCAGATAA
CGGCGGCGTGCATACAAATAGCGGCATCCCTAACAAAGCATATTACCTGC
TTGCGCAAGGAGGAACATTTGGCGGCGTGAATGTTACGGGCATTGGCAGA
TCACAAGCGATTCAGATCGTTTACAGAGCGCTGACGTACTACCTTACGAG
CACGAGCAATTTTAGCAACTACAGAAGCGCAATGGTGCAGGCAAGCACGG
ATCTGTATGGCGCAAATTCAACACAAACGACGGCGGTCAAGAATAGCCTT
TCAGCAGTGGGCATTAACTAA

The amino acid sequence of the PhuPro1 precursor protein expressed from plasmid pGX149(AprE-PhuPro1) is depicted in SEQ ID NO: 35. The predicted signal sequence is shown in italics, the three residue addition (AGK) is shown in bold, and the predicted pro-peptide is shown in underlined text.

*MRSKKLWISLLFALTLIFTMAFSNMSAQA*AGK<u>AEANDLAPLGDYTPKLIT</u>
<u>QATGITGASGDAKVWKFLEKQKRTIVTDDAASADVKELFEITKRQSDSQT</u>
<u>GTEHYRLNQTFKGIPVYGAEQTLHFDKSGNVSLYMGQVVEDVSAKLEASD</u>
<u>SKKGVTEDVYASDTKNDLVTPEISASQAISIAEKDAASKIGSLGEAQKTP</u>

-continued

EAKLYIYAPEDQAARLAYVTEVNVLEPSPLRTRYFVDAKTGSILFQYDLI

EHATGTGKGVLGDTKSFTVGTSGSSYVMTDSTRGKGIQTYTASNRTSLPG

STVTSSSSTFNDPASVDAHAYAQKVYDFYKSNFNRNSIDGNGLAIRSTTH

YSTRYNNAFWNGSQMVYGDGDGSQFIAFSGDLDVVGHELTHGVTEYTANL

EYYGQSGALNESISDIFGNTIEGKNWMVGDAIYTPGVSGDALRYMDDPTK

GGQPARMADYNNTSADNGGVHTNSGIPNKAYYLLAQGGTFGGVNVTGIGR

SQAIQIVYRALTYYLTSTSNFSNYRSAMVQASTDLYGANSTQTTAVKNSL

SAVGIN

Example 7.3

Proteolytic Activity of Metalloprotease PhuPro1

The proteolytic activity of purified metalloprotease PhuPro1 was measured in 50 mM Tris (pH 7), using azo-casein (Cat #74H7165, Megazyme) as a substrate. Prior to the reaction, the enzyme was diluted with Milli-Q water (Millipore) to specific concentrations. The azo-casein was dissolved in 100 mM Tris buffer (pH 7) to a final concentration of 1.5% (w/v). To initiate the reaction, 50 µl of the diluted enzyme (or Milli-Q $H_2O$ alone as the blank control) was added to the non-binding 96-well Microtiter Plate (96-MTP) (Corning Life Sciences, #3641) placed on ice, followed by the addition of 50 µl of 1.5% azo-casein. After sealing the 96-MTP, the reaction was carried out in a Thermomixer (Eppendorf) at 40° C. and 650 rpm for 10 min. The reaction was terminated by adding 100 µl of 5% Trichloroacetic Acid (TCA). Following equilibration (5 min at the room temperature) and subsequent centrifugation (2000 g for 10 min at 4° C.), 120 µl supernatant was transferred to a new 96-MTP, and absorbance of the supernatant was measured at 440 nm ($A_{440}$) using a SpectraMax 190. Net $A_{440}$ was calculated by subtracting the $A_{440}$ of the blank control from that of enzyme, and then plotted against different protein concentrations (from 1.25 ppm to 40 ppm). Each value was the mean of triplicate assays. The proteolytic activity is shown as Net A440. The proteolytic assay with azo-casein as the substrate (shown in FIG. 7.2) indicates that PhuPro1 is an active protease.

Example 7.4 pH Profile of Metalloprotease PhuPro1

With azo-casein as the substrate, the pH profile of metalloprotease PhuPro1 was studied in 12.5 mM acetate/Bis-Tris/HEPES/CHES buffer with different pH values (ranging from pH 4 to 11). To initiate the assay, 50 µl of 25 mM acetate/Bis-Tris/HEPES/CHES buffer with a specific pH was first mixed with 2 µl Milli-Q $H_2O$ diluted enzyme (125 ppm) in a 96-MTP placed on ice, followed by the addition of 48 µl of 1.5% (w/v) azo-casein prepared in $H_2O$. The reaction was performed and analyzed as described in Example 3. Enzyme activity at each pH was reported as the relative activity, where the activity at the optimal pH was set to be 100%. The pH values tested were 4, 5, 6, 7, 8, 9, 10 and 11. Each value was the mean of triplicate assays. As shown in FIG. 7.3, the optimal pH of PhuPro1 is about 6, with greater than 70% of maximal activity retained between 5 and 8.

Example 7.5

Temperature Profile of Metalloprotease PhuPro1

The temperature profile of metalloprotease PhuPro1 was analyzed in 50 mM Tris buffer (pH 7) using the azo-casein assays. The enzyme sample and azo-casein substrate were prepared as in Example 7.3. Prior to the reaction, 50 µl of 1.5% azo-casein and 45 µl Milli-Q $H_2O$ were mixed in a 200 µl PCR tube, which was then subsequently incubated in a Peltier Thermal Cycler (BioRad) at desired temperatures (i.e. 20-90° C.) for 5 min. After the incubation, 5 µl of diluted enzyme (50 ppm) or $H_2O$ (the blank control) was added to the substrate mixture, and the reaction was carried out in the Peltier Thermal Cycle for 10 min at different temperatures. To terminate the reaction, each assay mixture was transferred to a 96-MTP containing 100 µl of 5% TCA per well. Subsequent centrifugation and absorbance measurement were performed as described in Example 7.3. The activity was reported as the relative activity, where the activity at the optimal temperature was set to be 100%. The tested temperatures are 20, 30, 40, 50, 60, 70, 80, and 90° C. Each value was the mean of duplicate assays (the value varies no more than 5%). The data in FIG. 7.4 suggests that PhuPro1 showed an optimal temperature at 60° C., and retained greater than 70% of its maximum activity between 45 and 65° C.

Example 7.6

Cleaning Performance of Metalloprotease PhuPro1

The cleaning performance of PhuPro1 was tested using PA-S-38 (egg yolk, with pigment, aged by heating) microswatches (CFT-Vlaardingen, The Netherlands) at pH 6 and 8 using a model automatic dishwashing (ADW) detergent. Prior to the reaction, purified protease samples were diluted with a dilution solution containing 10 mM NaCl, 0.1 mM $CaCl_2$, 0.005% TWEEN® 80 and 10% propylene glycol to the desired concentrations. The reactions were performed in AT detergent with 100 ppm water hardness ($Ca^{2+}:Mg^{2+}=3:1$) (detergent composition shown in Table 7.1). To initiate the reaction, 180 µl of the AT detergent buffered at pH 6 or pH 8 was added to a 96-MTP placed with PA-S-38 microswatches, followed by the addition of 20 µl of diluted enzymes (or the dilution solution as the blank control). The 96-MTP was sealed and incubated in an incubator/shaker for 30 min at 50° C. and 1150 rpm. After incubation, 100 µl of wash liquid from each well was transferred to a new 96-MTP, and its absorbance was measured at 405 nm (referred here as the "Initial performance") using a spectrophotometer. The remaining wash liquid in the 96-MTP was discarded and the microswatches were rinsed once with 200 µl water. Following the addition of 180 µl of 0.1 M CAPS buffer (pH 10), the second incubation was carried out in the incubator/shaker at 50° C. and 1150 rpm for 10 min. One hundred microliters of the resulting wash liquid was transferred to a new 96-MTP, and its absorbance measured at 405 nm (referred here as the "Wash-off"). The sum of two absorbance measurements ("Initial performance" plus "Wash-off") gives the "Total performance", which measures the protease activity on the model stain; and Net $A_{405}$ was subsequently calculated by subtracting the $A_{405}$ of the "Total performance" of the blank control from that of the enzyme. Dose response in cleaning the PA-S-38 microswatches at pH 6 and pH 8 in AT detergent for PhuPro1 is shown in FIGS. 7.5A and 7.5B.

TABLE 7.1

Composition of AT detergent

| Ingredient | Concentration (mg/ml) |
| --- | --- |
| MGDA (methylglycinediacetic acid) | 0.143 |
| Sodium citrate | 1.86 |
| Citric acid* | varies |
| Plurafac ® LF 18B (a non-ionic surfactant) | 0.029 |
| Bismuthcitrate | 0.006 |
| Bayhibit ® S (Phosphonobutantricarboxylic acid sodium salt) | 0.006 |
| Acusol ™ 587 (a calcium polyphosphate inhibitor) | 0.029 |
| PEG 6000 | 0.043 |
| PEG 1500 | 0.1 |

*The pH of the AT formula detergent is adjusted to the desired value (pH 6 or 8) by the addition of 0.9M citric acid.

Example 7.7

Comparison of PhuPro1 to Other Proteases

A. Identification of Homologous Proteases

Homologs were identified by a BLAST search (Altschul et al., Nucleic Acids Res, 25:3389-402, 1997) against the NCBI non-redundant protein database and the Genome Quest Patent database with search parameters set to default values. The predicted mature protein amino acid sequence for PhuPro1 (SEQ ID NO: 33) was used as the query sequence. Percent identity (PID) for both search sets is defined as the number of identical residues divided by the number of aligned residues in the pairwise alignment. Tables 7.2A and 7.2B provide a list of sequences with the percent identity to PhuPro1. The length in Table 7.2 refers to the entire sequence length of the homologous proteases.

TABLE 7.2A

List of sequences with percent identity to PhuPro1 protein identified from the NCBI non-redundant protein database

| Accession # | PID to PhuPro1 | Organism | Length |
| --- | --- | --- | --- |
| P00800 | 55 | Bacillus thermoproteolyticus | 548 |
| AAB02774.1 | 55 | Geobacillus stearothermophilus | 552 |
| EJS73098.1 | 56 | Bacillus cereus BAG2X1-3 | 566 |
| BAD60997.1 | 56 | Bacillus megaterium | 562 |
| ZP_04216147.1 | 57 | Bacillus cereus Rock3-44 | 566 |
| YP_893436.1 | 56 | Bacillus thuringiensis str. Al Hakam | 566 |
| ZP_08640523.1 | 58 | Brevibacillus laterosporus | 564 |
| ZP_09069194.1 | 59 | Paenibacillus larvae subsp. larvae B-3650 | 502 |
| YP_002770810.1 | 60 | Brevibacillus brevis | 528 |
| ZP_08511445.1 | 61 | Paenibacillus sp. HGF7 | 525 |
| P43263 | 61 | Brevibacillus brevis | 527 |
| ZP_09775365.1 | 62 | Paenibacillus sp. Aloe-11 | 580 |
| ZP_09077634.1 | 66 | Paenibacillus elgii B69 | 524 |
| P29148 | 68 | NPRE_PAEPO | 590 |
| ZP_09775364.1 | 69 | Paenibacillus sp. Aloe-11 | 593 |
| ZP_10241030.1 | 69 | Paenibacillus peoriae KCTC 3763 | 593 |
| YP_005073223.1 | 69 | Paenibacillus terrae HPL-003 | 591 |

TABLE 7.2B

List of sequences with percent identity to PhuPro1 protein identified from the Genome Quest Patent database

| Patent ID # | PID to PhuPro1 | Organism | Length |
| --- | --- | --- | --- |
| WO2012110562-0003 | 56.23 | Geobacillus stearothermophilus | 319 |
| US6518054-0001 | 56.55 | Bacillus sp. | 319 |
| JP2002272453-0002 | 56.69 | Bacillus megaterium | 562 |
| US20090123467-0184 | 56.73 | Bacillus anthracis | 566 |
| US6103512-0003 | 56.87 | | 319 |
| EP0867512-0002 | 56.96 | | 316 |
| WO2012110562-0005 | 57.1 | Bacillus cereus | 320 |
| WO2012110563-0005 | 58.06 | Bacillus cereus | 320 |
| US20120107907-0187 | 68.44 | Bacillus polymyxa | 302 |

B. Alignment of Homologous Protease Sequences

The amino acid sequence of predicted mature PhuPro1 (SEQ ID NO: 33) protein was aligned with Proteinase T (P00800, Bacillus thermoproteolyticus), and protease from Paenibacillus terrae HPL-003 (YP_005073223.1) using CLUSTALW software (Thompson et al., Nucleic Acids Research, 22:4673-4680, 1994) with the default parameters. FIG. 7.6 shows the alignment of PhuPro1 with these protease sequences.

C. Phylogenetic Tree

A phylogenetic tree for full length sequence of PhuPro1 (SEQ ID NO: 2) was built using sequences of representative homologs from Table 2A and the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 7.7.

Example 7.8

Terg-o-Tometer Performance Evaluation of PhuPro1

The wash performance of PhuPro1 was tested in a laundry detergent application using a Terg-o-Tometer (Instrument Marketing Services, Inc, Fairfield, N.J.). The performance evaluation was conducted at 32° C. and 16° C. The soil load consisted of two of each of the following stain swatches: EMPA116 Blood, Milk, Ink on cotton (Test materials AG, St. Gallen, Switzerland), EMPA117 Blood, Milk, Ink on polycotton (Test materials AG, St. Gallen, Switzerland), EMPA112 Cocoa on cotton (Test materials AG, St. Gallen, Switzerland), and CFT C-10 Pigment, Oil, and Milk content on cotton (Center for Testmaterials BV, Vlaardingen, Netherlands), plus extra white interlock knit fabric to bring the total fabric load to 40 g per beaker of the Terg-o-Tometer, which was filled with 1 L of deionized water. The water hardness was adjusted to 6 grains per gallon, and the pH in the beaker was buffered with 5 mM HEPES, pH 8.2. Heat inactivated Tide Regular HDL (Proctor & Gamble), a commercial liquid detergent purchased in a local US supermarket, was used at 0.8 g/L. The detergent was inactivated before use by treatment at 92° C. in a water bath for 2-3 hours followed by cooling to room temperature. Heat inactivation of commercial detergents serves to destroy the activity of enzymatic components while retaining the properties of the non-enzymatic components. Enzyme activity in the heat inactivated detergent was measured using the Suc-AAPF-pNA assay for measuring protease activity. The Purafect® Prime HA, (Genencor Int'l) and PhuPro1 proteases were each added to final concentrations of 1 ppm. A control sample with no enzyme was included. The wash time was 12 minutes. After the wash treatment, all swatches were rinsed for 3 minutes and machine-dried at low heat.

Four of each type of swatch were measured before and after treatment by optical reflectance using a Tristimulus Minolta Meter CR-400. The difference in the L, a, b values was converted to total color difference (dE), as defined by the CIE-LAB color space. Cleaning of the stains is expressed as percent stain removal index (% SRI) by taking a ratio between the color difference before and after washing, and comparing it to the difference of unwashed soils (before wash) to unsoiled fabric, and averaging the eight values obtained by reading two different regions of each washed swatch. Cleaning performances of PhuPro1 and Purafect® Prime HA proteases at 32° C. are shown in Tables 7.8A and FIG. 7.8A and at 16° C. are shown in Table 7.8B and FIG. 7.8B.

TABLE 7.8A

Cleaning performance of PhuPro1 at 32° C.

| ppm enzyme | Purafect Prime HA | | PhuPro1 | | Purafect Prime HA | | PhuPro1 | |
| --- | --- | --- | --- | --- | --- | --- | --- | --- |
| | Average % SRI (dE) | 95CI [% SRI (dE)] | Average % SRI (dE) | 95CI [% SRI (dE)] | Average % SRI (dE) | 95CI [% SRI (dE)] | Average % SRI (dE) | 95CI [% SRI (dE)] |
| | EMPA-116 | | | | EMPA-117 | | | |
| 0 | 0.25 | 0.02 | 0.25 | 0.02 | 0.19 | 0.02 | 0.19 | 0.02 |
| 0.2 | 0.31 | 0.02 | 0.31 | 0.01 | 0.31 | 0.03 | 0.32 | 0.04 |
| 0.5 | 0.34 | 0.02 | 0.33 | 0.03 | 0.34 | 0.02 | 0.37 | 0.02 |
| 1 | 0.35 | 0.03 | 0.36 | 0.02 | 0.38 | 0.03 | 0.42 | 0.03 |
| 1.5 | 0.36 | 0.02 | 0.37 | 0.03 | 0.35 | 0.03 | 0.43 | 0.03 |
| | EMPA-112 | | | | CFT C-10 | | | |
| 0 | 0.15 | 0.03 | 0.15 | 0.03 | 0.07 | 0.01 | 0.07 | 0.01 |
| 0.2 | 0.17 | 0.04 | 0.14 | 0.02 | 0.11 | 0.01 | 0.15 | 0.01 |
| 0.5 | 0.19 | 0.02 | 0.19 | 0.04 | 0.13 | 0.01 | 0.16 | 0.03 |
| 1 | 0.20 | 0.03 | 0.22 | 0.03 | 0.17 | 0.01 | 0.17 | 0.01 |
| 1.5 | 0.24 | 0.03 | 0.25 | 0.04 | 0.17 | 0.02 | 0.20 | 0.02 |

TABLE 7.8B

Cleaning performance of PhuPro1 at 16° C.

| ppm enzyme | Purafect Prime HA | | PhuPro1 | | Purafect Prime HA | | PhuPro1 | |
| --- | --- | --- | --- | --- | --- | --- | --- | --- |
| | CAverage % SRI (dE) | 95CI [% SRI (dE)] | Average % SRI (dE) | 95CI [% SRI (dE)] | Average % SRI (dE) | 95CI [% SRI (dE)] | Average % SRI (dE) | 95CI [% SRI (dE)] |
| | EMPA-116 | | | | EMPA-117 | | | |
| 0 | 0.14 | 0.02 | 0.14 | 0.02 | 0.12 | 0.01 | 0.12 | 0.01 |
| 0.2 | 0.19 | 0.02 | 0.17 | 0.03 | 0.17 | 0.02 | 0.14 | 0.03 |
| 0.5 | 0.22 | 0.03 | 0.28 | 0.04 | 0.20 | 0.03 | 0.22 | 0.01 |
| 1 | 0.24 | 0.02 | 0.26 | 0.02 | 0.20 | 0.01 | 0.24 | 0.04 |
| 1.5 | 0.23 | 0.03 | 0.26 | 0.03 | 0.23 | 0.02 | 0.25 | 0.02 |
| | EMPA-112 | | | | CFT C-10 | | | |
| 0 | 0.09 | 0.03 | 0.09 | 0.03 | 0.07 | 0.01 | 0.07 | 0.01 |
| 0.2 | 0.07 | 0.01 | 0.09 | 0.02 | 0.08 | 0.02 | 0.06 | 0.01 |
| 0.5 | 0.11 | 0.02 | 0.12 | 0.03 | 0.10 | 0.01 | 0.09 | 0.01 |
| 1 | 0.11 | 0.02 | 0.12 | 0.02 | 0.13 | 0.01 | 0.15 | 0.01 |
| 1.5 | 0.13 | 0.03 | 0.19 | 0.03 | 0.13 | 0.01 | 0.11 | 0.01 |

TABLE 7.8B-continued

Cleaning performance of PhuPro1 at 16° C.

| | Purafect Prime HA | | PhuPro1 | | Purafect Prime HA | | PhuPro1 | |
|---|---|---|---|---|---|---|---|---|
| ppm enzyme | CAverage % SRI (dE) | 95CI [% SRI (dE)] | Average % SRI (dE) | 95CI [% SRI (dE)] | Average % SRI (dE) | 95CI [% SRI (dE)] | Average % SRI (dE) | 95CI [% SRI (dE)] |

Example 8.1

Cloning of *Paenibacillus amylolyticus* Metalloprotease PamPro1

A strain (DSM11747) of *Paenibacillus amylolyticus* was selected as a potential source of enzymes which may be useful in various industrial applications. Genomic DNA for sequencing was obtained by first growing the strain on Heart Infusion agar plates (Difco) at 37° C. for 24 hr. Cell material was scraped from the plates and used to prepare genomic DNA with the ZF Fungal/Bacterial DNA miniprep kit from Zymo (Cat No. D6005). The genomic DNA was used for genome sequencing. The entire genome of the *Paenibacillus amylolyticus* strain was sequenced by BaseClear (Leiden, The Netherlands) using the Illumina's next generation sequencing technology. After assembly of the data, contigs were annotated by BioXpr (Namur, Belgium). One of the genes identified after annotation in *Paenibacillus amylolyticus* encodes a metalloprotease and the sequence of this gene, called PamPro1, is provided in SEQ ID NO: 36. The corresponding protein encoded by the PamPro1 gene is shown in SEQ ID NO: 37. At the N-terminus, the protein has a signal peptide with a length of 25 amino acids as predicted by SignalP version 4.0 (Nordahl Petersen et al. (2011) Nature Methods, 8:785-786). The presence of a signal sequence suggests that PamPro1 is a secreted enzyme. The propeptide region was predicted based on protein sequence alignment with the *Paenibacillus polymyxa* Npr protein (Takekawa et al. (1991) Journal of Bacteriology, 173 (21): 6820-6825). The predicted mature region of PamPro1 protein is shown in SEQ ID NO: 3.

The nucleotide sequence of the PamPro1 gene isolated from *Paenibacillus amylolyticus* is set forth as SEQ ID NO: 36. The sequence encoding the predicted native signal peptide is shown in italics:

```
ATGAAATTCGCCAAAGTTATGCCAACAATTCTTGGAGGAGCTCTTTTGCT

CGCTTCCGTATCCTCTGCTACTGCAGCTCCAGTGTCTGATCAATCCATTC

CACTTCAGGCCCCTTATGCCTCTGAGGGGGGTATTCCATTGAACAGTGGA

ACAGATGACACTATCTTTAATTATCTTGGACAGCAGGAACAATTTCTGAA

TTCCGATGTGAAATCCCAGCTCAAAATTGTCAAAAGAAACACAGATACAT

CTGGCGTAAGACACTTCCGCCTGAAACAGTATATTAAAGGTATCCCGGTT

TATGGTGCAGAACAGACGGTCCACCTGGACAAAACCGGAGCCGTGAGCTC

CGCACTTGGCGATCTTCCACCGATTGAAGAGCAGGCCATTCCGAATGATG

GTGTAGCCGAGATCAGCGGAGAAGACGCGATCCAGATTGCAACCGAAGAA

GCAACCTCCCGGATTGGAGAGCTTGGTGCCGCGGAAATCACGCCTCAAGC
```

```
TGAATTGAACATCTATCATCATGAAGAAGATGGTCAGACATATCTGGTTT

ACATTACGGAAGTAAACGTACTGGAACCTGCCCCTCTACGGACCAAATAT

TTCATTAACGCAGTGGATGGCAGTATCGTATCCCAGTTTGACCTCATTAA

CTTCGCTACTGGAACAGGTACAGGTGTACTCGGTGATACCAAAACCCTGA

CAACCACCCAATCCGGCAGCACCTTCCAACTGAAAGACACCACTCGTGGC

AATGGCATCCAAACGTATACGGCAAACAATGGCTCCTCACTGCCTGGTAG

CTTGCTTACAGATTCGGATAATGTATGGACCGATCGTGCAGGTGTAGATG

CTCATGCTCATGCCGCTGCTACGTATGATTTCTACAAAAACAAATTCAAC

CGTAACGGTATTAATGGTAACGGATTGTTGATCAGATCAACCGTGCACTA

CGGCTCCAATTACAATAACGCCTTCTGGAACGGGGCACAGATTGTCTTTG

GTGACGGAGATGGAACGATGTTCCGATCCCTGTCTGGTGATCTGGATGTT

GTGGGTCATGAATTGACGCATGGTGTTATTGAATATACAGCCAATCTGGA

ATATCGCAATGAACCAGGTGCACTCAATGAAGCCTTTGCCGATATTTTCG

GTAATACGATCCAAAGCAAAAACTGGCTGCTCGGTGATGATATCTACACA

CCTAACACTCCAGGAGATGCGCTGCGCTCCCTCTCCAACCCTACATTGTA

TGGTCAACCTGACAAATACAGCGATCGCTACACAGGCTCACAGGACAACG

GCGGTGTCCATATCAACAGTGGTATCATCAATAAAGCCTATTTCCTTGCT

GCTCAAGGCGGAACACATAATGGTGTGACTGTTACCGGAATCGGCCGGGA

TAAAGCGATCCAGATTTTCTACAGCACACTGGTGAACTACCTGACACCAA

CGTCCAAATTTGCCGCTGCCAAAACAGCTACCATTCAAGCAGCCAAAGAT

CTGTACGGAGCAACTTCCGCTGAAGCTACTGCTATTACCAAAGCATATCA

AGCTGTAGGCCTG
```

The amino acid sequence of the PamPro1 precursor protein is set forth as SEQ ID NO: 37. The predicted signal sequence is shown in italics, and the predicted propeptide is shown in underlined text:

*MKFAKVMPTILGGALLLASVSSATA*<u>APVSDQSIPLQAPYASEGGIPLNSG</u>

<u>TDDTIFNYLGQQEQFLNSDVKSQLKIVKRNTDTSGVRHFRLKQYIKGIPV</u>

<u>YGAEQTVHLDKTGAVSSALGDLPPIEEQAIPNDGVAEISGEDAIQIATEE</u>

<u>ATSRIGELGAAEITPQAELNIYHHEEDGQTYLVYITEVNVLEPAPLRTKY</u>

<u>FINAVDGSIVSQFDLINFATGTGTGVLGDTKTLTTTQSGSTFQLKDTTRG</u>

NGIQTYTANNGSSLPGSLLTDSDNVWTDRAGVDAHAHAAATYDFYKNKFN

RNGINGNGLLIRSTVHYGSNYNNAFWNGAQIVFGDGDGTMFRSLSGDLDV

VGHELTHGVIEYTANLEYRNEPGALNEAFADIFGNTIQSKNWLLGDDIYT

-continued

PNTPGDALRSLSNPTLYGQPDKYSDRYTGSQDNGGVHINSGIINKAYFLA

AQGGTHNGVTVTGIGRDKAIQIFYSTLVNYLTPTSKFAAAKTATIQAAKD

LYGATSAEATAITKAYQAVGL

The amino acid sequence of the predicted mature form of PamPro1 is set forth as SEQ ID NO: 38:

ATGTGTGVLGDTKTLTTTQSGSTFQLKDTTRGNGIQTYTANNGSSLPGSL

LTDSDNVWTDRAGVDAHAHAAATYDFYKNKFNRNGINGNGLLIRSTVHYG

SNYNNAFWNGAQIVFGDGDGTMFRSLSGDLDVVGHELTHGVIEYTANLEY

RNEPGALNEAFADIFGNTIQSKNWLLGDDIYTPNTPGDALRSLSNPTLYG

QPDKYSDRYTGSQDNGGVHINSGIINKAYFLAAQGGTHNGVTVTGIGRDK

AIQIFYSTLVNYLTPTSKFAAAKTATIQAAKDLYGATSAEATAITKAYQA

VGL

Example 8.2

Expression of *Paenibacillus amylolyticus* Metalloprotease PamPro1

The DNA sequence of the propeptide-mature form of PamPro1 was synthesized and inserted into the *Bacillus subtilis* expression vector p2JM103BBI (Vogtentanz, *Protein Expr Purif*, 55:40-52, 2007) by Generay (Shanghai, China), resulting in plasmid pGX146(AprE-PamPro1) (FIG. 1). Ligation of this gene encoding the PamPro1 protein into the digested vector resulted in the addition of three codons (Ala-Gly-Lys) between the 3' end of the *B. subtilis* AprE signal sequence and the 5' end of the predicted PamPro1 native propeptide. The gene has an alternative start codon (GTG). The resulting plasmid shown in FIG. 8.1, labeled pGX146(AprE-PamPro1) contains an AprE promoter, an AprE signal sequence used to direct target protein secretion in *B. subtilis*, and the synthetic nucleotide sequence encoding the predicted propeptide and mature regions of PamPro1 (SEQ ID NO: 39). The translation product of the synthetic AprE-PamPro1 gene is shown in SEQ ID NO: 40.

The pGX146(AprE-PamPro1) plasmid was then transformed into *B. subtilis* cells (degU$^{Hy}$ 32, ΔscoC) and the transformed cells were spread on Luria Agar plates supplemented with 5 ppm Chloramphenicol and 1.2% skim milk (Cat #232100, Difco). Colonies with the largest clear halos on the plates were selected and subjected to fermentation in a 250 ml shake flask with MBD medium (a MOPS based defined medium, supplemented with additional 5 mM CaCl$_2$).

The broth from the shake flasks was concentrated and buffer-exchanged into the loading buffer containing 20 mM Tris-HCl (pH 8.5), 1 mM CaCl$_2$ and 10% propylene glycol using a VivaFlow 200 ultra filtration device (Sartorius Stedim). After filtering, this sample was applied to an 80 ml Q Sepharose High Performance column pre-equilibrated with the loading buffer above; and the active flow-through fractions were collected and concentrated. The sample was loaded onto a 320 ml Superdex 75 gel filtration column pre-equilibrated with the loading buffer described above containing 0.15 M NaCl. The corresponding active purified protein fractions were further pooled and concentrated via 10K Amicon Ultra for further analyses.

The nucleotide sequence of the synthesized PamPro1 gene in plasmid pGX146(AprE-PamPro1) is depicted in SEQ ID NO: 39. The sequence encoding the three residue addition (AGK) is shown in bold:

GTGAGAAGCAAAAAATTGTGGATCAGCTTGTTGTTTGCGTTAACGTTAAT

CTTTACGATGGCGTTCAGCAACATGAGCGCGCAGGCTGCTGGAAAAGCTC

CGGTTAGCGACCAGTCAATCCCTCTTCAAGCACCGTATGCCAGCGAAGGA

GGCATTCCGCTTAACAGCGGCACGGACGACACGATTTTCAATTACCTGGG

CCAACAGGAGCAGTTCCTGAACAGCGACGTCAAGAGCCAGCTGAAGATCG

TCAAAAGAAACACAGACACATCAGGCGTGAGACACTTCAGACTGAAGCAA

TACATCAAGGGCATCCCGGTTTATGGCGCTGAACAAACGGTTCACCTGGA

CAAAACAGGCGCAGTTTCATCAGCACTGGGAGATCTGCCGCCGATTGAAG

AGCAAGCAATCCCGAATGATGGAGTTGCGGAAATTAGCGGCGAGGATGCA

ATCCAAATCGCGACGGAGGAGGCTACATCAAGAATTGGAGAACTTGGCGC

AGCGGAGATTACACCGCAGGCTGAACTGAACATCTATCACCATGAGGAAG

ACGGCCAGACGTACCTGGTTTACATTACGGAAGTGAACGTGCTGGAACCG

GCACCTCTGAGAACAAAGTACTTTATCAACGCGGTTGACGGCAGCATCGT

CTCACAGTTCGACCTGATTAACTTCGCCACGGGAACAGGAACGGGCGTTC

TTGGAGACACAAAGACGCTGACGACGACGCAGTCAGGCAGCACATTCCAG

CTGAAGGACACAACAAGAGGCAACGGCATCCAAACGTACACGGCGAACAA

TGGATCATCACTGCCGGGCTCACTGCTGACGGATTCAGATAACGTGTGGA

CGGATAGAGCTGGCGTTGACGCGCATGCTCACGCTGCTGCGACGTACGAC

TTCTACAAGAACAAGTTCAACAGAAACGGCATTAACGGAAATGGCCTGCT

GATCAGAAGCACGGTGCATTATGGCTCAAACTACAACAACGCTTTTTGGA

ACGGCGCACAGATCGTGTTTGGCGACGGCGATGGCACAATGTTTAGAAGC

CTGTCAGGAGACCTGGATGTGGTGGGCCACGAACTGACGCACGGCGTGAT

CGAGTATACGGCGAACCTTGAATATAGAAACGAGCCGGGAGCACTGAATG

AGGCGTTCGCGGACATTTTCGGCAACACAATCCAGAGCAAAAACTGGCTG

CTGGGCGACGATATCTATACACCGAACACACCGGGCGATGCACTGAGATC

ACTGTCAAATCCGACGCTGTATGGCCAACCGGATAAGTACTCAGACAGAT

ATACGGGCAGCCAAGACAATGGCGGCGTTCACATCAACTCAGGCATCATC

AACAAGGCTTACTTCCTTGCGGCCCAAGGAGGAACACATAACGGCGTTAC

AGTTACAGGCATTGGCAGAGACAAGGCGATCCAGATCTTTTACAGCACGC

TGGTGAACTACCTGACACCTACGTCAAAGTTTGCCGCAGCGAAAACAGCA

ACAATTCAGGCGGCTAAAGACCTGTACGGAGCGACATCAGCCGAGGCCAC

AGCAATTACAAAAGCATATCAAGCAGTTGGCCTTTAA

The amino acid sequence of the PamPro1 precursor protein expressed from plasmid pGX146(AprE-PamPro1) is depicted in SEQ ID NO: 40. The predicted signal sequence is shown in italics, the three residue addition (AGK) is shown in bold, and the predicted pro-peptide is shown in underlined text.

*MRSKKLWISLLFALTLIFTMAFSNMSAQ*AAGKAPVSDQSIPLQAPYASEG

GIPLNSGTDDTIFNYLGQQEQFLNSDVKSQLKIVKRNTDTSGVRHFRLKQ

YIKGIPVYGAEQTVHLDKTGAVSSALGDLPPIEEQAIPNDGVAEISGEDA

IQIATEEATSRIGELGAAEITPQAELNIYHHEEDGQTYLVYITEVNVLEP

APLRTKYFINAVDGSIVSQFDLINFATGTGTGVLGDTKTLTTTQSGSTFQ

LKDTTRGNGIQTYTANNGSSLPGSLLTDSDNVWTDRAGVDAHAHAAATYD

FYKNKFNRNGINGNGLLIRSTVHYGSNYNNAFWNGAQIVFGDGDGTMFRS

LSGDLDVVGHELTHGVIEYTANLEYRNEPGALNEAFADIFGNTIQSKNWL

LGDDIYTPNTPGDALRSLSNPTLYGQPDKYSDRYTGSQDNGGVHINSGII

NKAYFLAAQGGTHNGVTVTGIGRDKAIQIFYSTLVNYLTPTSKFAAAKTA

TIQAAKDLYGATSAEATAITKAYQAVGL

Example 8.3

Proteolytic Activity of Metalloprotease PamPro1

The proteolytic activity of purified metalloprotease PamPro1 was measured in 50 mM Tris (pH 7), using azo-casein (Cat #74H7165, Megazyme) as a substrate. Prior to the reaction, the enzyme was diluted with Milli-Q water (Millipore) to specific concentrations. The azo-casein was dissolved in 100 mM Tris buffer (pH 7) to a final concentration of 1.5% (w/v). To initiate the reaction, 50 µl of the diluted enzyme (or Milli-Q H$_2$O alone as the blank control) was added to the non-binding 96-well Microtiter Plate (96-MTP) (Corning Life Sciences, #3641) placed on ice, followed by the addition of 50 µl of 1.5% azo-casein. After sealing the 96-MTP, the reaction was carried out in a Thermomixer (Eppendorf) at 40° C. and 650 rpm for 10 min. The reaction was terminated by adding 100 µl of 5% Trichloroacetic Acid (TCA). Following equilibration (5 min at the room temperature) and subsequent centrifugation (2000 g for 10 min at 4° C.), 120 µl supernatant was transferred to a new 96-MTP, and absorbance of the supernatant was measured at 440 nm (A$_{440}$) using a SpectraMax 190. Net A$_{440}$ was calculated by subtracting the A$_{440}$ of the blank control from that of enzyme, and then plotted against different protein concentrations (from 1.25 ppm to 40 ppm). Each value was the mean of triplicate assays. The proteolytic activity is shown as Net A$_{440}$. The proteolytic assay with azo-casein as the substrate (shown in FIG. 8.2) indicates that PamPro1 is an active protease.

Example 8.4 pH Profiles of Metalloprotease PamPro1

With azo-casein as the substrate, the pH profiles of metalloprotease PamPro1 were studied in 12.5 mM acetate/Bis-Tris/HEPES/CHES buffer with different pH values (ranging from pH 4 to 11). To initiate the assay, 50 µl of 25 mM acetate/Bis-Tris/HEPES/CHES buffer with a specific pH was first mixed with 2 µl Milli-Q H$_2$O diluted enzyme (125 ppm) in a 96-MTP placed on ice, followed by the addition of 48 µl of 1.5% (w/v) azo-casein prepared in H$_2$O. The reaction was performed and analyzed as described in Example 8.3. Enzyme activity at each pH was reported as the relative activity, where the activity at the optimal pH was set to be 100%. The pH values tested were 4, 5, 6, 7, 8, 9, 10 and 11. Each value was the mean of triplicate assays. As shown in FIG. 8.3, the optimal pH of PamPro1 is about 8, with greater than 70% of maximal activity retained between 7 and 9.5.

Example 8.5

Temperature Profile of Metalloprotease PamPro1

The temperature profile of metalloprotease PamPro1 was analyzed in 50 mM Tris buffer (pH 7) using the azo-casein assays. The enzyme sample and azo-casein substrate were prepared as in Example 8.3. Prior to the reaction, 50 µl of 1.5% azo-casein and 45 µl Milli-Q H$_2$O were mixed in a 200 µl PCR tube, which was then subsequently incubated in a Peltier Thermal Cycler (BioRad) at desired temperatures (i.e. 20~90° C.) for 5 min. After the incubation, 5 µl of diluted enzyme (50 ppm) or H$_2$O (the blank control) was added to the substrate mixture, and the reaction was carried out in the Peltier Thermal Cycle for 10 min at different temperatures. To terminate the reaction, each assay mixture was transferred to a 96-MTP containing 100 µl of 5% TCA per well. Subsequent centrifugation and absorbance measurement were performed as described in Example 8.3. The activity was reported as the relative activity, where the activity at the optimal temperature was set to be 100%. The tested temperatures are 20, 30, 40, 50, 60, 70, 80, and 90° C. Each value was the mean of duplicate assays (the value varies no more than 5%). The data in FIG. 8.4 suggest that PamPro1 showed an optimal temperature at about 50° C., and retained greater than 70% of its maximum activity between 45 and 55° C.

Example 8.6

Cleaning Performance of Metalloprotease PamPro1

The cleaning performance of PamPro1 was tested using PA-S-38 (egg yolk, with pigment, aged by heating) microswatches (CFT-Vlaardingen, The Netherlands) at pH 6 and 8 using a model automatic dishwashing (ADW) detergent. Prior to the reaction, purified protease samples were diluted with a dilution solution containing 10 mM NaCl, 0.1 mM CaCl$_2$, 0.005% TWEEN® 80 and 10% propylene glycol to the desired concentrations. The reactions were performed in AT detergent with 100 ppm water hardness (Ca$^{2+}$:Mg$^{2+}$=3:1) (detergent composition shown in Table 8.1). To initiate the reaction, 180 µl of the AT detergent buffered at pH 6 or pH 8 was added to a 96-MTP placed with PA-S-38 microswatches, followed by the addition of 20 µl of diluted enzymes (or the dilution solution as the blank control). The 96-MTP was sealed and incubated in an incubator/shaker for 30 min at 50° C. and 1150 rpm. After incubation, 100 µl of wash liquid from each well was transferred to a new 96-MTP, and its absorbance was measured at 405 nm (referred here as the "Initial performance") using a spectrophotometer. The remaining wash liquid in the 96-MTP was discarded and the microswatches were rinsed once with 200 µl water. Following the addition of 180 µl of 0.1 M CAPS buffer (pH 10), the second incubation was carried out in the incubator/shaker at 50° C. and 1150 rpm for 10 min. One hundred microliters of the resulting wash liquid was transferred to a new 96-MTP, and its absorbance measured at 405 nm (referred here as the "Wash-off"). The sum of two absorbance measurements ("Initial performance" plus "Wash-off") gives the "Total performance", which measures the protease activity on the model stain; and Net A$_{405}$ was subsequently calculated by subtracting the $A_{405}$ of the "Total performance" of the blank control from that of the enzyme. Dose response in cleaning the PA-S-38 microswatches at pH 6 and pH 8 in AT dish detergent for PamPro1 is shown in FIGS. 5A and 5B.

TABLE 8.1

Composition of AT dish detergent formula with bleach

| Ingredient | Concentration (mg/ml) |
|---|---|
| MGDA (methylglycinediacetic acid) | 0.143 |
| Sodium citrate | 1.86 |
| Citric acid* | varies |
| PAP (peracid N,N-phthaloylaminoperoxycaproic acid) | 0.057 |
| Plurafac ® LF 18B (a non-ionic surfactant) | 0.029 |
| Bismuthcitrate | 0.006 |
| Bayhibit ® S (Phosphonobutantricarboxylic acid sodium salt) | 0.006 |
| Acusol ™ 587 (a calcium polyphosphate inhibitor) | 0.029 |
| PEG 6000 | 0.043 |
| PEG 1500 | 0.1 |

*The pH of the AT formula detergent is adjusted to the desired value (pH 6 or 8) by the addition of 0.9M citric acid.

Example 8.7

Comparison of PamPro1 to Other Proteases

A. Identification of Homologous Proteases

Homologs were identified by a BLAST search (Altschul et al., Nucleic Acids Res, 25:3389-402, 1997) against the NCBI non-redundant protein database and the Genome Quest Patent database with search parameters set to default values. The predicted mature protein amino acid sequence for PamPro1 (SEQ ID NO: 38) was used as the query sequence. Percent identity (PID) for both search sets is defined as the number of identical residues divided by the number of aligned residues in the pairwise alignment. Tables 8.2A and 8.2B provide a list of sequences with the percent identity to PamPro1. The length in Table 8.2 refers to the entire sequence length of the homologous proteases.

TABLE 8.2A

List of sequences with percent identity to PamPro1 protein identified from the NCBI non-redundant protein database

| Accession # | PID to PamPro1 | Organism | Length |
|---|---|---|---|
| P23384 | 56 | Bacillus caldolyticus | 544 |
| P00800 | 56 | Bacillus thermoproteolyticus | 548 |
| ZP_08640523.1 | 57 | Brevibacillus laterosporus LMG 15441 | 564 |
| BAA06144.1 | 57 | Lactobacillus sp. | 566 |
| YP_003872180.1 | 58 | Paenibacillus polymyxa E681 | 587 |
| ZP_04149724.1 | 59 | Bacillus pseudomycoides DSM 12442 | 566 |
| EJR46541.1 | 60 | Bacillus cereus VD107 | 566 |
| YP_001373863.1 | 60 | Bacillus cytotoxicus NVH 391-98 | 565 |
| ZP_10738945.1 | 61 | Brevibacillus sp. CF 112 | 528 |
| YP_004646155.1 | 61 | Paenibacillus mucilaginosus KNP414 | 525 |
| ZP_02326602.1 | 62 | Paenibacillus larvae subsp. larvae BRL-230010 | 520 |
| P43263 | 63 | Brevi bacillus brevis | 527 |
| ZP_09775365.1 | 64 | Paenibacillus sp. Aloe-11 | 580 |
| ZP_09077634.1 | 65 | Paenibacillus elgii B69 | 529 |
| ZP_09071078.1 | 68 | Paenibacillus larvae subsp. larvae B-3650 | 529 |

TABLE 8.2A-continued

List of sequences with percent identity to PamPro1 protein identified from the NCBI non-redundant protein database

| Accession # | PID to PamPro1 | Organism | Length |
|---|---|---|---|
| ZP_08511445.1 | 69 | Paenibacillus sp. HGF7 | 525 |
| YP_005073223.1 | 70 | Paenibacillus terrae HPL-003 | 591 |
| YP_003948511.1 | 71 | Paenibacillus polymyxa SC2 | 592 |
| ZP_10241030.1 | 71 | Paenibacillus peoriae KCTC 3763 | 593 |

TABLE 8.2B

List of sequences with percent identity to PamPro1 protein identified from the Genome Quest Patent database

| Patent # | PID to PamPro1 | Organism | Length |
|---|---|---|---|
| US7335504-0030 | 56.63 | Bacillus thermoproteolyticus | 316 |
| US20120107907-0184 | 56.91 | Bacillus caldoyticus | 319 |
| JP2006124323-0003 | 56.96 | Bacillus thermoproteolyticus | 316 |
| JP1993199872-0001 | 56.96 | Bacillus sp. | 316 |
| JP1997000255-0001 | 56.96 | empty | 548 |
| US6518054-0001 | 57.23 | Bacillus sp. | 319 |
| US20120107907-0176 | 57.23 | Bacillus stearothermophilis | 548 |
| US8114656-0183 | 57.28 | Bacillus stearothermophilis | 316 |
| US20120009651-0002 | 57.28 | Geobacillus caldoproteolyticus | 548 |
| JP2011103791-0020 | 57.28 | Geobacillus stearothermophilus | 552 |
| WO2012110562-0006 | 57.88 | Bacillus megaterium | 320 |
| EP2390321-0178 | 57.88 | Bacillus thuringiensis | 566 |
| US6518054-0002 | 57.93 | Bacillus sp. | 316 |
| WO2012110562-0007 | 58.25 | Bacillus cereus | 320 |
| JP1995184649-0001 | 58.52 | Lactobacillus sp. | 566 |
| EP2178896-0184 | 58.52 | Bacillus anthracis | 566 |
| EP2390321-0195 | 59.55 | Bacillus cereus | 317 |
| WO2012110563-0005 | 59.87 | Bacillus cereus | 320 |
| US20080293610-0186 | 63.25 | Bacillus brevis | 304 |
| JP2005229807-0018 | 71.19 | Paenibacillus polymyxa | 566 |
| US8114656-0187 | 71.43 | Bacillus polymyxa | 302 |

B. Alignment of Homologous Protease Sequences

The amino acid sequence of the predicted mature PamPro1 (SEQ ID NO: 38) was aligned with thermolysin (P00800, *Bacillus thermoproteolyticus*), and protease from *Paenibacillus peoriae* KCTC 3763 (YP_005073223.1) using CLUSTALW software (Thompson et al., Nucleic Acids Research, 22:4673-4680, 1994) with the default parameters. FIG. 8.6 shows the alignment of PamPro1 with these protease sequences.

C. Phylogenetic Tree

A phylogenetic tree for full length sequences of PamPro1 (SEQ ID NO: 37) was built using sequences of representative homologs from Table 8.2A and the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 8.7.

Example 9

Comparison of the Various *Paenibacillus* Metalloproteases with Other Bacterial Metalloprotease Homologs A. Alignment of Homologous Protease Sequences The amino acid sequence of the predicted mature sequences for the *Paenibacillus* proteases described in Examples 1.1 to 8.7 were aligned with related bacterial metalloproteases using CLUSTALW software (Thompson et al., Nucleic Acids Research, 22:4673-4680, 1994) with the default parameters. FIG. 9.1 shows the alignment of the various *Paenibacillus* metalloproteases with other bacterial metalloprotease homologs.

B. Phylogenetic Tree

A phylogenetic tree for full length sequences of the metalloproteases aligned in FIG. 9.1 was created using the Neighbor Joining method (NJ) (Saitou, N.; and Nei, M. (1987). The neighbor-joining method: a new method for reconstructing Guide Trees. MolBiol.Evol. 4, 406-425). The NJ method works on a matrix of distances between all pairs of sequences to be analyzed. These distances are related to the degree of divergence between the sequences. The phylodendron-phylogenetic tree printer software (http://iubio.bio.indiana.edu/treeapp/treeprint-form.html) was used to display the phylogenetic tree shown in FIG. 9.2, where one can observe the clustering of the sequences from *Paenibacillus* genus.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

---

The invention claimed is:

1. A composition comprising a polypeptide comprising an amino acid sequence having at least 90% sequence identity to the amino acid sequence of SEQ ID NO: 33 and at least one surfactant, wherein the surfactant is a non-ionic surfactant.

2. The composition of claim 1, wherein said composition comprises from about 0.001 to about 0.1 weight % of said polypeptide.

3. The composition of claim 1, wherein said composition is a granular, powder, solid, bar, liquid, tablet, gel, or paste composition.

4. The composition of claim 1, wherein said composition is formulated at a pH of from about 5.5 to about 8.5.

* * * * *